US012215338B2

(12) United States Patent
Kim et al.

(10) Patent No.: US 12,215,338 B2
(45) Date of Patent: Feb. 4, 2025

(54) ADENO-ASSOCIATED VIRUS (AAV) DELIVERY OF ANTI-FAM19A5 ANTIBODIES

(71) Applicants: Neuracle Science Co., Ltd., Seoul (KR); Neuracle Genetics, Seoul (KR)

(72) Inventors: Jong-Mook Kim, Seoul (KR); Dong Sik Kim, Seoul (KR); Juwon Shim, Seoul (KR); Soon-gu Kwon, Seoul (KR)

(73) Assignees: Neuracle Science Co., Ltd., Seoul (KR); Neuracle Genetics, Seoul (KR)

( * ) Notice: Subject to any disclaimer, the term of this patent is extended or adjusted under 35 U.S.C. 154(b) by 135 days.

(21) Appl. No.: 17/053,733

(22) PCT Filed: May 8, 2019

(86) PCT No.: PCT/IB2019/053791
§ 371 (c)(1),
(2) Date: Nov. 6, 2020

(87) PCT Pub. No.: WO2019/215644
PCT Pub. Date: Nov. 14, 2019

(65) Prior Publication Data
US 2021/0388382 A1    Dec. 16, 2021

Related U.S. Application Data

(60) Provisional application No. 62/668,634, filed on May 8, 2018.

(51) Int. Cl.
*A61K 48/00*     (2006.01)
*C07K 16/24*    (2006.01)
(Continued)

(52) U.S. Cl.
CPC .............. *C12N 15/86* (2013.01); *C07K 16/24* (2013.01); *A61K 2039/505* (2013.01);
(Continued)

(58) Field of Classification Search
None
See application file for complete search history.

(56) References Cited

U.S. PATENT DOCUMENTS

| 414,209 | A | 11/1889 | Gonon |
| 4,044,126 | A | 8/1977 | Cook et al. |

(Continued)

FOREIGN PATENT DOCUMENTS

| JP | 2002503092 A | 1/2002 |
| WO | WO-1998022607 A1 | 5/1998 |

(Continued)

OTHER PUBLICATIONS

An, Z., et al., "IgG2m4, an engineered antibody isotype with reduced Fc function," mAbs 1(6):572-579, Taylor and Francis, United States (Nov.-Dec. 2009).

(Continued)

*Primary Examiner* — M Franco G Salvoza
(74) *Attorney, Agent, or Firm* — Sterne, Kessler, Goldstein & Fox P.L.L.C.

(57) ABSTRACT

The present disclosure provides adeno-associated vims (AAV) vectors and uses thereof. In certain embodiments, the AAV vectors comprise a nucleic acid that encodes an antagonist against a family with sequence similarity 19, member A5 (FAM19A5) protein, e.g., anti-FAM19A5 antibody, e.g., anti-FAM19A5 scFv.

20 Claims, 13 Drawing Sheets

Specification includes a Sequence Listing.

(51) Int. Cl.
  *C12N 15/86* (2006.01)
  *A61K 39/00* (2006.01)
(52) U.S. Cl.
  CPC .... *C07K 2317/622* (2013.01); *C07K 2317/76* (2013.01); *C12N 2750/14141* (2013.01); *C12N 2800/22* (2013.01)

(56) References Cited

U.S. PATENT DOCUMENTS

| | | | |
|---|---|---|---|
| 4,364,923 | A | 12/1982 | Cook et al. |
| 5,693,780 | A | 12/1997 | Newman et al. |
| 5,709,874 | A | 1/1998 | Hanson et al. |
| 5,759,542 | A | 6/1998 | Gurewich |
| 5,840,674 | A | 11/1998 | Yatvin et al. |
| 5,900,252 | A | 5/1999 | Calanchi et al. |
| 5,972,366 | A | 10/1999 | Haynes et al. |
| 5,985,307 | A | 11/1999 | Hanson et al. |
| 6,004,534 | A | 12/1999 | Langer et al. |
| 6,039,975 | A | 3/2000 | Shah et al. |
| 6,048,736 | A | 4/2000 | Kosak |
| 6,060,082 | A | 5/2000 | Chen et al. |
| 6,071,495 | A | 6/2000 | Unger et al. |
| 6,120,751 | A | 9/2000 | Unger |
| 6,131,570 | A | 10/2000 | Schuster et al. |
| 6,139,865 | A | 10/2000 | Friend et al. |
| 6,271,359 | B1 | 8/2001 | Norris |
| 6,274,552 | B1 | 8/2001 | Tamarkin et al. |
| 6,316,652 | B1 | 11/2001 | Steliou |
| 9,074,002 | B2 | 7/2015 | Tonks et al. |
| 9,579,398 | B2 | 2/2017 | Seong et al. |
| 11,155,613 | B2 * | 10/2021 | Kim .................. C07K 16/24 |
| 2004/0014194 | A1 | 1/2004 | Beyer et al. |
| 2009/0221670 | A1 | 9/2009 | Borglum et al. |
| 2012/0100140 | A1 | 4/2012 | Reyes et al. |
| 2015/0118230 | A1 | 4/2015 | Seong et al. |

FOREIGN PATENT DOCUMENTS

| | | | |
|---|---|---|---|
| WO | WO-9844955 A1 | 10/1998 | |
| WO | WO-199906562 A1 | 2/1999 | |
| WO | WO-200028004 A1 | 5/2000 | |
| WO | WO-200073316 A2 | 12/2000 | |
| WO | WO-200123001 A2 | 4/2001 | |
| WO | WO-2004112727 A2 | 12/2004 | |
| WO | WO-2005005610 A2 | 12/2005 | |
| WO | WO-2005072364 A2 | 12/2005 | |
| WO | WO-2012115980 A1 | 8/2012 | |
| WO | WO-2017040528 A1 | 3/2017 | |
| WO | WO-2017075119 A1 * | 5/2017 | .......... A61K 39/395 |
| WO | WO-2018083538 A1 | 5/2018 | |
| WO | WO-2019003159 A1 * | 1/2019 | .......... A61K 39/395 |
| WO | WO-2019207513 A1 * | 10/2019 | .............. A61P 25/02 |
| WO | WO-2019215644 A1 | 11/2019 | |

OTHER PUBLICATIONS

Bird, R.E., et al., "Single-chain antigen-binding proteins," Science 242:423-426, American Association for the Advancement of Science, United States (Oct. 1988).
Bricogne, G., et al., "Direct phase determination by entropy maximization and likelihood ranking: status report and perspectives," Acta Crystallogr D Bio Crystallogr 49(1):37-60, Wiley Publishing, United States (Jan. 1993).
Campbell, J.N., et al., "Mechanisms of neuropathic pain," Neuron 52(1):77-92, Cell Press, United States (Oct. 2006).
Chames, P., et al., "Therapeutic antibodies: successes, limitations and hopes for the future," Br J. Pharmacol 157(2):220-223, British Journal of Pharmacology, England (May 2009).
Champe, M., et al., "Monoclonal antibodies that block the activity of leukocyte function-associated antigen 1 recognize three discrete epitopes in the inserted domain of CD11a," J Biol Chem 270:1388-1394, Elsevier, Netherlands (Jan. 1995).

Chayen, N.E., et al., "The role of oil in macromolecular crystallization," Structure 5:1269-1274, Europe PMC, England (Oct. 1997).
Cunningham, B.C., et al., "High-resolution epitope mapping of hGH-receptor interactions by alanine-scanning mutagenesis," Science 244:1081-1085, American Association for the Advancement of Science, United States (Jun. 1989).
Daya, S., et al., "Gene therapy using adeno-associated virus vectors," Clin Microbiol Rev 21(4):583-593, American Society for Microbiology, United States (Oct. 2008).
Ecker, D.M., et al., "The therapeutic monoclonal antibody market," MAbs 7:9-14, Taylor and Francis, United States (Jan.-Feb. 2015).
Finnerup, N.B., et al., "Neuropathic pain: an updated grading system for research and clinical practice," Pain 157(8):1599-1606, Wolters Kluwer, Netherlands (Aug. 2016).
Giege, R., et al., "The CCP4 suite: programs for protein crystallography," Acta Crystallogr D Biol Crystallogr 50(4):339-350, Wiley Publishing, United States (Sep. 1994).
Goncalves, M., et al., "Adeno-associated virus: from defective virus to effective vector," Virol J 2:43, BioMed Central, England (May 2005).
Harmsen, M.M., et al., "Properties, production, and applications of camelid single-domain antibody fragments," App Microbiol Biotechnol 77(1):13-22, SpringerLink, Germany (Aug. 2007).
Huston, U.S., et al., "Protein engineering of antibody binding sites: recovery of specific activity in an anti-digoxin single-chain Fv analogue produced in Escherichia coli," Proc. Natl. Acad. Sci. USA 85:5879-5883, United States National Academy of Sciences, United States (Aug. 1988).
Inoue, N., et al., "Packaging Cells Based on Inducible Gene Amplification for the Production of Adeno-Associated Virus Vectors," J. Virol 72:7024-7031, American Society for Microbiology, United States (Sep. 1998).
International Search Report and Written Opinion for International Application No. PCT/IB2019/053791, Korean Intellectual Property Office, Korea, mailed on Sep. 23, 2019, 12 pages.
Jefferis, R., et al., "Human immunoglobulin allotypes," mAbs 1:1, Taylor and Francis, United States (Jul .- Aug. 2009).
Korea University, "Discovery and functional characterization of novel peptidome," Brain Science Source Technology Development Project Final Report; 1-46 (Nov. 2017).
Kostelny, S.A., et al., "Formation of a bispecific antibody by the use of leucine zippers," J. Immunol. 148:1547-1553, American Association of Immunologists (Mar. 1992).
Lau, C., et al., "Chimeric Anti-CD14 IGG2/4 Hybrid Antibodies for Therapeutic Intervention in Pig and Human Models of Inflammation," J. of Immunology 191:4769-4777, American Association of Immunologists, United States (Nov. 2013).
Lonberg, T., et al., "Human antibodies from transgenic animals," Nature Biotech 23(9):1117-1125, Nature Publishing Group, England (Sep. 2005).
McPherson, A., et al., "Current approaches to macromolecular crystallization," Eur J. Biochem 189:1-23, Wiley Publishing, United States (Apr. 1990).
McPherson, A., et al., "Crystallization of proteins from polyethylene glycol," J Bio Chem 251:6300-6303, American Society for Biochemistry and Molecular Biology, United States (Oct. 1976).
Roux, K.H., et al., "Comparisons of the Ability of Human IgG3 Hinge Mutants, IgM, IgE, and IgA2, to Form Small Immune Complexes: A Role for Flexibility and Geometry," J. Immunol. 161:4083, American Association of Immunologists, United States (Oct. 1998).
Roversi, P., et al., "Modelling prior distributions of atoms for macromolecular refinement and completion," Acta Crystallogr D Biol Crystallogr 56(10):1316-1323, Wiley Publishing, United States (Oct. 2000).
Samulski, R.J., et al., "Helper-free stocks of recombinant adeno-associated viruses: normal integration does not require viral gene expression," Virology 63: 3822-3828, American Society for Microbiology, United States (Sep. 1989).
Songsivilai, S., et al., "Bispecific antibody: a tool for diagnosis and treatment of disease," Clin. Exp. Immunol. 79:315-321, British Society for Immunology, England (Mar. 1990).

(56) References Cited

OTHER PUBLICATIONS

Tang, T., et al., "TAFA: a novel secreted family with conserved cysteine residues and restricted expression in the brain," Genomis 83(4):727-734, Elsevier, Netherlands (Apr. 2004).
Vidarsson, G., et al., "IgG subclasses and allotypes: from structure to effector functions," Front Immunol 5:520, Frontiers, United States (Oct. 2014).
Xiao,X., et al., "Production of high-titer recombinant adeno-associated virus vectors in the absence of helper adenovirus," Virology 72:2224, American Society for Microbiology, United States(Mar. 1998).

* cited by examiner

SEQUENCE LISTING

```
<160> NUMBER OF SEQ ID NOS: 301

<210> SEQ ID NO 1
<211> LENGTH: 132
<212> TYPE: PRT
<213> ORGANISM: Homo Sapiens

<400> SEQUENCE: 1

Met Ala Pro Ser Pro Arg Thr Gly Ser Arg Gln Asp Ala Thr Ala Leu
1               5                   10                  15

Pro Ser Met Ser Ser Thr Phe Trp Ala Phe Met Ile Leu Ala Ser Leu
                20                  25                  30

Leu Ile Ala Tyr Cys Ser Gln Leu Ala Ala Gly Thr Cys Glu Ile Val
            35                  40                  45

Thr Leu Asp Arg Asp Ser Ser Gln Pro Arg Arg Thr Ile Ala Arg Gln
        50                  55                  60

Thr Ala Arg Cys Ala Cys Arg Lys Gly Gln Ile Ala Gly Thr Thr Arg
65                  70                  75                  80

Ala Arg Pro Ala Cys Val Asp Ala Arg Ile Ile Lys Thr Lys Gln Trp
                85                  90                  95

Cys Asp Met Leu Pro Cys Leu Glu Gly Glu Gly Cys Asp Leu Leu Ile
                100                 105                 110

Asn Arg Ser Gly Trp Thr Cys Thr Gln Pro Gly Gly Arg Ile Lys Thr
            115                 120                 125

Thr Thr Val Ser
        130

<210> SEQ ID NO 2
<211> LENGTH: 125
<212> TYPE: PRT
<213> ORGANISM: Homo Sapiens

<400> SEQUENCE: 2

Met Gln Leu Leu Lys Ala Leu Trp Ala Leu Ala Gly Ala Ala Leu Cys
1               5                   10                  15

Cys Phe Leu Val Leu Val Ile His Ala Gln Phe Leu Lys Glu Gly Gln
                20                  25                  30

Leu Ala Ala Gly Thr Cys Glu Ile Val Thr Leu Asp Arg Asp Ser Ser
            35                  40                  45

Gln Pro Arg Arg Thr Ile Ala Arg Gln Thr Ala Arg Cys Ala Cys Arg
        50                  55                  60

Lys Gly Gln Ile Ala Gly Thr Thr Arg Ala Arg Pro Ala Cys Val Asp
65                  70                  75                  80
```

```
Ala Arg Ile Ile Lys Thr Lys Gln Trp Cys Asp Met Leu Pro Cys Leu
                85                  90                  95

Glu Gly Glu Gly Cys Asp Leu Leu Ile Asn Arg Ser Gly Trp Thr Cys
            100                 105                 110

Thr Gln Pro Gly Gly Arg Ile Lys Thr Thr Thr Val Ser
        115                 120                 125

<210> SEQ ID NO 3
<211> LENGTH: 53
<212> TYPE: PRT
<213> ORGANISM: Homo Sapiens

<400> SEQUENCE: 3

Met Tyr His His Arg Glu Trp Pro Ala Arg Ile Ile Lys Thr Lys Gln
1               5                   10                  15

Trp Cys Asp Met Leu Pro Cys Leu Glu Gly Glu Gly Cys Asp Leu Leu
                20                  25                  30

Ile Asn Arg Ser Gly Trp Thr Cys Thr Gln Pro Gly Gly Arg Ile Lys
                35                  40                  45

Thr Thr Thr Val Ser
        50

<210> SEQ ID NO 4
<211> LENGTH: 1501
<212> TYPE: DNA
<213> ORGANISM: Homo Sapiens

<400> SEQUENCE: 4
ggcggcggag gatggcgcgc gcggggcccg cacgtggagg ccggcgcggg ggcgcgggca     60
gggccggctg ctgagacgcg ctgctgcccc ccgcgcgggc gccgcggctt caatggcgcc    120
atcgcccagg accggcagcc ggcaagatgc gaccgccctg cccagcatgt cctcaacttt    180
ctgggcgttc atgatcctgg ccagcctgct catcgcctac tgcagtcagc tggccgccgg    240
cacctgtgag attgtgacct ggaccgggga cagcagccag cctcggagga cgatcgcccg    300
gcagaccgcc cgctgtgcgt gtagaaaggg gcagatcgcc ggcaccacga gagcccggcc    360
cgcctgtgtg gacgcaagaa tcatcaagac caagcagtgg tgtgacatgc ttccgtgtct    420
ggagggggaa ggctgcgact tgttaatcaa ccggtcaggc tggacgtgca cgcagccccgg   480
cgggaggata aagaccacca cggtctcctg acaaacacag cccctgaggg ggccccggga    540
gtggccttgg ctccctggag agcccacgtc tcagccacag ttctccactc gcctcggact    600
tcaccccgttc tctgccgccc gcccactccg tttccctgtg gtccgtgaag acggcctca    660
ggccttggca tcctgagctt cggtctgtcc agccgacccg aggaggccgg actcagacac    720
ataggcgggg ggcggcacct ggcatcagca atacgcagtc tgtgggagcc cggccgcgcc    780
cagcccccgc cgaccgtggc gttggccctg ctgtcctcag aggaggagga ggaggagca    840
gctccggcag ccacagaagg ctgcagccca gcccgcctga cacgacgc ctgccccagg      900
ggactgtcag gcacagaagc ggcctcctcc cgtgcccag actgtccgaa ttgcttttat    960
tttcttatac tttcagtata ctccatagac caaagagcaa aatctatctg aacctggacg   1020
caccctcact gtcagggtcc ctggggtcgc ttgtgcgggc gggagggcaa tggtggcaga   1080
gacatgctgg tggccccggc ggagcggaga gggcggccgt ggtggaggcc tccaccccag   1140
gagcaccccg cacaccctcg gaggacgggc ttcggctgcg cggaggccgt ggcacacctg   1200
cgggaggcag cgacggcccc cacgcagacg ccgggaacgc aggccgcttt attcctctgt   1260
```

```
acttagatca acttgaccgt actaaaatcc ctttctgttt taaccagtta aacatgcctc    1320
ttctacagct ccattttga tagttggata atccagtatc tgccaagagc atgttgggtc    1380
tcccgtgact gctgcctcat cgatacccca tttagctcca gaaagcaaag aaaactcgag    1440
taacacttgt ttgaaagaga tcattaaatg tattttgcaa agcccaaaaa aaaaaaaaaa    1500
a                                                                    1501
```

<210> SEQ ID NO 5
<211> LENGTH: 14
<212> TYPE: PRT
<213> ORGANISM: Artificial Sequence
<220> FEATURE:
<223> OTHER INFORMATION: Epitope F1

<400> SEQUENCE: 5

Gln Leu Ala Ala Gly Thr Cys Glu Ile Val Thr Leu Asp Arg
1               5                   10

<210> SEQ ID NO 6
<211> LENGTH: 20
<212> TYPE: PRT
<213> ORGANISM: Artificial Sequence
<220> FEATURE:
<223> OTHER INFORMATION: Epitope F2

<400> SEQUENCE: 6

Thr Leu Asp Arg Asp Ser Ser Gln Pro Arg Arg Thr Ile Ala Arg Gln
1               5                   10                  15

Thr Ala Arg Cys
            20

<210> SEQ ID NO 7
<211> LENGTH: 20
<212> TYPE: PRT
<213> ORGANISM: Artificial Sequence
<220> FEATURE:
<223> OTHER INFORMATION: Epitope F3

<400> SEQUENCE: 7

Thr Ala Arg Cys Ala Cys Arg Lys Gly Gln Ile Ala Gly Thr Thr Arg
1               5                   10                  15

Ala Arg Pro Ala
            20

<210> SEQ ID NO 8
<211> LENGTH: 20
<212> TYPE: PRT
<213> ORGANISM: Artificial Sequence
<220> FEATURE:
<223> OTHER INFORMATION: Epitope F4

<400> SEQUENCE: 8

Ala Arg Pro Ala Cys Val Asp Ala Arg Ile Ile Lys Thr Lys Gln Trp
1               5                   10                  15

Cys Asp Met Leu
            20

<210> SEQ ID NO 9
<211> LENGTH: 20
<212> TYPE: PRT
<213> ORGANISM: Artificial Sequence
<220> FEATURE:
<223> OTHER INFORMATION: Epitope F5

```
<400> SEQUENCE: 9

Cys Asp Met Leu Pro Cys Leu Glu Gly Glu Gly Cys Asp Leu Leu Ile
1               5                   10                  15

Asn Arg Ser Gly
            20

<210> SEQ ID NO 10
<211> LENGTH: 20
<212> TYPE: PRT
<213> ORGANISM: Artificial Sequence
<220> FEATURE:
<223> OTHER INFORMATION: Epitope F6

<400> SEQUENCE: 10

Asn Arg Ser Gly Trp Thr Cys Thr Gln Pro Gly Gly Arg Ile Lys Thr
1               5                   10                  15

Thr Thr Val Ser
            20

<210> SEQ ID NO 11
<211> LENGTH: 5
<212> TYPE: PRT
<213> ORGANISM: Artificial Sequence
<220> FEATURE:
<223> OTHER INFORMATION: 2-13 Antibody VH-CDR1

<400> SEQUENCE: 11

Ser His Gly Met Phe
1               5

<210> SEQ ID NO 12
<211> LENGTH: 17
<212> TYPE: PRT
<213> ORGANISM: Artificial Sequence
<220> FEATURE:
<223> OTHER INFORMATION: 2-13; 2-13D; 2-13D-37; 2-13D-37-1.5W-41; 2-13D-
      37-3W-16 VH-CDR2

<400> SEQUENCE: 12

Glu Ile Thr Asn Asp Gly Ser Gly Thr Asn Tyr Gly Ser Ala Val Lys
1               5                   10                  15

Gly

<210> SEQ ID NO 13
<211> LENGTH: 20
<212> TYPE: PRT
<213> ORGANISM: Artificial Sequence
<220> FEATURE:
<223> OTHER INFORMATION: 2-13; 2-13D; 2-13D-37 VH-CDR3

<400> SEQUENCE: 13

Ser Thr Tyr Glu Cys Pro Gly Gly Phe Ser Cys Trp Gly Asp Thr Gly
1               5                   10                  15

Gln Ile Asp Ala
            20

<210> SEQ ID NO 14
<211> LENGTH: 5
<212> TYPE: PRT
<213> ORGANISM: Artificial Sequence
<220> FEATURE:
<223> OTHER INFORMATION: 3-2 Antibody VH-CDR1

<400> SEQUENCE: 14
```

```
Ser Phe Asn Met Phe
1               5

<210> SEQ ID NO 15
<211> LENGTH: 17
<212> TYPE: PRT
<213> ORGANISM: Artificial Sequence
<220> FEATURE:
<223> OTHER INFORMATION: 3-2 Antibody VH-CDR2

<400> SEQUENCE: 15

Gln Ile Ser Ser Ser Gly Ser Ser Thr Asn Tyr Ala Pro Ala Val Arg
1               5                   10                  15

Gly

<210> SEQ ID NO 16
<211> LENGTH: 22
<212> TYPE: PRT
<213> ORGANISM: Artificial Sequence
<220> FEATURE:
<223> OTHER INFORMATION: 3-2; 1-7A-IT; Low-PI; 1-30; 1-17; 1-32; 4-11;
      6-10 VH-CDR3

<400> SEQUENCE: 16

Ser Ser Tyr Asp Cys Pro Tyr Gly His Cys Ser Ser Gly Val Asp Ser
1               5                   10                  15

Ala Gly Glu Ile Asp Ala
            20

<210> SEQ ID NO 17
<211> LENGTH: 5
<212> TYPE: PRT
<213> ORGANISM: Artificial Sequence
<220> FEATURE:
<223> OTHER INFORMATION: 1-65; SS01-13; SS01-13-s5; S5-2.GKNG VH-CDR1

<400> SEQUENCE: 17

Ser Tyr Gln Met Gly
1               5

<210> SEQ ID NO 18
<211> LENGTH: 10
<212> TYPE: PRT
<213> ORGANISM: Artificial Sequence
<220> FEATURE:
<223> OTHER INFORMATION: 1-65; SS01-13 VH-CDR2

<400> SEQUENCE: 18

Val Ile Asn Lys Ser Gly Ser Asp Thr Ser
1               5                   10

<210> SEQ ID NO 19
<211> LENGTH: 13
<212> TYPE: PRT
<213> ORGANISM: Artificial Sequence
<220> FEATURE:
<223> OTHER INFORMATION: 1-65; SS01-13; SS01-13-s5; S5-2.GKNG VH-CDR3

<400> SEQUENCE: 19

Gly Ser Ala Ser Tyr Ile Thr Ala Ala Thr Ile Asp Ala
1               5                   10

<210> SEQ ID NO 20
<211> LENGTH: 8
<212> TYPE: PRT
```

```
<213> ORGANISM: Artificial Sequence
<220> FEATURE:
<223> OTHER INFORMATION: 1-28 Antibody VH-CDR1

<400> SEQUENCE: 20

Gly Phe Asp Phe Ser Asp Tyr Gly
1               5

<210> SEQ ID NO 21
<211> LENGTH: 8
<212> TYPE: PRT
<213> ORGANISM: Artificial Sequence
<220> FEATURE:
<223> OTHER INFORMATION: 1-28 Antibody VH-CDR2

<400> SEQUENCE: 21

Ile Arg Ser Asp Gly Ser Asn Pro
1               5

<210> SEQ ID NO 22
<211> LENGTH: 29
<212> TYPE: PRT
<213> ORGANISM: Artificial Sequence
<220> FEATURE:
<223> OTHER INFORMATION: 1-28 Antibody VH-CDR3

<400> SEQUENCE: 22

Ala Lys Asp Gly Asn Gly Tyr Cys Ala Leu Asp Ala Tyr Arg Ser Gly
1               5                   10                  15

Gly Tyr Ser Cys Gly Val Tyr Pro Gly Ser Ile Asp Ala
            20                  25

<210> SEQ ID NO 23
<211> LENGTH: 8
<212> TYPE: PRT
<213> ORGANISM: Artificial Sequence
<220> FEATURE:
<223> OTHER INFORMATION: 2-13 Antibody VL-CDR1

<400> SEQUENCE: 23

Ser Gly Gly Ser Tyr Ser Tyr Gly
1               5

<210> SEQ ID NO 24
<211> LENGTH: 7
<212> TYPE: PRT
<213> ORGANISM: Artificial Sequence
<220> FEATURE:
<223> OTHER INFORMATION: 2-13; 2-13D; 2-13D-37; 2-13D-37-1.5W-41; 2-13D-
      37-3W-16 VL-CDR2

<400> SEQUENCE: 24

Trp Asp Asp Glu Arg Pro Ser
1               5

<210> SEQ ID NO 25
<211> LENGTH: 11
<212> TYPE: PRT
<213> ORGANISM: Artificial Sequence
<220> FEATURE:
<223> OTHER INFORMATION: 2-13; 2-13D; 2-13D-37; 2-13D-37-1.5W-41; 2-13D-
      37-3W-16 VL-CDR3

<400> SEQUENCE: 25

Gly Thr Glu Asp Ile Ser Gly Thr Ala Gly Val
1               5                   10
```

```
<210> SEQ ID NO 26
<211> LENGTH: 13
<212> TYPE: PRT
<213> ORGANISM: Artificial Sequence
<220> FEATURE:
<223> OTHER INFORMATION: 3-2; 1-7A-IT; 1-17; 1-32; 4-11; 6-10 VL-CDR1

<400> SEQUENCE: 26

Ser Gly Gly Gly Ser Tyr Ala Gly Ser Tyr Tyr Tyr Gly
1               5                   10

<210> SEQ ID NO 27
<211> LENGTH: 7
<212> TYPE: PRT
<213> ORGANISM: Artificial Sequence
<220> FEATURE:
<223> OTHER INFORMATION: 3-2 Antibody VL-CDR2

<400> SEQUENCE: 27

Glu Ser Asn Lys Arg Pro Ser
1               5

<210> SEQ ID NO 28
<211> LENGTH: 10
<212> TYPE: PRT
<213> ORGANISM: Artificial Sequence
<220> FEATURE:
<223> OTHER INFORMATION: 3-2; 1-7A-IT VL-CDR3

<400> SEQUENCE: 28

Gly Ser Trp Asp Ser Ser Asn Gly Gly Ile
1               5                   10

<210> SEQ ID NO 29
<211> LENGTH: 11
<212> TYPE: PRT
<213> ORGANISM: Artificial Sequence
<220> FEATURE:
<223> OTHER INFORMATION: 1-65 Antibody VL-CDR1

<400> SEQUENCE: 29

Ser Gly Gly Gly Ser Ser Gly Tyr Gly Tyr Gly
1               5                   10

<210> SEQ ID NO 30
<211> LENGTH: 7
<212> TYPE: PRT
<213> ORGANISM: Artificial Sequence
<220> FEATURE:
<223> OTHER INFORMATION: 1-65 Antibody VL-CDR2

<400> SEQUENCE: 30

Trp Asn Asp Lys Arg Pro Ser
1               5

<210> SEQ ID NO 31
<211> LENGTH: 14
<212> TYPE: PRT
<213> ORGANISM: Artificial Sequence
<220> FEATURE:
<223> OTHER INFORMATION: 1-65; ss01-13; SS01-13-S5; S5-2.GKNG VL-CDR3

<400> SEQUENCE: 31

Gly Asn Asp Asp Tyr Ser Ser Asp Ser Gly Tyr Val Gly Val
1               5                   10
```

```
<210> SEQ ID NO 32
<211> LENGTH: 5
<212> TYPE: PRT
<213> ORGANISM: Artificial Sequence
<220> FEATURE:
<223> OTHER INFORMATION: 1-28 Antibody VL-CDR1

<400> SEQUENCE: 32

Gly Tyr Gly Tyr Gly
1               5

<210> SEQ ID NO 33
<211> LENGTH: 3
<212> TYPE: PRT
<213> ORGANISM: Artificial Sequence
<220> FEATURE:
<223> OTHER INFORMATION: 1-28 Antibody VL-CDR2

<400> SEQUENCE: 33

Gln Asn Asp
1

<210> SEQ ID NO 34
<211> LENGTH: 11
<212> TYPE: PRT
<213> ORGANISM: Artificial Sequence
<220> FEATURE:
<223> OTHER INFORMATION: 1-28 Antibody VL-CDR3

<400> SEQUENCE: 34

Gly Ser Glu Asp Ser Ser Thr Leu Ala Gly Ile
1               5                   10

<210> SEQ ID NO 35
<211> LENGTH: 129
<212> TYPE: PRT
<213> ORGANISM: Artificial Sequence
<220> FEATURE:
<223> OTHER INFORMATION: 2-13 Antibody VH

<400> SEQUENCE: 35

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser His
                20                  25                  30

Gly Met Phe Trp Val Arg Gln Thr Pro Gly Lys Gly Leu Glu Tyr Val
            35                  40                  45

Ala Glu Ile Thr Asn Asp Gly Ser Gly Thr Asn Tyr Gly Ser Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Arg Ser Thr Tyr Glu Cys Pro Gly Phe Ser Cys Trp Gly Asp
            100                 105                 110

Thr Gly Gln Ile Asp Ala Trp Gly His Gly Thr Glu Val Ile Val Ser
        115                 120                 125

Ser

<210> SEQ ID NO 36
<211> LENGTH: 131
<212> TYPE: PRT
<213> ORGANISM: Artificial Sequence
```

```
<220> FEATURE:
<223> OTHER INFORMATION: 3-2 Antibody VH

<400> SEQUENCE: 36

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Phe
            20                  25                  30

Asn Met Phe Trp Val Arg Gln Ala Pro Gly Lys Gly Leu Glu Tyr Val
        35                  40                  45

Ala Gln Ile Ser Ser Ser Gly Ser Ser Thr Asn Tyr Ala Pro Ala Val
    50                  55                  60

Arg Gly Arg Ala Thr Ile Ser Arg Asp Asn Gly Gln Ser Thr Val Arg
65                  70                  75                  80

Leu Gln Leu Asn Asn Pro Gly Ala Glu Asp Thr Gly Thr Tyr Tyr Cys
                85                  90                  95

Ala Lys Ser Ser Tyr Asp Cys Pro Tyr Gly His Cys Ser Ser Gly Val
            100                 105                 110

Asp Ser Ala Gly Glu Ile Asp Ala Trp Gly His Gly Thr Glu Val Ile
        115                 120                 125

Val Ser Ser
    130

<210> SEQ ID NO 37
<211> LENGTH: 122
<212> TYPE: PRT
<213> ORGANISM: Artificial Sequence
<220> FEATURE:
<223> OTHER INFORMATION: 1-65 Antibody VH

<400> SEQUENCE: 37

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Gln Met Gly Trp Val Arg Gln Ala Pro Gly Lys Gly Leu Glu Trp Val
        35                  40                  45

Gly Val Ile Asn Lys Ser Gly Ser Asp Thr Ser Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Lys Gly Ser Ala Ser Tyr Ile Thr Ala Ala Thr Ile Asp Ala Trp
            100                 105                 110

Gly His Gly Thr Glu Val Ile Val Ser Ser
        115                 120

<210> SEQ ID NO 38
<211> LENGTH: 136
<212> TYPE: PRT
<213> ORGANISM: Artificial Sequence
<220> FEATURE:
<223> OTHER INFORMATION: 1-28 Antibody VH

<400> SEQUENCE: 38

Ala Val Thr Leu Asp Glu Ser Gly Gly Gly Leu Gln Thr Pro Gly Gly
1               5                   10                  15
```

```
Ala Leu Ser Leu Val Cys Lys Ala Ser Gly Phe Asp Phe Ser Asp Tyr
            20                  25                  30

Gly Met Gly Trp Val Arg Gln Ala Pro Gly Lys Gly Leu Glu Trp Val
        35                  40                  45

Ala Ala Ile Arg Ser Asp Gly Ser Asn Pro Ser Tyr Gly Ser Ala Val
50                  55                  60

Lys Gly Arg Ala Thr Ile Ser Lys Asp Asn Gly Arg Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Asp Gly Asn Gly Tyr Cys Ala Leu Asp Ala Tyr Arg Ser Gly
            100                 105                 110

Gly Tyr Ser Cys Gly Val Tyr Pro Gly Ser Ile Asp Ala Trp Gly His
        115                 120                 125

Gly Thr Glu Val Ile Val Ser Ser
        130                 135

<210> SEQ ID NO 39
<211> LENGTH: 104
<212> TYPE: PRT
<213> ORGANISM: Artificial Sequence
<220> FEATURE:
<223> OTHER INFORMATION: 2-13 Antibody VL

<400> SEQUENCE: 39

Ala Leu Thr Gln Pro Ser Ser Val Ser Ala Asn Pro Gly Glu Thr Val
1               5                   10                  15

Lys Ile Thr Cys Ser Gly Gly Ser Tyr Ser Tyr Gly Trp Phe Gln Gln
            20                  25                  30

Lys Ser Pro Gly Ser Ala Leu Val Thr Val Ile Tyr Trp Asp Asp Glu
        35                  40                  45

Arg Pro Ser Asp Ile Pro Ser Arg Phe Ser Gly Ala Leu Ser Gly Ser
    50                  55                  60

Thr Asn Thr Leu Thr Ile Thr Gly Val Gln Ala Asp Asp Glu Ala Val
65                  70                  75                  80

Tyr Phe Cys Gly Thr Glu Asp Ile Ser Gly Thr Ala Gly Val Phe Gly
                85                  90                  95

Ala Gly Thr Thr Leu Thr Val Leu
            100

<210> SEQ ID NO 40
<211> LENGTH: 108
<212> TYPE: PRT
<213> ORGANISM: Artificial Sequence
<220> FEATURE:
<223> OTHER INFORMATION: 3-2 Antibody VL

<400> SEQUENCE: 40

Ala Leu Thr Gln Pro Ser Ser Val Ser Ala Asn Pro Gly Glu Thr Val
1               5                   10                  15

Lys Ile Thr Cys Ser Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
        35                  40                  45

Tyr Glu Ser Asn Lys Arg Pro Ser Asp Ile Pro Ser Arg Phe Ser Gly
    50                  55                  60

Ser Thr Ser Gly Ser Thr Ala Thr Leu Thr Ile Thr Gly Val Gln Ala
65                  70                  75                  80
```

Asp Asp Glu Ala Ile Tyr Tyr Cys Gly Ser Trp Asp Ser Ser Asn Gly
                85                  90                  95

Gly Ile Phe Gly Ala Gly Thr Thr Leu Thr Val Leu
            100                 105

<210> SEQ ID NO 41
<211> LENGTH: 110
<212> TYPE: PRT
<213> ORGANISM: Artificial Sequence
<220> FEATURE:
<223> OTHER INFORMATION: 1-65 Antibody VL

<400> SEQUENCE: 41

Ala Leu Thr Gln Pro Ser Ser Val Ser Ala Asn Pro Gly Glu Thr Val
1               5                   10                  15

Lys Ile Thr Cys Ser Gly Gly Ser Gly Tyr Gly Tyr Gly Trp
            20                  25                  30

Tyr Gln Gln Lys Ser Pro Ser Ala Pro Leu Thr Val Ile Tyr Trp
            35                  40                  45

Asn Asp Lys Arg Pro Ser Asp Ile Pro Ser Arg Phe Ser Gly Ser Lys
50                  55                  60

Ser Gly Ser Thr His Thr Leu Thr Ile Thr Gly Val Gln Ala Glu Asp
65                  70                  75                  80

Glu Ala Val Tyr Phe Cys Gly Asn Asp Asp Tyr Ser Ser Asp Ser Gly
                85                  90                  95

Tyr Val Gly Val Phe Gly Ala Gly Thr Thr Leu Thr Val Leu
            100                 105                 110

<210> SEQ ID NO 42
<211> LENGTH: 104
<212> TYPE: PRT
<213> ORGANISM: Artificial Sequence
<220> FEATURE:
<223> OTHER INFORMATION: 1-28 Antibody VL

<400> SEQUENCE: 42

Ala Leu Thr Gln Pro Ser Ser Val Ser Ala Asn Leu Gly Thr Val
1               5                   10                  15

Glu Ile Thr Cys Ser Gly Ser Gly Tyr Gly Tyr Gly Trp Tyr Gln Gln
            20                  25                  30

Lys Ser Pro Gly Ser Ala Pro Val Thr Val Ile Tyr Gln Asn Asp Lys
            35                  40                  45

Arg Pro Ser Asp Ile Pro Ser Arg Phe Ser Gly Ser Lys Ser Gly Ser
50                  55                  60

Thr Gly Thr Leu Thr Ile Thr Gly Val Gln Val Glu Asp Glu Ala Val
65                  70                  75                  80

Tyr Tyr Cys Gly Ser Glu Asp Ser Ser Thr Leu Ala Gly Ile Phe Gly
                85                  90                  95

Ala Gly Thr Thr Leu Thr Val Leu
            100

<210> SEQ ID NO 43
<211> LENGTH: 388
<212> TYPE: DNA
<213> ORGANISM: Artificial Sequence
<220> FEATURE:
<223> OTHER INFORMATION: 2-13 Antibody VH

<400> SEQUENCE: 43

| | |
|---|---|
| gccgtgacgt tggacgagtc cggggggcggc ctccagacgc ccggaggagc gctcagcctc | 60 |
| gtctgcaagg cctccgggtt caccttcagc agccatggca tgttctgggt gcgacagacg | 120 |
| cccggcaagg ggttggaata tgtcgctgaa attaccaatg atggtagtgg cacaaactac | 180 |
| gggtcggcgg tgaagggccg tgccaccatc tcgaggaca acgggcagag cacagtgagg | 240 |
| ctgcagctga caaacctcag ggctgaggac accggcacct acttctgcgc cagatctact | 300 |
| tatgaatgtc ctggtggttt tagttgttgg ggtgatactg gtcaaataga cgcatggggc | 360 |
| cacgggaccg aagtcatcgt ctcctcca | 388 |

<210> SEQ ID NO 44
<211> LENGTH: 394
<212> TYPE: DNA
<213> ORGANISM: Artificial Sequence
<220> FEATURE:
<223> OTHER INFORMATION: 3-2 Antibody VH

<400> SEQUENCE: 44

| | |
|---|---|
| gccgtgacgt tggacgagtc cggggggcggc ctccagacgc ccggaggagc gctcagcctc | 60 |
| gtctgcaagg cctccgggtt caccttcagc agcttcaaca tgttctgggt gcgacaggcg | 120 |
| cccggcaagg ggctggaata cgtcgctcaa attagcagca gtggtagtag cacaaactac | 180 |
| gcacccgcgg tgaggggccg tgccaccatc tcgaggaca acgggcagag cacagtgagg | 240 |
| ctgcagctga acaaccccgg ggctgaagac accggcacct actactgcgc caaaagtagt | 300 |
| tatgactgtc cttacggtca ttgtagtagt ggtgttgata gtgctggtga gatcgacgca | 360 |
| tggggccacg ggaccgaagt catcgtctcc tcca | 394 |

<210> SEQ ID NO 45
<211> LENGTH: 366
<212> TYPE: DNA
<213> ORGANISM: Artificial Sequence
<220> FEATURE:
<223> OTHER INFORMATION: 1-65 Antibody VH

<400> SEQUENCE: 45

| | |
|---|---|
| gccgtgacgt tggacgagtc cggggggcggc ctccagacgc ccggaggagc gctcagcctc | 60 |
| gtctgcaagg cctccgggtt caccttcagc agctatcaga tgggctgggt gcgacaggcg | 120 |
| cccggcaagg ggctggaatg ggtcggtgtt attaacaaga gtggtagtga cacatcatac | 180 |
| gggtcggcgg tgaagggccg tgccaccatc tcgaggaca acgggcagag cacagtgagg | 240 |
| ctgcagctga caaacctcag ggctgaggac accggcacct acttctgcgc caaaggttct | 300 |
| gctagttata aactgctgc taccatcgac gcatggggcc acgggaccga agtcatcgtc | 360 |
| tcctcc | 366 |

<210> SEQ ID NO 46
<211> LENGTH: 408
<212> TYPE: DNA
<213> ORGANISM: Artificial Sequence
<220> FEATURE:
<223> OTHER INFORMATION: 1-28 Antibody VH

<400> SEQUENCE: 46

| | |
|---|---|
| gccgtgacgt tggacgagtc cggggggcggc ctccagacgc ccggaggagc gctcagcctc | 60 |
| gtctgcaagg cctccgggtt cgacttcagc gattatggca tgggttgggt gcgacaggct | 120 |
| ccaggcaagg ggctggagtg ggttgctgct attagaagtg atggtagtaa cccatcatac | 180 |
| gggtcggcgg tgaagggccg tgccaccatc tcgaaggaca acgggcgaag cacagtgagg | 240 |

```
ctgcagctga acaacctcag ggctgaggac accgccacct actactgcgc caaggatggt    300
aatggttact gtgctctcga tgcttatcgt agtggtggtt atagttgtgg tgtttatcct    360
ggtagcatcg acgcatgggg ccacgggacc gaagtcatcg tctcctcc                 408
```

```
<210> SEQ ID NO 47
<211> LENGTH: 315
<212> TYPE: DNA
<213> ORGANISM: Artificial Sequence
<220> FEATURE:
<223> OTHER INFORMATION: 2-13 Antibody VL

<400> SEQUENCE: 47
ggccctgact cagccgtcct cggtgtcagc aaacccagga gaaaccgtca agataacctg     60 ctccggggt agctatagct atggctggtt ccagcagaag tctcctggca gtgcccttgt    120
cactgtgatc tactgggatg atgagagacc ctcggacatc ccttcacgat tctccggtgc    180
cctatccggc tccacaaaca cattaaccat cactggggtc aagccgacg acgaggctgt    240 ctatttctgt gggactgaag acatcagcgg cactgctggt gtatttgggg ccgggacaac    300
cctgaccgtc ctggg                                                     315
```

```
<210> SEQ ID NO 48
<211> LENGTH: 327
<212> TYPE: DNA
<213> ORGANISM: Artificial Sequence
<220> FEATURE:
<223> OTHER INFORMATION: 3-2 Antibody VL

<400> SEQUENCE: 48
ggccctgact cagccgtcct cggtgtcagc aaacccagga gaaaccgtca agatcacctg     60 ctccggggt ggcagctatg ctggaagtta ctattatggc tggtaccagc agaaggcacc    120
tggcagtgcc cctgtcactc tgatctatga aagcaacaag agaccctcgg acatcccttc    180
acgattctcc ggttccacat ctggctccac agccacacta accatcactg ggtccaagc    240 cgatgacgag gctatctatt actgtgggag ctgggacagt agcaatggtg gtatatttgg    300
ggccgggaca accctgaccg tcctagg                                        327
```

```
<210> SEQ ID NO 49
<211> LENGTH: 331
<212> TYPE: DNA
<213> ORGANISM: Artificial Sequence
<220> FEATURE:
<223> OTHER INFORMATION: 1-65 Antibody VL

<400> SEQUENCE: 49
ggccctgact cagccgtcct cggtgtcagc aaaccctggg gaaactgtca agatcacctg     60 ctccggggt ggtagcagtg ctatggctta tggctggtat cagcagaagt cacctagcag    120
tgcccctctc actgtgatct actggaacga caagagaccc tcggacatcc cttcacgatt    180
ctccggttcc aaatccggct ccacacacac attaaccatc actggggtcc aagccgagga    240
cgaggctgta tatttctgtg ggaatgatga ctacagcagt gatagtggat atgtcggtgt    300
atttggggcc gggacaaccc tgaccgtcct a                                   331
```

```
<210> SEQ ID NO 50
<211> LENGTH: 312
<212> TYPE: DNA
<213> ORGANISM: Artificial Sequence
<220> FEATURE:
```

<223> OTHER INFORMATION: 1-28 Antibody VL

<400> SEQUENCE: 50

```
gccctgactc agccgtcctc ggtgtcagca aacctggaag gaaccgtcga gatcacctgc      60
tccgggagtg gctatggtta tggctggtat cagcagaagt ctcctggcag tgcccctgtc     120
actgtgatct atcagaacga caagagaccc tcggacatcc cttcacgatt ctccggttcc     180
aaatccggct ccacgggcac attaaccatc actgggtcc aagtcgagga cgaggctgtc      240
tattactgtg ggagtgaaga cagcagcact cttgctggta tatttggggc cgggacaacc     300
ctgaccgtcc ta                                                         312
```

<210> SEQ ID NO 51
<211> LENGTH: 100
<212> TYPE: PRT
<213> ORGANISM: Artificial Sequence
<220> FEATURE:
<223> OTHER INFORMATION: M3 mutant

<400> SEQUENCE: 51

```
Gln Phe Leu Lys Glu Gly Gln Leu Ala Ala Gly Thr Cys Glu Ile Val
1               5                   10                  15

Thr Leu Asp Arg Asp Ser Ser Gln Pro Arg Ile Glu Glu Arg Ser Gln
                20                  25                  30

Thr Ala Arg Cys Ala Cys Arg Lys Gly Gln Ile Ala Gly Thr Thr Arg
                35                  40                  45

Ala Arg Pro Ala Cys Val Asp Ala Arg Ile Ile Lys Thr Lys Gln Trp
        50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100
```

<210> SEQ ID NO 52
<211> LENGTH: 100
<212> TYPE: PRT
<213> ORGANISM: Artificial Sequence
<220> FEATURE:
<223> OTHER INFORMATION: M4 mutant

<400> SEQUENCE: 52

```
Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
                20                  25                  30

Thr Val Lys Cys Ser Cys Phe Pro Gly Gln Ile Ala Gly Thr Thr Arg
                35                  40                  45

Ala Arg Pro Ala Cys Val Asp Ala Arg Ile Ile Lys Thr Lys Gln Trp
        50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100
```

```
<210> SEQ ID NO 53
<211> LENGTH: 100
<212> TYPE: PRT
<213> ORGANISM: Artificial Sequence
<220> FEATURE:
<223> OTHER INFORMATION: M5 mutant

<400> SEQUENCE: 53

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Asn Lys Pro Ser Cys Val Asp Ala Arg Ile Ile Lys Thr Lys Gln Trp
    50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 54
<211> LENGTH: 100
<212> TYPE: PRT
<213> ORGANISM: Artificial Sequence
<220> FEATURE:
<223> OTHER INFORMATION: M6 mutant

<400> SEQUENCE: 54

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Leu Gln Arg Trp Trp
    50                  55                  60

Cys Gln Met Glu Leu Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 55
<211> LENGTH: 100
<212> TYPE: PRT
<213> ORGANISM: Artificial Sequence
<220> FEATURE:
<223> OTHER INFORMATION: M7 mutant

<400> SEQUENCE: 55

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45
```

```
Ala Arg Pro Ala Cys Val Asp Ala Arg Ile Ile Lys Thr Lys Gln Trp
        50                  55                  60

Cys Asp Met Leu Pro Cys Leu Glu Gly Glu Glu Cys Lys Thr Leu Pro
65                  70                  75                  80

Asp Asn Ser Gly Trp Thr Cys Thr Gln Pro Gly Gly Arg Ile Lys Thr
                85                  90                  95

Thr Thr Val Ser
            100

<210> SEQ ID NO 56
<211> LENGTH: 101
<212> TYPE: PRT
<213> ORGANISM: Artificial Sequence
<220> FEATURE:
<223> OTHER INFORMATION: M8 mutant

<400> SEQUENCE: 56

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Lys Thr Lys Gln Trp
        50                  55                  60

Cys Asp Met Leu Pro Cys Leu Glu Gly Glu Gly Cys Asp Leu Leu Ile
65                  70                  75                  80

Asn Arg Ser Gly Trp Thr Cys Ser Cys Ser Ser Gly Asn Lys Ile Lys
                85                  90                  95

Thr Thr Thr Val Ser
            100

<210> SEQ ID NO 57
<211> LENGTH: 459
<212> TYPE: PRT
<213> ORGANISM: Artificial Sequence
<220> FEATURE:
<223> OTHER INFORMATION: 2-13 Antibody HC

<400> SEQUENCE: 57

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser His
            20                  25                  30

Gly Met Phe Trp Val Arg Gln Thr Pro Gly Lys Gly Leu Glu Tyr Val
        35                  40                  45

Ala Glu Ile Thr Asn Asp Gly Ser Gly Thr Asn Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Arg Ser Thr Tyr Glu Cys Pro Gly Gly Phe Ser Cys Trp Gly Asp
            100                 105                 110

Thr Gly Gln Ile Asp Ala Trp Gly His Gly Thr Glu Val Ile Val Ser
        115                 120                 125

Ser Ala Ser Thr Lys Gly Pro Ser Val Phe Pro Leu Ala Pro Ser Ser
```

130                 135                 140
Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
                180                 185                 190

Ser Leu Ser Ser Val Val Thr Val Pro Ser Ser Ser Leu Gly Thr Gln
                195                 200                 205

Thr Tyr Ile Cys Asn Val Asn His Lys Pro Ser Asn Thr Lys Val Asp
                210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser His Glu Asp Pro Glu Val Lys Phe Asn
                275                 280                 285

Trp Tyr Val Asp Gly Val Glu Val His Asn Ala Lys Thr Lys Pro Arg
                290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
                340                 345                 350

Gly Gln Pro Arg Glu Pro Gln Val Tyr Thr Leu Pro Pro Ser Arg Glu
                355                 360                 365

Glu Met Thr Lys Asn Gln Val Ser Leu Thr Cys Leu Val Lys Gly Phe
                370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
                420                 425                 430

Asn Val Phe Ser Cys Ser Val Met His Glu Ala Leu His Asn His Tyr
                435                 440                 445

Thr Gln Lys Ser Leu Ser Leu Ser Pro Gly Lys
450                 455

<210> SEQ ID NO 58
<211> LENGTH: 461
<212> TYPE: PRT
<213> ORGANISM: Artificial Sequence
<220> FEATURE:
<223> OTHER INFORMATION: 3-2 Antibody HC

<400> SEQUENCE: 58

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Phe
                20                  25                  30

Asn Met Phe Trp Val Arg Gln Ala Pro Gly Lys Gly Leu Glu Tyr Val

-continued

```
                35                  40                  45
Ala Gln Ile Ser Ser Ser Gly Ser Ser Thr Asn Tyr Ala Pro Ala Val
 50                  55                  60
Arg Gly Arg Ala Thr Ile Ser Arg Asp Asn Gly Gln Ser Thr Val Arg
 65                  70                  75                  80
Leu Gln Leu Asn Asn Pro Gly Ala Glu Asp Thr Gly Thr Tyr Tyr Cys
                 85                  90                  95
Ala Lys Ser Ser Tyr Asp Cys Pro Tyr Gly His Cys Ser Ser Gly Val
                100                 105                 110
Asp Ser Ala Gly Glu Ile Asp Ala Trp Gly His Gly Thr Glu Val Ile
                115                 120                 125
Val Ser Ser Ala Ser Thr Lys Gly Pro Ser Val Phe Pro Leu Ala Pro
130                 135                 140
Ser Ser Lys Ser Thr Ser Gly Gly Thr Ala Ala Leu Gly Cys Leu Val
145                 150                 155                 160
Lys Asp Tyr Phe Pro Glu Pro Val Thr Val Ser Trp Asn Ser Gly Ala
                165                 170                 175
Leu Thr Ser Gly Val His Thr Phe Pro Ala Val Leu Gln Ser Ser Gly
                180                 185                 190
Leu Tyr Ser Leu Ser Ser Val Val Thr Val Pro Ser Ser Ser Leu Gly
                195                 200                 205
Thr Gln Thr Tyr Ile Cys Asn Val Asn His Lys Pro Ser Asn Thr Lys
                210                 215                 220
Val Asp Lys Lys Val Glu Pro Lys Ser Cys Asp Lys Thr His Thr Cys
225                 230                 235                 240
Pro Pro Cys Pro Ala Pro Glu Leu Leu Gly Gly Pro Ser Val Phe Leu
                245                 250                 255
Phe Pro Pro Lys Pro Lys Asp Thr Leu Met Ile Ser Arg Thr Pro Glu
                260                 265                 270
Val Thr Cys Val Val Val Asp Val Ser His Glu Asp Pro Glu Val Lys
                275                 280                 285
Phe Asn Trp Tyr Val Asp Gly Val Glu Val His Asn Ala Lys Thr Lys
                290                 295                 300
Pro Arg Glu Glu Gln Tyr Asn Ser Thr Tyr Arg Val Val Ser Val Leu
305                 310                 315                 320
Thr Val Leu His Gln Asp Trp Leu Asn Gly Lys Glu Tyr Lys Cys Lys
                325                 330                 335
Val Ser Asn Lys Ala Leu Pro Ala Pro Ile Glu Lys Thr Ile Ser Lys
                340                 345                 350
Ala Lys Gly Gln Pro Arg Glu Pro Gln Val Tyr Thr Leu Pro Pro Ser
                355                 360                 365
Arg Glu Glu Met Thr Lys Asn Gln Val Ser Leu Thr Cys Leu Val Lys
                370                 375                 380
Gly Phe Tyr Pro Ser Asp Ile Ala Val Glu Trp Glu Ser Asn Gly Gln
385                 390                 395                 400
Pro Glu Asn Asn Tyr Lys Thr Thr Pro Pro Val Leu Asp Ser Asp Gly
                405                 410                 415
Ser Phe Phe Leu Tyr Ser Lys Leu Thr Val Asp Lys Ser Arg Trp Gln
                420                 425                 430
Gln Gly Asn Val Phe Ser Cys Ser Val Met His Glu Ala Leu His Asn
                435                 440                 445
His Tyr Thr Gln Lys Ser Leu Ser Leu Ser Pro Gly Lys
                450                 455                 460
```

<210> SEQ ID NO 59
<211> LENGTH: 452
<212> TYPE: PRT
<213> ORGANISM: Artificial Sequence
<220> FEATURE:
<223> OTHER INFORMATION: 1-65 Antibody HC

<400> SEQUENCE: 59

```
Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Gln Met Gly Trp Val Arg Gln Ala Pro Gly Lys Gly Leu Glu Trp Val
        35                  40                  45

Gly Val Ile Asn Lys Ser Gly Ser Asp Thr Ser Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Lys Gly Ser Ala Ser Tyr Ile Thr Ala Ala Thr Ile Asp Ala Trp
            100                 105                 110

Gly His Gly Thr Glu Val Ile Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365
```

```
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
            435                 440                 445

Ser Pro Gly Lys
    450

<210> SEQ ID NO 60
<211> LENGTH: 466
<212> TYPE: PRT
<213> ORGANISM: Artificial Sequence
<220> FEATURE:
<223> OTHER INFORMATION: 1-28 Antibody HC

<400> SEQUENCE: 60

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Asp Phe Ser Asp Tyr
            20                  25                  30

Gly Met Gly Trp Val Arg Gln Ala Pro Gly Lys Gly Leu Glu Trp Val
        35                  40                  45

Ala Ala Ile Arg Ser Asp Gly Ser Asn Pro Ser Tyr Gly Ser Ala Val
    50                  55                  60

Lys Gly Arg Ala Thr Ile Ser Lys Asp Asn Gly Arg Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Asp Gly Asn Gly Tyr Cys Ala Leu Asp Ala Tyr Arg Ser Gly
            100                 105                 110

Gly Tyr Ser Cys Gly Val Tyr Pro Gly Ser Ile Asp Ala Trp Gly His
        115                 120                 125

Gly Thr Glu Val Ile Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270
```

```
Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
    355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
    435                 440                 445

Glu Ala Leu His Asn His Tyr Thr Gln Lys Ser Leu Ser Leu Ser Pro
    450                 455                 460

Gly Lys
465

<210> SEQ ID NO 61
<211> LENGTH: 211
<212> TYPE: PRT
<213> ORGANISM: Artificial Sequence
<220> FEATURE:
<223> OTHER INFORMATION: 2-13 Antibody LC

<400> SEQUENCE: 61

Ala Leu Thr Gln Pro Ser Ser Val Ser Ala Asn Pro Gly Glu Thr Val
1               5                   10                  15

Lys Ile Thr Cys Ser Gly Gly Tyr Ser Tyr Gly Trp Phe Gln Gln
            20                  25                  30

Lys Ser Pro Gly Ser Ala Leu Val Thr Val Ile Tyr Trp Asp Asp Glu
    35                  40                  45

Arg Pro Ser Asp Ile Pro Ser Arg Phe Ser Gly Ala Leu Ser Gly Ser
50                  55                  60

Thr Asn Thr Leu Thr Ile Thr Gly Val Gln Ala Asp Asp Glu Ala Val
65                  70                  75                  80

Tyr Phe Cys Gly Thr Glu Asp Ile Ser Gly Thr Ala Gly Val Phe Gly
                85                  90                  95

Ala Gly Thr Thr Leu Thr Val Leu Arg Ser Val Ala Ala Pro Ser Val
            100                 105                 110

Phe Ile Phe Pro Pro Ser Asp Glu Gln Leu Lys Ser Gly Thr Ala Ser
    115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160
```

```
Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
        210

<210> SEQ ID NO 62
<211> LENGTH: 215
<212> TYPE: PRT
<213> ORGANISM: Artificial Sequence
<220> FEATURE:
<223> OTHER INFORMATION: 3-2 Antibody LC

<400> SEQUENCE: 62

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
        35                  40                  45

Tyr Glu Ser Asn Lys Arg Pro Ser Asp Ile Pro Ser Arg Phe Ser Gly
    50                  55                  60

Ser Thr Ser Gly Ser Thr Ala Thr Leu Thr Ile Thr Gly Val Gln Ala
65                  70                  75                  80

Asp Asp Glu Ala Ile Tyr Tyr Cys Gly Ser Trp Asp Ser Ser Asn Gly
                85                  90                  95

Gly Ile Phe Gly Ala Gly Thr Thr Leu Thr Val Leu Arg Ser Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 63
<211> LENGTH: 217
<212> TYPE: PRT
<213> ORGANISM: Artificial Sequence
<220> FEATURE:
<223> OTHER INFORMATION: 1-65 Antibody LC

<400> SEQUENCE: 63

Ala Leu Thr Gln Pro Ser Ser Val Ser Ala Asn Pro Gly Glu Thr Val
1               5                   10                  15

Lys Ile Thr Cys Ser Gly Gly Gly Ser Ser Gly Tyr Gly Tyr Gly Trp
```

```
                20                  25                  30
Tyr Gln Gln Lys Ser Pro Ser Ser Ala Pro Leu Thr Val Ile Tyr Trp
            35                  40                  45
Asn Asp Lys Arg Pro Ser Asp Ile Pro Ser Arg Phe Ser Gly Ser Lys
        50                  55                  60
Ser Gly Ser Thr His Thr Leu Thr Ile Thr Gly Val Gln Ala Glu Asp
65                  70                  75                  80
Glu Ala Val Tyr Phe Cys Gly Asn Asp Asp Tyr Ser Ser Asp Ser Gly
                85                  90                  95
Tyr Val Gly Val Phe Gly Ala Gly Thr Thr Leu Thr Val Leu Arg Ser
            100                 105                 110
Val Ala Ala Pro Ser Val Phe Ile Phe Pro Pro Ser Asp Glu Gln Leu
            115                 120                 125
Lys Ser Gly Thr Ala Ser Val Val Cys Leu Leu Asn Asn Phe Tyr Pro
        130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Gln Gly Leu Ser Ser Pro Val
            195                 200                 205
Thr Lys Ser Phe Asn Arg Gly Glu Cys
        210                 215

<210> SEQ ID NO 64
<211> LENGTH: 211
<212> TYPE: PRT
<213> ORGANISM: Artificial Sequence
<220> FEATURE:
<223> OTHER INFORMATION: 1-28 Antibody LC

<400> SEQUENCE: 64

Ala Leu Thr Gln Pro Ser Ser Val Ser Ala Asn Leu Glu Gly Thr Val
1               5                   10                  15
Glu Ile Thr Cys Ser Gly Ser Gly Tyr Gly Tyr Gly Trp Tyr Gln Gln
                20                  25                  30
Lys Ser Pro Gly Ser Ala Pro Val Thr Val Ile Tyr Gln Asn Asp Lys
            35                  40                  45
Arg Pro Ser Asp Ile Pro Ser Arg Phe Ser Gly Ser Lys Ser Gly Ser
        50                  55                  60
Thr Gly Thr Leu Thr Ile Thr Gly Val Gln Val Glu Asp Glu Ala Val
65                  70                  75                  80
Tyr Tyr Cys Gly Ser Glu Asp Ser Ser Thr Leu Ala Gly Ile Phe Gly
                85                  90                  95
Ala Gly Thr Thr Leu Thr Val Leu Arg Ser Val Ala Ala Pro Ser Val
            100                 105                 110
Phe Ile Phe Pro Pro Ser Asp Glu Gln Leu Lys Ser Gly Thr Ala Ser
            115                 120                 125
Val Val Cys Leu Leu Asn Asn Phe Tyr Pro Arg Glu Ala Lys Val Gln
        130                 135                 140
Trp Lys Val Asp Asn Ala Leu Gln Ser Gly Asn Ser Gln Glu Ser Val
145                 150                 155                 160
Thr Glu Gln Asp Ser Lys Asp Ser Thr Tyr Ser Leu Ser Ser Thr Leu
```

```
                165                 170                 175
Thr Leu Ser Lys Ala Asp Tyr Glu Lys His Lys Val Tyr Ala Cys Glu
        180                 185                 190

Val Thr His Gln Gly Leu Ser Ser Pro Val Thr Lys Ser Phe Asn Arg
        195                 200                 205

Gly Glu Cys
    210

<210> SEQ ID NO 65
<211> LENGTH: 5
<212> TYPE: PRT
<213> ORGANISM: Artificial Sequence
<220> FEATURE:
<223> OTHER INFORMATION: EP1 Epitope

<400> SEQUENCE: 65

Ile Val Thr Leu Asp
1               5

<210> SEQ ID NO 66
<211> LENGTH: 5
<212> TYPE: PRT
<213> ORGANISM: Artificial Sequence
<220> FEATURE:
<223> OTHER INFORMATION: EP2 Epitope

<400> SEQUENCE: 66

Asp Ser Ser Gln Pro
1               5

<210> SEQ ID NO 67
<211> LENGTH: 5
<212> TYPE: PRT
<213> ORGANISM: Artificial Sequence
<220> FEATURE:
<223> OTHER INFORMATION: EP3 Epitope

<400> SEQUENCE: 67

Arg Thr Ile Ala Arg
1               5

<210> SEQ ID NO 68
<211> LENGTH: 7
<212> TYPE: PRT
<213> ORGANISM: Artificial Sequence
<220> FEATURE:
<223> OTHER INFORMATION: EP4 Epitope

<400> SEQUENCE: 68

Ala Arg Cys Ala Cys Arg Lys
1               5

<210> SEQ ID NO 69
<211> LENGTH: 4
<212> TYPE: PRT
<213> ORGANISM: Artificial Sequence
<220> FEATURE:
<223> OTHER INFORMATION: EP5 Epitope

<400> SEQUENCE: 69

Ala Arg Pro Ala
1

<210> SEQ ID NO 70
<211> LENGTH: 9
```

```
<212> TYPE: PRT
<213> ORGANISM: Artificial Sequence
<220> FEATURE:
<223> OTHER INFORMATION: EP6 Epitope

<400> SEQUENCE: 70

Lys Thr Lys Gln Trp Cys Asp Met Leu
1               5

<210> SEQ ID NO 71
<211> LENGTH: 8
<212> TYPE: PRT
<213> ORGANISM: Artificial Sequence
<220> FEATURE:
<223> OTHER INFORMATION: EP7 Epitope

<400> SEQUENCE: 71

Gly Cys Asp Leu Leu Ile Asn Arg
1               5

<210> SEQ ID NO 72
<211> LENGTH: 8
<212> TYPE: PRT
<213> ORGANISM: Artificial Sequence
<220> FEATURE:
<223> OTHER INFORMATION: EP8 Epitope

<400> SEQUENCE: 72

Thr Cys Thr Gln Pro Gly Gly Arg
1               5

<210> SEQ ID NO 73
<211> LENGTH: 20
<212> TYPE: PRT
<213> ORGANISM: Artificial Sequence
<220> FEATURE:
<223> OTHER INFORMATION: F2-01-BSA (#1)

<400> SEQUENCE: 73

Thr Ala Asp Arg Asp Ser Ser Gln Pro Arg Arg Thr Ile Ala Arg Gln
1               5                   10                  15

Thr Ala Arg Cys
            20

<210> SEQ ID NO 74
<211> LENGTH: 20
<212> TYPE: PRT
<213> ORGANISM: Artificial Sequence
<220> FEATURE:
<223> OTHER INFORMATION: F2-02-BSA (#2)

<400> SEQUENCE: 74

Thr Leu Ala Arg Asp Ser Ser Gln Pro Arg Arg Thr Ile Ala Arg Gln
1               5                   10                  15

Thr Ala Arg Cys
            20

<210> SEQ ID NO 75
<211> LENGTH: 20
<212> TYPE: PRT
<213> ORGANISM: Artificial Sequence
<220> FEATURE:
<223> OTHER INFORMATION: F2-03-BSA (#3)

<400> SEQUENCE: 75

Thr Leu Asp Arg Ala Ser Ser Gln Pro Arg Arg Thr Ile Ala Arg Gln
```

```
Thr Ala Arg Cys
        20

<210> SEQ ID NO 76
<211> LENGTH: 20
<212> TYPE: PRT
<213> ORGANISM: Artificial Sequence
<220> FEATURE:
<223> OTHER INFORMATION: F2-04-BSA (#4)

<400> SEQUENCE: 76

Thr Leu Asp Arg Asp Ala Ser Gln Pro Arg Arg Thr Ile Ala Arg Gln
1               5                   10                  15

Thr Ala Arg Cys
        20

<210> SEQ ID NO 77
<211> LENGTH: 20
<212> TYPE: PRT
<213> ORGANISM: Artificial Sequence
<220> FEATURE:
<223> OTHER INFORMATION: F2-05-BSA (#5)

<400> SEQUENCE: 77

Thr Leu Asp Arg Asp Ser Ala Gln Pro Arg Arg Thr Ile Ala Arg Gln
1               5                   10                  15

Thr Ala Arg Cys
        20

<210> SEQ ID NO 78
<211> LENGTH: 20
<212> TYPE: PRT
<213> ORGANISM: Artificial Sequence
<220> FEATURE:
<223> OTHER INFORMATION: F2-06-BSA (#6)

<400> SEQUENCE: 78

Thr Leu Asp Arg Asp Ser Ser Ala Pro Arg Arg Thr Ile Ala Arg Gln
1               5                   10                  15

Thr Ala Arg Cys
        20

<210> SEQ ID NO 79
<211> LENGTH: 20
<212> TYPE: PRT
<213> ORGANISM: Artificial Sequence
<220> FEATURE:
<223> OTHER INFORMATION: F2-07-BSA (#7)

<400> SEQUENCE: 79

Thr Leu Asp Arg Asp Ser Ser Gln Ala Arg Arg Thr Ile Ala Arg Gln
1               5                   10                  15

Thr Ala Arg Cys
        20

<210> SEQ ID NO 80
<211> LENGTH: 20
<212> TYPE: PRT
<213> ORGANISM: Artificial Sequence
<220> FEATURE:
<223> OTHER INFORMATION: F2-08-BSA (#8)

<400> SEQUENCE: 80
```

Thr Leu Asp Arg Asp Ser Ser Gln Pro Arg Ala Thr Ile Ala Arg Gln
1               5                   10                  15

Thr Ala Arg Cys
            20

<210> SEQ ID NO 81
<211> LENGTH: 20
<212> TYPE: PRT
<213> ORGANISM: Artificial Sequence
<220> FEATURE:
<223> OTHER INFORMATION: F2-09-BSA (#9)

<400> SEQUENCE: 81

Thr Leu Asp Arg Asp Ser Ser Gln Pro Arg Arg Ala Ile Ala Arg Gln
1               5                   10                  15

Thr Ala Arg Cys
            20

<210> SEQ ID NO 82
<211> LENGTH: 20
<212> TYPE: PRT
<213> ORGANISM: Artificial Sequence
<220> FEATURE:
<223> OTHER INFORMATION: F2-10-BSA (#10)

<400> SEQUENCE: 82

Thr Leu Asp Arg Asp Ser Ser Gln Pro Arg Arg Thr Ala Ala Arg Gln
1               5                   10                  15

Thr Ala Arg Cys
            20

<210> SEQ ID NO 83
<211> LENGTH: 20
<212> TYPE: PRT
<213> ORGANISM: Artificial Sequence
<220> FEATURE:
<223> OTHER INFORMATION: F2-11-BSA (#11)

<400> SEQUENCE: 83

Thr Leu Asp Arg Asp Ser Ser Gln Pro Arg Arg Thr Ile Arg Arg Gln
1               5                   10                  15

Thr Ala Arg Cys
            20

<210> SEQ ID NO 84
<211> LENGTH: 20
<212> TYPE: PRT
<213> ORGANISM: Artificial Sequence
<220> FEATURE:
<223> OTHER INFORMATION: F2-12-BSA (#12)

<400> SEQUENCE: 84

Thr Leu Asp Arg Asp Ser Ser Gln Pro Arg Arg Thr Ile Ala Ala Gln
1               5                   10                  15

Thr Ala Arg Cys
            20

<210> SEQ ID NO 85
<211> LENGTH: 20
<212> TYPE: PRT
<213> ORGANISM: Artificial Sequence
<220> FEATURE:
<223> OTHER INFORMATION: F2-12-BSA (#13)

<400> SEQUENCE: 85

```
Thr Leu Asp Arg Asp Ser Ser Gln Pro Arg Arg Thr Ile Ala Arg Gln
1               5                   10                  15

Thr Val Arg Cys
            20

<210> SEQ ID NO 86
<211> LENGTH: 100
<212> TYPE: PRT
<213> ORGANISM: Artificial Sequence
<220> FEATURE:
<223> OTHER INFORMATION: Wild-type FAM19A5 Isoform 2 (without signal
      peptide)

<400> SEQUENCE: 86

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
                20                  25                  30

Thr Ala Arg Cys Ala Cys Arg Lys Gly Gln Ile Ala Gly Thr Thr Arg
            35                  40                  45

Ala Arg Pro Ala Cys Val Asp Ala Arg Ile Ile Lys Thr Lys Gln Trp
        50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 87
<211> LENGTH: 100
<212> TYPE: PRT
<213> ORGANISM: Artificial Sequence
<220> FEATURE:
<223> OTHER INFORMATION: M1 mutant

<400> SEQUENCE: 87

Gln Phe Leu Lys Glu Gly Gln Leu Ala Ala Gly Thr Cys Glu Val Ile
1               5                   10                  15

Ala Ala His Arg Asp Ser Ser Gln Pro Arg Arg Thr Ile Ala Arg Gln
                20                  25                  30

Thr Ala Arg Cys Ala Cys Arg Lys Gly Gln Ile Ala Gly Thr Thr Arg
            35                  40                  45

Ala Arg Pro Ala Cys Val Asp Ala Arg Ile Ile Lys Thr Lys Gln Trp
        50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 88
<211> LENGTH: 100
<212> TYPE: PRT
<213> ORGANISM: Artificial Sequence
<220> FEATURE:
<223> OTHER INFORMATION: M2 mutant

<400> SEQUENCE: 88
```

```
Gln Phe Leu Lys Glu Gly Gln Leu Ala Ala Gly Thr Cys Glu Ile Val
1               5                   10                  15

Thr Leu Asp Arg Cys Cys Asn Lys Asn Arg Arg Thr Ile Ala Arg Gln
                20                  25                  30

Thr Ala Arg Cys Ala Cys Arg Lys Gly Gln Ile Ala Gly Thr Thr Arg
            35                  40                  45

Ala Arg Pro Ala Cys Val Asp Ala Arg Ile Ile Lys Thr Lys Gln Trp
        50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 89
<211> LENGTH: 5
<212> TYPE: PRT
<213> ORGANISM: Artificial Sequence
<220> FEATURE:
<223> OTHER INFORMATION: P2-C12 antibodyVH CDR1

<400> SEQUENCE: 89

Thr Tyr Ala Val Thr
1               5

<210> SEQ ID NO 90
<211> LENGTH: 16
<212> TYPE: PRT
<213> ORGANISM: Artificial Sequence
<220> FEATURE:
<223> OTHER INFORMATION: P2-C12antibodyVH CDR2

<400> SEQUENCE: 90

Tyr Ile Asn Trp Arg Gly Gly Thr Ser Tyr Ala Asn Trp Ala Lys Gly
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: P2-C12antibodyVH CDR3

<400> SEQUENCE: 91

Asp Ala Ser Ser Gly Ala Ala Phe Gly Ser Tyr Gly Met Asp Pro
1               5                   10                  15

<210> SEQ ID NO 92
<211> LENGTH: 11
<212> TYPE: PRT
<213> ORGANISM: Artificial Sequence
<220> FEATURE:
<223> OTHER INFORMATION: P2-C12 antibodyVL CDR1

<400> SEQUENCE: 92

Gln Ala Ser Gln Ser Ile Ser Ser Tyr Leu Ser
1               5                   10

<210> SEQ ID NO 93
<211> LENGTH: 7
<212> TYPE: PRT
<213> ORGANISM: Artificial Sequence
```

```
<220> FEATURE:
<223> OTHER INFORMATION: P2-C12antibodyVL CDR2

<400> SEQUENCE: 93

Glu Ala Ser Lys Leu Ala Ser
1               5

<210> SEQ ID NO 94
<211> LENGTH: 12
<212> TYPE: PRT
<213> ORGANISM: Artificial Sequence
<220> FEATURE:
<223> OTHER INFORMATION: P2-C12antibodyVL CDR3

<400> SEQUENCE: 94

Gln Gln Gly Tyr Ser Ser Thr Asn Val Trp Asn Ala
1               5                   10

<210> SEQ ID NO 95
<211> LENGTH: 6
<212> TYPE: PRT
<213> ORGANISM: Artificial Sequence
<220> FEATURE:
<223> OTHER INFORMATION: 13B4antibodyVH CDR1

<400> SEQUENCE: 95

Ser Ser Asn Trp Trp Ser
1               5

<210> SEQ ID NO 96
<211> LENGTH: 16
<212> TYPE: PRT
<213> ORGANISM: Artificial Sequence
<220> FEATURE:
<223> OTHER INFORMATION: 13B4antibodyVH CDR2

<400> SEQUENCE: 96

Glu Ile Tyr His Gly Gly Thr Thr Asn Tyr Asn Pro Ser Leu Lys Gly
1               5                   10                  15

<210> SEQ ID NO 97
<211> LENGTH: 9
<212> TYPE: PRT
<213> ORGANISM: Artificial Sequence
<220> FEATURE:
<223> OTHER INFORMATION: 13B4antibodyVH CDR3

<400> SEQUENCE: 97

Trp Gln Leu Val Gly Gly Leu Asp Val
1               5

<210> SEQ ID NO 98
<211> LENGTH: 11
<212> TYPE: PRT
<213> ORGANISM: Artificial Sequence
<220> FEATURE:
<223> OTHER INFORMATION: 13B4antibodyVL CDR1

<400> SEQUENCE: 98

Ser Gly Asp Lys Leu Gly Asn Val Tyr Ala Ser
1               5                   10

<210> SEQ ID NO 99
<211> LENGTH: 7
<212> TYPE: PRT
<213> ORGANISM: Artificial Sequence
<220> FEATURE:
```

<223> OTHER INFORMATION: 13B4antibodyVL CDR2

<400> SEQUENCE: 99

Gln Asp Asn Lys Arg Pro Ser
1               5

<210> SEQ ID NO 100
<211> LENGTH: 9
<212> TYPE: PRT
<213> ORGANISM: Artificial Sequence
<220> FEATURE:
<223> OTHER INFORMATION: 13B4antibodyVL CDR3

<400> SEQUENCE: 100

Gln Ala Trp Asp Ser Ser Thr Ala Val
1               5

<210> SEQ ID NO 101
<211> LENGTH: 5
<212> TYPE: PRT
<213> ORGANISM: Artificial Sequence
<220> FEATURE:
<223> OTHER INFORMATION: 13F7antibodyVH CDR1

<400> SEQUENCE: 101

Gly Tyr Ser Trp Thr
1               5

<210> SEQ ID NO 102
<211> LENGTH: 16
<212> TYPE: PRT
<213> ORGANISM: Artificial Sequence
<220> FEATURE:
<223> OTHER INFORMATION: 13F7antibodyVH CDR2

<400> SEQUENCE: 102

Glu Ile Ser His Phe Gly Ser Ala Asn Tyr Asn Pro Ser Leu Lys Ser
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: 13F7antibodyVH CDR3

<400> SEQUENCE: 103

Ala Leu Arg Gly Thr Tyr Ser Arg Phe Tyr Tyr Gly Met Asp Val
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: 13F7antibodyVL CDR1

<400> SEQUENCE: 104

Arg Ser Ser Gln Ser Leu Leu His Ser Asn Gly Tyr Asn Tyr Leu Asp
1               5                   10                  15

<210> SEQ ID NO 105
<211> LENGTH: 7
<212> TYPE: PRT
<213> ORGANISM: Artificial Sequence
<220> FEATURE:
<223> OTHER INFORMATION: 13F7antibodyVL CDR2

```
<400> SEQUENCE: 105

Leu Gly Ser Asn Arg Ala Ser
1               5

<210> SEQ ID NO 106
<211> LENGTH: 9
<212> TYPE: PRT
<213> ORGANISM: Artificial Sequence
<220> FEATURE:
<223> OTHER INFORMATION: 13F7antibodyVL CDR3

<400> SEQUENCE: 106

Met Gln Ala Arg Gln Thr Pro Leu Thr
1               5

<210> SEQ ID NO 107
<211> LENGTH: 5
<212> TYPE: PRT
<213> ORGANISM: Artificial Sequence
<220> FEATURE:
<223> OTHER INFORMATION: 15A9antibodyVH CDR1

<400> SEQUENCE: 107

Ser Tyr Tyr Trp Ser
1               5

<210> SEQ ID NO 108
<211> LENGTH: 16
<212> TYPE: PRT
<213> ORGANISM: Artificial Sequence
<220> FEATURE:
<223> OTHER INFORMATION: 15A9antibodyVH CDR2

<400> SEQUENCE: 108

Tyr Ile Tyr Pro Ser Gly Ser Thr Asn Tyr Asn Pro Ser Leu Lys Ser
1               5                   10                  15

<210> SEQ ID NO 109
<211> LENGTH: 12
<212> TYPE: PRT
<213> ORGANISM: Artificial Sequence
<220> FEATURE:
<223> OTHER INFORMATION: 15A9antibodyVH CDR3

<400> SEQUENCE: 109

Val Asn Pro Phe Gly Tyr Tyr Tyr Ala Met Asp Val
1               5                   10

<210> SEQ ID NO 110
<211> LENGTH: 11
<212> TYPE: PRT
<213> ORGANISM: Artificial Sequence
<220> FEATURE:
<223> OTHER INFORMATION: 15A9antibodyVL CDR1

<400> SEQUENCE: 110

Arg Ala Ser Gln Ser Ile Ser Thr Ser Leu Asn
1               5                   10

<210> SEQ ID NO 111
<211> LENGTH: 7
<212> TYPE: PRT
<213> ORGANISM: Artificial Sequence
<220> FEATURE:
<223> OTHER INFORMATION: 15A9antibodyVL CDR2
```

<400> SEQUENCE: 111

Gly Ala Ser Thr Leu Gln Ser
1               5

<210> SEQ ID NO 112
<211> LENGTH: 9
<212> TYPE: PRT
<213> ORGANISM: Artificial Sequence
<220> FEATURE:
<223> OTHER INFORMATION: 15A9antibodyVL CDR3

<400> SEQUENCE: 112

Gln Glu Ser Ala Ser Ile Pro Arg Thr
1               5

<210> SEQ ID NO 113
<211> LENGTH: 5
<212> TYPE: PRT
<213> ORGANISM: Artificial Sequence
<220> FEATURE:
<223> OTHER INFORMATION: P1-A03antibodyVH CDR1

<400> SEQUENCE: 113

Ser Asp Tyr Met Ser
1               5

<210> SEQ ID NO 114
<211> LENGTH: 16
<212> TYPE: PRT
<213> ORGANISM: Artificial Sequence
<220> FEATURE:
<223> OTHER INFORMATION: P1-A03antibodyVH CDR2

<400> SEQUENCE: 114

Ile Ile Tyr Pro Ser Thr Thr Thr Tyr Tyr Ala Ser Trp Ala Lys Gly
1               5                   10                  15

<210> SEQ ID NO 115
<211> LENGTH: 10
<212> TYPE: PRT
<213> ORGANISM: Artificial Sequence
<220> FEATURE:
<223> OTHER INFORMATION: P1-A03antibodyVH CDR3

<400> SEQUENCE: 115

Gly Ser Asn Trp Ser Ser Gly Met Asn Leu
1               5                   10

<210> SEQ ID NO 116
<211> LENGTH: 11
<212> TYPE: PRT
<213> ORGANISM: Artificial Sequence
<220> FEATURE:
<223> OTHER INFORMATION: P1-A03antibodyVL CDR1

<400> SEQUENCE: 116

Leu Ala Ser Glu Asp Ile Tyr Ser Gly Ile Ser
1               5                   10

<210> SEQ ID NO 117
<211> LENGTH: 7
<212> TYPE: PRT
<213> ORGANISM: Artificial Sequence
<220> FEATURE:
<223> OTHER INFORMATION: P1-A03antibodyVL CDR2

<400> SEQUENCE: 117

```
Gly Ala Ser Asn Leu Glu Ser
1               5

<210> SEQ ID NO 118
<211> LENGTH: 12
<212> TYPE: PRT
<213> ORGANISM: Artificial Sequence
<220> FEATURE:
<223> OTHER INFORMATION: P1-A03antibodyVL CDR3

<400> SEQUENCE: 118

Leu Gly Gly Tyr Ser Tyr Ser Ser Thr Gly Leu Thr
1               5                   10

<210> SEQ ID NO 119
<211> LENGTH: 5
<212> TYPE: PRT
<213> ORGANISM: Artificial Sequence
<220> FEATURE:
<223> OTHER INFORMATION: P1-A08antibodyVH CDR1

<400> SEQUENCE: 119

Thr Tyr Tyr Met Ser
1               5

<210> SEQ ID NO 120
<211> LENGTH: 16
<212> TYPE: PRT
<213> ORGANISM: Artificial Sequence
<220> FEATURE:
<223> OTHER INFORMATION: P1-A08antibodyVH CDR2

<400> SEQUENCE: 120

Ile Val Tyr Pro Ser Gly Thr Thr Tyr Tyr Ala Asn Trp Ala Lys Gly
1               5                   10                  15

<210> SEQ ID NO 121
<211> LENGTH: 8
<212> TYPE: PRT
<213> ORGANISM: Artificial Sequence
<220> FEATURE:
<223> OTHER INFORMATION: P1-A08antibodyVH CDR3

<400> SEQUENCE: 121

Gly Asp Ser Phe Gly Tyr Gly Leu
1               5

<210> SEQ ID NO 122
<211> LENGTH: 11
<212> TYPE: PRT
<213> ORGANISM: Artificial Sequence
<220> FEATURE:
<223> OTHER INFORMATION: P1-A08antibodyVL CDR1

<400> SEQUENCE: 122

Thr Ala Asp Thr Leu Ser Arg Ser Tyr Ala Ser
1               5                   10

<210> SEQ ID NO 123
<211> LENGTH: 7
<212> TYPE: PRT
<213> ORGANISM: Artificial Sequence
<220> FEATURE:
<223> OTHER INFORMATION: P1-A08antibodyVL CDR2

<400> SEQUENCE: 123
```

```
Arg Asp Thr Ser Arg Pro Ser
1               5

<210> SEQ ID NO 124
<211> LENGTH: 13
<212> TYPE: PRT
<213> ORGANISM: Artificial Sequence
<220> FEATURE:
<223> OTHER INFORMATION: P1-A08antibodyVL CDR3

<400> SEQUENCE: 124

Ala Thr Ser Asp Gly Ser Gly Ser Asn Tyr Gln Tyr Val
1               5                   10

<210> SEQ ID NO 125
<211> LENGTH: 5
<212> TYPE: PRT
<213> ORGANISM: Artificial Sequence
<220> FEATURE:
<223> OTHER INFORMATION: P1-F02antibodyVH CDR1

<400> SEQUENCE: 125

Asn Tyr Tyr Met Gly
1               5

<210> SEQ ID NO 126
<211> LENGTH: 16
<212> TYPE: PRT
<213> ORGANISM: Artificial Sequence
<220> FEATURE:
<223> OTHER INFORMATION: P1-F02antibodyVH CDR2

<400> SEQUENCE: 126

Ile Ile Tyr Ala Ser Gly Ser Thr Tyr Tyr Ala Ser Trp Ala Lys Gly
1               5                   10                  15

<210> SEQ ID NO 127
<211> LENGTH: 17
<212> TYPE: PRT
<213> ORGANISM: Artificial Sequence
<220> FEATURE:
<223> OTHER INFORMATION: P1-F02antibodyVH CDR3

<400> SEQUENCE: 127

Ile Asp Ile Gly Val Gly Asp Tyr Gly Trp Ala Tyr Asp Arg Leu Asp
1               5                   10                  15

Leu

<210> SEQ ID NO 128
<211> LENGTH: 11
<212> TYPE: PRT
<213> ORGANISM: Artificial Sequence
<220> FEATURE:
<223> OTHER INFORMATION: P1-F02antibodyVL CDR1

<400> SEQUENCE: 128

Leu Ala Ser Glu Asp Ile Tyr Ser Gly Ile Ser
1               5                   10

<210> SEQ ID NO 129
<211> LENGTH: 7
<212> TYPE: PRT
<213> ORGANISM: Artificial Sequence
<220> FEATURE:
<223> OTHER INFORMATION: P1-F02antibodyVL CDR2

<400> SEQUENCE: 129
```

```
Gly Ala Ser Asn Leu Glu Ser
1               5

<210> SEQ ID NO 130
<211> LENGTH: 10
<212> TYPE: PRT
<213> ORGANISM: Artificial Sequence
<220> FEATURE:
<223> OTHER INFORMATION: P1-F02antibodyVL CDR3

<400> SEQUENCE: 130

Leu Gly Gly Tyr Ser Tyr Ser Ser Ile Thr
1               5                   10

<210> SEQ ID NO 131
<211> LENGTH: 5
<212> TYPE: PRT
<213> ORGANISM: Artificial Sequence
<220> FEATURE:
<223> OTHER INFORMATION: P2-A01antibodyVH CDR1

<400> SEQUENCE: 131

Gly Tyr Tyr Met Ser
1               5

<210> SEQ ID NO 132
<211> LENGTH: 16
<212> TYPE: PRT
<213> ORGANISM: Artificial Sequence
<220> FEATURE:
<223> OTHER INFORMATION: P2-A01antibodyVH CDR2

<400> SEQUENCE: 132

Ile Ile Tyr Pro Ser Gly Ser Thr Asp Tyr Ala Ser Trp Ala Lys Gly
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: P2-A01antibodyVH CDR3

<400> SEQUENCE: 133

Val Ala Gly Tyr Val Gly Tyr Gly Tyr Glu Thr Phe Phe Asp Ile
1               5                   10                  15

<210> SEQ ID NO 134
<211> LENGTH: 11
<212> TYPE: PRT
<213> ORGANISM: Artificial Sequence
<220> FEATURE:
<223> OTHER INFORMATION: P2-A01antibodyVL CDR1

<400> SEQUENCE: 134

Leu Ala Ser Glu Asp Ile Tyr Ser Gly Ile Ser
1               5                   10

<210> SEQ ID NO 135
<211> LENGTH: 7
<212> TYPE: PRT
<213> ORGANISM: Artificial Sequence
<220> FEATURE:
<223> OTHER INFORMATION: P2-A01antibodyVL CDR2

<400> SEQUENCE: 135
```

Gly Ala Ser Asn Leu Glu Ser
1               5

<210> SEQ ID NO 136
<211> LENGTH: 14
<212> TYPE: PRT
<213> ORGANISM: Artificial Sequence
<220> FEATURE:
<223> OTHER INFORMATION: P2-A01antibodyVL CDR3

<400> SEQUENCE: 136

Leu Gly Gly Val Thr Tyr Ser Ser Thr Gly Thr His Leu Thr
1               5                   10

<210> SEQ ID NO 137
<211> LENGTH: 5
<212> TYPE: PRT
<213> ORGANISM: Artificial Sequence
<220> FEATURE:
<223> OTHER INFORMATION: P2-A03antibodyVH CDR1

<400> SEQUENCE: 137

Asn Tyr Asp Met Ser
1               5

<210> SEQ ID NO 138
<211> LENGTH: 16
<212> TYPE: PRT
<213> ORGANISM: Artificial Sequence
<220> FEATURE:
<223> OTHER INFORMATION: P2-A03antibodyVH CDR2

<400> SEQUENCE: 138

Phe Met Asp Thr Asp Gly Ser Ala Tyr Tyr Ala Thr Trp Ala Lys Gly
1               5                   10                  15

<210> SEQ ID NO 139
<211> LENGTH: 11
<212> TYPE: PRT
<213> ORGANISM: Artificial Sequence
<220> FEATURE:
<223> OTHER INFORMATION: P2-A03antibodyVH CDR3

<400> SEQUENCE: 139

Arg Gly Ser Ser Tyr Tyr Gly Gly Ile Asp Ile
1               5                   10

<210> SEQ ID NO 140
<211> LENGTH: 11
<212> TYPE: PRT
<213> ORGANISM: Artificial Sequence
<220> FEATURE:
<223> OTHER INFORMATION: P2-A03antibodyVL CDR1

<400> SEQUENCE: 140

Gln Ala Ser Gln Ser Ile Gly Gly Asn Leu Ala
1               5                   10

<210> SEQ ID NO 141
<211> LENGTH: 7
<212> TYPE: PRT
<213> ORGANISM: Artificial Sequence
<220> FEATURE:
<223> OTHER INFORMATION: P2-A03antibodyVL CDR2

<400> SEQUENCE: 141

Arg Ala Ser Thr Leu Ala Ser

```
<210> SEQ ID NO 142
<211> LENGTH: 14
<212> TYPE: PRT
<213> ORGANISM: Artificial Sequence
<220> FEATURE:
<223> OTHER INFORMATION: P2-A03antibodyVL CDR3

<400> SEQUENCE: 142

Gln Ser Pro Ala Tyr Asp Pro Ala Ala Tyr Val Gly Asn Ala
1               5                   10

<210> SEQ ID NO 143
<211> LENGTH: 5
<212> TYPE: PRT
<213> ORGANISM: Artificial Sequence
<220> FEATURE:
<223> OTHER INFORMATION: P2-F07antibodyVH CDR1

<400> SEQUENCE: 143

Ser Tyr Tyr Met Asn
1               5

<210> SEQ ID NO 144
<211> LENGTH: 16
<212> TYPE: PRT
<213> ORGANISM: Artificial Sequence
<220> FEATURE:
<223> OTHER INFORMATION: P2-F07antibodyVH CDR2

<400> SEQUENCE: 144

Ile Ile Tyr Pro Ser Gly Thr Thr Tyr Tyr Ala Gly Trp Ala Lys Gly
1               5                   10                  15

<210> SEQ ID NO 145
<211> LENGTH: 8
<212> TYPE: PRT
<213> ORGANISM: Artificial Sequence
<220> FEATURE:
<223> OTHER INFORMATION: P2-F07antibodyVH CDR3

<400> SEQUENCE: 145

Thr Val Ser Gly Tyr Phe Asp Ile
1               5

<210> SEQ ID NO 146
<211> LENGTH: 11
<212> TYPE: PRT
<213> ORGANISM: Artificial Sequence
<220> FEATURE:
<223> OTHER INFORMATION: P2-F07antibodyVL CDR1

<400> SEQUENCE: 146

Leu Ala Ser Glu Asp Ile Tyr Ser Ala Leu Ala
1               5                   10

<210> SEQ ID NO 147
<211> LENGTH: 7
<212> TYPE: PRT
<213> ORGANISM: Artificial Sequence
<220> FEATURE:
<223> OTHER INFORMATION: P2-F07antibodyVL CDR2

<400> SEQUENCE: 147

Gly Thr Ser Asn Leu Glu Ser
1               5
```

```
<210> SEQ ID NO 148
<211> LENGTH: 9
<212> TYPE: PRT
<213> ORGANISM: Artificial Sequence
<220> FEATURE:
<223> OTHER INFORMATION: P2-F07antibodyVL CDR3

<400> SEQUENCE: 148

Gln Gly Tyr Ser Ser Tyr Pro Leu Thr
1               5

<210> SEQ ID NO 149
<211> LENGTH: 5
<212> TYPE: PRT
<213> ORGANISM: Artificial Sequence
<220> FEATURE:
<223> OTHER INFORMATION: P2-F11antibodyVH CDR1

<400> SEQUENCE: 149

Ser Tyr Gly Val Ser
1               5

<210> SEQ ID NO 150
<211> LENGTH: 16
<212> TYPE: PRT
<213> ORGANISM: Artificial Sequence
<220> FEATURE:
<223> OTHER INFORMATION: P2-F11antibodyVH CDR2

<400> SEQUENCE: 150

Tyr Ile Ala Asn Asn Tyr Asn Pro His Tyr Ala Ser Trp Ala Lys Gly
1               5                   10                  15

<210> SEQ ID NO 151
<211> LENGTH: 7
<212> TYPE: PRT
<213> ORGANISM: Artificial Sequence
<220> FEATURE:
<223> OTHER INFORMATION: P2-F11antibodyVH CDR3

<400> SEQUENCE: 151

Asp Asn Tyr Gly Met Asp Pro
1               5

<210> SEQ ID NO 152
<211> LENGTH: 13
<212> TYPE: PRT
<213> ORGANISM: Artificial Sequence
<220> FEATURE:
<223> OTHER INFORMATION: P2-F11antibodyVL CDR1

<400> SEQUENCE: 152

Gln Ala Ser Gln Ser Val Tyr Asn Asn Lys Asn Leu Ala
1               5                   10

<210> SEQ ID NO 153
<211> LENGTH: 7
<212> TYPE: PRT
<213> ORGANISM: Artificial Sequence
<220> FEATURE:
<223> OTHER INFORMATION: P2-F11antibodyVL CDR2

<400> SEQUENCE: 153

Ala Ala Ser Thr Leu Ala Ser
1               5
```

<210> SEQ ID NO 154
<211> LENGTH: 13
<212> TYPE: PRT
<213> ORGANISM: Artificial Sequence
<220> FEATURE:
<223> OTHER INFORMATION: P2-F11antibodyVL CDR3

<400> SEQUENCE: 154

Gln Gly Glu Phe Ser Cys Ser Ser Ala Asp Cys Asn Ala
1               5                   10

<210> SEQ ID NO 155
<211> LENGTH: 121
<212> TYPE: PRT
<213> ORGANISM: Artificial Sequence
<220> FEATURE:
<223> OTHER INFORMATION: P2-C12antibodyVH

<400> SEQUENCE: 155

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Val Thr Trp Val Arg Gln Ala Pro Gly Lys Gly Leu Glu Trp Ile Gly
        35                  40                  45

Tyr Ile Asn Trp Arg Gly Gly Thr Ser Tyr Ala Asn Trp Ala Lys Gly
    50                  55                  60

Arg Phe Thr Ile Ser Lys Thr Ser Ser Thr Thr Val Asp Leu Lys Met
65                  70                  75                  80

Thr Ser Pro Thr Thr Glu Asp Thr Ala Thr Tyr Phe Cys Ala Arg Asp
                85                  90                  95

Ala Ser Ser Gly Ala Ala Phe Gly Ser Tyr Gly Met Asp Pro Trp Gly
            100                 105                 110

Pro Gly Thr Leu Val Thr Val Ser Ser
        115                 120

<210> SEQ ID NO 156
<211> LENGTH: 118
<212> TYPE: PRT
<213> ORGANISM: Artificial Sequence
<220> FEATURE:
<223> OTHER INFORMATION: 13B4antibodyVH

<400> SEQUENCE: 156

Gln Val Gln Leu Gln Glu Ser Gly Pro Gly Leu Val Lys Pro Ser Gly
1               5                   10                  15

Thr Leu Ser Leu Asn Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Gly Thr Thr Asn Tyr Asn Pro Ser Leu
    50                  55                  60

Lys Gly Arg Val Thr Met Ser Val Asp Lys Thr Lys Asn Gln Phe Ser
65                  70                  75                  80

Leu Arg Leu Ser Ser Val Thr Ala Val Asp Thr Ala Val Tyr Tyr Cys
                85                  90                  95

Ala Arg Trp Gln Leu Val Gly Gly Leu Asp Val Trp Gly Gln Gly Thr
            100                 105                 110

Thr Val Thr Val Ser Ser

<210> SEQ ID NO 157
<211> LENGTH: 123
<212> TYPE: PRT
<213> ORGANISM: Artificial Sequence
<220> FEATURE:
<223> OTHER INFORMATION: 13F7antibodyVH

<400> SEQUENCE: 157

Gln Val Gln Leu Gln Glu Trp Gly Ala Gly Leu Leu Lys Pro Ser Glu
1               5                   10                  15

Thr Leu Ser Leu Thr Cys Ala Ile Asn Ala Glu Ser Phe Asn Gly Tyr
            20                  25                  30

Ser Trp Thr Trp Ile Arg Gln Thr Pro Gly Lys Gly Leu Glu Trp Ile
        35                  40                  45

Gly Glu Ile Ser His Phe Gly Ser Ala Asn Tyr Asn Pro Ser Leu Lys
    50                  55                  60

Ser Arg Ala Thr Ile Ser Ala Asp Lys Ser Lys Asn Gln Phe Ser Leu
65                  70                  75                  80

Lys Leu Thr Ser Val Thr Ala Val Asp Thr Ala Val Tyr Tyr Cys Ala
                85                  90                  95

Arg Ala Leu Arg Gly Thr Tyr Ser Arg Phe Tyr Tyr Gly Met Asp Val
            100                 105                 110

Trp Gly Gln Gly Thr Thr Val Thr Val Ser Ser
        115                 120

<210> SEQ ID NO 158
<211> LENGTH: 120
<212> TYPE: PRT
<213> ORGANISM: Artificial Sequence
<220> FEATURE:
<223> OTHER INFORMATION: 15A9antibodyVH

<400> SEQUENCE: 158

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Pro Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Asn Leu Lys Ser Val Thr Ala Val Asp Thr Ala Val Tyr Tyr Cys Ala
                85                  90                  95

Arg Val Asn Pro Phe Gly Tyr Tyr Tyr Ala Met Asp Val Trp Gly Gln
            100                 105                 110

Gly Thr Thr Val Thr Val Ser Ser
        115                 120

<210> SEQ ID NO 159
<211> LENGTH: 116
<212> TYPE: PRT
<213> ORGANISM: Artificial Sequence
<220> FEATURE:
<223> OTHER INFORMATION: P1-A03antibodyVH

<400> SEQUENCE: 159

-continued

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asp Tyr
            20                  25                  30

Met Ser Trp Val Arg Gln Ala Pro Gly Glu Gly Leu Glu Trp Ile Gly
            35                  40                  45

Ile Ile Tyr Pro Ser Thr Thr Thr Tyr Tyr Ala Ser Trp Ala Lys Gly
        50                  55                  60

Arg Phe Thr Ile Ser Lys Thr Ser Ser Thr Thr Val Glu Leu Lys Met
65              70                  75                  80

Thr Ser Leu Thr Thr Glu Asp Thr Ala Thr Tyr Phe Cys Ala Arg Gly
            85                  90                  95

Ser Asn Trp Ser Ser Gly Met Asn Leu Trp Gly Pro Gly Thr Leu Val
            100                 105                 110

Thr Val Ser Ser
        115

<210> SEQ ID NO 160
<211> LENGTH: 113
<212> TYPE: PRT
<213> ORGANISM: Artificial Sequence
<220> FEATURE:
<223> OTHER INFORMATION: P1-A08antibodyVH

<400> SEQUENCE: 160

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Thr Tyr Tyr
            20                  25                  30

Met Ser Trp Val Arg Gln Ala Pro Gly Lys Gly Leu Glu Trp Ile Gly
            35                  40                  45

Ile Val Tyr Pro Ser Gly Thr Tyr Tyr Ala Asn Trp Ala Lys Gly
        50                  55                  60

Arg Phe Thr Ile Ser Thr Ala Ser Thr Thr Val Asp Leu Met Ile Thr
65              70                  75                  80

Ser Pro Thr Thr Glu Asp Thr Ala Thr Tyr Phe Cys Ala Arg Gly Asp
            85                  90                  95

Ser Phe Gly Tyr Gly Leu Trp Gly Pro Gly Thr Leu Val Thr Val Ser
            100                 105                 110

Ser

<210> SEQ ID NO 161
<211> LENGTH: 122
<212> TYPE: PRT
<213> ORGANISM: Artificial Sequence
<220> FEATURE:
<223> OTHER INFORMATION: P1-F02antibodyVH

<400> SEQUENCE: 161

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Tyr Tyr
            20                  25                  30

Met Gly Trp Val Arg Gln Ala Pro Gly Glu Gly Leu Glu Trp Ile Gly
            35                  40                  45

Ile Ile Tyr Ala Ser Gly Ser Thr Tyr Tyr Ala Ser Trp Ala Lys Gly
        50                  55                  60
```

Arg Phe Thr Ile Ser Lys Ser Thr Thr Val Asp Leu Lys Met Thr
65                  70                  75                  80

Ser Leu Thr Thr Glu Asp Ala Thr Tyr Phe Cys Ala Arg Ile Asp
            85                  90                  95

Ile Gly Val Gly Asp Tyr Gly Trp Ala Tyr Asp Arg Leu Asp Leu Trp
            100                 105                 110

Gly Gln Gly Thr Leu Val Thr Val Ser Ser
        115                 120

<210> SEQ ID NO 162
<211> LENGTH: 121
<212> TYPE: PRT
<213> ORGANISM: Artificial Sequence
<220> FEATURE:
<223> OTHER INFORMATION: P2-A01antibodyVH

<400> SEQUENCE: 162

Gln Glu Gln Leu Val Glu Ser Gly Gly Arg Leu Val Thr Pro Gly Thr
1               5                   10                  15

Pro Leu Thr Leu Ser Cys Thr Ala Ser Gly Phe Phe Leu Ser Gly Tyr
            20                  25                  30

Tyr Met Ser Trp Val Arg Gln Ala Pro Gly Lys Gly Leu Glu Trp Ile
        35                  40                  45

Gly Ile Ile Tyr Pro Ser Gly Ser Thr Asp Tyr Ala Ser Trp Ala Lys
    50                  55                  60

Gly Arg Phe Thr Ile Ser Lys Thr Ser Thr Thr Val Asp Leu Lys Ile
65                  70                  75                  80

Thr Thr Pro Thr Thr Glu Asp Thr Ala Thr Tyr Phe Cys Ala Arg Val
            85                  90                  95

Ala Gly Tyr Val Gly Tyr Gly Tyr Glu Thr Phe Phe Asp Ile Trp Gly
            100                 105                 110

Pro Gly Thr Leu Val Thr Val Ser Leu
        115                 120

<210> SEQ ID NO 163
<211> LENGTH: 116
<212> TYPE: PRT
<213> ORGANISM: Artificial Sequence
<220> FEATURE:
<223> OTHER INFORMATION: P2-A03antibodyVH

<400> SEQUENCE: 163

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Asp
            20                  25                  30

Met Ser Trp Val Arg Gln Ala Pro Gly Lys Gly Leu Glu Tyr Ile Gly
        35                  40                  45

Phe Met Asp Thr Asp Gly Ser Ala Tyr Tyr Ala Thr Trp Ala Lys Gly
    50                  55                  60

Arg Phe Thr Ile Ser Arg Thr Ser Thr Thr Val Asp Leu Lys Met Thr
65                  70                  75                  80

Ser Pro Thr Thr Glu Asp Thr Ala Thr Tyr Phe Cys Ala Arg Arg Gly
            85                  90                  95

Ser Ser Tyr Tyr Gly Gly Ile Asp Ile Trp Gly Pro Gly Thr Pro Val
            100                 105                 110

Thr Val Ser Leu

115

<210> SEQ ID NO 164
<211> LENGTH: 113
<212> TYPE: PRT
<213> ORGANISM: Artificial Sequence
<220> FEATURE:
<223> OTHER INFORMATION: P2-F07antibodyVH

<400> SEQUENCE: 164

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Asn Trp Val Arg Gln Ala Pro Gly Lys Gly Leu Glu Trp Ile Gly
        35                  40                  45

Ile Ile Tyr Pro Ser Gly Thr Thr Tyr Tyr Ala Gly Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Ser Glu Asp Thr Ala Thr Tyr Phe Cys Ala Arg Thr Val
                85                  90                  95

Ser Gly Tyr Phe Asp Ile Trp Gly Pro Gly Thr Leu Val Thr Val Ser
            100                 105                 110

Leu

<210> SEQ ID NO 165
<211> LENGTH: 114
<212> TYPE: PRT
<213> ORGANISM: Artificial Sequence
<220> FEATURE:
<223> OTHER INFORMATION: P2-F11antibodyVH

<400> SEQUENCE: 165

Gln Glu Gln Leu Val Glu Ser Gly Gly Arg Leu Val Thr Pro Gly Thr
1               5                   10                  15

Thr Leu Thr Leu Thr Cys Thr Val Ser Gly Phe Ser Leu Ser Ser Tyr
            20                  25                  30

Gly Val Ser Trp Val Arg Gln Ala Pro Gly Lys Gly Leu Glu Trp Ile
        35                  40                  45

Gly Tyr Ile Ala Asn Asn Tyr Asn Pro His Tyr Ala Ser Trp Ala Lys
    50                  55                  60

Gly Arg Phe Thr Ile Ser Lys Thr Ser Ser Thr Thr Val Asp Leu Lys
65                  70                  75                  80

Met Thr Ser Leu Thr Thr Glu Asp Thr Ala Thr Tyr Phe Cys Ala Arg
                85                  90                  95

Asp Asn Tyr Gly Met Asp Pro Trp Gly Pro Gly Thr Leu Val Thr Val
            100                 105                 110

Ser Ser

<210> SEQ ID NO 166
<211> LENGTH: 110
<212> TYPE: PRT
<213> ORGANISM: Artificial Sequence
<220> FEATURE:
<223> OTHER INFORMATION: P2-C12antibodyVL

<400> SEQUENCE: 166

Glu Leu Asp Met Thr Gln Thr Pro Ser Ser Val Ser Ala Ala Val Gly

```
               1               5                  10                 15
Gly Thr Val Thr Ile Lys Cys Gln Ala Ser Gln Ser Ile Ser Ser Tyr
                20                  25                 30

Leu Ser Trp Tyr Gln Gln Lys Pro Gly Gln Pro Pro Lys Leu Leu Ile
        35                  40                 45

Tyr Glu Ala Ser Lys Leu Ala Ser Gly Val Pro Ser Arg Phe Ser Gly
        50                  55                 60

Ser Gly Tyr Gly Thr Glu Phe Thr Leu Thr Ile Ser Asp Leu Glu Cys
65                  70                  75                 80

Ala Asp Ala Ala Thr Tyr Tyr Cys Gln Gln Gly Tyr Ser Ser Thr Asn
                85                  90                 95

Val Trp Asn Ala Phe Gly Gly Gly Thr Asn Val Glu Ile Lys
                100                 105                110
```

<210> SEQ ID NO 167
<211> LENGTH: 106
<212> TYPE: PRT
<213> ORGANISM: Artificial Sequence
<220> FEATURE:
<223> OTHER INFORMATION: 13B4antibodyVL

<400> SEQUENCE: 167

```
Ser Tyr Glu Leu Thr Gln Pro Leu Ser Val Ser Val Ser Pro Gly Gln
1               5                  10                 15

Thr Ala Ser Ile Thr Cys Ser Gly Asp Lys Leu Gly Asn Val Tyr Ala
                20                  25                 30

Ser Trp Tyr Gln Gln Lys Pro Gly Gln Ser Pro Thr Leu Val Ile Tyr
        35                  40                 45

Gln Asp Asn Lys Arg Pro Ser Gly Ile Pro Glu Arg Phe Ser Gly Ser
        50                  55                 60

Asn Ser Gly Lys Thr Ala Thr Leu Thr Ile Ser Gly Thr Gln Ala Leu
65                  70                  75                 80

Asp Glu Ala Asp Tyr Tyr Cys Gln Ala Trp Asp Ser Ser Thr Ala Val
                85                  90                 95

Phe Gly Gly Gly Thr Lys Leu Thr Val Leu
                100                 105
```

<210> SEQ ID NO 168
<211> LENGTH: 112
<212> TYPE: PRT
<213> ORGANISM: Artificial Sequence
<220> FEATURE:
<223> OTHER INFORMATION: 13F7antibodyVL

<400> SEQUENCE: 168

```
Asp Ile Val Met Thr Gln Thr Pro Leu Ser Leu Pro Val Ala Pro Gly
1               5                  10                 15

Glu Pro Ala Ser Ile Ser Cys Arg Ser Ser Gln Ser Leu Leu His Ser
                20                  25                 30

Asn Gly Tyr Asn Tyr Leu Asp Trp Tyr Val Gln Lys Pro Gly Gln Pro
        35                  40                 45

Pro Gln Leu Leu Ile Tyr Leu Gly Ser Asn Arg Ala Ser Gly Val Pro
        50                  55                 60

Asp Arg Phe Ser Gly Ser Gly Ser Gly Thr Asp Phe Thr Leu Lys Ile
65                  70                  75                 80

Ser Arg Val Glu Ala Glu Asp Val Gly Val Tyr Tyr Cys Met Gln Ala
                85                  90                 95
```

```
Arg Gln Thr Pro Leu Thr Phe Gly Gly Gly Thr Lys Val Glu Ile Lys
            100                 105                 110
```

<210> SEQ ID NO 169
<211> LENGTH: 107
<212> TYPE: PRT
<213> ORGANISM: Artificial Sequence
<220> FEATURE:
<223> OTHER INFORMATION: 15A9antibodyVL

<400> SEQUENCE: 169

```
Asp Ile Gln Met Thr Gln Ser Pro Ser Ser Leu Ser Ala Ser Val Gly
1               5                   10                  15

Asp Arg Ile Thr Ile Ser Cys Arg Ala Ser Gln Ser Ile Ser Thr Ser
            20                  25                  30

Leu Asn Trp Tyr Gln Gln Thr Pro Gly Lys Ala Pro Arg Leu Leu Ile
        35                  40                  45

Tyr Gly Ala Ser Thr Leu Gln Ser Gly Val Pro Ser Arg Phe Ser Gly
    50                  55                  60

Gly Gly Ser Gly Thr Asp Phe Ser Leu Thr Ile Thr Ser Leu Gln Pro
65                  70                  75                  80

Glu Asp Phe Ala Thr Tyr Tyr Cys Gln Glu Ser Ala Ser Ile Pro Arg
                85                  90                  95

Thr Phe Gly Gln Gly Thr Lys Leu Asp Ile Lys
            100                 105
```

<210> SEQ ID NO 170
<211> LENGTH: 110
<212> TYPE: PRT
<213> ORGANISM: Artificial Sequence
<220> FEATURE:
<223> OTHER INFORMATION: P1-A03antibodyVL

<400> SEQUENCE: 170

```
Glu Leu Val Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Glu Lys Pro Pro Thr Leu Leu Ile
        35                  40                  45

Ser Gly Ala Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Tyr Ser Tyr Ser Ser
                85                  90                  95

Thr Gly Leu Thr Phe Gly Ala Gly Thr Asn Val Glu Ile Lys
            100                 105                 110
```

<210> SEQ ID NO 171
<211> LENGTH: 110
<212> TYPE: PRT
<213> ORGANISM: Artificial Sequence
<220> FEATURE:
<223> OTHER INFORMATION: P1-A08antibodyVL

<400> SEQUENCE: 171

```
Glu Leu Val Leu Thr Gln Ser Pro Ser Val Gln Val Asn Leu Gly Gln
1               5                   10                  15

Thr Val Ser Leu Thr Cys Thr Ala Asp Thr Leu Ser Arg Ser Tyr Ala
```

```
                20                  25                  30

Ser Trp Tyr Gln Gln Lys Pro Gly Gln Ala Pro Val Leu Leu Ile Tyr
            35                  40                  45

Arg Asp Thr Ser Arg Pro Ser Gly Val Pro Asp Arg Phe Ser Gly Ser
        50                  55                  60

Ser Ser Gly Asn Thr Ala Thr Leu Thr Ile Ser Gly Ala Gln Ala Gly
65                  70                  75                  80

Asp Glu Ala Asp Tyr Tyr Cys Ala Thr Ser Asp Gly Ser Gly Ser Asn
                85                  90                  95

Tyr Gln Tyr Val Phe Gly Gly Gly Thr Gln Leu Thr Val Thr
            100                 105                 110

<210> SEQ ID NO 172
<211> LENGTH: 108
<212> TYPE: PRT
<213> ORGANISM: Artificial Sequence
<220> FEATURE:
<223> OTHER INFORMATION: P1-F02antibodyVL

<400> SEQUENCE: 172

Glu Leu Asp Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Pro Thr Leu Leu Ile
        35                  40                  45

Tyr Gly Ala Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Tyr Ser Tyr Ser Ser
                85                  90                  95

Ile Thr Phe Gly Ala Gly Thr Asn Val Glu Ile Lys
            100                 105

<210> SEQ ID NO 173
<211> LENGTH: 112
<212> TYPE: PRT
<213> ORGANISM: Artificial Sequence
<220> FEATURE:
<223> OTHER INFORMATION: P2-A01antibodyVL

<400> SEQUENCE: 173

Glu Leu Val Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Pro Thr Leu Leu Ile
        35                  40                  45

Tyr Gly Ala Ser Asn Leu Glu Ser Gly Val Pro Pro Arg Phe Ser Gly
    50                  55                  60

Ser Gly Ser Gly Ser Asp Tyr Thr Leu Thr Ile Gly Gly Val Gln Ala
65                  70                  75                  80

Glu Asp Ala Ala Thr Tyr Tyr Cys Leu Gly Gly Val Thr Tyr Ser Ser
                85                  90                  95

Thr Gly Thr His Leu Thr Phe Gly Ala Gly Thr Asn Val Glu Ile Lys
            100                 105                 110
```

<210> SEQ ID NO 174
<211> LENGTH: 112
<212> TYPE: PRT
<213> ORGANISM: Artificial Sequence
<220> FEATURE:
<223> OTHER INFORMATION: P2-A03antibodyVL

<400> SEQUENCE: 174

```
Glu Leu Asp Leu Thr Gln Thr Pro Ala Ser Val Ser Glu Pro Val Gly
1               5                   10                  15

Gly Thr Val Thr Ile Lys Cys Gln Ala Ser Gln Ser Ile Gly Gly Asn
            20                  25                  30

Leu Ala Trp Tyr Gln Gln Lys Pro Gly Gln Pro Lys Leu Leu Ile
        35                  40                  45

Tyr Arg Ala Ser Thr Leu Ala Ser Gly Val Pro Ser Arg Phe Lys Gly
 50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Ser Pro Ala Tyr Asp Pro Ala
                85                  90                  95

Ala Tyr Val Gly Asn Ala Phe Gly Gly Thr Glu Leu Glu Ile Leu
            100                 105                 110
```

<210> SEQ ID NO 175
<211> LENGTH: 107
<212> TYPE: PRT
<213> ORGANISM: Artificial Sequence
<220> FEATURE:
<223> OTHER INFORMATION: P2-F07antibodyVL

<400> SEQUENCE: 175

```
Glu Leu Asp Leu Thr Gln Thr Pro Pro Ser Leu Ser Ala Ser Val Gly
1               5                   10                  15

Gly Thr Val Thr Ile Asn Cys Leu Ala Ser Glu Asp Ile Tyr Ser Ala
            20                  25                  30

Leu Ala Trp Tyr Gln Gln Lys Pro Gly Lys Pro Pro Thr Leu Leu Ile
        35                  40                  45

Ser Gly Thr Ser Asn Leu Glu Ser Gly Val Pro Pro Arg Phe Ser Gly
 50                  55                  60

Ser Gly Ser Gly Thr Asp Tyr Thr Leu Thr Ile Gly Gly Val Gln Ala
65                  70                  75                  80

Glu Asp Ala Ala Thr Tyr Phe Cys Gln Gly Tyr Ser Ser Tyr Pro Leu
                85                  90                  95

Thr Phe Gly Ala Gly Thr Asn Val Glu Ile Lys
            100                 105
```

<210> SEQ ID NO 176
<211> LENGTH: 113
<212> TYPE: PRT
<213> ORGANISM: Artificial Sequence
<220> FEATURE:
<223> OTHER INFORMATION: P2-F11antibodyVL

<400> SEQUENCE: 176

```
Glu Leu Asp Leu Thr Gln Thr Pro Ser Ser Val Ser Ala Ala Val Gly
1               5                   10                  15

Gly Thr Val Thr Ile Asn Cys Gln Ala Ser Gln Ser Val Tyr Asn Asn
            20                  25                  30

Lys Asn Leu Ala Trp Tyr Gln Gln Lys Pro Gly Gln Pro Pro Lys Leu
```

```
                    35                  40                  45
Leu Ile Tyr Ala Ala Ser Thr Leu Ala Ser Gly Val Ser Ser Arg Phe
            50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Gln Gly Glu Phe Ser Cys
                    85                  90                  95

Ser Ser Ala Asp Cys Asn Ala Phe Gly Gly Gly Thr Glu Leu Glu Ile
            100                 105                 110

Leu
```

<210> SEQ ID NO 177
<211> LENGTH: 363
<212> TYPE: DNA
<213> ORGANISM: Artificial Sequence
<220> FEATURE:
<223> OTHER INFORMATION: P2-C12antibodyVH

<400> SEQUENCE: 177

```
cagtcgctgg aggagtccgg gggtcgcctg gtcacgcctg gacacccct gacactcacc      60
tgcaccgtct ctggattctc cctcagtacc tatgcagtga cctgggtccg ccaggctcca     120
gggaagggc tggaatggat cggatacatt aattggcgtg gtgggacatc ctacgcgaac     180
tgggcgaaag gccgattcac catctccaaa acctcgtcga ccacggtgga tctgaaaatg     240
accagtccga caaccgagga cacggccacc tatttctgtg ccagagatgc tagtagtggt     300
gctgcttttg ggtcttacgg catggacccc tggggcccag gaccctcgt caccgtctct     360
tca                                                                   363
```

<210> SEQ ID NO 178
<211> LENGTH: 330
<212> TYPE: DNA
<213> ORGANISM: Artificial Sequence
<220> FEATURE:
<223> OTHER INFORMATION: P2-C12antibodyVL

<400> SEQUENCE: 178

```
gagctcgata tgacccagac tccatcctcc gtgtctgcag ctgtgggagg cacagtcacc      60
atcaagtgcc aggccagtca gagcattagt agctacttat cctggtatca gcagaaacca     120
gggcagcctc ccaagctcct gatctatgaa gcatccaaac tggcctctgg ggtcccatcg     180
cggttcagcg gcagtggata tgggacagag ttcactctca ccatcagcga cctggagtgt     240
gccgatgctg ccacttacta ctgtcaacag ggttatagta gtactaatgt ttggaatgct     300
ttcggcggag gcaccaatgt ggaaatcaaa                                      330
```

<210> SEQ ID NO 179
<211> LENGTH: 451
<212> TYPE: PRT
<213> ORGANISM: Artificial Sequence
<220> FEATURE:
<223> OTHER INFORMATION: P2-C12HC

<400> SEQUENCE: 179

```
Gln Ser Leu Glu Glu Ser Gly Gly Arg Leu Val Thr Pro Gly Thr Pro
1               5                  10                  15

Leu Thr Leu Thr Cys Thr Val Ser Gly Phe Ser Leu Ser Thr Tyr Ala
            20                  25                  30

Val Thr Trp Val Arg Gln Ala Pro Gly Lys Gly Leu Glu Trp Ile Gly
```

-continued

```
                35                  40                  45
Tyr Ile Asn Trp Arg Gly Gly Thr Ser Tyr Ala Asn Trp Ala Lys Gly
 50                  55                  60

Arg Phe Thr Ile Ser Lys Thr Ser Ser Thr Thr Val Asp Leu Lys Met
 65                  70                  75                  80

Thr Ser Pro Thr Thr Glu Asp Thr Ala Thr Tyr Phe Cys Ala Arg Asp
                 85                  90                  95

Ala Ser Ser Gly Ala Ala Phe Gly Ser Tyr Gly Met Asp Pro Trp Gly
                100                 105                 110

Pro Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
450
```

<210> SEQ ID NO 180
<211> LENGTH: 448
<212> TYPE: PRT
<213> ORGANISM: Artificial Sequence
<220> FEATURE:
<223> OTHER INFORMATION: 13B4HC

<400> SEQUENCE: 180

Gln Val Gln Leu Gln Glu Ser Gly Pro Gly Leu Val Lys Pro Ser Gly
1               5                   10                  15

Thr Leu Ser Leu Asn Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Gly Gly Thr Thr Asn Tyr Asn Pro Ser Leu
    50                  55                  60

Lys Gly Arg Val Thr Met Ser Val Asp Lys Thr Lys Asn Gln Phe Ser
65                  70                  75                  80

Leu Arg Leu Ser Ser Val Thr Ala Val Asp Thr Ala Val Tyr Tyr Cys
                85                  90                  95

Ala Arg Trp Gln Leu Val Gly Gly Leu Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

```
Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 181
<211> LENGTH: 453
<212> TYPE: PRT
<213> ORGANISM: Artificial Sequence
<220> FEATURE:
<223> OTHER INFORMATION: 13F7HC

<400> SEQUENCE: 181

Gln Val Gln Leu Gln Glu Trp Gly Ala Gly Leu Leu Lys Pro Ser Glu
1               5                   10                  15

Thr Leu Ser Leu Thr Cys Ala Ile Asn Ala Glu Ser Phe Asn Gly Tyr
            20                  25                  30

Ser Trp Thr Trp Ile Arg Gln Thr Pro Gly Lys Gly Leu Glu Trp Ile
        35                  40                  45

Gly Glu Ile Ser His Phe Gly Ser Ala Asn Tyr Asn Pro Ser Leu Lys
    50                  55                  60

Ser Arg Ala Thr Ile Ser Ala Asp Lys Ser Lys Asn Gln Phe Ser Leu
65                  70                  75                  80

Lys Leu Thr Ser Val Thr Ala Val Asp Thr Ala Val Tyr Tyr Cys Ala
                85                  90                  95

Arg Ala Leu Arg Gly Thr Tyr Ser Arg Phe Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
    450

<210> SEQ ID NO 182
<211> LENGTH: 450
<212> TYPE: PRT
<213> ORGANISM: Artificial Sequence
<220> FEATURE:
<223> OTHER INFORMATION: 15A9HC

<400> SEQUENCE: 182

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Pro Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Asn Leu Lys Ser Val Thr Ala Val Asp Thr Ala Val Tyr Tyr Cys Ala
                85                  90                  95

Arg Val Asn Pro Phe Gly Tyr Tyr Tyr Ala Met Asp Val Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 183
<211> LENGTH: 446
<212> TYPE: PRT
<213> ORGANISM: Artificial Sequence
<220> FEATURE:
<223> OTHER INFORMATION: P1-A03HC

<400> SEQUENCE: 183

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asp Tyr
                20                  25                  30

Met Ser Trp Val Arg Gln Ala Pro Gly Glu Gly Leu Glu Trp Ile Gly
            35                  40                  45

Ile Ile Tyr Pro Ser Thr Thr Tyr Tyr Ala Ser Trp Ala Lys Gly
    50                  55                  60

Arg Phe Thr Ile Ser Lys Thr Ser Ser Thr Val Glu Leu Lys Met
65                  70                  75                  80

Thr Ser Leu Thr Thr Glu Asp Thr Ala Thr Tyr Phe Cys Ala Arg Gly
                85                  90                  95
```

Ser Asn Trp Ser Ser Gly Met Asn Leu Trp Gly Pro Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 184
<211> LENGTH: 443
<212> TYPE: PRT
<213> ORGANISM: Artificial Sequence
<220> FEATURE:
<223> OTHER INFORMATION: P1-A08HC

<400> SEQUENCE: 184

Gln Ser Leu Glu Glu Ser Gly Gly Arg Leu Val Thr Pro Gly Thr Pro
1               5                   10                  15

```
Leu Thr Leu Thr Cys Thr Ala Ser Gly Phe Ser Leu Ser Thr Tyr Tyr
            20                  25                  30

Met Ser Trp Val Arg Gln Ala Pro Gly Lys Gly Leu Glu Trp Ile Gly
            35                  40                  45

Ile Val Tyr Pro Ser Gly Thr Thr Tyr Tyr Ala Asn Trp Ala Lys Gly
50                  55                  60

Arg Phe Thr Ile Ser Thr Ala Ser Thr Thr Val Asp Leu Met Ile Thr
65                  70                  75                  80

Ser Pro Thr Thr Glu Asp Thr Ala Thr Tyr Phe Cys Ala Arg Gly Asp
                85                  90                  95

Ser Phe Gly Tyr Gly Leu Trp Gly Pro Gly Thr Leu Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Lys Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430
```

Thr Gln Lys Ser Leu Ser Leu Ser Pro Gly Lys
            435                 440

<210> SEQ ID NO 185
<211> LENGTH: 452
<212> TYPE: PRT
<213> ORGANISM: Artificial Sequence
<220> FEATURE:
<223> OTHER INFORMATION: P1-F02HC

<400> SEQUENCE: 185

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Tyr Tyr
            20                  25                  30

Met Gly Trp Val Arg Gln Ala Pro Gly Glu Gly Leu Glu Trp Ile Gly
        35                  40                  45

Ile Ile Tyr Ala Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Ala Arg Ile Asp
                85                  90                  95

Ile Gly Val Gly Asp Tyr Gly Trp Ala Tyr Asp Arg Leu Asp Leu Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

```
Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 186
<211> LENGTH: 451
<212> TYPE: PRT
<213> ORGANISM: Artificial Sequence
<220> FEATURE:
<223> OTHER INFORMATION: P2-A01HC

<400> SEQUENCE: 186

Gln Glu Gln Leu Val Glu Ser Gly Gly Arg Leu Val Thr Pro Gly Thr
1               5                   10                  15

Pro Leu Thr Leu Ser Cys Thr Ala Ser Gly Phe Phe Leu Ser Gly Tyr
            20                  25                  30

Tyr Met Ser Trp Val Arg Gln Ala Pro Gly Lys Gly Leu Glu Trp Ile
        35                  40                  45

Gly Ile Ile Tyr Pro Ser Gly Ser Thr Asp Tyr Ala Ser Trp Ala Lys
    50                  55                  60

Gly Arg Phe Thr Ile Ser Lys Thr Ser Thr Thr Val Asp Leu Lys Ile
65                  70                  75                  80

Thr Thr Pro Thr Thr Glu Asp Thr Ala Thr Tyr Phe Cys Ala Arg Val
                85                  90                  95

Ala Gly Tyr Val Gly Tyr Gly Tyr Glu Thr Phe Phe Asp Ile Trp Gly
            100                 105                 110

Pro Gly Thr Leu Val Thr Val Ser Leu Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 187
<211> LENGTH: 446
<212> TYPE: PRT
<213> ORGANISM: Artificial Sequence
<220> FEATURE:
<223> OTHER INFORMATION: P2-A03HC

<400> SEQUENCE: 187

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Asp
            20                  25                  30

Met Ser Trp Val Arg Gln Ala Pro Gly Lys Gly Leu Glu Tyr Ile Gly
            35                  40                  45

Phe Met Asp Thr Asp Gly Ser Ala Tyr Tyr Ala Thr Trp Ala Lys Gly
    50                  55                  60

Arg Phe Thr Ile Ser Arg Thr Ser Thr Thr Val Asp Leu Lys Met Thr
65                  70                  75                  80

Ser Pro Thr Thr Glu Asp Thr Ala Thr Tyr Phe Cys Ala Arg Arg Gly
                85                  90                  95

Ser Ser Tyr Tyr Gly Gly Ile Asp Ile Trp Gly Pro Gly Thr Pro Val
            100                 105                 110

Thr Val Ser Leu Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 188
<211> LENGTH: 443
<212> TYPE: PRT
<213> ORGANISM: Artificial Sequence
<220> FEATURE:
<223> OTHER INFORMATION: P2-F07HC

<400> SEQUENCE: 188

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
                20                  25                  30

Met Asn Trp Val Arg Gln Ala Pro Gly Lys Gly Leu Glu Trp Ile Gly
            35                  40                  45

Ile Ile Tyr Pro Ser Gly Thr Thr Tyr Tyr Ala Gly Trp Ala Lys Gly
        50                  55                  60

Arg Phe Thr Ile Ser Lys Thr Ser Thr Thr Val Asp Leu Lys Ile Thr
65                  70                  75                  80
```

```
Ser Pro Thr Ser Glu Asp Thr Ala Thr Tyr Phe Cys Ala Arg Thr Val
                85                  90                  95

Ser Gly Tyr Phe Asp Ile Trp Gly Pro Gly Thr Leu Val Thr Val Ser
            100                 105                 110

Leu Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
                180                 185                 190

Thr Tyr Ile Cys Asn Val Asn His Lys Pro Ser Asn Thr Lys Val Asp
                195                 200                 205

Lys Lys Val Glu Pro Lys Ser Cys Asp Lys Thr His Thr Cys Pro Pro
            210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
                260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 189
<211> LENGTH: 444
<212> TYPE: PRT
<213> ORGANISM: Artificial Sequence
<220> FEATURE:
<223> OTHER INFORMATION: P2-F11HC

<400> SEQUENCE: 189
```

-continued

```
Gln Glu Gln Leu Val Glu Ser Gly Gly Arg Leu Val Thr Pro Gly Thr
1               5                   10                  15

Thr Leu Thr Leu Thr Cys Thr Val Ser Gly Phe Ser Leu Ser Ser Tyr
            20                  25                  30

Gly Val Ser Trp Val Arg Gln Ala Pro Gly Lys Gly Leu Glu Trp Ile
        35                  40                  45

Gly Tyr Ile Ala Asn Asn Tyr Asn Pro His Tyr Ala Ser Trp Ala Lys
    50                  55                  60

Gly Arg Phe Thr Ile Ser Lys Thr Ser Ser Thr Val Asp Leu Lys
65                  70                  75                  80

Met Thr Ser Leu Thr Thr Glu Asp Thr Ala Thr Tyr Phe Cys Ala Arg
                85                  90                  95

Asp Asn Tyr Gly Met Asp Pro Trp Gly Pro Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
```

```
                    420             425             430
Tyr Thr Gln Lys Ser Leu Ser Leu Ser Pro Gly Lys
        435                 440

<210> SEQ ID NO 190
<211> LENGTH: 217
<212> TYPE: PRT
<213> ORGANISM: Artificial Sequence
<220> FEATURE:
<223> OTHER INFORMATION: P2-C12LC

<400> SEQUENCE: 190

Glu Leu Asp Met Thr Gln Thr Pro Ser Ser Val Ser Ala Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Pro Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Gln Gly Tyr Ser Ser Thr Asn
                85                  90                  95

Val Trp Asn Ala Phe Gly Gly Gly Thr Asn Val Glu Ile Lys Arg Ser
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 191
<211> LENGTH: 213
<212> TYPE: PRT
<213> ORGANISM: Artificial Sequence
<220> FEATURE:
<223> OTHER INFORMATION: 13B4LC

<400> SEQUENCE: 191

Ser Tyr Glu Leu Thr Gln Pro Leu Ser Val Ser Val Ser Pro Gly Gln
1               5                   10                  15

Thr Ala Ser Ile Thr Cys Ser Gly Asp Lys Leu Gly Asn Val Tyr Ala
            20                  25                  30

Ser Trp Tyr Gln Gln Lys Pro Gly Gln Ser Pro Thr Leu Val Ile Tyr
        35                  40                  45

Gln Asp Asn Lys Arg Pro Ser Gly Ile Pro Glu Arg Phe Ser Gly Ser
    50                  55                  60
```

```
Asn Ser Gly Lys Thr Ala Thr Leu Thr Ile Ser Gly Thr Gln Ala Leu
 65                  70                  75                  80

Asp Glu Ala Asp Tyr Tyr Cys Gln Ala Trp Asp Ser Ser Thr Ala Val
                 85                  90                  95

Phe Gly Gly Gly Thr Lys Leu Thr Val Leu Arg Ser Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 192
<211> LENGTH: 219
<212> TYPE: PRT
<213> ORGANISM: Artificial Sequence
<220> FEATURE:
<223> OTHER INFORMATION: 13F7LC

<400> SEQUENCE: 192

Asp Ile Val Met Thr Gln Thr Pro Leu Ser Leu Pro Val Ala Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Val Gln Lys Pro Gly Gln Pro
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Met Gln Ala
                 85                 90                  95

Arg Gln Thr Pro Leu Thr Phe Gly Gly Gly Thr Lys Val Glu Ile Lys
            100                 105                 110

Arg Ser Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

```
Pro Val Thr Lys Ser Phe Asn Arg Gly Glu Cys
    210                 215
```

<210> SEQ ID NO 193
<211> LENGTH: 214
<212> TYPE: PRT
<213> ORGANISM: Artificial Sequence
<220> FEATURE:
<223> OTHER INFORMATION: 15A9LC

<400> SEQUENCE: 193

```
Asp Ile Gln Met Thr Gln Ser Pro Ser Ser Leu Ser Ala Ser Val Gly
1               5                   10                  15

Asp Arg Ile Thr Ile Ser Cys Arg Ala Ser Gln Ser Ile Ser Thr Ser
            20                  25                  30

Leu Asn Trp Tyr Gln Gln Thr Pro Gly Lys Ala Pro Arg Leu Leu Ile
        35                  40                  45

Tyr Gly Ala Ser Thr Leu Gln Ser Gly Val Pro Ser Arg Phe Ser Gly
    50                  55                  60

Gly Gly Ser Gly Thr Asp Phe Ser Leu Thr Ile Thr Ser Leu Gln Pro
65                  70                  75                  80

Glu Asp Phe Ala Thr Tyr Tyr Cys Gln Glu Ser Ala Ser Ile Pro Arg
                85                  90                  95

Thr Phe Gly Gln Gly Thr Lys Leu Asp Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 194
<211> LENGTH: 217
<212> TYPE: PRT
<213> ORGANISM: Artificial Sequence
<220> FEATURE:
<223> OTHER INFORMATION: P1-A03LC

<400> SEQUENCE: 194

```
Glu Leu Val Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Glu Lys Pro Pro Thr Leu Leu Ile
        35                  40                  45

Ser Gly Ala Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80
```

Glu Asp Ala Ala Thr Tyr Tyr Cys Leu Gly Gly Tyr Ser Tyr Ser Ser
                85                  90                  95

Thr Gly Leu Thr Phe Gly Ala Gly Thr Asn Val Glu Ile Lys Arg Ser
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 195
<211> LENGTH: 217
<212> TYPE: PRT
<213> ORGANISM: Artificial Sequence
<220> FEATURE:
<223> OTHER INFORMATION: P1-A08LC

<400> SEQUENCE: 195

Glu Leu Val Leu Thr Gln Ser Pro Ser Val Gln Val Asn Leu Gly Gln
1               5                   10                  15

Thr Val Ser Leu Thr Cys Thr Ala Asp Thr Leu Ser Arg Ser Tyr Ala
            20                  25                  30

Ser Trp Tyr Gln Gln Lys Pro Gly Gln Ala Pro Val Leu Leu Ile Tyr
        35                  40                  45

Arg Asp Thr Ser Arg Pro Ser Gly Val Pro Asp Arg Phe Ser Gly Ser
    50                  55                  60

Ser Ser Gly Asn Thr Ala Thr Leu Thr Ile Ser Gly Ala Gln Ala Gly
65                  70                  75                  80

Asp Glu Ala Asp Tyr Tyr Cys Ala Thr Ser Asp Gly Ser Gly Ser Asn
                85                  90                  95

Tyr Gln Tyr Val Phe Gly Gly Gly Thr Gln Leu Thr Val Thr Arg Ser
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 196
<211> LENGTH: 215
<212> TYPE: PRT
<213> ORGANISM: Artificial Sequence
<220> FEATURE:
<223> OTHER INFORMATION: P1-F02LC

<400> SEQUENCE: 196

Glu Leu Asp Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Thr Leu Leu Ile
        35                  40                  45

Tyr Gly Ala Ser Asn Leu Glu Ser Gly Val Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Tyr Ser Tyr Ser Ser
                85                  90                  95

Ile Thr Phe Gly Ala Gly Thr Asn Val Glu Ile Lys Arg Ser Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 197
<211> LENGTH: 219
<212> TYPE: PRT
<213> ORGANISM: Artificial Sequence
<220> FEATURE:
<223> OTHER INFORMATION: P2-A01LC

<400> SEQUENCE: 197

Glu Leu Val Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Thr Leu Leu Ile
        35                  40                  45

Tyr Gly Ala Ser Asn Leu Glu Ser Gly Val Pro Arg Phe Ser Gly
    50                  55                  60

Ser Gly Ser Gly Ser Asp Tyr Thr Leu Thr Ile Gly Gly Val Gln Ala
65                  70                  75                  80

Glu Asp Ala Ala Thr Tyr Tyr Cys Leu Gly Gly Val Thr Tyr Ser Ser

```
                    85                  90                  95
Thr Gly Thr His Leu Thr Phe Gly Ala Gly Thr Asn Val Glu Ile Lys
                100                 105                 110

Arg Ser Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
                130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215
```

<210> SEQ ID NO 198
<211> LENGTH: 219
<212> TYPE: PRT
<213> ORGANISM: Artificial Sequence
<220> FEATURE:
<223> OTHER INFORMATION: P2-A03LC

<400> SEQUENCE: 198

```
Glu Leu Asp Leu Thr Gln Thr Pro Ala Ser Val Ser Glu Pro Val Gly
1               5                   10                  15

Gly Thr Val Thr Ile Lys Cys Gln Ala Ser Gln Ser Ile Gly Gly Asn
                20                  25                  30

Leu Ala Trp Tyr Gln Gln Lys Pro Gly Gln Pro Pro Lys Leu Leu Ile
            35                  40                  45

Tyr Arg Ala Ser Thr Leu Ala Ser Gly Val Pro Ser Arg Phe Lys Gly
50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Ser Pro Ala Tyr Asp Pro Ala
                85                  90                  95

Ala Tyr Val Gly Asn Ala Phe Gly Gly Thr Glu Leu Glu Ile Leu
                100                 105                 110

Arg Ser Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
                130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215
```

<210> SEQ ID NO 199
<211> LENGTH: 214
<212> TYPE: PRT
<213> ORGANISM: Artificial Sequence
<220> FEATURE:
<223> OTHER INFORMATION: P2-F07LC

<400> SEQUENCE: 199

```
Glu Leu Asp Leu Thr Gln Thr Pro Pro Ser Leu Ser Ala Ser Val Gly
1               5                   10                  15

Gly Thr Val Thr Ile Asn Cys Leu Ala Ser Glu Asp Ile Tyr Ser Ala
            20                  25                  30

Leu Ala Trp Tyr Gln Gln Lys Pro Gly Lys Pro Thr Leu Leu Ile
        35                  40                  45

Ser Gly Thr Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Phe Cys Gln Gly Tyr Ser Ser Tyr Pro Leu
                85                  90                  95

Thr Phe Gly Ala Gly Thr Asn Val Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 200
<211> LENGTH: 220
<212> TYPE: PRT
<213> ORGANISM: Artificial Sequence
<220> FEATURE:
<223> OTHER INFORMATION: P2-F11LC

<400> SEQUENCE: 200

```
Glu Leu Asp Leu Thr Gln Thr Pro Ser Ser Val Ser Ala Ala Val Gly
1               5                   10                  15

Gly Thr Val Thr Ile Asn Cys Gln Ala Ser Gln Ser Val Tyr Asn Asn
            20                  25                  30

Lys Asn Leu Ala Trp Tyr Gln Gln Lys Pro Gly Gln Pro Pro Lys Leu
        35                  40                  45

Leu Ile Tyr Ala Ala Ser Thr Leu Ala Ser Gly Val Ser Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Gln Gly Glu Phe Ser Cys
                85                  90                  95
```

Ser Ser Ala Asp Cys Asn Ala Phe Gly Gly Thr Glu Leu Glu Ile
            100                 105                 110

Leu Arg Ser Val Ala Ala Pro Ser Val Phe Ile Phe Pro Pro Ser Asp
115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 201
<211> LENGTH: 251
<212> TYPE: PRT
<213> ORGANISM: Artificial Sequence
<220> FEATURE:
<223> OTHER INFORMATION: 3-2 scFv

<400> SEQUENCE: 201

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
            35                  40                  45

Tyr Glu Ser Asn Lys Arg Pro Ser Asp Ile Pro Ser Arg Phe Ser Gly
50                  55                  60

Ser Thr Ser Gly Ser Thr Ala Thr Leu Thr Ile Thr Gly Val Gln Ala
65                  70                  75                  80

Asp Asp Glu Ala Ile Tyr Tyr Cys Gly Ser Trp Asp Ser Ser Asn Gly
            85                  90                  95

Gly Ile Phe Gly Ala Gly Thr Thr Leu Thr Val Leu Ser Gly Gly Gly
            100                 105                 110

Gly Ser Ser Gly Gly Gly Gly Ser Ala Val Thr Leu Asp Glu Ser Gly
            115                 120                 125

Gly Gly Leu Gln Thr Pro Gly Gly Ala Leu Ser Leu Val Cys Lys Ala
            130                 135                 140

Ser Gly Phe Thr Phe Ser Ser Phe Asn Met Phe Trp Val Arg Gln Ala
145                 150                 155                 160

Pro Gly Lys Gly Leu Glu Tyr Val Ala Gln Ile Ser Ser Ser Gly Ser
            165                 170                 175

Ser Thr Asn Tyr Ala Pro Ala Val Arg Gly Arg Ala Thr Ile Ser Arg
            180                 185                 190

Asp Asn Gly Gln Ser Thr Val Arg Leu Gln Leu Asn Asn Pro Gly Ala
            195                 200                 205

Glu Asp Thr Gly Thr Tyr Tyr Cys Ala Lys Ser Ser Tyr Asp Cys Pro
            210                 215                 220

Tyr Gly His Cys Ser Ser Gly Val Asp Ser Ala Gly Glu Ile Asp Ala
225                 230                 235                 240

Trp Gly His Gly Thr Glu Val Ile Val Ser Ser
                245                 250

<210> SEQ ID NO 202
<211> LENGTH: 244
<212> TYPE: PRT
<213> ORGANISM: Artificial Sequence
<220> FEATURE:
<223> OTHER INFORMATION: 1-65 scFv

<400> SEQUENCE: 202

Ala Leu Thr Gln Pro Ser Ser Val Ser Ala Asn Pro Gly Glu Thr Val
1               5                   10                  15

Lys Ile Thr Cys Ser Gly Gly Ser Gly Tyr Gly Tyr Gly Trp
            20                  25                  30

Tyr Gln Gln Lys Ser Pro Ser Ala Pro Leu Thr Val Ile Tyr Trp
                35                  40                  45

Asn Asp Lys Arg Pro Ser Asp Ile Pro Ser Arg Phe Ser Gly Ser Lys
        50                  55                  60

Ser Gly Ser Thr His Thr Leu Thr Ile Thr Gly Val Gln Ala Glu Asp
65                  70                  75                  80

Glu Ala Val Tyr Phe Cys Gly Asn Asp Asp Tyr Ser Ser Asp Ser Gly
                85                  90                  95

Tyr Val Gly Val Phe Gly Ala Gly Thr Thr Leu Thr Val Leu Ser Gly
                100                 105                 110

Gly Gly Gly Ser Ser Gly Gly Gly Ser Ala Val Thr Leu Asp Glu
            115                 120                 125

Ser Gly Gly Gly Leu Gln Thr Pro Gly Gly Ala Leu Ser Leu Val Cys
        130                 135                 140

Lys Ala Ser Gly Phe Thr Phe Ser Ser Tyr Gln Met Gly Trp Val Arg
145                 150                 155                 160

Gln Ala Pro Gly Lys Gly Leu Glu Trp Val Gly Val Ile Asn Lys Ser
                165                 170                 175

Gly Ser Asp Thr Ser Tyr Gly Ser Ala Val Lys Gly Arg Ala Thr Ile
            180                 185                 190

Ser Arg Asp Asn Gly Gln Ser Thr Val Arg Leu Gln Leu Asn Asn Leu
        195                 200                 205

Arg Ala Glu Asp Thr Gly Thr Tyr Phe Cys Ala Lys Gly Ser Ala Ser
    210                 215                 220

Tyr Ile Thr Ala Ala Thr Ile Asp Ala Trp Gly His Gly Thr Glu Val
225                 230                 235                 240

Ile Val Ser Ser

<210> SEQ ID NO 203
<211> LENGTH: 245
<212> TYPE: PRT
<213> ORGANISM: Artificial Sequence
<220> FEATURE:
<223> OTHER INFORMATION: 2-13 scFv

<400> SEQUENCE: 203

Ala Leu Thr Gln Pro Ser Ser Val Ser Ala Asn Pro Gly Glu Thr Val
1               5                   10                  15

Lys Ile Thr Cys Ser Gly Gly Ser Tyr Ser Tyr Gly Trp Phe Gln Gln
            20                  25                  30

Lys Ser Pro Gly Ser Ala Leu Val Thr Val Ile Tyr Trp Asp Glu
        35                  40                  45

```
Arg Pro Ser Asp Ile Pro Ser Arg Phe Ser Gly Ala Leu Ser Gly Ser
    50                  55                  60

Thr Asn Thr Leu Thr Ile Thr Gly Val Gln Ala Asp Asp Glu Ala Val
65                  70                  75                  80

Tyr Phe Cys Gly Thr Glu Asp Ile Ser Gly Thr Ala Gly Val Phe Gly
                85                  90                  95

Ala Gly Thr Thr Leu Thr Val Leu Ser Gly Gly Gly Ser Ser Gly
            100                 105                 110

Gly Gly Gly Ser Ala Val Thr Leu Asp Glu Ser Gly Gly Leu Gln
            115                 120                 125

Thr Pro Gly Gly Ala Leu Ser Leu Val Cys Lys Ala Ser Gly Phe Thr
130                 135                 140

Phe Ser Ser His Gly Met Phe Trp Val Arg Gln Thr Pro Gly Lys Gly
145                 150                 155                 160

Leu Glu Tyr Val Ala Glu Ile Thr Asn Asp Gly Ser Gly Thr Asn Tyr
                165                 170                 175

Gly Ser Ala Val Lys Gly Arg Ala Thr Ile Ser Arg Asp Asn Gly Gln
            180                 185                 190

Ser Thr Val Arg Leu Gln Leu Asn Asn Leu Arg Ala Glu Asp Thr Gly
            195                 200                 205

Thr Tyr Phe Cys Ala Arg Ser Thr Tyr Glu Cys Pro Gly Gly Phe Ser
210                 215                 220

Cys Trp Gly Asp Thr Gly Gln Ile Asp Ala Trp Gly His Gly Thr Glu
225                 230                 235                 240

Val Ile Val Ser Ser
            245

<210> SEQ ID NO 204
<211> LENGTH: 753
<212> TYPE: DNA
<213> ORGANISM: Artificial Sequence
<220> FEATURE:
<223> OTHER INFORMATION: 3-2 scFv

<400> SEQUENCE: 204
gcattgactc agccctcttc cgtgagtgct aatccaggtg aaacagtaaa ataacttgc      60 agtgggggag gtcttacgc aggatcttat tattatggat ggtaccagca aaaagcccct    120
gggtctgcac cagtcactct gatatacgag agcaataaac gccctccga catccccagc    180 cgcttttctg gttctacctc tggcagtact gctaccttga ctattaccgg ggtccaggct    240
gacgacgaag ccattattta ttgtggaagt tgggattcaa gcaacggggg tatattcggc    300
gctggtacta cccttaccgt gctgtccggt ggggtggga gcagtggagg tggaggaagt    360
gctgtaactc ttgatgaaag cggggagggg ctgcaaaccc ctggcggggc cttgtccttg    420
gtttgtaagg cttccggatt tactttctca agttttaata tgttttgggt gcgacaggcc    480
ccagggaaag ggttggaata tgttgcacag atctccagct caggttcatc accaattat    540 gcacctgccg tccgagggag ggctacaatt tctagggaca cgggcagtc aactgtacgg    600 ttgcagctta caatcccgg agcagaagat acaggtacct attactgtgc taagagttca    660
tacgactgtc cctatggtca ctgttcctca ggtgttgact ccgcagggga gatagatgct    720
tgggggcatg ggaccgaagt gattgtgtca tct                                 753

<210> SEQ ID NO 205
<211> LENGTH: 732
<212> TYPE: DNA
```

```
<213> ORGANISM: Artificial Sequence
<220> FEATURE:
<223> OTHER INFORMATION: 1-65 scFv

<400> SEQUENCE: 205
gccttgacac aaccctcatc agtatctgct aaccccggcg aaacagttaa ataacatgc      60
tcaggaggtg gttcatctgg ctatggatat gggtggtatc aacagaaatc accaagttcc    120
gccccttga ccgtgattta ttggaatgat aagcgcccct cagacattcc cagtcgcttc     180
tcaggcagta atcaggctc aacccatact cttactatca ccggtgtcca agcagaagat     240
gaagccgtgt atttttgtgg gaatgatgac tattccagcg attctggcta tgtaggagtg    300
ttcggtgccg gtactaccct cacagtattg agtggtggtg gcggaagttc aggtggtggt    360
ggaagcgctg tcactttgga tgaatcaggt ggaggcctcc aaaccccagg tggcgcactc    420
agtctcgtat gtaaagcctc tggtttcact ttcagctcat atcaaatggg atgggtgcgg   480
caggctcccg gcaaggggtt ggagtgggtc ggtgttatca acaagagcgg ctctgatact    540
agctatggaa gcgcagtcaa ggggagagct actataagca gggataatgg caaagtacc    600
gtcaggcttc aattgaacaa tctcagggct gaggatacag gaacctactt ctgcgccaaa    660
gggtcagcat cttatatcac agcagctacc attgacgcat ggggacatgg cacagaggtc    720
attgtttcca gt                                                         732

<210> SEQ ID NO 206
<211> LENGTH: 735
<212> TYPE: DNA
<213> ORGANISM: Artificial Sequence
<220> FEATURE:
<223> OTHER INFORMATION: 2-13 scFv

<400> SEQUENCE: 206
gctctgacac aaccaagctc tgtcagtgca aatccaggag agaccgttaa atcacttgc      60
agcggaggct cttattccta cggatggttc agcaaaaaaa gtcctggttc agccctcgtt    120
actgtcatct actgggacga cgagcgccct agcgatattc ctagtagatt ctcaggggct    180
cttagcggct ccactaatac tttgaccatt actggagtac aggctgatga cgaagcagtt    240
tacttctgtg gcaccgaaga tataagcgga actgcagggg tatttggggc tggtacaaca    300
ctcacagtgc tctccggggg gggcgggagc tcaggaggcg gcggatcagc tgtaaccctg    360
gacgaatctg gtgggggct tcaaacaccc ggaggagccc tctccctcgt atgcaaagct    420
tcaggattca ccttctcttc acatggaatg ttctgggtaa ggcagacacc tggcaaaggg    480
cttgaatatg tagctgagat cactaatgac ggtagcggta caaactatgg gtctgctgtg    540
aaaggccggg ctacaataag tcgagacaat ggacaaagta ccgttagact ccagctcaac    600
aacctgcgag ctgaggacac aggcacttac ttttgtgcac gcagtactta cgagtgtcca    660
ggtggatttt catgttgggg agataccgga cagatcgacg cttgggggca cggcaccgag    720
gtcattgtaa gtagc                                                      735

<210> SEQ ID NO 207
<211> LENGTH: 12
<212> TYPE: PRT
<213> ORGANISM: Artificial Sequence
<220> FEATURE:
<223> OTHER INFORMATION: Linker

<400> SEQUENCE: 207

Ser Gly Gly Gly Gly Ser Ser Gly Gly Gly Gly Ser
```

```
1               5                   10

<210> SEQ ID NO 208
<211> LENGTH: 10
<212> TYPE: PRT
<213> ORGANISM: Artificial sequence
<220> FEATURE:
<223> OTHER INFORMATION: SS01-13-s5 Ab VH-CDR2

<400> SEQUENCE: 208

Ala Ile Asn Lys Ser Gly Ser Asp Thr Ser
1               5                   10

<210> SEQ ID NO 209
<211> LENGTH: 10
<212> TYPE: PRT
<213> ORGANISM: Artificial sequence
<220> FEATURE:
<223> OTHER INFORMATION: S5-2.GKNG Ab VH-CDR2

<400> SEQUENCE: 209

Ala Ile Asn Lys Gly Gly Ser Asp Thr Ser
1               5                   10

<210> SEQ ID NO 210
<211> LENGTH: 10
<212> TYPE: PRT
<213> ORGANISM: Artificial sequence
<220> FEATURE:
<223> OTHER INFORMATION: 1-7A-IT Ab VH-CDR1

<400> SEQUENCE: 210

Gly Phe Thr Phe Ser Ser Phe Asn Met Phe
1               5                   10

<210> SEQ ID NO 211
<211> LENGTH: 17
<212> TYPE: PRT
<213> ORGANISM: Artificial sequence
<220> FEATURE:
<223> OTHER INFORMATION: 1-7A-IT Ab VH-CDR2

<400> SEQUENCE: 211

Gln Ile Ser Ser Ser Gly Ser Ser Thr Asn Tyr Ala Pro Ala Val Lys
1               5                   10                  15

Gly

<210> SEQ ID NO 212
<211> LENGTH: 10
<212> TYPE: PRT
<213> ORGANISM: Artificial sequence
<220> FEATURE:
<223> OTHER INFORMATION: Low-PI; 1-30; 1-17; 1-32; 4-11; 6-10 Abs
      VH-CDR1

<400> SEQUENCE: 212

Gly Phe Asp Phe Glu Ser Phe Asn Met Phe
1               5                   10

<210> SEQ ID NO 213
<211> LENGTH: 17
<212> TYPE: PRT
<213> ORGANISM: Artificial sequence
<220> FEATURE:
<223> OTHER INFORMATION: Low-PI; 1-30; 1-17; 1-32; 4-11; 6-10 Abs
      VH-CDR2
```

```
<400> SEQUENCE: 213

Gln Ile Ser Ser Glu Glu Asp Glu Asn Tyr Ala Pro Ala Val Lys
1               5                   10                  15

Gly

<210> SEQ ID NO 214
<211> LENGTH: 10
<212> TYPE: PRT
<213> ORGANISM: Artificial sequence
<220> FEATURE:
<223> OTHER INFORMATION: 2-13D Ab VH-CDR1

<400> SEQUENCE: 214

Gly Phe Thr Phe Ser Ser His Gly Met Phe
1               5                   10

<210> SEQ ID NO 215
<211> LENGTH: 10
<212> TYPE: PRT
<213> ORGANISM: Artificial sequence
<220> FEATURE:
<223> OTHER INFORMATION: 2-13D-37; 2-13D-37-1.5W-41; 2-13D-37-3W-16
      VH-CDR1

<400> SEQUENCE: 215

Gly Phe Asp Phe Ser Ser His Gly Met Phe
1               5                   10

<210> SEQ ID NO 216
<211> LENGTH: 20
<212> TYPE: PRT
<213> ORGANISM: Artificial sequence
<220> FEATURE:
<223> OTHER INFORMATION: 2-13D-37-1.5W-41 VH-CDR3

<400> SEQUENCE: 216

Ser Ser Tyr Val Cys Pro Gly Gly Phe Ser Cys Trp Gly Asp Thr Gly
1               5                   10                  15

Gln Ile Asp Ala
            20

<210> SEQ ID NO 217
<211> LENGTH: 20
<212> TYPE: PRT
<213> ORGANISM: Artificial sequence
<220> FEATURE:
<223> OTHER INFORMATION: 2-13D-37-3W-16 VH-CDR3

<400> SEQUENCE: 217

Ser Asn Tyr Ala Cys Pro Gly Gly Phe Ser Cys Trp Gly Asp Thr Gly
1               5                   10                  15

Gln Ile Asp Ala
            20

<210> SEQ ID NO 218
<211> LENGTH: 11
<212> TYPE: PRT
<213> ORGANISM: Artificial sequence
<220> FEATURE:
<223> OTHER INFORMATION: ss01-13; SS01-13-S5; S5-2.GKNG Abs VL-CDR1

<400> SEQUENCE: 218

Ser Gly Gly Ala Ser Ser Gly Tyr Gly Tyr Gly
1               5                   10
```

```
<210> SEQ ID NO 219
<211> LENGTH: 7
<212> TYPE: PRT
<213> ORGANISM: Artificial sequence
<220> FEATURE:
<223> OTHER INFORMATION: ss01-13 Ab VL-CDR2

<400> SEQUENCE: 219

Lys Asp Asp Glu Arg Pro Ser
1               5

<210> SEQ ID NO 220
<211> LENGTH: 7
<212> TYPE: PRT
<213> ORGANISM: Artificial sequence
<220> FEATURE:
<223> OTHER INFORMATION: ss01-13-S5; S5-2.GKNG Ab VL-CDR2

<400> SEQUENCE: 220

Lys Asp Ser Glu Arg Pro Ser
1               5

<210> SEQ ID NO 221
<211> LENGTH: 7
<212> TYPE: PRT
<213> ORGANISM: Artificial sequence
<220> FEATURE:
<223> OTHER INFORMATION: 1-7A-IT Ab VL-CDR2

<400> SEQUENCE: 221

Glu Asn Asn Lys Arg Pro Ser
1               5

<210> SEQ ID NO 222
<211> LENGTH: 13
<212> TYPE: PRT
<213> ORGANISM: Artificial sequence
<220> FEATURE:
<223> OTHER INFORMATION: Low-PI; 1-30 Abs VL-CDR1

<400> SEQUENCE: 222

Ser Gly Gly Gly Ser Glu Glu Glu Gln Tyr Tyr Tyr Gly
1               5                   10

<210> SEQ ID NO 223
<211> LENGTH: 7
<212> TYPE: PRT
<213> ORGANISM: Artificial sequence
<220> FEATURE:
<223> OTHER INFORMATION: Low-PI VL-CDR2

<400> SEQUENCE: 223

Glu Asp Glu Glu Arg Pro Ser
1               5

<210> SEQ ID NO 224
<211> LENGTH: 10
<212> TYPE: PRT
<213> ORGANISM: Artificial sequence
<220> FEATURE:
<223> OTHER INFORMATION: Low-PI; 1-30; 1-17; 1-32 Abs VL-CDR3

<400> SEQUENCE: 224

Gly Ser Trp Asp Ser Glu Asp Glu Asp His
1               5                   10
```

```
<210> SEQ ID NO 225
<211> LENGTH: 7
<212> TYPE: PRT
<213> ORGANISM: Artificial sequence
<220> FEATURE:
<223> OTHER INFORMATION: 1-30; 1-32 Abs VL-CDR2

<400> SEQUENCE: 225

Gln Asp Glu Glu Arg Pro Ser
1               5

<210> SEQ ID NO 226
<211> LENGTH: 7
<212> TYPE: PRT
<213> ORGANISM: Artificial sequence
<220> FEATURE:
<223> OTHER INFORMATION: 1-17 Ab VL-CDR2

<400> SEQUENCE: 226

Glu Asp Glu Gln Arg Pro Ser
1               5

<210> SEQ ID NO 227
<211> LENGTH: 7
<212> TYPE: PRT
<213> ORGANISM: Artificial sequence
<220> FEATURE:
<223> OTHER INFORMATION: 4-11 Ab VL-CDR2

<400> SEQUENCE: 227

Glu Asp His Glu Arg Pro Ser
1               5

<210> SEQ ID NO 228
<211> LENGTH: 10
<212> TYPE: PRT
<213> ORGANISM: Artificial sequence
<220> FEATURE:
<223> OTHER INFORMATION: 4-11 Ab VL-CDR3

<400> SEQUENCE: 228

Gly Ser Trp Asp Ser Ser Asp Glu Asp His
1               5                   10

<210> SEQ ID NO 229
<211> LENGTH: 7
<212> TYPE: PRT
<213> ORGANISM: Artificial sequence
<220> FEATURE:
<223> OTHER INFORMATION: 6-10 Ab VL-CDR2

<400> SEQUENCE: 229

Gln Asp Leu Leu Arg Pro Ser
1               5

<210> SEQ ID NO 230
<211> LENGTH: 10
<212> TYPE: PRT
<213> ORGANISM: Artificial sequence
<220> FEATURE:
<223> OTHER INFORMATION: 6-10 Ab VL-CDR3

<400> SEQUENCE: 230

Gly Ser Trp Asp Ser Leu Ser Ser Ser His
1               5                   10

<210> SEQ ID NO 231
```

```
<211> LENGTH: 8
<212> TYPE: PRT
<213> ORGANISM: Artificial sequence
<220> FEATURE:
<223> OTHER INFORMATION: 2-13D; 2-13D-37; 2-13D-37-1.5W-41; 2-13D-37-3W-
      16 Abs VL-CDR1

<400> SEQUENCE: 231

Ser Gly Gly Val Tyr Ser Tyr Gly
1               5

<210> SEQ ID NO 232
<211> LENGTH: 122
<212> TYPE: PRT
<213> ORGANISM: Artificial sequence
<220> FEATURE:
<223> OTHER INFORMATION: SS01-13 Ab VH

<400> SEQUENCE: 232

Ala Val Thr Leu Asp Glu Ser Gly Gly Gly Leu Gln Thr Pro Gly Gly
1               5                   10                  15

Ala Leu Ser Leu Ser Cys Lys Ala Ser Gly Phe Thr Phe Ser Ser Tyr
            20                  25                  30

Gln Met Gly Trp Val Arg Gln Ala Pro Gly Lys Gly Leu Glu Trp Val
        35                  40                  45

Gly Val Ile Asn Lys Ser Gly Ser Asp Thr Ser Tyr Gly Ser Ala Val
    50                  55                  60

Lys Gly Arg Ala Thr Ile Ser Arg Asp Asn Gly Gln Ser Thr Leu Tyr
65                  70                  75                  80

Leu Gln Met Asn Asn Leu Arg Ala Glu Asp Thr Ala Val Tyr Phe Cys
                85                  90                  95

Ala Lys Gly Ser Ala Ser Tyr Ile Thr Ala Ala Thr Ile Asp Ala Trp
            100                 105                 110

Gly His Gly Thr Glu Val Ile Val Ser Ser
        115                 120

<210> SEQ ID NO 233
<211> LENGTH: 122
<212> TYPE: PRT
<213> ORGANISM: Artificial sequence
<220> FEATURE:
<223> OTHER INFORMATION: SS01-13-s5 Ab VH

<400> SEQUENCE: 233

Ala Val Thr Leu Asp Glu Ser Gly Gly Gly Leu Gln Thr Pro Gly Gly
1               5                   10                  15

Ala Leu Arg Leu Ser Cys Lys Ala Ser Gly Phe Thr Phe Ser Ser Tyr
            20                  25                  30

Gln Met Gly Trp Val Arg Gln Ala Pro Gly Lys Gly Leu Glu Trp Val
        35                  40                  45

Ser Ala Ile Asn Lys Ser Gly Ser Asp Thr Ser Tyr Gly Ser Ala Val
    50                  55                  60

Lys Gly Arg Ala Thr Ile Ser Arg Asp Asn Gly Gln Ser Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ser Ala Ser Tyr Ile Thr Ala Ala Thr Ile Asp Ala Trp
            100                 105                 110

Gly His Gly Thr Glu Val Ile Val Ser Ser
        115                 120
```

```
<210> SEQ ID NO 234
<211> LENGTH: 122
<212> TYPE: PRT
<213> ORGANISM: Artificial sequence
<220> FEATURE:
<223> OTHER INFORMATION: S5-2.GKNG Ab VH

<400> SEQUENCE: 234

Ala Val Thr Leu Asp Glu Ser Gly Gly Gly Leu Gln Thr Pro Gly Gly
1               5                   10                  15

Ala Leu Arg Leu Ser Cys Lys Ala Ser Gly Phe Thr Phe Ser Ser Tyr
            20                  25                  30

Gln Met Gly Trp Val Arg Gln Ala Pro Gly Lys Gly Leu Glu Trp Val
        35                  40                  45

Ser Ala Ile Asn Lys Gly Gly Ser Asp Thr Ser Tyr Gly Ser Ala Val
    50                  55                  60

Lys Gly Arg Ala Thr Ile Ser Arg Asp Asn Gly Gln Ser Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ser Ala Ser Tyr Ile Thr Ala Ala Thr Ile Asp Ala Trp
            100                 105                 110

Gly His Gly Thr Glu Val Ile Val Ser Ser
        115                 120

<210> SEQ ID NO 235
<211> LENGTH: 131
<212> TYPE: PRT
<213> ORGANISM: Artificial sequence
<220> FEATURE:
<223> OTHER INFORMATION: 1-7A-IT Ab VH

<400> SEQUENCE: 235

Ala Val Thr Leu Asp Glu Ser Gly Gly Gly Leu Gln Thr Pro Gly Gly
1               5                   10                  15

Ala Leu Arg Leu Ser Cys Lys Ala Ser Gly Phe Thr Phe Ser Ser Phe
            20                  25                  30

Asn Met Phe Trp Val Arg Gln Ala Pro Gly Lys Gly Leu Glu Tyr Val
        35                  40                  45

Ser Gln Ile Ser Ser Ser Gly Ser Ser Thr Asn Tyr Ala Pro Ala Val
    50                  55                  60

Lys Gly Arg Ala Thr Ile Ser Arg Asp Asn Gly Gln Ser Thr Leu Tyr
65                  70                  75                  80

Leu Gln Met Asn Ser Leu Arg Ala Glu Asp Thr Gly Thr Tyr Tyr Cys
                85                  90                  95

Ala Lys Ser Ser Tyr Asp Cys Pro Tyr Gly His Cys Ser Ser Gly Val
            100                 105                 110

Asp Ser Ala Gly Glu Ile Asp Ala Trp Gly His Gly Thr Glu Val Ile
        115                 120                 125

Val Ser Ser
    130

<210> SEQ ID NO 236
<211> LENGTH: 131
<212> TYPE: PRT
<213> ORGANISM: Artificial sequence
<220> FEATURE:
<223> OTHER INFORMATION: Low-PI; 1-30; 1-17; 1-31; 4-11; 6-10 Abs VH
```

<400> SEQUENCE: 236

```
Ala Val Thr Leu Asp Glu Ser Gly Gly Gly Leu Gln Thr Pro Gly Gly
1               5                   10                  15
Ala Leu Arg Leu Ser Cys Lys Ala Ser Gly Phe Asp Phe Glu Ser Phe
            20                  25                  30
Asn Met Phe Trp Val Arg Gln Ala Pro Gly Lys Gly Leu Glu Tyr Val
        35                  40                  45
Ser Gln Ile Ser Ser Ser Glu Asp Glu Asn Tyr Ala Pro Ala Val
    50                  55                  60
Lys Gly Arg Ala Thr Ile Ser Arg Asp Asn Gly Gln Ser Thr Leu Tyr
65                  70                  75                  80
Leu Gln Met Asn Ser Leu Arg Ala Glu Asp Thr Gly Thr Tyr Tyr Cys
                85                  90                  95
Ala Lys Ser Ser Tyr Asp Cys Pro Tyr Gly His Cys Ser Ser Gly Val
            100                 105                 110
Asp Ser Ala Gly Glu Ile Asp Ala Trp Gly His Gly Thr Glu Val Ile
        115                 120                 125
Val Ser Ser
    130
```

<210> SEQ ID NO 237
<211> LENGTH: 129
<212> TYPE: PRT
<213> ORGANISM: Artificial sequence
<220> FEATURE:
<223> OTHER INFORMATION: 2-13D VH

<400> SEQUENCE: 237

```
Ala Val Thr Leu Asp Glu Ser Gly Gly Gly Leu Gln Thr Pro Gly Gly
1               5                   10                  15
Ala Leu Arg Leu Ser Cys Ser Ala Ser Gly Phe Thr Phe Ser Ser His
            20                  25                  30
Gly Met Phe Trp Val Arg Gln Ala Pro Gly Lys Gly Leu Glu Tyr Val
        35                  40                  45
Ser Glu Ile Thr Asn Asp Gly Ser Gly Thr Asn Tyr Gly Ser Ala Val
    50                  55                  60
Lys Gly Arg Ala Thr Ile Ser Arg Asp Asn Gly Gln Ser Thr Leu Tyr
65                  70                  75                  80
Leu Gln Met Asn Ser Leu Arg Ala Glu Asp Thr Gly Thr Tyr Phe Cys
                85                  90                  95
Ala Arg Ser Thr Tyr Glu Cys Pro Gly Gly Phe Ser Cys Trp Gly Asp
            100                 105                 110
Thr Gly Gln Ile Asp Ala Trp Gly His Gly Thr Glu Val Ile Val Ser
        115                 120                 125
Ser
```

<210> SEQ ID NO 238
<211> LENGTH: 129
<212> TYPE: PRT
<213> ORGANISM: Artificial sequence
<220> FEATURE:
<223> OTHER INFORMATION: 2-13D-37 VH

<400> SEQUENCE: 238

```
Ala Val Thr Leu Asp Glu Ser Gly Gly Gly Leu Gln Thr Pro Gly Gly
1               5                   10                  15
```

```
Ala Leu Arg Leu Ser Cys Ser Ala Ser Gly Phe Asp Phe Ser Ser His
            20                  25                  30

Gly Met Phe Trp Val Arg Gln Ala Pro Gly Lys Gly Leu Glu Tyr Val
        35                  40                  45

Ser Glu Ile Thr Asn Asp Gly Ser Gly Thr Asn Tyr Gly Ser Ala Val
 50                  55                  60

Lys Gly Arg Ala Thr Ile Ser Arg Asp Asn Gly Gln Ser Thr Leu Tyr
 65                  70                  75                  80

Leu Gln Met Asn Ser Leu Arg Ala Glu Asp Thr Gly Thr Tyr Phe Cys
                85                  90                  95

Ala Arg Ser Thr Tyr Glu Cys Pro Gly Gly Phe Ser Cys Trp Gly Asp
            100                 105                 110

Thr Gly Gln Ile Asp Ala Trp Gly His Gly Thr Glu Val Ile Val Ser
        115                 120                 125

Ser
```

<210> SEQ ID NO 239
<211> LENGTH: 129
<212> TYPE: PRT
<213> ORGANISM: Artificial sequence
<220> FEATURE:
<223> OTHER INFORMATION: 2-13D-37-1.5W-41 VH

<400> SEQUENCE: 239

```
Ala Val Thr Leu Asp Glu Ser Gly Gly Gly Leu Gln Thr Pro Gly Gly
 1               5                  10                  15

Ala Leu Arg Leu Ser Cys Ser Ala Ser Gly Phe Asp Phe Ser Ser His
            20                  25                  30

Gly Met Phe Trp Val Arg Gln Ala Pro Gly Lys Gly Leu Glu Tyr Val
        35                  40                  45

Ser Glu Ile Thr Asn Asp Gly Ser Gly Thr Asn Tyr Gly Ser Ala Val
 50                  55                  60

Lys Gly Arg Ala Thr Ile Ser Arg Asp Asn Gly Gln Ser Thr Leu Tyr
 65                  70                  75                  80

Leu Gln Met Asn Ser Leu Arg Ala Glu Asp Thr Gly Thr Tyr Phe Cys
                85                  90                  95

Ala Arg Ser Ser Tyr Val Cys Pro Gly Gly Phe Ser Cys Trp Gly Asp
            100                 105                 110

Thr Gly Gln Ile Asp Ala Trp Gly His Gly Thr Glu Val Ile Val Ser
        115                 120                 125

Ser
```

<210> SEQ ID NO 240
<211> LENGTH: 129
<212> TYPE: PRT
<213> ORGANISM: Artificial sequence
<220> FEATURE:
<223> OTHER INFORMATION: 2-13D-37-3W-16 VH

<400> SEQUENCE: 240

```
Ala Val Thr Leu Asp Glu Ser Gly Gly Gly Leu Gln Thr Pro Gly Gly
 1               5                  10                  15

Ala Leu Arg Leu Ser Cys Ser Ala Ser Gly Phe Asp Phe Ser Ser His
            20                  25                  30

Gly Met Phe Trp Val Arg Gln Ala Pro Gly Lys Gly Leu Glu Tyr Val
        35                  40                  45

Ser Glu Ile Thr Asn Asp Gly Ser Gly Thr Asn Tyr Gly Ser Ala Val
```

```
                    50                  55                  60
Lys Gly Arg Ala Thr Ile Ser Arg Asp Asn Gly Gln Ser Thr Leu Tyr
 65                  70                  75                  80

Leu Gln Met Asn Ser Leu Arg Ala Glu Asp Thr Gly Thr Tyr Phe Cys
                 85                  90                  95

Ala Arg Ser Asn Tyr Ala Cys Pro Gly Gly Phe Ser Cys Trp Gly Asp
                100                 105                 110

Thr Gly Gln Ile Asp Ala Trp Gly His Gly Thr Glu Val Ile Val Ser
            115                 120                 125

Ser

<210> SEQ ID NO 241
<211> LENGTH: 109
<212> TYPE: PRT
<213> ORGANISM: Artificial sequence
<220> FEATURE:
<223> OTHER INFORMATION: SS01-13 VL

<400> SEQUENCE: 241

Ala Leu Thr Gln Pro Ser Ser Val Ser Ala Asn Pro Gly Glu Thr Val
 1               5                  10                  15

Arg Ile Thr Cys Ser Gly Gly Ala Ser Ser Gly Tyr Gly Tyr Gly Trp
                 20                  25                  30

Tyr Gln Gln Lys Pro Ser Ser Ala Pro Leu Thr Val Ile Tyr Lys Asp
             35                  40                  45

Asp Glu Arg Pro Ser Asp Ile Pro Ser Arg Phe Ser Gly Ser Ser Ser
         50                  55                  60

Gly Ser Thr His Thr Leu Thr Ile Thr Gly Val Gln Ala Glu Asp Glu
 65                  70                  75                  80

Ala Val Tyr Phe Cys Gly Asn Asp Asp Tyr Ser Ser Asp Ser Gly Tyr
                 85                  90                  95

Val Gly Val Phe Gly Ala Gly Thr Thr Leu Thr Val Leu
                100                 105

<210> SEQ ID NO 242
<211> LENGTH: 109
<212> TYPE: PRT
<213> ORGANISM: Artificial sequence
<220> FEATURE:
<223> OTHER INFORMATION: SS01-13-s5; S5-2.GKNG VL

<400> SEQUENCE: 242

Ala Leu Thr Gln Pro Ser Ser Val Ser Ala Asn Pro Gly Glu Thr Ala
 1               5                  10                  15

Arg Ile Thr Cys Ser Gly Gly Ala Ser Ser Gly Tyr Gly Tyr Gly Trp
                 20                  25                  30

Tyr Gln Gln Lys Pro Ser Ser Ala Pro Leu Thr Val Ile Tyr Lys Asp
             35                  40                  45

Ser Glu Arg Pro Ser Asp Ile Pro Ser Arg Phe Ser Gly Ser Ser Ser
         50                  55                  60

Gly Ser Thr His Thr Leu Thr Ile Ser Gly Val Gln Ala Glu Asp Glu
 65                  70                  75                  80

Ala Val Tyr Phe Cys Gly Asn Asp Asp Tyr Ser Ser Asp Ser Gly Tyr
                 85                  90                  95

Val Gly Val Phe Gly Ala Gly Thr Thr Leu Thr Val Leu
                100                 105
```

```
<210> SEQ ID NO 243
<211> LENGTH: 107
<212> TYPE: PRT
<213> ORGANISM: Artificial sequence
<220> FEATURE:
<223> OTHER INFORMATION: 1-7A-IT VL

<400> SEQUENCE: 243

Ala Leu Thr Gln Pro Ser Ser Val Ser Ala Asn Pro Gly Glu Thr Val
1               5                   10                  15

Lys Ile Thr Cys Ser Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
        35                  40                  45

Glu Asn Asn Lys Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Ser Asn Gly Gly
                85                  90                  95

Ile Phe Gly Ala Gly Thr Thr Leu Thr Val Leu
            100                 105

<210> SEQ ID NO 244
<211> LENGTH: 107
<212> TYPE: PRT
<213> ORGANISM: Artificial sequence
<220> FEATURE:
<223> OTHER INFORMATION: Low-PI VL

<400> SEQUENCE: 244

Ala Leu Thr Gln Pro Ser Ser Val Ser Ala Asn Pro Gly Glu Thr Val
1               5                   10                  15

Lys Ile Thr Cys Ser Gly Gly Ser Glu Glu Gln Tyr Tyr Tyr
            20                  25                  30

Gly Trp Tyr Gln Gln Lys Pro Gly Ser Ala Pro Val Thr Leu Ile Tyr
        35                  40                  45

Glu Asp Glu Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu
            100                 105

<210> SEQ ID NO 245
<211> LENGTH: 107
<212> TYPE: PRT
<213> ORGANISM: Artificial sequence
<220> FEATURE:
<223> OTHER INFORMATION: 1-30 VL

<400> SEQUENCE: 245

Ala Leu Thr Gln Pro Ser Ser Val Ser Ala Asn Pro Gly Glu Thr Val
1               5                   10                  15

Lys Ile Thr Cys Ser Gly Gly Ser Glu Glu Gln Tyr Tyr Tyr
            20                  25                  30

Gly Trp Tyr Gln Gln Lys Pro Gly Ser Ala Pro Val Thr Leu Ile Tyr
        35                  40                  45
```

```
Gln Asp Glu Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu
                100                 105
```

<210> SEQ ID NO 246
<211> LENGTH: 107
<212> TYPE: PRT
<213> ORGANISM: Artificial sequence
<220> FEATURE:
<223> OTHER INFORMATION: 1-17 VL

<400> SEQUENCE: 246

```
Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
                20                  25                  30

Gly Trp Tyr Gln Gln Lys Pro Gly Ser Ala Pro Val Thr Leu Ile Tyr
            35                  40                  45

Glu Asp Glu Gln Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu
                100                 105
```

<210> SEQ ID NO 247
<211> LENGTH: 107
<212> TYPE: PRT
<213> ORGANISM: Artificial sequence
<220> FEATURE:
<223> OTHER INFORMATION: 1-32 VL

<400> SEQUENCE: 247

```
Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
                20                  25                  30

Gly Trp Tyr Gln Gln Lys Pro Gly Ser Ala Pro Val Thr Leu Ile Tyr
            35                  40                  45

Gln Asp Glu Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu
                100                 105
```

<210> SEQ ID NO 248
<211> LENGTH: 107
<212> TYPE: PRT

<213> ORGANISM: Artificial sequence
<220> FEATURE:
<223> OTHER INFORMATION: 4-11 VL

<400> SEQUENCE: 248

```
Ala Leu Thr Gln Pro Ser Ser Val Ser Ala Asn Pro Gly Glu Thr Val
1               5                   10                  15

Lys Ile Thr Cys Ser Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
        35                  40                  45

Glu Asp His Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Ser Asp Glu Asp
                85                  90                  95

His Phe Gly Ala Gly Thr Thr Leu Thr Val Leu
            100                 105
```

<210> SEQ ID NO 249
<211> LENGTH: 107
<212> TYPE: PRT
<213> ORGANISM: Artificial sequence
<220> FEATURE:
<223> OTHER INFORMATION: 6-10 VL

<400> SEQUENCE: 249

```
Ala Leu Thr Gln Pro Ser Ser Val Ser Ala Asn Pro Gly Glu Thr Val
1               5                   10                  15

Lys Ile Thr Cys Ser Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
        35                  40                  45

Gln Asp Leu Leu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Leu Ser Ser Ser
                85                  90                  95

His Phe Gly Ala Gly Thr Thr Leu Thr Val Leu
            100                 105
```

<210> SEQ ID NO 250
<211> LENGTH: 103
<212> TYPE: PRT
<213> ORGANISM: Artificial sequence
<220> FEATURE:
<223> OTHER INFORMATION: 2-13D; 2-13D-37; 2-13D-37-1.5W-41; 2-13D-37-3W-16 VL

<400> SEQUENCE: 250

```
Ala Leu Thr Gln Pro Ser Ser Val Ser Ala Asn Pro Gly Glu Thr Ala
1               5                   10                  15

Lys Ile Thr Cys Ser Gly Gly Val Tyr Ser Tyr Gly Trp Phe Gln Gln
            20                  25                  30

Lys Pro Gly Ser Ala Leu Val Thr Val Ile Tyr Trp Asp Asp Glu Arg
        35                  40                  45

Pro Ser Asp Ile Pro Ser Arg Phe Ser Gly Ala Leu Ser Gly Ser Thr
```

-continued

```
                50                  55                  60
Asn Thr Leu Thr Ile Thr Gly Val Gln Ala Glu Asp Glu Ala Asp Tyr
 65                  70                  75                  80

Tyr Cys Gly Thr Glu Asp Ile Ser Gly Thr Ala Gly Val Phe Gly Ala
                 85                  90                  95

Gly Thr Thr Leu Thr Val Leu
            100
```

<210> SEQ ID NO 251
<211> LENGTH: 249
<212> TYPE: PRT
<213> ORGANISM: Artificial sequence
<220> FEATURE:
<223> OTHER INFORMATION: SS01-13 scFv

<400> SEQUENCE: 251

```
Ala Leu Thr Gln Pro Ser Ser Val Ser Ala Asn Pro Gly Glu Thr Val
 1               5                  10                  15

Arg Ile Thr Cys Ser Gly Gly Ala Ser Ser Gly Tyr Gly Tyr Gly Trp
                20                  25                  30

Tyr Gln Gln Lys Pro Ser Ser Ala Pro Leu Thr Val Ile Tyr Lys Asp
             35                  40                  45

Asp Glu Arg Pro Ser Asp Ile Pro Ser Arg Phe Ser Gly Ser Ser Ser
         50                  55                  60

Gly Ser Thr His Thr Leu Thr Ile Thr Gly Val Gln Ala Glu Asp Glu
 65                  70                  75                  80

Ala Val Tyr Phe Cys Gly Asn Asp Asp Tyr Ser Ser Asp Ser Gly Tyr
                 85                  90                  95

Val Gly Val Phe Gly Ala Gly Thr Thr Leu Thr Val Leu Gly Gln Ser
                100                 105                 110

Ser Arg Ser Ser Gly Gly Gly Ser Ser Gly Gly Gly Gly Ser Ala
            115                 120                 125

Val Thr Leu Asp Glu Ser Gly Gly Gly Leu Gln Thr Pro Gly Gly Ala
        130                 135                 140

Leu Ser Leu Ser Cys Lys Ala Ser Gly Phe Thr Phe Ser Ser Tyr Gln
145                 150                 155                 160

Met Gly Trp Val Arg Gln Ala Pro Gly Lys Gly Leu Glu Trp Val Gly
                165                 170                 175

Val Ile Asn Lys Ser Gly Ser Asp Thr Ser Tyr Gly Ser Ala Val Lys
                180                 185                 190

Gly Arg Ala Thr Ile Ser Arg Asp Asn Gly Gln Ser Thr Leu Tyr Leu
            195                 200                 205

Gln Met Asn Asn Leu Arg Ala Glu Asp Thr Ala Val Tyr Phe Cys Ala
        210                 215                 220

Lys Gly Ser Ala Ser Tyr Ile Thr Ala Ala Thr Ile Asp Ala Trp Gly
225                 230                 235                 240

His Gly Thr Glu Val Ile Val Ser Ser
                245
```

<210> SEQ ID NO 252
<211> LENGTH: 249
<212> TYPE: PRT
<213> ORGANISM: Artificial sequence
<220> FEATURE:
<223> OTHER INFORMATION: SS01-13-s5 scFv

<400> SEQUENCE: 252

Ala Leu Thr Gln Pro Ser Ser Val Ser Ala Asn Pro Gly Glu Thr Ala
1               5                   10                  15

Arg Ile Thr Cys Ser Gly Gly Ala Ser Ser Gly Tyr Gly Tyr Gly Trp
                20                  25                  30

Tyr Gln Gln Lys Pro Ser Ser Ala Pro Leu Thr Val Ile Tyr Lys Asp
            35                  40                  45

Ser Glu Arg Pro Ser Asp Ile Pro Ser Arg Phe Ser Gly Ser Ser Ser
        50                  55                  60

Gly Ser Thr His Thr Leu Thr Ile Ser Gly Val Gln Ala Glu Asp Glu
65                  70                  75                  80

Ala Val Tyr Phe Cys Gly Asn Asp Asp Tyr Ser Ser Asp Ser Gly Tyr
                85                  90                  95

Val Gly Val Phe Gly Ala Gly Thr Thr Leu Thr Val Leu Gly Gln Ser
            100                 105                 110

Ser Arg Ser Ser Gly Gly Gly Ser Gly Gly Gly Ser Ala
        115                 120                 125

Val Thr Leu Asp Glu Ser Gly Gly Leu Gln Thr Pro Gly Gly Ala
        130                 135                 140

Leu Arg Leu Ser Cys Lys Ala Ser Gly Phe Thr Phe Ser Ser Tyr Gln
145                 150                 155                 160

Met Gly Trp Val Arg Gln Ala Pro Gly Lys Gly Leu Glu Trp Val Ser
                165                 170                 175

Ala Ile Asn Lys Ser Gly Ser Asp Thr Ser Tyr Gly Ser Ala Val Lys
                180                 185                 190

Gly Arg Ala Thr Ile Ser Arg Asp Asn Gly Gln Ser Thr Leu Tyr Leu
            195                 200                 205

Gln Met Asn Ser Leu Arg Ala Glu Asp Thr Ala Val Tyr Phe Cys Ala
        210                 215                 220

Lys Gly Ser Ala Ser Tyr Ile Thr Ala Ala Thr Ile Asp Ala Trp Gly
225                 230                 235                 240

His Gly Thr Glu Val Ile Val Ser Ser
                245

<210> SEQ ID NO 253
<211> LENGTH: 249
<212> TYPE: PRT
<213> ORGANISM: Artificial sequence
<220> FEATURE:
<223> OTHER INFORMATION: S5-2.GKNG scFv

<400> SEQUENCE: 253

Ala Leu Thr Gln Pro Ser Ser Val Ser Ala Asn Pro Gly Glu Thr Ala
1               5                   10                  15

Arg Ile Thr Cys Ser Gly Gly Ala Ser Ser Gly Tyr Gly Tyr Gly Trp
                20                  25                  30

Tyr Gln Gln Lys Pro Ser Ser Ala Pro Leu Thr Val Ile Tyr Lys Asp
            35                  40                  45

Ser Glu Arg Pro Ser Asp Ile Pro Ser Arg Phe Ser Gly Ser Ser Ser
        50                  55                  60

Gly Ser Thr His Thr Leu Thr Ile Ser Gly Val Gln Ala Glu Asp Glu
65                  70                  75                  80

Ala Val Tyr Phe Cys Gly Asn Asp Asp Tyr Ser Ser Asp Ser Gly Tyr
                85                  90                  95

Val Gly Val Phe Gly Ala Gly Thr Thr Leu Thr Val Leu Gly Gln Ser
            100                 105                 110

```
Ser Arg Ser Ser Gly Gly Gly Ser Ser Gly Gly Gly Ser Ala
        115                 120                 125

Val Thr Leu Asp Glu Ser Gly Gly Gly Leu Gln Thr Pro Gly Gly Ala
130                 135                 140

Leu Arg Leu Ser Cys Lys Ala Ser Gly Phe Thr Phe Ser Ser Tyr Gln
145                 150                 155                 160

Met Gly Trp Val Arg Gln Ala Pro Gly Lys Gly Leu Glu Trp Val Ser
                165                 170                 175

Ala Ile Asn Lys Gly Gly Ser Asp Thr Ser Tyr Gly Ser Ala Val Lys
            180                 185                 190

Gly Arg Ala Thr Ile Ser Arg Asp Asn Gly Gln Ser Thr Leu Tyr Leu
        195                 200                 205

Gln Met Asn Ser Leu Arg Ala Glu Asp Thr Ala Val Tyr Phe Cys Ala
210                 215                 220

Lys Gly Ser Ala Ser Tyr Ile Thr Ala Ala Thr Ile Asp Ala Trp Gly
225                 230                 235                 240

His Gly Thr Glu Val Ile Val Ser Ser
                245

<210> SEQ ID NO 254
<211> LENGTH: 256
<212> TYPE: PRT
<213> ORGANISM: Artificial sequence
<220> FEATURE:
<223> OTHER INFORMATION: 1-7A-IT scFv

<400> SEQUENCE: 254

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
                20                  25                  30

Gly Trp Tyr Gln Gln Lys Pro Gly Ser Ala Pro Val Thr Leu Ile Tyr
            35                  40                  45

Glu Asn Asn Lys Arg Pro Ser Asp Ile Pro Ser Arg Phe Ser Gly Ser
        50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Ser Asn Gly Gly
                85                  90                  95

Ile Phe Gly Ala Gly Thr Thr Leu Thr Val Leu Gly Gln Ser Ser Arg
            100                 105                 110

Ser Ser Gly Gly Gly Ser Ser Gly Gly Gly Ser Ala Val Thr
        115                 120                 125

Leu Asp Glu Ser Gly Gly Gly Leu Gln Thr Pro Gly Gly Ala Leu Arg
    130                 135                 140

Leu Ser Cys Lys Ala Ser Gly Phe Thr Phe Ser Ser Phe Asn Met Phe
145                 150                 155                 160

Trp Val Arg Gln Ala Pro Gly Lys Gly Leu Glu Tyr Val Ser Gln Ile
                165                 170                 175

Ser Ser Ser Gly Ser Ser Thr Asn Tyr Ala Pro Ala Val Lys Gly Arg
            180                 185                 190

Ala Thr Ile Ser Arg Asp Asn Gly Gln Ser Thr Leu Tyr Leu Gln Met
        195                 200                 205

Asn Ser Leu Arg Ala Glu Asp Thr Gly Thr Tyr Tyr Cys Ala Lys Ser
        210                 215                 220
```

Ser Tyr Asp Cys Pro Tyr Gly His Cys Ser Ser Gly Val Asp Ser Ala
225                 230                 235                 240

Gly Glu Ile Asp Ala Trp Gly His Gly Thr Glu Val Ile Val Ser Ser
            245                 250                 255

<210> SEQ ID NO 255
<211> LENGTH: 256
<212> TYPE: PRT
<213> ORGANISM: Artificial sequence
<220> FEATURE:
<223> OTHER INFORMATION: Low-PI scFv

<400> SEQUENCE: 255

Ala Leu Thr Gln Pro Ser Ser Val Ser Ala Asn Pro Gly Glu Thr Val
1               5                   10                  15

Lys Ile Thr Cys Ser Gly Gly Gly Ser Glu Glu Glu Gln Tyr Tyr Tyr
            20                  25                  30

Gly Trp Tyr Gln Gln Lys Pro Gly Ser Ala Pro Val Thr Leu Ile Tyr
            35                  40                  45

Glu Asp Glu Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu Gly Gln Ser Ser Arg
            100                 105                 110

Ser Ser Gly Gly Gly Gly Ser Gly Gly Gly Gly Ser Ala Val Thr
            115                 120                 125

Leu Asp Glu Ser Gly Gly Gly Leu Gln Thr Pro Gly Gly Ala Leu Arg
            130                 135                 140

Leu Ser Cys Lys Ala Ser Gly Phe Asp Phe Glu Ser Phe Asn Met Phe
145                 150                 155                 160

Trp Val Arg Gln Ala Pro Gly Lys Gly Leu Glu Tyr Val Ser Gln Ile
                165                 170                 175

Ser Ser Ser Glu Glu Asp Glu Asn Tyr Ala Pro Ala Val Lys Gly Arg
            180                 185                 190

Ala Thr Ile Ser Arg Asp Asn Gly Gln Ser Thr Leu Tyr Leu Gln Met
            195                 200                 205

Asn Ser Leu Arg Ala Glu Asp Thr Gly Thr Tyr Tyr Cys Ala Lys Ser
    210                 215                 220

Ser Tyr Asp Cys Pro Tyr Gly His Cys Ser Ser Gly Val Asp Ser Ala
225                 230                 235                 240

Gly Glu Ile Asp Ala Trp Gly His Gly Thr Glu Val Ile Val Ser Ser
            245                 250                 255

<210> SEQ ID NO 256
<211> LENGTH: 256
<212> TYPE: PRT
<213> ORGANISM: Artificial sequence
<220> FEATURE:
<223> OTHER INFORMATION: 1-30 scFv

<400> SEQUENCE: 256

Ala Leu Thr Gln Pro Ser Ser Val Ser Ala Asn Pro Gly Glu Thr Val
1               5                   10                  15

Lys Ile Thr Cys Ser Gly Gly Gly Ser Glu Glu Glu Gln Tyr Tyr Tyr
            20                  25                  30

Gly Trp Tyr Gln Gln Lys Pro Gly Ser Ala Pro Val Thr Leu Ile Tyr
                35                  40                  45

Gln Asp Glu Glu Arg Pro Ser Asp Ile Pro Ser Arg Phe Ser Gly Ser
 50                  55                  60

Thr Ser Gly Ser Thr Ala Thr Leu Thr Ile Thr Gly Val Gln Ala Gly
 65                  70                  75                  80

Asp Glu Ala Asp Tyr Tyr Cys Gly Ser Trp Asp Ser Glu Asp Glu Asp
                 85                  90                  95

His Phe Gly Ala Gly Thr Thr Leu Thr Val Leu Gly Gln Ser Ser Arg
                100                 105                 110

Ser Ser Gly Gly Gly Gly Ser Gly Gly Gly Ser Ala Val Thr
                115                 120                 125

Leu Asp Glu Ser Gly Gly Leu Gln Thr Pro Gly Gly Ala Leu Arg
 130                 135                 140

Leu Ser Cys Lys Ala Ser Gly Phe Asp Phe Glu Ser Phe Asn Met Phe
145                 150                 155                 160

Trp Val Arg Gln Ala Pro Gly Lys Gly Leu Glu Tyr Val Ser Gln Ile
                165                 170                 175

Ser Ser Ser Glu Glu Asp Glu Asn Tyr Ala Pro Ala Val Lys Gly Arg
                180                 185                 190

Ala Thr Ile Ser Arg Asp Asn Gly Gln Ser Thr Leu Tyr Leu Gln Met
                195                 200                 205

Asn Ser Leu Arg Ala Glu Asp Thr Gly Thr Tyr Tyr Cys Ala Lys Ser
210                 215                 220

Ser Tyr Asp Cys Pro Tyr Gly His Cys Ser Gly Val Asp Ser Ala
225                 230                 235                 240

Gly Glu Ile Asp Ala Trp Gly His Gly Thr Glu Val Ile Val Ser Ser
                245                 250                 255

<210> SEQ ID NO 257
<211> LENGTH: 256
<212> TYPE: PRT
<213> ORGANISM: Artificial sequence
<220> FEATURE:
<223> OTHER INFORMATION: 1-17 scFv

<400> SEQUENCE: 257

Ala Leu Thr Gln Pro Ser Ser Val Ser Ala Asn Pro Gly Glu Thr Val
 1               5                  10                  15

Lys Ile Thr Cys Ser Gly Gly Gly Ser Tyr Ala Gly Ser Tyr Tyr Tyr
                20                  25                  30

Gly Trp Tyr Gln Gln Lys Pro Gly Ser Ala Pro Val Thr Leu Ile Tyr
                35                  40                  45

Glu Asp Glu Gln Arg Pro Ser Asp Ile Pro Ser Arg Phe Ser Gly Ser
 50                  55                  60

Thr Ser Gly Ser Thr Ala Thr Leu Thr Ile Thr Gly Val Gln Ala Gly
 65                  70                  75                  80

Asp Glu Ala Asp Tyr Tyr Cys Gly Ser Trp Asp Ser Glu Asp Glu Asp
                 85                  90                  95

His Phe Gly Ala Gly Thr Thr Leu Thr Val Leu Gly Gln Ser Ser Arg
                100                 105                 110

Ser Ser Gly Gly Gly Gly Ser Ser Gly Gly Gly Ser Ala Val Thr
                115                 120                 125

Leu Asp Glu Ser Gly Gly Gly Leu Gln Thr Pro Gly Gly Ala Leu Arg
 130                 135                 140

Leu Ser Cys Lys Ala Ser Gly Phe Asp Phe Glu Ser Phe Asn Met Phe
145                 150                 155                 160

Trp Val Arg Gln Ala Pro Gly Lys Gly Leu Glu Tyr Val Ser Gln Ile
            165                 170                 175

Ser Ser Ser Glu Glu Asp Glu Asn Tyr Ala Pro Ala Val Lys Gly Arg
            180                 185                 190

Ala Thr Ile Ser Arg Asp Asn Gly Gln Ser Thr Leu Tyr Leu Gln Met
        195                 200                 205

Asn Ser Leu Arg Ala Glu Asp Thr Gly Thr Tyr Tyr Cys Ala Lys Ser
    210                 215                 220

Ser Tyr Asp Cys Pro Tyr Gly His Cys Ser Ser Gly Val Asp Ser Ala
225                 230                 235                 240

Gly Glu Ile Asp Ala Trp Gly His Gly Thr Glu Val Ile Val Ser Ser
            245                 250                 255

<210> SEQ ID NO 258
<211> LENGTH: 256
<212> TYPE: PRT
<213> ORGANISM: Artificial sequence
<220> FEATURE:
<223> OTHER INFORMATION: 1-32 scFv

<400> SEQUENCE: 258

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
        35                  40                  45

Gln Asp Glu Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu Gly Gln Ser Ser Arg
            100                 105                 110

Ser Ser Gly Gly Gly Gly Ser Gly Gly Gly Ser Ala Val Thr
            115                 120                 125

Leu Asp Glu Ser Gly Gly Gly Leu Gln Thr Pro Gly Gly Ala Leu Arg
130                 135                 140

Leu Ser Cys Lys Ala Ser Gly Phe Asp Phe Glu Ser Phe Asn Met Phe
145                 150                 155                 160

Trp Val Arg Gln Ala Pro Gly Lys Gly Leu Glu Tyr Val Ser Gln Ile
            165                 170                 175

Ser Ser Ser Glu Glu Asp Glu Asn Tyr Ala Pro Ala Val Lys Gly Arg
            180                 185                 190

Ala Thr Ile Ser Arg Asp Asn Gly Gln Ser Thr Leu Tyr Leu Gln Met
        195                 200                 205

Asn Ser Leu Arg Ala Glu Asp Thr Gly Thr Tyr Tyr Cys Ala Lys Ser
    210                 215                 220

Ser Tyr Asp Cys Pro Tyr Gly His Cys Ser Ser Gly Val Asp Ser Ala
225                 230                 235                 240

Gly Glu Ile Asp Ala Trp Gly His Gly Thr Glu Val Ile Val Ser Ser
            245                 250                 255

<210> SEQ ID NO 259
<211> LENGTH: 256
<212> TYPE: PRT
<213> ORGANISM: Artificial sequence
<220> FEATURE:
<223> OTHER INFORMATION: 4-11 scFv

<400> SEQUENCE: 259

Ala Leu Thr Gln Pro Ser Ser Val Ser Ala Asn Pro Gly Glu Thr Val
1               5                   10                  15

Lys Ile Thr Cys Ser Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
                35                  40                  45

Glu Asp His Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Ser Asp Glu Asp
                85                  90                  95

His Phe Gly Ala Gly Thr Thr Leu Thr Val Leu Gly Gln Ser Ser Arg
            100                 105                 110

Ser Ser Gly Gly Gly Gly Ser Gly Gly Gly Ser Ala Val Thr
            115                 120                 125

Leu Asp Glu Ser Gly Gly Gly Leu Gln Thr Pro Gly Gly Ala Leu Arg
    130                 135                 140

Leu Ser Cys Lys Ala Ser Gly Phe Asp Phe Glu Ser Phe Asn Met Phe
145                 150                 155                 160

Trp Val Arg Gln Ala Pro Gly Lys Gly Leu Glu Tyr Val Ser Gln Ile
                165                 170                 175

Ser Ser Ser Glu Glu Asp Glu Asn Tyr Ala Pro Ala Val Lys Gly Arg
            180                 185                 190

Ala Thr Ile Ser Arg Asp Asn Gly Gln Ser Thr Leu Tyr Leu Gln Met
                195                 200                 205

Asn Ser Leu Arg Ala Glu Asp Thr Gly Thr Tyr Tyr Cys Ala Lys Ser
    210                 215                 220

Ser Tyr Asp Cys Pro Tyr Gly His Cys Ser Ser Gly Val Asp Ser Ala
225                 230                 235                 240

Gly Glu Ile Asp Ala Trp Gly His Gly Thr Glu Val Ile Val Ser Ser
                245                 250                 255

<210> SEQ ID NO 260
<211> LENGTH: 256
<212> TYPE: PRT
<213> ORGANISM: Artificial sequence
<220> FEATURE:
<223> OTHER INFORMATION: 6-10 scFv

<400> SEQUENCE: 260

Ala Leu Thr Gln Pro Ser Ser Val Ser Ala Asn Pro Gly Glu Thr Val
1               5                   10                  15

Lys Ile Thr Cys Ser Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
                35                  40                  45

Gln Asp Leu Leu Arg Pro Ser Asp Ile Pro Ser Arg Phe Ser Gly Ser

```
                 50                  55                  60
Thr Ser Gly Ser Thr Ala Thr Leu Thr Ile Thr Gly Val Gln Ala Gly
 65                  70                  75                  80

Asp Glu Ala Asp Tyr Tyr Cys Gly Ser Trp Asp Ser Leu Ser Ser Ser
                 85                  90                  95

His Phe Gly Ala Gly Thr Thr Leu Thr Val Leu Gly Gln Ser Ser Arg
                100                 105                 110

Ser Ser Gly Gly Gly Gly Ser Gly Gly Gly Ser Ala Val Thr
            115                 120                 125

Leu Asp Glu Ser Gly Gly Leu Gln Thr Pro Gly Gly Ala Leu Arg
130                 135                 140

Leu Ser Cys Lys Ala Ser Gly Phe Asp Phe Glu Ser Phe Asn Met Phe
145                 150                 155                 160

Trp Val Arg Gln Ala Pro Gly Lys Gly Leu Glu Tyr Val Ser Gln Ile
                165                 170                 175

Ser Ser Ser Glu Glu Asp Glu Asn Tyr Ala Pro Ala Val Lys Gly Arg
                180                 185                 190

Ala Thr Ile Ser Arg Asp Asn Gly Gln Ser Thr Leu Tyr Leu Gln Met
                195                 200                 205

Asn Ser Leu Arg Ala Glu Asp Thr Gly Thr Tyr Tyr Cys Ala Lys Ser
210                 215                 220

Ser Tyr Asp Cys Pro Tyr Gly His Cys Ser Ser Gly Val Asp Ser Ala
225                 230                 235                 240

Gly Glu Ile Asp Ala Trp Gly His Gly Thr Glu Val Ile Val Ser Ser
                245                 250                 255

<210> SEQ ID NO 261
<211> LENGTH: 250
<212> TYPE: PRT
<213> ORGANISM: Artificial sequence
<220> FEATURE:
<223> OTHER INFORMATION: 2-13D scFv

<400> SEQUENCE: 261

Ala Leu Thr Gln Pro Ser Ser Val Ser Ala Asn Pro Gly Glu Thr Ala
 1               5                  10                  15

Lys Ile Thr Cys Ser Gly Gly Val Tyr Ser Tyr Gly Trp Phe Gln Gln
                20                  25                  30

Lys Pro Gly Ser Ala Leu Val Thr Val Ile Tyr Trp Asp Asp Glu Arg
            35                  40                  45

Pro Ser Asp Ile Pro Ser Arg Phe Ser Gly Ala Leu Ser Gly Ser Thr
 50                  55                  60

Asn Thr Leu Thr Ile Thr Gly Val Gln Ala Glu Asp Glu Ala Asp Tyr
 65                  70                  75                  80

Tyr Cys Gly Thr Glu Asp Ile Ser Gly Thr Ala Gly Val Phe Gly Ala
                 85                  90                  95

Gly Thr Thr Leu Thr Val Leu Gly Gln Ser Ser Arg Ser Ser Gly Gly
                100                 105                 110

Gly Gly Ser Ser Gly Gly Gly Ser Ala Val Thr Leu Asp Glu Ser
            115                 120                 125

Gly Gly Gly Leu Gln Thr Pro Gly Gly Ala Leu Arg Leu Ser Cys Ser
            130                 135                 140

Ala Ser Gly Phe Thr Phe Ser Ser His Gly Met Phe Trp Val Arg Gln
145                 150                 155                 160

Ala Pro Gly Lys Gly Leu Glu Tyr Val Ser Glu Ile Thr Asn Asp Gly
```

Ser Gly Thr Asn Tyr Gly Ser Ala Val Lys Gly Arg Ala Thr Ile Ser
            165                 170                 175

Arg Asp Asn Gly Gln Ser Thr Leu Tyr Leu Gln Met Asn Ser Leu Arg
        180                 185                 190

Ala Glu Asp Thr Gly Thr Tyr Phe Cys Ala Arg Ser Thr Tyr Glu Cys
    195                 200                 205

Pro Gly Gly Phe Ser Cys Trp Gly Asp Thr Gly Gln Ile Asp Ala Trp
210                 215                 220

Gly His Gly Thr Glu Val Ile Val Ser Ser
225                 230                 235                 240

245                 250

Gly His Gly Thr Glu Val Ile Val Ser Ser
                245                 250

<210> SEQ ID NO 262
<211> LENGTH: 250
<212> TYPE: PRT
<213> ORGANISM: Artificial sequence
<220> FEATURE:
<223> OTHER INFORMATION: 2-13D-37 scFv

<400> SEQUENCE: 262

Ala Leu Thr Gln Pro Ser Ser Val Ser Ala Asn Pro Gly Glu Thr Ala
1               5                   10                  15

Lys Ile Thr Cys Ser Gly Gly Val Tyr Ser Tyr Gly Trp Phe Gln Gln
            20                  25                  30

Lys Pro Gly Ser Ala Leu Val Thr Val Ile Tyr Trp Asp Asp Glu Arg
        35                  40                  45

Pro Ser Asp Ile Pro Ser Arg Phe Ser Gly Ala Leu Ser Gly Ser Thr
    50                  55                  60

Asn Thr Leu Thr Ile Thr Gly Val Gln Ala Glu Asp Glu Ala Asp Tyr
65                  70                  75                  80

Tyr Cys Gly Thr Glu Asp Ile Ser Gly Thr Ala Gly Val Phe Gly Ala
                85                  90                  95

Gly Thr Thr Leu Thr Val Leu Gly Gln Ser Ser Arg Ser Ser Gly Gly
            100                 105                 110

Gly Gly Ser Ser Gly Gly Gly Gly Ser Ala Val Thr Leu Asp Glu Ser
        115                 120                 125

Gly Gly Gly Leu Gln Thr Pro Gly Gly Ala Leu Arg Leu Ser Cys Ser
    130                 135                 140

Ala Ser Gly Phe Asp Phe Ser Ser His Gly Met Phe Trp Val Arg Gln
145                 150                 155                 160

Ala Pro Gly Lys Gly Leu Glu Tyr Val Ser Glu Ile Thr Asn Asp Gly
                165                 170                 175

Ser Gly Thr Asn Tyr Gly Ser Ala Val Lys Gly Arg Ala Thr Ile Ser
            180                 185                 190

Arg Asp Asn Gly Gln Ser Thr Leu Tyr Leu Gln Met Asn Ser Leu Arg
        195                 200                 205

Ala Glu Asp Thr Gly Thr Tyr Phe Cys Ala Arg Ser Thr Tyr Glu Cys
    210                 215                 220

Pro Gly Gly Phe Ser Cys Trp Gly Asp Thr Gly Gln Ile Asp Ala Trp
225                 230                 235                 240

Gly His Gly Thr Glu Val Ile Val Ser Ser
                245                 250

<210> SEQ ID NO 263
<211> LENGTH: 250
<212> TYPE: PRT

<213> ORGANISM: Artificial sequence
<220> FEATURE:
<223> OTHER INFORMATION: 2-13D-37-1.5W-41 scFv

<400> SEQUENCE: 263

```
Ala Leu Thr Gln Pro Ser Ser Val Ser Ala Asn Pro Gly Glu Thr Ala
1               5                   10                  15

Lys Ile Thr Cys Ser Gly Gly Val Tyr Ser Tyr Gly Trp Phe Gln Gln
            20                  25                  30

Lys Pro Gly Ser Ala Leu Val Thr Val Ile Tyr Trp Asp Asp Glu Arg
        35                  40                  45

Pro Ser Asp Ile Pro Ser Arg Phe Ser Gly Ala Leu Ser Gly Ser Thr
    50                  55                  60

Asn Thr Leu Thr Ile Thr Gly Val Gln Ala Glu Asp Glu Ala Asp Tyr
65                  70                  75                  80

Tyr Cys Gly Thr Glu Asp Ile Ser Gly Thr Ala Gly Val Phe Gly Ala
                85                  90                  95

Gly Thr Thr Leu Thr Val Leu Gly Gln Ser Ser Arg Ser Ser Gly Gly
            100                 105                 110

Gly Gly Ser Ser Gly Gly Gly Ser Ala Val Thr Leu Asp Glu Ser
        115                 120                 125

Gly Gly Gly Leu Gln Thr Pro Gly Gly Ala Leu Arg Leu Ser Cys Ser
    130                 135                 140

Ala Ser Gly Phe Asp Phe Ser Ser His Gly Met Phe Trp Val Arg Gln
145                 150                 155                 160

Ala Pro Gly Lys Gly Leu Glu Tyr Val Ser Glu Ile Thr Asn Asp Gly
                165                 170                 175

Ser Gly Thr Asn Tyr Gly Ser Ala Val Lys Gly Arg Ala Thr Ile Ser
            180                 185                 190

Arg Asp Asn Gly Gln Ser Thr Leu Tyr Leu Gln Met Asn Ser Leu Arg
        195                 200                 205

Ala Glu Asp Thr Gly Thr Tyr Phe Cys Ala Arg Ser Ser Tyr Val Cys
    210                 215                 220

Pro Gly Gly Phe Ser Cys Trp Gly Asp Thr Gly Gln Ile Asp Ala Trp
225                 230                 235                 240

Gly His Gly Thr Glu Val Ile Val Ser Ser
                245                 250
```

<210> SEQ ID NO 264
<211> LENGTH: 250
<212> TYPE: PRT
<213> ORGANISM: Artificial sequence
<220> FEATURE:
<223> OTHER INFORMATION: 2-13D-37-3W-16 scFv

<400> SEQUENCE: 264

```
Ala Leu Thr Gln Pro Ser Ser Val Ser Ala Asn Pro Gly Glu Thr Ala
1               5                   10                  15

Lys Ile Thr Cys Ser Gly Gly Val Tyr Ser Tyr Gly Trp Phe Gln Gln
            20                  25                  30

Lys Pro Gly Ser Ala Leu Val Thr Val Ile Tyr Trp Asp Asp Glu Arg
        35                  40                  45

Pro Ser Asp Ile Pro Ser Arg Phe Ser Gly Ala Leu Ser Gly Ser Thr
    50                  55                  60

Asn Thr Leu Thr Ile Thr Gly Val Gln Ala Glu Asp Glu Ala Asp Tyr
65                  70                  75                  80
```

```
Tyr Cys Gly Thr Glu Asp Ile Ser Gly Thr Ala Gly Val Phe Gly Ala
                 85                  90                  95

Gly Thr Thr Leu Thr Val Leu Gly Gln Ser Ser Arg Ser Ser Gly Gly
            100                 105                 110

Gly Gly Ser Gly Gly Gly Ser Ala Val Thr Leu Asp Glu Ser
        115                 120                 125

Gly Gly Gly Leu Gln Thr Pro Gly Gly Ala Leu Arg Leu Ser Cys Ser
        130                 135                 140

Ala Ser Gly Phe Asp Phe Ser Ser His Gly Met Phe Trp Val Arg Gln
145                 150                 155                 160

Ala Pro Gly Lys Gly Leu Glu Tyr Val Ser Glu Ile Thr Asn Asp Gly
                165                 170                 175

Ser Gly Thr Asn Tyr Gly Ser Ala Val Lys Gly Arg Ala Thr Ile Ser
            180                 185                 190

Arg Asp Asn Gly Gln Ser Thr Leu Tyr Leu Gln Met Asn Ser Leu Arg
        195                 200                 205

Ala Glu Asp Thr Gly Thr Tyr Phe Cys Ala Arg Ser Asn Tyr Ala Cys
    210                 215                 220

Pro Gly Gly Phe Ser Cys Trp Gly Asp Thr Gly Gln Ile Asp Ala Trp
225                 230                 235                 240

Gly His Gly Thr Glu Val Ile Val Ser Ser
                245                 250

<210> SEQ ID NO 265
<211> LENGTH: 366
<212> TYPE: DNA
<213> ORGANISM: Artificial sequence
<220> FEATURE:
<223> OTHER INFORMATION: SS01-13 VH

<400> SEQUENCE: 265
gccgtgacgt tggacgagtc cggggggcggc ctccagacgc ccggaggagc gctctctctc      60
tcttgcaaag cctccgggtt caccttcagc agctatcaga tgggctgggt gcgacaggcg     120
cccggcaagg ggctggaatg ggtcggtgtt attaacaagt ctggtagtga cacatcatac     180
gggtcggcgg tgaagggccg tgccaccatc tcgagggaca cgggcagag cacactgtac      240 ctgcagatga caacctcag ggctgaggac accgctgttt acttctgcgc caaaggttct      300
gctagttaca taactgctgc taccatcgac gcatggggcc acgggaccga agtcatcgtc     360
tcctcc                                                                  366

<210> SEQ ID NO 266
<211> LENGTH: 366
<212> TYPE: DNA
<213> ORGANISM: Artificial sequence
<220> FEATURE:
<223> OTHER INFORMATION: SS01-13-S5 VH

<400> SEQUENCE: 266
gccgtgacgt tggacgagtc cggggggcggc ctccagacgc ccggaggagc gctccgcctc      60
tcttgcaagg cctccgggtt caccttcagc agctatcaga tgggctgggt gcgacaggcg     120
cccggcaagg ggctggaatg ggtcagcgcg attaataaga gcgtagtga cacatcatac      180 gggtcggcgg tgaagggccg tgccaccatc tcgagggaca cgggcagag cacactgtac      240 ctgcagatga cagcctcag ggctgaggac accgctgttt acttctgcgc caaaggttct      300
gctagttaca taactgctgc taccatcgac gcatggggcc acgggaccga agtcatcgtc     360
``` tcctcc                                                                    366

<210> SEQ ID NO 267
<211> LENGTH: 366
<212> TYPE: DNA
<213> ORGANISM: Artificial sequence
<220> FEATURE:
<223> OTHER INFORMATION: S5-2.GKNG VH

<400> SEQUENCE: 267
gccgtgacgt tggacgagtc cggggcggc ctccagacgc ccggaggagc gctccgcctc        60
tcttgcaagg cctccgggtt caccttcagc agctatcaga tgggctgggt gcgacaggcg       120
cccggcaagg ggctggaatg ggtcagcgcg attaataagg gcggtagtga cacatcatac       180
gggtcggcgg tgaagggccg tgccaccatc tcgaggaca acgggcagag cacactgtac        240
ctgcagatga acagcctcag ggctgaggac accgctgttt acttctgcgc caaaggttct      300
gctagttaca taactgctgc taccatcgac gcatggggcc acgggaccga agtcatcgtc       360
tcctcc                                                                    366

<210> SEQ ID NO 268
<211> LENGTH: 393
<212> TYPE: DNA
<213> ORGANISM: Artificial sequence
<220> FEATURE:
<223> OTHER INFORMATION: 1-7A-IT VH

<400> SEQUENCE: 268
gccgtgacgt tggatgaatc cggggcggc ctccagacgc ccggaggagc gctccgcctc        60
agctgcaagg cctctgggtt caccttcagc agcttcaaca tgttctgggt gcgacaggcg       120
cccggcaagg ggctggaata cgtctcgcag attagcagca gtggtagtag cacaaactac      180
gcacccgcgg tgaaaggccg tgccaccatc tcgagggaca acgggcagag cacactgtat      240
ctgcagatga acagcctgcg cgctgaagac accggcacct actactgcgc caaaagtagt      300
tatgactgtc cttacggtca ttgtagtagt ggtgttgata gtgctggtga gatcgacgca      360
tggggccacg ggaccgaagt catcgtctcc tcc                                     393

<210> SEQ ID NO 269
<211> LENGTH: 393
<212> TYPE: DNA
<213> ORGANISM: Artificial sequence
<220> FEATURE:
<223> OTHER INFORMATION: Low-PI VH

<400> SEQUENCE: 269
gccgtgacgt tggatgaatc cggggcggc ctccagacgc ccggaggagc gctccgcctc        60
agctgcaagg cctctgggtt caccttcagc agcttcaaca tgttctgggt gcgacaggcg       120
cccggcaagg ggctggaata cgtctcgcag attagcagca gtggtagtag cacaaactac      180
gcacccgcgg tgaaaggccg tgccaccatc tcgagggaca acgggcagag cacactgtat      240
ctgcagatga acagcctgcg cgctgaagac accggcacct actactgcgc caaaagtagt      300
tatgactgtc cttacggtca ttgtagtagt ggtgttgata gtgctggtga gatcgacgca      360
tggggccacg ggaccgaagt catcgtctcc tcc                                     393

<210> SEQ ID NO 270
<211> LENGTH: 393
<212> TYPE: DNA
<213> ORGANISM: Artificial sequence

```
<220> FEATURE:
<223> OTHER INFORMATION: 1-30 VH

<400> SEQUENCE: 270
gccgtgacgt tggatgaatc cgggggcggc ctccagacgc ccggaggagc gctccgcctc    60
agctgcaagg cctctggctt tgattttgaa agcttcaaca tgttctgggt gcgacaggcg   120
cccggcaagg ggctggaata cgtctcgcag attagcagca gtgaagaaga tgaaaactac   180
gcacccgcgg tgaaaggccg tgccaccatc tcgaggaca acgggcagag cacactgtat    240
ctgcagatga acagcctgcg cgctgaagac accggcacct actactgcgc caaaagtagt   300
tatgactgtc cttacggtca ttgtagtagt ggtgttgata gtgctggtga gatcgacgca   360
tggggccacg ggaccgaagt catcgtctcc tcc                                393

<210> SEQ ID NO 271
<211> LENGTH: 393
<212> TYPE: DNA
<213> ORGANISM: Artificial sequence
<220> FEATURE:
<223> OTHER INFORMATION: 1-17 VH

<400> SEQUENCE: 271
gccgtgacgt tggatgaatc cgggggcggc ctccagacgc ccggaggagc gctccgcctc    60
agctgcaagg cctctggctt tgattttgaa agcttcaaca tgttctgggt gcgacaggcg   120
cccggcaagg ggctggaata cgtctcgcag attagcagca gtgaagaaga tgaaaactac   180
gcacccgcgg tgaaaggccg tgccaccatc tcgaggaca acgggcagag cacactgtat    240
ctgcagatga acagcctgcg cgctgaagac accggcacct actactgcgc caaaagtagt   300
tatgactgtc cttacggtca ttgtagtagt ggtgttgata gtgctggtga gatcgacgca   360
tggggccacg ggaccgaagt catcgtctcc tcc                                393

<210> SEQ ID NO 272
<211> LENGTH: 393
<212> TYPE: DNA
<213> ORGANISM: Artificial sequence
<220> FEATURE:
<223> OTHER INFORMATION: 1-32 VH

<400> SEQUENCE: 272
gccgtgacgt tggatgaatc cgggggcggc ctccagacgc ccggaggagc gctccgcctc    60
agctgcaagg cctctggctt tgattttgaa agcttcaaca tgttctgggt gcgacaggcg   120
cccggcaagg ggctggaata cgtctcgcag attagcagca gtgaagaaga tgaaaactac   180
gcacccgcgg tgaaaggccg tgccaccatc tcgagggaca acgggcagag cacactgtat   240
ctgcagatga acagcctgcg cgctgaagac accggcacct actactgcgc caaaagtagt   300
tatgactgtc cttacggtca ttgtagtagt ggtgttgata gtgctggtga gatcgacgca   360
tggggccacg ggaccgaagt catcgtctcc tcc                                393

<210> SEQ ID NO 273
<211> LENGTH: 393
<212> TYPE: DNA
<213> ORGANISM: Artificial sequence
<220> FEATURE:
<223> OTHER INFORMATION: 4-11 VH

<400> SEQUENCE: 273
gccgtgacgt tggatgaatc cgggggcggc ctccagacgc ccggaggagc gctccgcctc    60
```

```
agctgcaagg cctctggctt tgattttgaa agcttcaaca tgttctgggt gcgacaggcg      120
cccggcaagg ggctggaata cgtctcgcag attagcagca gtgaagaaga tgaaaactac      180
gcacccgcgg tgaaaggccg tgccaccatc tcgagggaca cgggcagag cacactgtat       240 ctgcagatga acagcctgcg cgctgaagac accggcacct actactgcgc caaaagtagt      300
tatgactgtc cttacggtca ttgtagtagt ggtgttgata gtgctggtga gatcgacgca      360
tggggccacg ggaccgaagt catcgtctcc tcc                                    393
```

<210> SEQ ID NO 274
<211> LENGTH: 393
<212> TYPE: DNA
<213> ORGANISM: Artificial sequence
<220> FEATURE:
<223> OTHER INFORMATION: 6-10 VH

<400> SEQUENCE: 274

```
gccgtgacgt tggatgaatc cggggggcggc ctccagacgc ccggaggagc gctccgcctc      60
agctgcaagg cctctggctt tgattttgaa agcttcaaca tgttctgggt gcgacaggcg      120
cccggcaagg ggctggaata cgtctcgcag attagcagca gtgaagaaga tgaaaactac      180
gcacccgcgg tgaaaggccg tgccaccatc tcgagggaca cgggcagag cacactgtat       240 ctgcagatga acagcctgcg cgctgaagac accggcacct actactgcgc caaaagtagt      300
tatgactgtc cttacggtca ttgtagtagt ggtgttgata gtgctggtga gatcgacgca      360
tggggccacg ggaccgaagt catcgtctcc tcc                                    393
```

<210> SEQ ID NO 275
<211> LENGTH: 387
<212> TYPE: DNA
<213> ORGANISM: Artificial sequence
<220> FEATURE:
<223> OTHER INFORMATION: 2-13D VH

<400> SEQUENCE: 275

```
gccgtgacgt tggacgagtc cggggggcggc ctccagacgc ccggaggagc gctccgcctt      60
agctgcagcg cctccgggtt caccttcagc agccatggca tgttctgggt gcgacaggcg      120
cccggcaagg ggttggaata tgtctcggag attaccaatg atggtagtgg cacaaactac      180
gggtcggcgg tgaagggccg tgccaccatc tcgagggaca cgggcagag cacactgtat       240 ctgcagatga acagcctcag ggctgaggac accggcacct acttctgcgc cagatctact      300
tatgaatgtc ctggtggttt tagttgttgg ggtgatactg gtcaaataga cgcatggggc      360
cacgggaccg aagtcatcgt ctcctcc                                           387
```

<210> SEQ ID NO 276
<211> LENGTH: 387
<212> TYPE: DNA
<213> ORGANISM: Artificial sequence
<220> FEATURE:
<223> OTHER INFORMATION: 2-13D-37 VH

<400> SEQUENCE: 276

```
gccgtgacgt tggacgagtc cggggggcggc ctccagacgc ccggaggagc gctccgcctt      60
agctgcagcg cctccgggtt cgatttcagc agccatggca tgttctgggt gcgacaggcg      120
cccggcaagg ggttggaata tgtctcggag attaccaatg atggtagtgg cacaaactac      180
gggtcggcgg tgaagggccg tgccaccatc tcgagggaca cgggcagag cacactgtat       240 ctgcagatga acagcctcag ggctgaggac accggcacct acttctgcgc cagatctact      300
```
tatgaatgtc ctggtggttt tagttgttgg ggtgatactg gtcaaataga cgcatggggc      360
cacgggaccg aagtcatcgt ctcctcc                                          387

<210> SEQ ID NO 277
<211> LENGTH: 387
<212> TYPE: DNA
<213> ORGANISM: Artificial sequence
<220> FEATURE:
<223> OTHER INFORMATION: 2-13D-37-1.5W-41 VH

<400> SEQUENCE: 277
gccgtgacgt tggacgagtc cgggggcggc ctccagacgc ccggaggagc gctccgcctt      60
agctgcagcg cctccgggtt cgatttcagc agccatggca tgttctgggt gcgacaggcg     120
cccggcaagg ggttggaata tgtctcggag attaccaatg atggtagtgg cacaaactac     180
gggtcggcgg tgaagggccg tgccaccatc tcgagggaca cgggcagag cacactgtat      240 ctgcagatga acagcctcag ggctgaggac accggcacct acttctgcgc cagatcttct    300
tatgtttgtc ctggtggttt tagttgttgg ggtgatactg gtcaaataga cgcatggggc     360
cacgggaccg aagtcatcgt ctcctcc                                          387

<210> SEQ ID NO 278
<211> LENGTH: 387
<212> TYPE: DNA
<213> ORGANISM: Artificial sequence
<220> FEATURE:
<223> OTHER INFORMATION: 2-13D-37-3W-16 VH

<400> SEQUENCE: 278
gccgtgacgt tggacgagtc cgggggcggc ctccagacgc ccggaggagc gctccgcctt      60
agctgcagcg cctccgggtt cgatttcagc agccatggca tgttctgggt gcgacaggcg     120
cccggcaagg ggttggaata tgtctcggag attaccaatg atggtagtgg cacaaactac     180
gggtcggcgg tgaagggccg tgccaccatc tcgagggaca cgggcagag cacactgtat      240 ctgcagatga acagcctcag ggctgaggac accggcacct acttctgcgc cagatctaat    300
tatgcttgtc ctggtggttt tagttgttgg ggtgatactg gtcaaataga cgcatggggc     360
cacgggaccg aagtcatcgt ctcctcc                                          387

<210> SEQ ID NO 279
<211> LENGTH: 327
<212> TYPE: DNA
<213> ORGANISM: Artificial sequence
<220> FEATURE:
<223> OTHER INFORMATION: SS01-13 VL

<400> SEQUENCE: 279
gccctgactc agccgtcctc ggtgtcagca aaccctgggg aaactgttcg tatcacctgc      60
tccgggggtg ctagcagtgg ctatggttat ggctggtatc agcagaagcc tagcagtgcc     120
cctctcactg tgatctacaa agacgacgaa agaccctcgg acatcccttc acgattctcc     180
ggttcctctt ccggctccac acacacatta accatcactg gggtccaagc cgaggacgag     240
gctgtatatt tctgtgggaa tgatgactac agcagtgata tggatatgt cggtgtattt      300 ggggccggga caaccctgac cgtccta                                          327

<210> SEQ ID NO 280
<211> LENGTH: 327
<212> TYPE: DNA

```
<213> ORGANISM: Artificial sequence
<220> FEATURE:
<223> OTHER INFORMATION: SS01-13-S5 VL

<400> SEQUENCE: 280
gccctgactc agccgtcctc ggtgtcagca aaccctgggg aaactgcgcg tatcacctgc      60
tccggtggtg ctagcagtgg ctatggttat ggctggtatc agcagaagcc tagcagtgcc     120
cctctcactg tgatctacaa agactctgaa agaccctcgg acatcccttc acgattctcc     180
ggttcctctt ccggctccac acacacatta accatcagcg gggtccaagc cgaggacgag     240
gctgtatatt tctgtgggaa tgatgactac agcagtgata gtggatatgt cggtgtattt     300
ggggccggga caaccctgac cgtccta                                         327

<210> SEQ ID NO 281
<211> LENGTH: 327
<212> TYPE: DNA
<213> ORGANISM: Artificial sequence
<220> FEATURE:
<223> OTHER INFORMATION: S5-2.GKNG VL

<400> SEQUENCE: 281
gccctgactc agccgtcctc ggtgtcagca aaccctgggg aaactgcgcg tatcacctgc      60
tccggtggtg ctagcagtgg ctatggttat ggctggtatc agcagaagcc tagcagtgcc     120
cctctcactg tgatctacaa agactctgaa agaccctcgg acatcccttc acgattctcc     180
ggttcctctt ccggctccac acacacatta accatcagcg gggtccaagc cgaggacgag     240
gctgtatatt tctgtgggaa tgatgactac agcagtgata gtggatatgt cggtgtattt     300
ggggccggga caaccctgac cgtccta                                         327

<210> SEQ ID NO 282
<211> LENGTH: 321
<212> TYPE: DNA
<213> ORGANISM: Artificial sequence
<220> FEATURE:
<223> OTHER INFORMATION: 1-7A-IT VL

<400> SEQUENCE: 282
gccctgactc agccgtcctc ggtgtcagca aacccaggag aaaccgtcaa gatcacctgc      60
tccgggggtg gcagctatgc tggaagttac tattatggct ggtatcagca gaagcctggc     120
agtgcccctg tcactctgat ctatgaaaac aacaagagac cctcggacat cccttcacga     180
ttctccggtt ccacatctgg ctccacagcc acactaacca tcactggggt ccaagccggc     240
gacgaggctg attattactg tgggagctgg gacagtagca atggtggtat atttggggcc     300
gggacaaccc tgaccgtcct a                                               321

<210> SEQ ID NO 283
<211> LENGTH: 321
<212> TYPE: DNA
<213> ORGANISM: Artificial sequence
<220> FEATURE:
<223> OTHER INFORMATION: Low-PI VL

<400> SEQUENCE: 283
gccctgactc agccgtcctc ggtgtcagca aacccaggag aaaccgtcaa gatcacctgc      60
tccgggggtg gcagctatgc tggaagttac tattatggct ggtatcagca gaagcctggc     120
agtgcccctg tcactctgat ctatgaaaac aacaagagac cctcggacat cccttcacga     180
ttctccggtt ccacatctgg ctccacagcc acactaacca tcactggggt ccaagccggc     240
```
gacgaggctg attattactg tgggagctgg dacagtagca atggtggtat atttggggcc    300
gggacaaccc tgaccgtcct a    321

<210> SEQ ID NO 284
<211> LENGTH: 321
<212> TYPE: DNA
<213> ORGANISM: Artificial sequence
<220> FEATURE:
<223> OTHER INFORMATION: 1-30 VL

<400> SEQUENCE: 284
gccctgactc agccgtcctc ggtgtcagca aacccaggag aaaccgtcaa gatcacctgc    60 tccggggtg gcagcgaaga agaacagtac tattatggct ggtatcagca gaagcctggc    120
agtgcccctg tcactctgat ctatcaggat gaagaaagac cctcggacat cccttcacga    180
ttctccggtt ccacatctgg ctccacagcc acactaacca tcactggggt ccaagccggc    240
gacgaggctg attattactg tgggagctgg dacagtgaag atgaagatca ttttggggcc    300
gggacaaccc tgaccgtcct a    321

<210> SEQ ID NO 285
<211> LENGTH: 321
<212> TYPE: DNA
<213> ORGANISM: Artificial sequence
<220> FEATURE:
<223> OTHER INFORMATION: 1-17 VL

<400> SEQUENCE: 285
gccctgactc agccgtcctc ggtgtcagca aacccaggag aaaccgtcaa gatcacctgc    60 tccggggtg gcagctatgc tggaagttac tattatggct ggtatcagca gaagcctggc    120
agtgcccctg tcactctgat ctatgaagat gaacagagac cctcggacat cccttcacga    180
ttctccggtt ccacatctgg ctccacagcc acactaacca tcactggggt ccaagccggc    240
gacgaggctg attattactg tgggagctgg dacagtgaag atgaagatca ttttggggcc    300
gggacaaccc tgaccgtcct a    321

<210> SEQ ID NO 286
<211> LENGTH: 321
<212> TYPE: DNA
<213> ORGANISM: Artificial sequence
<220> FEATURE:
<223> OTHER INFORMATION: 1-32 VL

<400> SEQUENCE: 286
gccctgactc agccgtcctc ggtgtcagca aacccaggag aaaccgtcaa gatcacctgc    60 tccggggtg gcagctatgc tggaagttac tattatggct ggtatcagca gaagcctggc    120
agtgcccctg tcactctgat ctatcaggat gaagaaagac cctcggacat cccttcacga    180
ttctccggtt ccacatctgg ctccacagcc acactaacca tcactggggt ccaagccggc    240
gacgaggctg attattactg tgggagctgg dacagtgaag atgaagatca ttttggggcc    300
gggacaaccc tgaccgtcct a    321

<210> SEQ ID NO 287
<211> LENGTH: 321
<212> TYPE: DNA
<213> ORGANISM: Artificial sequence
<220> FEATURE:
<223> OTHER INFORMATION: 4-11 VL

<400> SEQUENCE: 287

```
gccctgactc agccgtcctc ggtgtcagca acccaggag aaaccgtcaa gatcacctgc      60
tccgggggtg gcagctatgc tggaagttac tattatggct ggtatcagca gaagcctggc    120
agtgccctg tcactctgat ctatgaagac cacgagagac cctcggacat cccttcacga    180
ttctccggtt ccacatctgg ctccacagcc acactaacca tcactggggt ccaagccggc    240
gacgaggctg attattactg tgggagctgg gacagtagcg atgaagatca ttttggggcc    300
gggacaaccc tgaccgtcct a                                              321
```

<210> SEQ ID NO 288
<211> LENGTH: 321
<212> TYPE: DNA
<213> ORGANISM: Artificial sequence
<220> FEATURE:
<223> OTHER INFORMATION: 6-10 VL

<400> SEQUENCE: 288

```
gccctgactc agccgtcctc ggtgtcagca acccaggag aaaccgtcaa gatcacctgc      60
tccgggggtg gcagctatgc tggaagttac tattatggct ggtatcagca gaagcctggc    120
agtgccctg tcactctgat ctatcaggat ctgctgagac cctcggacat cccttcacga    180
ttctccggtt ccacatctgg ctccacagcc acactaacca tcactggggt ccaagccggc    240
gacgaggctg attattactg tgggagctgg gacagtctga gcagcagcca ttttggggcc    300
gggacaaccc tgaccgtcct a                                              321
```

<210> SEQ ID NO 289
<211> LENGTH: 309
<212> TYPE: DNA
<213> ORGANISM: Artificial sequence
<220> FEATURE:
<223> OTHER INFORMATION: 2-13D VL

<400> SEQUENCE: 289

```
gccctgactc agccgtcctc ggtgtcagca acccaggag aaaccgcgaa gataacctgc      60
tccgggggtg tgtatagcta tggctggttc cagcagaagc ctggcagtgc ccttgtcact    120
gtgatctact gggatgatga gagaccctcg gacatccctt cacgattctc cggtgcccta    180
tccggctcca caaacacatt aaccatcact ggggtccaag ccgaagacga ggctgattat    240
tattgtggga ctgaagacat cagcggcact gctggtgtat ttggggccgg gacaaccctg    300
accgtcctg                                                            309
```

<210> SEQ ID NO 290
<211> LENGTH: 309
<212> TYPE: DNA
<213> ORGANISM: Artificial sequence
<220> FEATURE:
<223> OTHER INFORMATION: 2-13D-37 VL

<400> SEQUENCE: 290

```
gccctgactc agccgtcctc ggtgtcagca acccaggag aaaccgcgaa gataacctgc      60
tccgggggtg tgtatagcta tggctggttc cagcagaagc ctggcagtgc ccttgtcact    120
gtgatctact gggatgatga gagaccctcg gacatccctt cacgattctc cggtgcccta    180
tccggctcca caaacacatt aaccatcact ggggtccaag ccgaagacga ggctgattat    240
tattgtggga ctgaagacat cagcggcact gctggtgtat ttggggccgg gacaaccctg    300
accgtcctg                                                            309
```

<210> SEQ ID NO 291
<211> LENGTH: 309
<212> TYPE: DNA
<213> ORGANISM: Artificial sequence
<220> FEATURE:
<223> OTHER INFORMATION: 2-13D-37-1.5W-41 VL

<400> SEQUENCE: 291

```
gccctgactc agccgtcctc ggtgtcagca aacccaggag aaaccgcgaa gataacctgc      60
tccgggggtg tgtatagcta tggctggttc cagcagaagc ctggcagtgc ccttgtcact     120
gtgatctact gggatgatga gagaccctcg gacatccctt cacgattctc cggtgcccta     180
tccggctcca caaacacatt aaccatcact ggggtccaag ccgaagacga ggctgattat     240
tattgtggga ctgaagacat cagcggcact gctggtgtat ttggggccgg gacaaccctg     300
accgtcctg                                                             309
```

<210> SEQ ID NO 292
<211> LENGTH: 309
<212> TYPE: DNA
<213> ORGANISM: Artificial sequence
<220> FEATURE:
<223> OTHER INFORMATION: 2-13D-37-3W-16 VL

<400> SEQUENCE: 292

```
gccctgactc agccgtcctc ggtgtcagca aacccaggag aaaccgcgaa gataacctgc      60
tccgggggtg tgtatagcta tggctggttc cagcagaagc ctggcagtgc ccttgtcact     120
gtgatctact gggatgatga gagaccctcg gacatccctt cacgattctc cggtgcccta     180
tccggctcca caaacacatt aaccatcact ggggtccaag ccgaagacga ggctgattat     240
tattgtggga ctgaagacat cagcggcact gctggtgtat ttggggccgg gacaaccctg     300
accgtcctg                                                             309
```

<210> SEQ ID NO 293
<211> LENGTH: 747
<212> TYPE: DNA
<213> ORGANISM: Artificial sequence
<220> FEATURE:
<223> OTHER INFORMATION: SS01-13 scFv

<400> SEQUENCE: 293

```
gccctgactc agccgtcctc ggtgtcagca aaccctgggg aaactgttcg tatcacctgc      60
tccgggggtg ctagcagtgg ctatggttat ggctggtatc agcagaagcc tagcagtgcc     120
cctctcactg tgatctacaa agacgacgaa agaccctcgg acatcccttc acgattctcc     180
ggttcctctt ccggctccac acacacatta accatcactg gggtccaagc cgaggacgag     240
gctgtatatt tctgtgggaa tgatgactac agcagtgata gtggatatgt cggtgtattt     300
ggggccggga caaccctgac cgtcctaggt cagtcctcta gatcttccgg cggtggtggc     360
agctccggtg gtggcggttc cgccgtgacg ttggacgagt ccggggcgg cctccagacg     420
cccggaggag cgctctctct ctcttgcaaa gcctccgggt tcaccttcag cagctatcag     480
atgggctggg tgcgacaggc gcccggcaag ggctgaat gggtcggtgt tattaacaag     540
tctggtagtg acacatcata cgggtcggcg gtgaagggcc gtgccaccat ctcgagggac     600
aacgggcaga gcacactgta cctgcagatg aacaacctca gggctgagga caccgctgtt     660
tacttctgcg ccaaaggttc tgctagttac ataactgctg ctaccatcga cgcatgggc     720
```

```
cacgggaccg aagtcatcgt ctcctcc                                          747
```

<210> SEQ ID NO 294
<211> LENGTH: 747
<212> TYPE: DNA
<213> ORGANISM: Artificial sequence
<220> FEATURE:
<223> OTHER INFORMATION: SS01-13-s5 scFv

<400> SEQUENCE: 294

```
gccctgactc agccgtcctc ggtgtcagca aaccctgggg aaactgcgcg tatcacctgc        60
tccggtggtg ctagcagtgg ctatggttat ggctggtatc agcagaagcc tagcagtgcc       120
cctctcactg tgatctacaa agactctgaa agaccctcgg acatcccttc acgattctcc       180
ggttcctctt ccggctccac acacacatta accatcagcg gggtccaagc cgaggacgag       240
gctgtatatt tctgtgggaa tgatgactac agcagtgata gtggatatgt cggtgtattt       300
ggggccggga caaccctgac cgtcctaggt cagtcctcta gatcttccgg cggtggtgga       360
tcctctggtg gtggtggttc cgccgtgacg ttggacgagt ccggggggcgg cctccagacg       420
cccggaggag cgctccgcct ctcttgcaag gcctccgggt tcaccttcag cagctatcag       480
atgggctggg tgcgacaggc gcccggcaag gggctggaat gggtcagcgc gattaataag       540
agcggtagtg acacatcata cgggtcggcg gtgaagggcc gtgccaccat ctcgagggac       600
aacgggcaga gcacactgta cctgcagatg aacagcctca gggctgagga caccgctgtt       660
tacttctgcg ccaaaggttc tgctagttac ataactgctg ctaccatcga cgcatggggc       720
cacgggaccg aagtcatcgt ctcctcc                                          747
```

<210> SEQ ID NO 295
<211> LENGTH: 747
<212> TYPE: DNA
<213> ORGANISM: Artificial sequence
<220> FEATURE:
<223> OTHER INFORMATION: S5-2.GKNG scFv

<400> SEQUENCE: 295

```
gccctgactc agccgtcctc ggtgtcagca aaccctgggg aaactgcgcg tatcacctgc        60
tccggtggtg ctagcagtgg ctatggttat ggctggtatc agcagaagcc tagcagtgcc       120
cctctcactg tgatctacaa agactctgaa agaccctcgg acatcccttc acgattctcc       180
ggttcctctt ccggctccac acacacatta accatcagcg gggtccaagc cgaggacgag       240
gctgtatatt tctgtgggaa tgatgactac agcagtgata gtggatatgt cggtgtattt       300
ggggccggga caaccctgac cgtcctaggt cagtcctcta gatcttccgg cggtggtgga       360
tcctctggtg gtggtggttc cgccgtgacg ttggacgagt ccggggggcgg cctccagacg       420
cccggaggag cgctccgcct ctcttgcaag gcctccgggt tcaccttcag cagctatcag       480
atgggctggg tgcgacaggc gcccggcaag gggctggaat gggtcagcgc gattaataag       540
ggcggtagtg acacatcata cgggtcggcg gtgaagggcc gtgccaccat ctcgagggac       600
aacgggcaga gcacactgta cctgcagatg aacagcctca gggctgagga caccgctgtt       660
tacttctgcg ccaaaggttc tgctagttac ataactgctg ctaccatcga cgcatggggc       720
cacgggaccg aagtcatcgt ctcctcc                                          747
```

<210> SEQ ID NO 296
<211> LENGTH: 747
<212> TYPE: DNA
<213> ORGANISM: Artificial sequence
<220> FEATURE:
<223> OTHER INFORMATION: 2-13D scFv

<400> SEQUENCE: 296

```
ctgactcagc cgtcctcggt gtcagcaaac ccaggagaaa ccgcgaagat aacctgctcc      60
gggggtgtgt atagctatgg ctggttccag cagaagcctg gcagtgccct tgtcactgtg     120
atctactggg atgatgagag accctcggac atcccttcac gattctccgg tgccctatcc     180
ggctccacaa acacattaac catcactggg gtccaagccg aagacgaggc tgattattat     240
tgtgggactg aagacatcag cggcactgct ggtgtatttg gggccgggac aaccctgacc     300
gtcctgggtc agtcctctag atcttccggc ggtggtggat cctctggtgg tggtggttcc     360
gccgtgacgt tggacgagtc cggggggggc ctccagacgc ccggaggagc gctccgcctt     420
agctgcagcg cctccgggtt caccttcagc agccatggca tgttctgggt gcgacaggcg     480
cccggcaagg ggttggaata tgtctcggag attaccaatg atggtagtgg cacaaactac     540
gggtcggcgg tgaagggccg tgccaccatc tcgaggaca acgggcagag cacactgtat     600
ctgcagatga acagcctcag ggctgaggac accggcacct acttctgcgc cagatctact     660
tatgaatgtc ctggtggttt tagttgttgg ggtgatactg gtcaaataga cgcatggggc     720
cacgggaccg aagtcatcgt ctcctcc                                         747
```

<210> SEQ ID NO 297
<211> LENGTH: 747
<212> TYPE: DNA
<213> ORGANISM: Artificial sequence
<220> FEATURE:
<223> OTHER INFORMATION: 2-13D-37 scFv

<400> SEQUENCE: 297

```
ctgactcagc cgtcctcggt gtcagcaaac ccaggagaaa ccgcgaagat aacctgctcc      60
gggggtgtgt atagctatgg ctggttccag cagaagcctg gcagtgccct tgtcactgtg     120
atctactggg atgatgagag accctcggac atcccttcac gattctccgg tgccctatcc     180
ggctccacaa acacattaac catcactggg gtccaagccg aagacgaggc tgattattat     240
tgtgggactg aagacatcag cggcactgct ggtgtatttg gggccgggac aaccctgacc     300
gtcctgggtc agtcctctag atcttccggc ggtggtggat cctctggtgg tggtggttcc     360
gccgtgacgt tggacgagtc cggggggggc ctccagacgc ccggaggagc gctccgcctt     420
agctgcagcg cctccgggtt cgatttcagc agccatggca tgttctgggt gcgacaggcg     480
cccggcaagg ggttggaata tgtctcggag attaccaatg atggtagtgg cacaaactac     540
gggtcggcgg tgaagggccg tgccaccatc tcgaggaca acgggcagag cacactgtat     600
ctgcagatga acagcctcag ggctgaggac accggcacct acttctgcgc cagatctact     660
tatgaatgtc ctggtggttt tagttgttgg ggtgatactg gtcaaataga cgcatggggc     720
cacgggaccg aagtcatcgt ctcctcc                                         747
```

<210> SEQ ID NO 298
<211> LENGTH: 750
<212> TYPE: DNA
<213> ORGANISM: Artificial sequence
<220> FEATURE:
<223> OTHER INFORMATION: 2-13D-37-1.5W-41 scFv

<400> SEQUENCE: 298

```
gccctgactc agccgtcctc ggtgtcagca aacccaggag aaaccgcgaa gataacctgc      60
```

```
tccggggtg tgtatagcta tggctggttc cagcagaagc ctggcagtgc ccttgtcact    120
gtgatctact gggatgatga gagaccctcg gacatcccttc acgattctc cggtgcccta   180 tccggctcca caaacacatt aaccatcact ggggtccaag ccgaagacga ggctgattat   240
tattgtggga ctgaagacat cagcggcact gctggtgtat ttggggccgg acaaccctg   300 accgtcctgg gtcagtcctc tagatcttcc ggcggtggtg gatcctctgg tggtggtggt   360
tccgccgtga cgttggacga gtccgggggc ggcctccaga cgcccggagg agcgctccgc   420
cttagctgca gcgcctccgg gttcgatttc agcagccatg gcatgttctg ggtgcgacag   480
gcgcccggca aggggttgga atatgtctcg gagattacca atgatggtag tggcacaaac   540
tacgggtcgg cggtgaaggg ccgtgccacc atctcgaggg acaacgggca gagcacactg   600
tatctgcaga tgaacagcct cagggctgag gacaccggca cctacttctg cgccagatct   660
tcttatgttt gtcctggtgg ttttagttgt tggggtgata ctggtcaaat agacgcatgg   720
ggccacggga ccgaagtcat cgtctcctcc                                   750
```

<210> SEQ ID NO 299
<211> LENGTH: 750
<212> TYPE: DNA
<213> ORGANISM: Artificial sequence
<220> FEATURE:
<223> OTHER INFORMATION: 2-13D-37-3W-16 scFv

<400> SEQUENCE: 299

```
gccctgactc agccgtcctc ggtgtcagca acccaggag aaaccgcgaa gataacctgc    60 tccggggtg tgtatagcta tggctggttc cagcagaagc ctggcagtgc ccttgtcact   120
gtgatctact gggatgatga gagaccctcg gacatcccttc acgattctc cggtgcccta   180 tccggctcca caaacacatt aaccatcact ggggtccaag ccgaagacga ggctgattat   240
tattgtggga ctgaagacat cagcggcact gctggtgtat ttggggccgg acaaccctg   300 accgtcctgg gtcagtcctc tagatcttcc ggcggtggtg gatcctctgg tggtggtggt   360
tccgccgtga cgttggacga gtccgggggc ggcctccaga cgcccggagg agcgctccgc   420
cttagctgca gcgcctccgg gttcgatttc agcagccatg gcatgttctg ggtgcgacag   480
gcgcccggca aggggttgga atatgtctcg gagattacca atgatggtag tggcacaaac   540
tacgggtcgg cggtgaaggg ccgtgccacc atctcgaggg acaacgggca gagcacactg   600
tatctgcaga tgaacagcct cagggctgag gacaccggca cctacttctg cgccagatct   660
aattatgctt gtcctggtgg ttttagttgt tggggtgata ctggtcaaat agacgcatgg   720
ggccacggga ccgaagtcat cgtctcctcc                                   750
```

<210> SEQ ID NO 300
<211> LENGTH: 18
<212> TYPE: PRT
<213> ORGANISM: Artificial sequence
<220> FEATURE:
<223> OTHER INFORMATION: Linker

<400> SEQUENCE: 300

Gly Gln Ser Ser Arg Ser Ser Gly Gly Gly Gly Ser Ser Gly Gly Gly
1               5                   10                  15

Gly Ser

<210> SEQ ID NO 301
<211> LENGTH: 768
<212> TYPE: DNA

<213> ORGANISM: Artificial Sequence
<220> FEATURE:
<223> OTHER INFORMATION: 1-30 scFv

<400> SEQUENCE: 301

```
gctctcacac aaccttcctc tgtctctgct aatcctggcg agactgttaa aatcacctgc         60 tccgggggg gtagtgagga agaacagtat tactatggat ggtaccaaca aaagcctggg        120
tctgcacccg taaccttat ataccaagat gaggagcgcc catccgatat accctcacgc        180
ttctcaggca gtacatctgg gtcaactgca accctcacca ttacaggagt gcaagcaggt        240
gatgaggcag attattattg tgggtcatgg gactccgagg acgaggatca ttttggagct        300
ggcactacat tgacagtact gggccagtca tcaagaagtt caggtggcgg cggaagctcc        360
gggggcggtg gatcagcagt aactctcgac gaatctggag gcggtcttca aacccctggg        420
ggggctctga gactctcatg taaagccagc ggattcgatt tcgagtcatt taacatgttt        480
tgggtccgcc aggcccccgg taaaggcctg gagtatgtgt cccaaatatc aagttcagag        540
gaggacgaga actatgcccc agccgtgaaa ggtcgagcta caatttcccg agacaacggc        600
cagtcaacac tctacttgca gatgaacagc ctgagagccg aagacactgg tacatactat        660
tgtgctaaat ccagctacga ctgtccatac ggccattgtt catcaggagt agactccgca        720
ggtgagatag acgcatgggg tcatggcact gaggtcattg tgtcctct                     768
```

ADENO-ASSOCIATED VIRUS (AAV) DELIVERY OF ANTI-FAM19A5 ANTIBODIES

REFERENCE TO SEQUENCE LISTING SUBMITTED ELECTRONICALLY

The content of the electronically submitted sequence listing in ASCII text file (Name: 3763_010PC01_SeqListing_ST25.txt; Size: 261,643 bytes; and Date of Creation: May 8, 2019) filed with the application is incorporated herein by reference in its entirety.

FIELD OF THE DISCLOSURE

The present disclosure relates to recombinant adeno-associated virus (AAV) vectors and uses thereof. More specifically, the present disclosure relates to AAV vectors comprising a nucleic acid that encodes an antagonist against a family with sequence similarity 19, member A5 (FAM19A5) protein. In certain aspects, the FAM19A5 antagonist is a single-chain variable fragment targeting a FAM19A5 protein.

BACKGROUND OF THE DISCLOSURE

FAM19A5 is a member of the TAFA subfamily of proteins which is composed of five highly homologous small proteins. Tang T. Y. et al., *Genomics* 83(4):727-34 (2004). These proteins contain conserved cysteine residues at fixed positions, and are distantly related to macrophage inflammatory protein 1-alpha (MIP-1-alpha), a member of the CC-chemokine family. Like many of the other TAFA proteins, FAM19A5 is predominantly expressed in specific regions of the brain and the spinal cord. It is thought to play an important role not only in the development, differentiation, and formation of a complete central nervous system but also in the pathogenesis of many diseases associated with the central nervous system. Accordingly, the in vivo administration of an anti-FAM19A5 antibody has been shown to improve symptoms associated with central nervous system damage or diseases. U.S. Pat. No. 9,579,398.

Therapeutic antibodies have successfully been used to treat various diseases. Ecker D. M., et al., *MAbs* 7: 9-14 (2015). However, despite their efficacy, there are known limitations to antibodies, which limit their widespread therapeutic use. For instance, many antibodies have been described as having inadequate pharmacokinetics and tissue accessibility, as well as impaired interactions with the immune system. Chames P., et al., *Br J Pharmacol* 157(2): 220-223 (2009). Moreover, antibodies often have to be administered in large amounts to achieve clinical efficacy, resulting in large manufacturing costs. Accordingly, there is a need for an alternative method, that is both efficacious and economical, for delivering therapeutic antibodies, e.g., anti-FAM19A5 antibodies, to a subject to treat diseases.

BRIEF SUMMARY OF THE DISCLOSURE

The present disclosure provides an adeno-associated virus (AAV) vector comprising a nucleic acid that encodes an antagonist against a family with sequence similarity 19, member A5 (FAM19A5) protein. In some embodiments, the AAV vector further comprises an intron, a signal peptide, and/or one or more adeno-associated virus inverted terminal repeats (ITRs).

In some embodiments, the FAM19A5 antagonist is an anti-FAM19A5 antibody. Accordingly, in some embodiments, the AAV vector comprises a nucleic acid that encodes an anti-FAM19A5 antibody. In some embodiments, the anti-FAM19A5 antibody comprises an Fab, an Fab', an F(ab')2, an Fv, or a single chain Fv (scFv). In certain embodiments, the anti-FAM19A5 antibody is a scFv.

In some embodiments, the AAV vector comprises a nucleic acid which has been codon optimized. In some embodiments, the nucleic acid comprises a nucleotide sequence as set forth in SEQ ID NO: 204, SEQ ID NO: 205, SEQ ID NO: 206, or SEQ ID NO: 301. In some embodiments, the scFv comprises an amino acid sequence as set forth in SEQ ID NO: 201, SEQ ID NO: 202, SEQ ID NO: 203, or SEQ ID NO: 256.

In some embodiments, the anti-FAM19A5 antibody exhibits a property selected from: (a) binds to soluble human FAM19A5 with a $K_D$ of 10 nM or less as measured by enzyme-linked immunosorbent assay (ELISA); (b) binds to membrane bound human FAM19A5 with a $K_D$ of 10 nM or less as measured by ELISA; or (c) both (a) and (b).

In some embodiments, the anti-FAM19A5 antibody cross-competes for binding to a human FAM19A5 epitope with a reference antibody comprising a heavy chain CDR1, CDR2, and CDR3 and a light chain CDR1, CDR2, and CDR3, (i) wherein the heavy chain CDR1 comprises the amino acid sequence set forth in SEQ ID NO: 17, the heavy chain CDR2 comprises the amino acid sequence set forth in SEQ ID NO: 18, the heavy chain CDR3 comprises the amino acid sequence set forth in SEQ ID NO: 19, the light chain CDR1 comprises the amino acid sequence set forth in SEQ ID NO: 29, the light chain CDR2 comprises the amino acid sequence set forth in SEQ ID NO: 30, and the light chain CDR3 comprises the amino acid sequence set forth in SEQ ID NO: 31; (ii) wherein the heavy chain CDR1 comprises the amino acid sequence set forth in SEQ ID NO: 14, the heavy chain CDR2 comprises the amino acid sequence set forth in SEQ ID NO: 15, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 27, and the light chain CDR3 comprises the amino acid sequence set forth in SEQ ID NO: 28; (iii) wherein the heavy chain CDR1 comprises the amino acid sequence set forth in SEQ ID NO: 11, the heavy chain CDR2 comprises the amino acid sequence set forth in SEQ ID NO: 12, the heavy chain CDR3 comprises the amino acid sequence set forth in SEQ ID NO: 13, the light chain CDR1 comprises the amino acid sequence set forth in SEQ ID NO: 23, the light chain CDR2 comprises the amino acid sequence set forth in SEQ ID NO: 24, and the light chain CDR3 comprises the amino acid sequence set forth in SEQ ID NO: 25; or (iv) wherein the heavy chain CDR1 comprises the amino acid sequence of SEQ ID NO: 212, the heavy chain CDR2 comprises the amino acid sequence of SEQ ID NO: 213, the heavy chain CDR3 comprises the amino acid sequence of SEQ ID NO: 16, the light chain CDR1 comprises the amino acid sequence of SEQ ID NO: 222, the light chain CDR2 comprises the amino acid sequence of SEQ ID NO: 225, and the light chain CDR3 comprises the amino acid sequence of SEQ ID NO: 224.

In some embodiments, the anti-FAM19A5 antibody binds to the same FAM19A5 epitope as a reference antibody comprising a heavy chain CDR1, CDR2, and CDR3 and a light chain CDR1, CDR2, and CDR3, (i) wherein the heavy chain CDR1 comprises the amino acid sequence set forth in SEQ ID NO: 17, the heavy chain CDR2 comprises the amino acid sequence set forth in SEQ ID NO: 18, the heavy chain CDR3 comprises the amino acid sequence set forth in SEQ ID NO: 19, the light chain CDR1 comprises the amino acid sequence set forth in SEQ ID NO: 29, the light chain CDR2 comprises the amino acid sequence set forth in SEQ ID NO: 30, and the light chain CDR3 comprises the amino acid sequence set forth in SEQ ID NO: 31; (ii) wherein the heavy chain CDR1 comprises the amino acid sequence set forth in SEQ ID NO: 14, the heavy chain CDR2 comprises the amino acid sequence set forth in SEQ ID NO: 15, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 27, and the light chain CDR3 comprises the amino acid sequence set forth in SEQ ID NO: 28; (iii) wherein the heavy chain CDR1 comprises the amino acid sequence set forth in SEQ ID NO: 11, the heavy chain CDR2 comprises the amino acid sequence set forth in SEQ ID NO: 12, the heavy chain CDR3 comprises the amino acid sequence set forth in SEQ ID NO: 13, the light chain CDR1 comprises the amino acid sequence set forth in SEQ ID NO: 23, the light chain CDR2 comprises the amino acid sequence set forth in SEQ ID NO: 24, and the light chain CDR3 comprises the amino acid sequence set forth in SEQ ID NO: 25; or (iv) wherein the heavy chain CDR1 comprises the amino acid sequence of SEQ ID NO: 212, the heavy chain CDR2 comprises the amino acid sequence of SEQ ID NO: 213, the heavy chain CDR3 comprises the amino acid sequence of SEQ ID NO: 16, the light chain CDR1 comprises the amino acid sequence of SEQ ID NO: 222, the light chain CDR2 comprises the amino acid sequence of SEQ ID NO: 225, and the light chain CDR3 comprises the amino acid sequence of SEQ ID NO: 224.

In some embodiments, the anti-FAM19A5 antibody binds to at least one FAM19A5 epitope, which is SEQ ID NO: 6 or SEQ ID NO: 9. In other embodiments, the anti-FAM19A5 antibody binds only to an FAM19A5 epitope, which is SEQ ID NO: 6 or SEQ ID NO: 9. In certain embodiments, the anti-FAM19A5 antibody further binds to an additional FAM19A5 epitope. In some embodiments, the additional FAM19A5 epitope is selected from the group consisting of SEQ ID NO: 5, SEQ ID NO: 6, SEQ ID NO: 7, SEQ ID NO: 8, SEQ ID NO: 9, SEQ ID NO: 10, and any combination thereof.

In some embodiments, the anti-FAM19A5 antibody comprises a heavy chain CDR1, CDR2, and CDR3 and a light chain CDR1, CDR2, and CDR3, wherein the heavy chain CDR3 comprises the amino acid sequence set forth in SEQ ID NO: 19, SEQ ID NO: 16, or SEQ ID NO: 13. In some embodiments, the heavy chain CDR1 of the anti-FAM19A5 antibody comprises the amino acid sequence set forth in SEQ ID NO: 17, SEQ ID NO: 14, SEQ ID NO: 11, or SEQ ID NO: 212. In some embodiments, the heavy chain CDR2 of the anti-FAM19A5 antibody comprises the amino acid sequence set forth in SEQ ID NO: 18, SEQ ID NO: 15, SEQ ID NO: 12, or SEQ ID NO: 213. In some embodiments, the light chain CDR1 of the anti-FAM19A5 antibody comprises the amino acid sequence set forth in SEQ ID NO: 29, SEQ ID NO: 26, SEQ ID NO: 23, or SEQ ID NO: 222. In some embodiments, the light chain CDR2 of the anti-FAM19A5 antibody comprises the amino acid sequence set forth in SEQ ID NO: 30, SEQ ID NO: 27, SEQ ID NO: 24, or SEQ ID NO: 225. In certain embodiments, the light chain CDR3 of the anti-FAM19A5 antibody comprises the amino acid sequence set forth in SEQ ID NO: 31, SEQ ID NO: 28, SEQ ID NO: 25, or SEQ ID NO: 224.

In some embodiments, the anti-FAM19A5 antibody comprises a heavy chain CDR1, CDR2, and CDR3, and a light chain CDR1, CDR2, and CDR3, wherein (i) the heavy chain CDR1, CDR2, and CDR3 comprise SEQ ID NOs: 17, 18, and 19, respectively, and the light chain CDR1, CDR2, and CDR3 comprise SEQ ID NOs: 29, 30, and 31, respectively; (ii) the heavy chain CDR1, CDR2, and CDR3 comprise SEQ ID NOs: 14, 15, and 16, respectively, and the light chain CDR1, CDR2, and CDR3 comprise SEQ ID NOs: 26, 27, and 28, respectively; (iii) the heavy chain CDR1, CDR2, and CDR3 comprise SEQ ID NOs: 11, 12, and 13, respectively, and the light chain CDR1, CDR2, and CDR3 comprise SEQ ID NOs: 23, 24, and 25, respectively; or (iv) the heavy chain CDR1, CDR2, and CDR3 comprise SEQ ID NOs: 212, 213, and 16, respectively, and the light chain CDR1, CDR2, and CDR3 comprise SEQ ID NOs: 222, 225, and 224, respectively.

In some embodiments, the anti-FAM19A5 antibody comprises a heavy chain variable domain comprising SEQ ID NO: 37, SEQ ID NO: 36, SEQ ID NO: 35, or SEQ ID NO: 236 and/or a light chain variable domain comprising SEQ ID NO: 41, SEQ ID NO: 40, SEQ ID NO: 39, or SEQ ID NO: 245. In certain embodiments, the anti-FAM19A5 antibody comprises a heavy chain variable domain comprising SEQ ID NO: 37 and a light chain variable domain comprising SEQ ID NO: 41. In other embodiments, the anti-FAM19A5 antibody comprises a heavy chain variable domain comprising SEQ ID NO: 36 and a light chain variable domain comprising SEQ ID NO: 40. In some embodiments, the anti-FAM19A5 antibody comprises a heavy chain variable domain comprising SEQ ID NO: 35 and a light chain variable domain comprising SEQ ID NO: 39. In some embodiments, the anti-FAM19A5 antibody comprises a heavy chain variable domain comprising SEQ ID NO: 236 and a light chain variable domain comprising SEQ ID NO: 245.

In some embodiments, the anti-FAM19A5 antibody comprises a heavy chain variable domain and a light chain variable domain, wherein the heavy chain variable domain comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 37, 36, 35, or 236. In some embodiments, the anti-FAM19A5 antibody comprises a heavy chain variable region and a light chain variable region, wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 41, 40, 39, or 245. In certain embodiments, the anti-FAM19A5 antibody comprises a heavy chain variable region and a light chain variable region, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 37, 36, 35, or 236; and wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 41, 40, 39, or 245.

In some embodiments, the anti-FAM19A5 antibody inhibits binding of a reference antibody to human FAM19A5 by at least 10%, 20%, 30%, 40%, 50%, 60%, 70%, 80%, 90%, or by 100%, as measured by a binding inhibition assay. In certain embodiments, the anti-FAM19A5 antibody reduces a concentration of FAM19A5 protein in a culture medium comprising an astrocyte cell line (e.g., C8-D1A) by at least 10%, 20%, 30%, 40%, 50%, 60%, 70%, 80%, 90%, or by 100%, as measured by ELISA.

Also disclosed herein is a method of producing a recombinant adeno-associated virus (AAV) particle, comprising (a) culturing a host cell that has been transfected with the AAV vector disclosed herein to provide a cell culture, and (b) recovering the recombinant AAV particle from a supernatant of the cell culture.

The present disclosure also provides a method for in vivo delivery of an antagonist against a FAM19A5 protein to a subject in need thereof, comprising administering to the subject an AAV vector described herein.

The present disclosure further provides method of treating a disease or condition in a subject in need thereof, comprising administering to the subject an AAV vector as disclosed herein.

Also disclosed herein is a method of treating a neuropathic pain in a subject in need thereof, comprising administering to the subject an AAV vector of the present disclosure. In some embodiments, the neuropathic pain is a peripheral neuropathic pain.

The present disclosure provides a method of increasing a threshold or latency to an external stimulus in a subject in need thereof, comprising administering to the subject an AAV vector disclosed herein. In some embodiments, the external stimulus is a mechanical stimulus. In other embodiments, the external stimulus is a thermal stimulus.

In some embodiments, the AAV vector of the present disclosure is administered intravenously, orally, parenterally, intrathecally, intra-cerebroventricularly, pulmonarily, intramuscularly, subcutaneously, intraperitoneally, intravitreally, epidurally, subretinally, or intraventricularly. In some embodiments, the subject is a human.

BRIEF DESCRIPTION OF THE DRAWINGS

As shown in FIG. 1, the pscAAV construct comprises the following key elements: (i) human beta globin under a CMV promoter; (ii) transgene encoding the 3-2, 1-65, or 2-13 scFv, and (iii) left and right inverted terminal repeats (ITRs).

In FIG. 2A, the HEK293 cells were transduced with scAAV8-CMV-3-2-ScFv at two different MOI: $5\times10^4$ (white bar) or $1\times10^5$ (black bar). Antibody levels were measured at day 1, 4, and 8 post-transduction. In FIG. 2B, HEK293 cells were transduced with scAAV9-CMV-3-2-ScFv (white bar: MOI=$1\times10^5$; black bar=$2\times10^5$). Antibody levels were measured at a single time point, i.e., day 8 post-transduction. In FIG. 2C, HEK293 cells were transfected with either scAAV9-CMV-1-65-ScFv (white bar: MOI=$1\times10^5$; black bar=$2\times10^5$) or scAAV9-2-13-ScFv (white bar with dots: MOI=$1\times10^5$; black bar with dots=$2\times10^5$).

FIG. 3A shows the data for scAAV9-CMV-1-65-ScFv. The number "1" indicates the control (GFP) and the number "2" indicates the 1-65 scFv. FIG. 3B shows the data for scAAV9-2-13-ScFv. The number "1" indicates the control (GFP) and the number "2" indicates the 2-13 scFv. FIG. 3C shows the data for scAAV8-CMV-3-2-ScFv. The number "1" indicates the control (PBS) and the number "2" indicates the 3-2 scFv.

FIG. 4A shows a comparison of FAM19A5 protein levels when the C8-D1A cells were cultured with either supernatant from cells transduced with scAAV8-CMV-3-2-ScFv or PBS alone. FIG. 4B shows a comparison of FAM19A5 levels when the C8-D1A cells were cultured with scAAV9-2-13-ScFv, scAAV9-CMV-1-65-ScFv, or the control construct (scAAV9-CMV-GFP). In FIGS. 4A and 4B, "Naïve" indicates C8-D1A cells that were not activated and therefore, produced minimal FAM19A5 protein into culture.

In FIG. 6A, the effect on mechanical allodynia is shown as the frequency in which the animals reacted in pain to stimulation with a Von Frey microfilament. In FIG. 6B, the effect on thermal hyperalgesia is shown as paw withdrawal latency (how long the animals took to pull away from the heat source). "*" indicates a statistical significance of $p<0.05$, compared to the control group.

In FIG. 7A, the effect on mechanical allodynia is shown as the frequency in which the animals reacted in pain to stimulation with a Von Frey microfilament. In FIG. 7B, the effect on thermal hyperalgesia is shown as paw withdrawal latency (how long the animals took to pull away from the heat source). "*" indicates a statistical significance of $p<0.05$, compared to the control group.

In FIG. 8A, the effect on mechanical allodynia is shown as the frequency in which the animals reacted in pain to stimulation with a Von Frey microfilament (out of 10 stimuli). In FIG. 8B, the effect on thermal hyperalgesia is shown as paw withdrawal latency (how long the animals took to pull away from the heat source). "*" indicates a statistical significance of $p<0.05$, compared to the control group.

In FIG. 9A, the effect on mechanical allodynia is shown as the frequency in which the animals reacted in pain to stimulation with a Von Frey microfilament (out of 10 stimuli). In FIG. 9B, the effect on thermal hyperalgesia is shown as paw withdrawal latency (how long the animals took to pull away from the heat source). "*" indicates a statistical significance of $p<0.05$, compared to the control group.

In FIG. 10A, the effect on mechanical allodynia is shown as the frequency in which the animals reacted in pain to stimulation with a Von Frey microfilament (out of 10 stimuli). In FIG. 10B, the effect on thermal hyperalgesia is shown as paw withdrawal latency (how long the animals took to pull away from the heat source). "*" indicates a statistical significance of p<0.05, compared to the control group.

In FIG. 11A, the animals received one of the following: (i) scAAV1-CMV-GFP (open circle); (ii) scAAV1-CMV-3-2-ScFv (closed circle); (iii) scAAV9-CMV-mIL-10 (open square); (iv) scAAV1-CMV-3-2-ScFv+scAAV9-CMV-mIL-10 (closed square). In FIG. 11B, the animals received one of the following: (i) scAAV9-CMV-GFP (open circle); (ii) scAAV9-CMV-2-13-ScFv (closed circle); (iii) scAAV9-CMV-mIL-10 (open square); (iv) scAAV9-CMV-2-13-ScFv+scAAV9-CMV-mIL-10 (closed square). In FIG. 11C, the animals received one of the following: (i) scAAV9-CMV-GFP (open circle); (ii) scAAV9-CMV-1-30-ScFv (closed circle); (iii) scAAV9-CMV-mIL-10 (open square); (iv) scAAV9-CMV-1-30-ScFv+scAAV9-CMV-mIL-10 (closed square). "*" indicates a statistical significance of $p<0.05$, compared to the control group.

DETAILED DESCRIPTION OF THE DISCLOSURE

Figure 1:
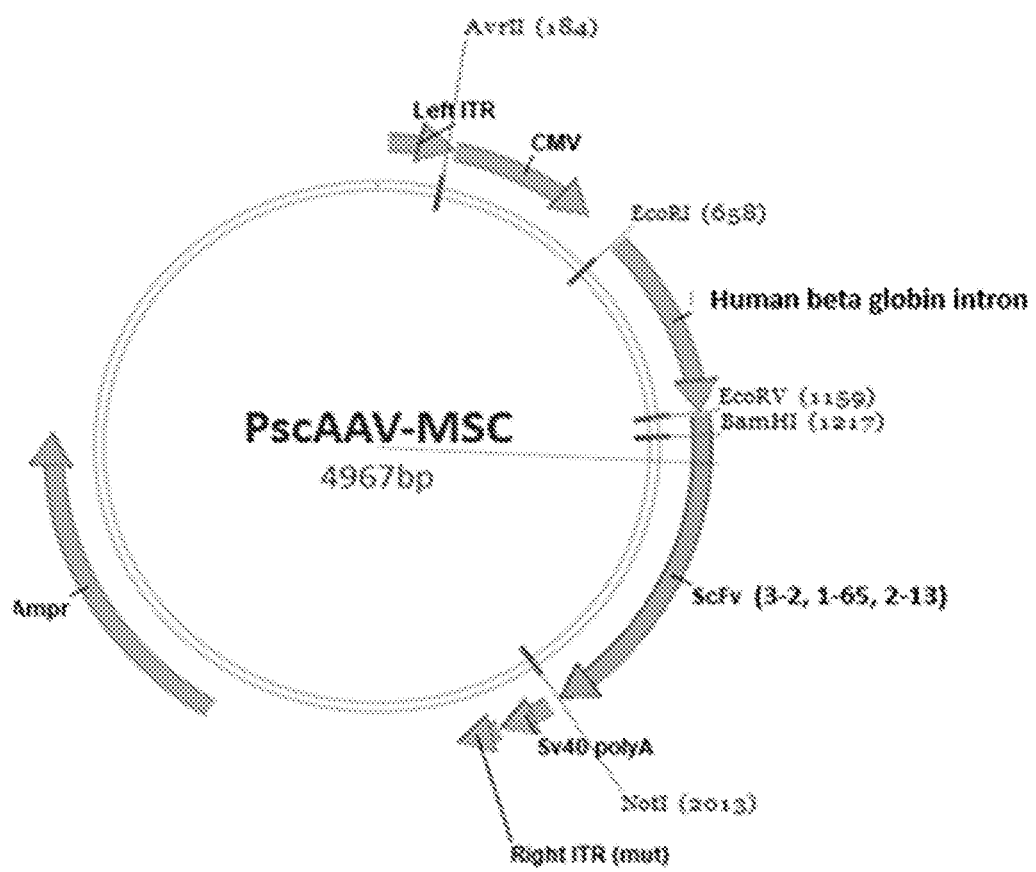
FIG. 1 provides a map of the pscAAV construct, which was used to generate the anti-FAM19A5 scFv AAV constructs described in the Examples.

Disclosed herein are compositions, e.g., adeno-associated virus (AAV) vector, comprising a nucleic acid that encodes an antagonist against a family with sequence similarity 19, member A5 (FAM19A5) protein. Also provided herein are methods of using such compositions as gene therapy for the treatment of a disease or disorder, e.g., neuropathic pain.

To facilitate an understanding of the disclosure provided herein, a number of terms and phrases are defined. Additional definitions are set forth throughout the detailed description.

I. Definitions

Throughout this disclosure, the term "a" or "an" entity refers to one or more of that entity; for example, "an antibody," is understood to represent one or more antibodies. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

As used herein, the term "adeno-associated virus" or "AAV" refers to all adeno-associated viruses that are used in gene therapy, including derivatives thereof, virus subtypes, and naturally occurring and recombinant forms. The various serotypes of AAVs can be used as recombinant gene transfer viruses to transduce many different cell types. Non-limiting examples of AAV serotypes include AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), avian AAV, bovine AAV, canine AAV, equine AAV, primate AAV, non-primate AAV, and ovine AAV. In some embodiments, the AAV is AAV type 8 (AAV-8) or AAV type 9 (AAV-9).

The genomic organization of all known AAV serotypes is very similar. The genome of AAV is a linear, single-stranded DNA molecule that is less than about 5,000 nucleotides (nt) in length. The genome comprises three genes, rep (Replication), cap (Capsid), and aap (Assembly). These three genes give rise to at least nine gene products through the use of three promoters, alternative translation start sites, and differential splicing. AAV vectors of the present disclosure can include additional elements that function in cis or in trans. In particular embodiments, an AAV vector that includes a vector genome also has one or more inverted terminal repeat (ITR) sequences that flank the 5' or 3' terminus of the donor sequence; an expression control element that drives transcription (e.g., a promoter or enhancer) of the donor sequence, such as a constitutive or regulatable control element, a tissue-specific expression control element, an intron sequence, a stuffer or filler polynucleotide sequence; and/or a poly-adenine sequence located at 3' of the donor sequence.

AAV possesses unique features that make it attractive as a vector for delivering foreign DNA to cells. AAV infection of cells in culture has generally been noncytopathic, and natural infection of humans and other animals is silent and asymptomatic. Moreover, AAV infects many different types of mammalian cells allowing the possibility of targeting many different tissues in vivo. AAV also possess additional advantages that make it a particularly attractive viral system for gene delivery, including promotion of a milder immune response compared to other forms of gene delivery and persistent expression in both dividing and quiescent cells as a non-integrating vector. Also, AAV withstands the conditions used to inactivate adenovirus (56° to 65° C. for several hours), making cold preservation of rAAV-based vaccines less critical. In some embodiments, the AAV of the present disclosure comprises one or more of these features.

The term "AAV vector," as used herein, refers to any vector that comprises or derives from components of an adeno-associated virus (AAV) and is suitable to infect mammalian cells, including human cells, of any of a number of tissue types, such as brain, heart, lung, skeletal muscle, liver, kidney, spleen, or pancreas, whether in vitro or in vivo. The term "AAV vector" can be used to refer to an AAV type viral particle (or virion) comprising at least a nucleic acid molecule encoding a protein of interest. In some embodiments, the AAV vector is a "recombinant AAV vector," which refers to an AAV vector comprising a polynucleotide sequence not of AAV origin (i.e., a polynucleotide heterologous to AAV, e.g., an anti-FAM19A5 antibody), typically a sequence of interest for the genetic transformation of a cell. In general, the heterologous polynucleotide is flanked by at least one, and generally by two AAV inverted terminal repeat sequences (ITRs). The term AAV vector encompasses both AAV vector particles and AAV vector plasmids.

As used herein, the term "ITR" refers to inverted terminal repeats. Typically, ITRs are involved in parvovirus (e.g., AAV) DNA replication and rescue, or excision, from prokaryotic plasmids (Daya, S., et al., *Clin Microbiol Rev* 21(4): 583-593 (2008). In addition, ITRs are generally thought to be the minimum sequences required for AAV proviral integration and for packaging of AAV DNA into virions. Accordingly, these elements are essential for efficient multiplication of a parvovirus genome.

As used herein, the term "serotype" refers to a subdivision of AAV that is identifiable by serologic or DNA sequencing methods and can be distinguishable by its antigenic character. In addition, the term "isolate," when used in reference to AAV, means a particular AAV serotype obtained from a specific source. The skilled artisan readily will recognize the difference between an "isolated AAV," which refers to the relative purity of an AAV sample, and an "AAV isolate," which refers to a clonally derived preparation of a particular AAV serotype, based on the context in which the term is used.

The term "capsid-free" or "capsid-less" (or variations thereof) vector or nucleic acid molecule refers to a vector construct free from a capsid. In some embodiments, the capsid-less vector or nucleic acid molecule does not contain sequences encoding, e.g., an AAV Rep protein.

In some embodiments, AAV disclosed herein replicates using a helper virus. As used herein, a "helper virus" for AAV refers to a virus that allows AAV (e.g. wild-type AAV) to be replicated and packaged by a mammalian cell. A variety of such helper viruses for AAV are known in the art, including adenoviruses, herpesviruses, and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

In some embodiments, AAV of the present disclosure has distinct tissue targeting capabilities (e.g., tissue tropisms). In some embodiments, the AAV further exhibit increased transduction or tropism in one or more human stem cell types as compared to non-variant parent capsid polypeptides. In some embodiments, the human stem cell types include but are not limited to embryonic stem cells, adult tissue stem cells (i.e., somatic stem cells), bone marrow, progenitor cells, induced pluripotent stem cells, and reprogrammed stem cells. In some embodiments, adult stem cells can include organoid stem cells (i.e., stem cells derived from any organ or organ system of interest within the body). In some embodiments, the target tissue of an AAV is gonad, diaphragm, heart, stomach, liver, spleen, pancreas, or kidney. In some embodiments, the AAV targets organs of the body include, but are not limited to, skin, hair, nails, sense receptors, sweat gland, oil glands, bones, muscles, brain, spinal cord, nerve, pituitary gland, pineal gland, hypothalamus, thyroid gland, parathyroid, thymus, adrenals, pancreas (islet tissue), heart, blood vessels, lymph nodes, lymph vessels, thymus, spleen, tonsils, nose, pharynx, larynx, trachea, bronchi, lungs, mouth, pharynx, esophagus, stomach, small intestine, large intestine, rectum, anal canal, teeth, salivary glands, tongue, liver, gallbladder, pancreas, appendix, kidneys, ureters, urinary bladder, urethra, testes, ductus (vas) deferens, urethra, prostate, penis, scrotum, ovaries, uterus, uterine (fallopian) tubes, vagina, vulva, and mammary glands (breasts). Organ systems of the body include but are not limited to the integumentary system, skeletal system, muscular system, nervous system, endocrine system, cardiovascular system, lymphatic system, respiratory system, digestive system, urinary system, and reproductive system. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%.

The phrases "tropism" and "transduction" are interrelated, but there are differences. The term "tropism" as used herein refers to the ability of an AAV vector or virion to infect one or more specified cell types, but can also encompass how the vector functions to transduce the cell in the one or more specified cell types; i.e., tropism refers to preferential entry of the AAV vector or virion into certain cell or tissue type(s) and/or preferential interaction with the cell surface that facilitates entry into certain cell or tissue types, optionally and preferably followed by expression (e.g., transcription and, optionally, translation) of sequences carried by the AAV vector or virion in the cell, e.g., for a recombinant virus, expression of the heterologous nucleotide sequence(s). As used herein, the term "transduction" refers to the ability of an AAV vector or virion to infect one or more particular cell types; i.e., transduction refers to entry of the AAV vector or virion into the cell and the transfer of genetic material contained within the AAV vector or virion into the cell to obtain expression from the vector genome. In some cases, but not all cases, transduction and tropism may correlate.

As used herein, the term "multiplicity of infection" or "MOI" refers to the ratio of integrating vectors:host cells used during transfection or transduction of host cells. For example, if 1,000,000 vectors are used to transduce 100,000 host cells, the multiplicity of infection is 10. The use of this term is not limited to events involving transduction, but instead encompasses introduction of a vector into a host by methods such as lipofection, microinjection, calcium phosphate precipitation, and electroporation.

The term "neuropathic pain" refers to a pain due to an injury, damage, and/or improper function affecting any level of the central nervous system (CNS) and/or the peripheral nervous system. The term "neuropathic pain" includes any and all types of neuropathic pain regardless of the cause and any and all symptoms of neuropathic pain.

Neuropathic pain includes central neuropathic pain and peripheral neuropathic pain. As used herein, the term "central neuropathic pain" refers to pain resulting from a disorder, congenital defect, or injury to the central nervous system (i.e., the brain or spinal cord). As used herein, the term "peripheral neuropathic pain" refers to pain resulting from an injury or an infection of the peripheral sensory nerves.

Symptoms of neuropathic pain can include persistent/chronic pain, spontaneous pain, as well as allodynia (e.g., a painful response to a stimulus that normally is not painful), hyperalgesia (e.g., an accentuated response to a painful stimulus that usually causes only a mild discomfort, such as a pin prick), hyperesthesia (e.g., excessive physical sensitivity to stimuli, especially of the skin), or hyperpathia (e.g., where a short discomfort becomes a prolonged severe pain). In some embodiments, symptoms can be long-lasting and persist after resolution of the primary cause, if one was present. Merck Manual, Neuropathic Pain, available at merckmanuals.com/professional/neurologic-disorders/pain/neuropathic-pain; Campbell J. N. and Meyer R. A. *Neuron* 52(1): 77-92 (2006).

In some embodiments, the types of neuropathic pain can include: (1) neuralgia, (2) deafferentation pain syndrome, (3) complex regional pain syndrome (CRPSs), and (4) neuropathy (central or peripheral).

In some embodiments, the neuropathic pain is a neuralgia, which refers to a pain that radiates along the course of one or more specific nerves (e.g., cranial nerves), usually without any demonstrable pathological change in the nerve structure. Neuralgia includes, without limitation, trigeminal neuralgia (TN), atypical trigeminal neuralgia (ATN), occipital neuralgia, glossopharyngeal neuralgia, postherpetic neuralgia (caused by shingles or herpes), peripheral nerve injury pain, sciatica, low back pain, and an atypical facial pain. Chemical irritation, chronic kidney disease, diabetes, inflammation, trauma (including surgery), compression of the nerves by nearby structures (for instance, tumors), certain medicines (e.g., cisplatin, paclitaxel, or vincristine), porphyria (blood disorder), and infections (e.g., herpes zoster (shingles), HIV/AIDS, Lyme disease, or syphilis) can all lead to neuralgia.

In some embodiments, the neuropathic pain is a deafferentation pain syndrome, which can result from a loss of the sensory input from a portion of the body (e.g., caused by interruption of either peripheral sensory fibers or nerves from the central nervous system). Deafferentation pain syndrome includes, without limitation, an injury to the brain or spinal cord, a post-stroke pain, a phantom pain, a paraplegia, a brachial plexus avulsion injuries, and lumbar radiculopathies.

In some embodiments, the neuropathic pain is a "Complex Regional Pain Syndrome" (CRPS), which is a chronic pain condition that most commonly affects an arm or a leg. In some embodiments, the CRPS develops after an injury, surgery, stroke, or heart attack. In certain embodiments, the CRPS is a type I CRPS (CRPS-I) (also known as reflex sympathetic dystrophy syndrome). Individuals without a confirmed nerve injury are often classified as having CRPS-I. In other embodiments, the CRPS is a type II CRPS (CRPS-II) (also known as causalgia), which is associated with a confirmed nerve injury.

In some embodiments, the neuropathic pain is a neuropathy, which refers to a pain resulting from a functional or pathological change (e.g., a disease or damage) in a nerve. Neuropathy can often be characterized clinically by sensory or motor neuron abnormalities. In certain embodiments, the neuropathy is a central neuropathy (e.g., a functional or pathological change in the central nervous system). In other embodiments, the neuropathy is a peripheral neuropathy (e.g., a functional or pathological change in one or more peripheral nerves, including a motor nerve, a sensory nerve, an autonomic nerve, or a combination thereof). In some embodiments, the peripheral neuropathy involves a functional or pathological change to a single nerve or nerve group (i.e., mononeuropathy). In some embodiments, the peripheral neuropathy involves a functional or pathological change affecting multiple nerves (locally or systemically) (i.e., polyneuropathy). In some embodiments, the peripheral neuropathy affects both sides of the body roughly the same (i.e., symmetrical polyneuropathy). In some embodiments, the peripheral neuropathy affects disparate areas of the body (e.g., mononeuritis multiplex, multifocal mononeuropathy, or multiple mononeuropathy).

As used herein, "mononeuropathy" is a peripheral neuropathy involving loss of movement or sensation to an area caused by damage or destruction to a single peripheral nerve or nerve group. Mononeuropathy is most often caused by an injury or trauma to a local area, which, e.g., results in prolonged pressure/compression on a single nerve. However, certain systemic disorders (e.g., mononeuritis multiplex) can also cause mononeuropathy. In some embodiment, the injury or trauma to a local area causes destruction of the myelin sheath (covering) of the nerve or of part of the nerve cell (the axon), which can slow down or prevent the conduction of impulses through the nerve. In some embodiment, the mononeuropathy can affect any part of the body. Examples of mononeuropathic pain include, without limitation, a sciatic nerve dysfunction, a common peroneal nerve dysfunction, a radial nerve dysfunction, an ulnar nerve dysfunction, a cranial mononeuropathy VI, a cranial mononeuropathy VII, a cranial mononeuropathy III (compression type), a cranial mononeuropathy III (diabetic type), an axillary nerve dysfunction, a carpal tunnel syndrome, a femoral nerve dysfunction, a tibial nerve dysfunction, a Bell's palsy, a thoracic outlet syndrome, a carpal tunnel syndrome, and a sixth (abducent) nerve palsy. Finnerup N. B. et al., *Pain* 157(8): 1599-1606 (2016); National Institute of Neurological Disorders and Stroke, Peripheral Neuropathy Fact Sheet, available at ninds.nih.gov/disorders/peripheralneuropathy/detail_peripheralneuropathy.htm. In some embodiments, the mononeuropathic pain is a sciatica.

As used herein, "polyneuropathy" is a peripheral neuropathy involving the loss of movement or sensation to an area caused by damage or destruction to multiple peripheral nerves. Polyneuropathic pain includes, without limitation, post-polio syndrome, postmastectomy syndrome, diabetic neuropathy, alcohol neuropathy, amyloid, toxins, AIDS, hypothyroidism, uremia, vitamin deficiencies, chemotherapy-induced pain, 2',3'-didexoycytidine (ddC) treatment, Guillain-Barre syndrome or Fabry's disease. Finnerup N. B. et al., *Pain* 157(8): 1599-1606 (2016); National Institute of Neurological Disorders and Stroke, Peripheral Neuropathy Fact Sheet, available at ninds.nih.gov/disorders/peripheralneuropathy/detail_peripheralneuropathy.htm. In some embodiments, the polyneuropathy is a diabetic peripheral neuropathy. In certain embodiments, the diabetic peripheral neuropathy is caused by the high blood glucose levels (blood sugar) and/or the high levels of fat (e.g., triglycerides) in the blood of diabetic subjects, which causes damage to the peripheral nerves of the subject.

In some embodiments, peripheral neuropathy disclosed herein can be classified based on the part of the nerve cell that is damaged or affected (e.g., axon, myelin sheath, or the cell body). In some embodiments, the peripheral neuropathy is a distal axonopathy, which results from a metabolic or toxic derangement of the axons. In some embodiments, the metabolic derangement comprises diabetes, renal failure, deficiency syndromes such as malnutrition and alcoholism. In some embodiments, the metabolic derangement is diabetes, and the distal axonopathy is diabetic neuropathy.

In some embodiments, the peripheral neuropathy is a myelinopathy, which results from a primary attack on myelin or the myelinating Schwann cells, causing an acute failure of impulse conduction. The most common cause is acute inflammatory demyelinating polyneuropathy (AIDP; aka Guillain-Barre syndrome), though other causes include chronic inflammatory demyelinating syndrome (CIDP), genetic metabolic disorders (e.g., leukodystrophy), or toxins.

In some embodiments, the peripheral neuropathy is a neuronopathy, which is due to a destruction of peripheral nervous system (PNS) neurons. In some embodiments, the neuronopathy is caused by motor neuron diseases, sensory neuronopathies (e.g., Herpes zoster), toxins or autonomic dysfunction. In some embodiments, the neuronopathy is caused by neurotoxins, such as the chemotherapy agent vincristine.

Neuropathic pain can result from or be associated with various etiologies (e.g., a physical injury (e.g., trauma or repetitive stress), a disease or disorder, exposure to a toxic agent, or a combination thereof). In some embodiments, the neuropathic pain results from or is associated with a traumatic injury or damage, such as, for example, a nerve compression injury (e.g., a nerve crush, a nerve stretch, a nerve entrapment or an incomplete nerve transsection); a spinal cord injury (e.g., a hemisection of the spinal cord); an injury or damage to a peripheral nerve (e.g., a motor nerve, sensory nerve, or autonomic nerve, or a combination thereof.), a limb amputation; a contusion; an inflammation (e.g., an inflammation of the spinal cord); or a surgical procedure. In some embodiments, the neuropathic pain results from or is associated with a repetitive stress, including, for example, repetitive, awkward, and/or forceful activities that require movement of any group of joints for prolonged periods. Not be bound by any one theory, the resulting irritation can cause ligaments, tendons, and muscles to become inflamed and swollen, constricting the narrow passageways through which nerves pass (e.g., ulnar neuropathy and carpal tunnel syndrome, which are neuropathy from trapped or compressed nerves at the elbow or wrist.). In some embodiments, the neuropathic pain results from or is associated with a disease or disorder including, for example, an ischemic event (e.g., a stroke or a heart attack), multiple sclerosis, a metabolic and/or endocrine disease or disorder (e.g., diabetes mellitus, metabolic disease, and acromegaly, a condition caused by overproduction of growth hormone and is characterized by the abnormal enlargement of parts of the skeleton, including the joints, leading to nerve entrapment and pain.), a small vessel disease that causes decreased oxygen supply to the peripheral nerves leading to nerve tissue damage (e.g., vasculitis, namely blood vessel inflammation), an autoimmune disease (e.g., Sjogren's syndrome, lupus, rheumatoid arthritis, and acute inflammatory demyelinating neuropathy, also known as Guillain-Barrè syndrome), a kidney disorder, a cancer or tumor (e.g., a neoplastic tumor, neuromas, paraneoplastic syndromes, and toxicity from the chemotherapeutic agents and radiation in cancer treatment), an infection (e.g., infections by viruses such as herpes varicellazoster (shingles), Epstein-Barr virus, West Nile virus, cytomegalovirus, and herpes simplex viruses, an acquired immune deficiency syndrome (AIDS), or by bacteria such as Lyme disease, diphtheria, and leprosy), an inflammatory disorder, a peripheral nerve disorder (e.g., neuroma), a genetic disorder, either hereditary or arise de novo (e.g., Charcot-Marie-Tooth disorders include extreme weakening and wasting of muscles in the lower legs and feet, gait abnormalities, loss of tendon reflexes, and numbness in the lower limbs), a mononeuropathy or a polyneuropathy. In some embodiments, the neuropathic pain results from or is associated with an infectious agent (e.g., tick-borne infection, herpes varicellazoster, Epstein-Barr virus, West Nile virus, cytomegalovirus, herpes simplex viruses, AIDS). In some embodiments, the neuropathic pain results from or is associated with an exposure to a toxic agent, including, for example, a drug, an alcohol, a heavy metal (e.g., lead, arsenic, mercury), an industrial agent (e.g., a solvent, fumes from a glue) or nitrous oxide.

The term "a neuropathic pain associated with" a disease or disorder refers to a neuropathic pain that accompanies a disease or disorder (e.g., those disclosed herein), or caused by or resulting from a disease or a disorder (e.g., those disclosed herein).

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

As used herein, "administering" refers to the physical introduction of a therapeutic agent or a composition comprising a therapeutic agent to a subject, using any of the various methods and delivery systems known to those skilled in the art. Preferred routes of administration for antibodies described herein include intravenous, intraperitoneal, intramuscular, subcutaneous, spinal, intravitreal, or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intravitreal, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The term "therapeutically effective amount" as used herein refers to an amount of a drug, alone or in combination with another therapeutic agent, effective to "treat" a disease or disorder in a subject or reduce the risk, potential, possibility or occurrence of a disease or disorder (e.g., a neuropathic pain). A "therapeutically effective amount" includes an amount of a drug or a therapeutic agent that provides some improvement or benefit to a subject having or at risk of having a disease or disorder (e.g., a neuropathic pain disclosed herein). Thus, a "therapeutically effective" amount is an amount that reduces the risk, potential, possibility or occurrence of a disease or provides disorder or some alleviation, mitigation, and/or reduces at least one indicator (e.g., a neuropathic pain), and/or decrease in at least one clinical symptom of a disease or disorder.

As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

The term "family with sequence similarity 19, member A5" or "FAM19A5" refers to a protein that belongs to the TAFA family (also known as FAM19 family) of five highly homologous proteins and is predominantly expressed in brain and the spinal cord. FAM19A5 is also known as TAFA5 or Chemokine-like protein TAFA-5.

In humans, the gene encoding FAM19A5 is located on chromosome 22. There are multiple human FAM19A5 (UniProt: Q7Z5A7) isoforms, which are believed to be produced by alternative splicing: isoform 1 (UniProt: Q7Z5A7-1), which consists of 132 amino acids, isoform 2 (UniProt: Q7Z5A7-2), which consists of 125 amino acids, and isoform 3 (UniProt: Q7Z5A7-3), which consists of 53 amino acids. Human FAM19A5 protein is believed to exist as both membrane bound and soluble (secreted) forms. Isoform 1 is believed to be a membrane with one transmembrane region. Isoform 2, which was reported in Tang T. Y. et al., *Genomics* 83(4):727-34 (2004) as a secreted protein (soluble), contains a signal peptide at amino acid positions 1-25. Isoform 1 is believed to be a membrane protein. Below are the amino acid sequences of the three known human FAM19A5 isoforms.

(I) Isoform 1 (UniProt: Q7Z5A7-1, transmembrane protein): this isoform has been chosen as the canonical sequence.
(SEQ ID NO: 1)
MAPSPRTGSR QDATALPSMS STFWAFMILA SLLIAYCSQL

AAGTCEIVTL DRDSSQPRRT IARQTARCAC RKGQIAGTTR

ARPACVDARI IKTKQWCDML PCLEGEGCDL LINRSGWTCT

QPGGRIKTTT VS (II) Isoform 2 (UniProt: Q7Z5A7-2, soluble protein):
(SEQ ID NO: 2)
MQLLKALWAL AGAALCCFLV LVIHAQFLKE GQLAAGTCEI

VTLDRDSSQP RRTIARQTAR CACRKGQIAG TTRARPACVD

ARIIKTKQWC DMLPCLEGEG CDLLINRSGW TCTQPGGRIK

TTTVS (III) Isoform 3 (UniProt: Q7Z5A7-3):
(SEQ ID NO: 3)
MYHHREWPAR IIKTKQWCDM LPCLEGEGCD LLINRSGWTC

TQPGGRIKTT TVS

The term "FAM19A5" includes any variants or isoforms of FAM19A5 which are naturally expressed by cells. Accordingly, antibodies described herein can cross-react with different isoforms in the same species (e.g., different isoforms of human FAM19A5), or cross-react with FAM19A5 from species other than human (e.g., mouse FAM19A5). Alternatively, the antibodies can be specific for human FAM19A5 and cannot exhibit any cross-reactivity with other species. FAM19A5 or any variants and isoforms thereof, can either be isolated from cells or tissues which naturally express them or be recombinantly produced. The polynucleotide encoding human FAM19A5 has the GenBank Accession No. BC039396 and the following sequence:

TABLE 1A

Polynucleotide sequence of human FAM19A5

Polynucleotide sequence (SEQ ID NO: 4)

FAM19A5
(GenBank
Accession
No.
BC039396)

ggcggcggag gatggcgcgc gcggggcccg
cacgtggagg ccggcgcggg ggcgcgggca
gggccggctg ctgagacgcg ctgctgcccc
ccgcgcgggc gccgcggctt caatggcgcc
atcgcccagg accggcagcc ggcaagatgc
gaccgccctg cccagcatgt cctcaacttt
ctgggcgttc atgatcctgg ccagcctgct
catcgcctac tgcagtcagc tggccgccgg
cacctgtgag attgtgacct tggaccggga
cagcagccag cctcggagga cgatcgcccg
gcagaccgcc cgctgtgcgt gtagaaaggg
gcagatcgcc ggcaccacga gagcccggcc
cgcctgtgtg gacgcaagaa tcatcaagac
caagcagtgt tgtgacatgc ttccgtgtct
ggaggggaa ggctgcgact tgttaatcaa
ccggtcaggc tggacgtgca cgcagcccgg
cgggaggata aagaccacca cggtctcctg
acaaacacag ccctgaggg ggcccgggga
gtggccttgg ctccctggag agcccacgtc
tcagccacag ttctccactc gcctcggact
tcacccgttc tctgccgccc gcccactccg
tttccctgtg gtccgtgaag gacggcctca
ggccttggca tcctgagctt cggtctgtcc
agccgacccg aggaggccgg actcagacac
ataggcgggg ggcggcacct ggcatcagca
atacgcagtc tgtgggagcc cggccgcgcc
cagccccgc cgaccgtggc gttggccctg
ctgtcctcag aggaggagga ggaggaggca
gctccggcag ccacagaagg ctgcagccca
gcccgcctga gacacgacgc ctgccccagg
ggactgtcag gcacagaagc ggcctcctcc
cgtgcccag actgtccgaa ttgcttttat
tttcttatac tttcagtata ctccatagac
caaagagcaa aatctatctg aacctggacg
caccctcact gtcagggtcc ctggggtcgc
ttgtgcgggc gggagggcaa tggtggcaga
gacatgctgg tggcccggc ggagcggaga
gggcggccgt ggtggaggcc tccacccag
gagcaccccg cacaccctcg gaggacgggc
ttcggctgcg cggaggccgt ggcacacctg
cgggaggcag cgacggcccc cacgcagacg
ccgggaacgc aggccgcttt attcctctgt
acttagatca acttgaccgt actaaaatcc
ctttctgttt taaccagtta aacatgcctc
ttctacagct ccattttga tagttggata
atccagtatc tgccaagagc atgttgggtc
tcccgtgact gctgcctcat cgataccca
tttagctcca gaaagcaaag aaaactcgag
taacacttgt ttgaaagaga tcattaaatg
tattttgcaa agcccaaaaa aaaaaaaaa a The term "antagonist against a FAM19A5 protein" refers to all antagonists that suppress the expression of the FAM19A5 protein. Such antagonist can be a peptide, a nucleic acid, or a compound. More specifically, the antagonist can be an antisense-oligonucleotide, siRNA, shRNA, miRNA, dsRNA, aptamer, PNA (peptide nucleic acid) targeting FAM19A5, or a vector including the same. In some embodiments, the antagonist can be an antibody, or an antigen-binding portion thereof, that specifically binds to the FAM19A5 protein.

The terms "antibody" and "antibodies" are terms of art and can be used interchangeably herein and refer to a molecule with an antigen binding site that specifically binds an antigen. The terms as used to herein include whole antibodies and any antigen binding fragments (i.e., "antigen-binding portions") or single chains thereof. An "antibody" refers, in some embodiments, to a glycoprotein comprising at least two heavy (H) chains and two light (L) chains inter-connected by disulfide bonds, or an antigen binding portion thereof. In other embodiments, an "antibody" refers to a single chain antibody comprising a single variable domain, e.g., VHH domain. Each heavy chain is comprised of a heavy chain variable region (abbreviated herein as VH) and a heavy chain constant region. In certain naturally occurring antibodies, the heavy chain constant region is comprised of three domains, CH1, CH2 and CH3. In certain naturally occurring antibodies, each light chain is comprised of a light chain variable region (abbreviated herein as VL) and a light chain constant region. The light chain constant region is comprised of one domain, CL.

The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "Kabat numbering" and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat E A & Wu T T (1971) *Ann NY Acad Sci* 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

The phrases "amino acid position numbering as in Kabat," "Kabat position," and grammatical variants thereof refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82. See TABLE 1B.

TABLE 1B

| Loop | Kabat | AbM | Chothia |
| --- | --- | --- | --- |
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35B | H26-H35B | H26-H32 |
| | | (Chothia Numbering) | |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See, e.g., Lefranc, M. P. et al., *Dev. Comp. Immunol.* 27: 55-77(2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

For all heavy chain constant region amino acid positions discussed in the present disclosure, numbering is according to the EU index first described in Edelman et al., 1969, *Proc. Natl. Acad. Sci. USA* 63(1):78-85, describing the amino acid sequence of myeloma protein EU, which is the first human IgG1 sequenced. The EU index of Edelman et al. is also set forth in Kabat et al., 1991, Sequences of Proteins of Immunological Interest, 5th Ed., United States Public Health Service, National Institutes of Health, Bethesda. Thus, the phrases "EU index as set forth in Kabat" or "EU index of Kabat" and "position . . . according to the EU index as set forth in Kabat," and grammatical variants thereof refer to the residue numbering system based on the human IgG1 EU antibody of Edelman et al., as set forth in Kabat 1991.

The numbering system used for the variable domains (both heavy chain and light chain) and light chain constant region amino acid sequence is that set forth in Kabat 1991.

Antibodies can be of any type (e.g., IgG, IgE, IgM, IgD, IgA or IgY), any class (e.g., IgD, IgG2, IgG3, IgG4, IgA1 or IgA2), or any subclass (e.g., IgG1, IgG2, IgG3 and IgG4 in humans, and IgG1, IgG2a, IgG2b and IgG3 in mice) of immunoglobulin molecule. Immunoglobulins, e.g., IgG1, exist in several allotypes, which differ from each other in at most a few amino acids. An antibody disclosed herein can be from any of the commonly known isotypes, classes, subclasses, or allotypes. In certain embodiments, the antibodies described herein are of the IgG1, IgG2, IgG3 or IgG4 subclass or any hybrid thereof. In certain embodiments, the antibodies are of the IgG2, IgG4 or IgG2/IgG4 subclass.

"Antibody" includes, by way of example, both naturally occurring and non-naturally occurring antibodies; monoclonal and polyclonal antibodies; chimeric and humanized antibodies; human and non-human antibodies; wholly synthetic antibodies; single chain antibodies; monospecific antibodies; multispecific antibodies (including bispecific antibodies); tetrameric antibodies comprising two heavy chain and two light chain molecules; an antibody light chain monomer; an antibody heavy chain monomer; an antibody light chain dimer, an antibody heavy chain dimer; an antibody light chain-antibody heavy chain pair; intrabodies; heteroconjugate antibodies; monovalent antibodies; single chain antibodies; camelized antibodies; affibodies; anti-idiotypic (anti-Id) antibodies (including, e.g., anti-anti-Id antibodies), and single-domain antibodies (sdAbs), which include binding molecules consisting of a single monomeric variable antibody domain that are fully capable of antigen binding (e.g., a VH domain or a VL domain). Harmen M. M. and Haard H. J. *Appl Microbiol Biotechnol.* 77(1): 13-22 (2007)).

The terms "antigen-binding portion" and "antigen-binding fragment" of an antibody, as used herein, are interchangeable and refer to one or more fragments of an antibody that retain the ability to specifically bind to an antigen (e.g., human FAM19A5). Such "fragments" are, for example, between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody, e.g., an anti-FAM19A5 antibody described herein, include (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, and disulfide-linked Fvs (sdFv) (v) a dAb fragment (Ward et al., (1989) *Nature* 341:544-546), which consists of a VH domain; and (vi) an isolated complementarity determining region (CDR) or (vii) a combination of two or more isolated CDRs which can optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR).

Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

As used herein, the term "heavy chain" (HC) when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "light chain" (LC) when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, a Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains; IgM and IgE Fc regions comprise three heavy chain constant domains (CH domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. The CH2 domain of a human IgG Fc region extends from about amino acid 231 to about amino acid 340, whereas the CH3 domain is positioned on C-terminal side of a Cm domain in a Fc region, i.e., it extends from about amino acid 341 to about amino acid 447 of an IgG. As used herein, the Fc region can be a native sequence Fc, including any allotypic variant, or a variant Fc (e.g., a non-naturally occurring Fc). Fc can also refer to this region in isolation or in the context of a Fc-comprising protein polypeptide such as a "binding protein comprising a Fc region," also referred to as an "Fc fusion protein" (e.g., an antibody or immunoadhesin).

A "native sequence Fc region" or "native sequence Fc" comprises an amino acid sequence that is identical to the amino acid sequence of a Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc includes the various allotypes of Fcs (see, e.g., Jefferis et al. (2009) *mAbs* 1:1; Vidarsson G. et al. *Front Immunol.* 5:520 (published online Oct. 20, 2014)).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Human IgG1 binds to most human Fc receptors and elicits the strongest Fc effector functions. It is considered equivalent to murine IgG2a with respect to the types of activating Fc receptors that it binds to. Conversely, human IgG4 elicits the least Fc effector functions. Vidarsson G. et al., *Front Immunol.* 5:520 (published online Oct. 20, 2014).

The constant region can be manipulated, e.g., by recombinant technology, to eliminate one or more effector functions. An "effector function" refers to the interaction of an antibody Fc region with a Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and down regulation of a cell surface receptor (e.g., the B cell receptor; BCR). Such effector functions generally require the Fc region to be combined with a binding domain (e.g., an antibody variable domain). Accordingly, the term "a constant region without the Fc function" include constant regions with reduced or without one or more effector functions mediated by Fc region.

Effector functions of an antibody can be reduced or avoided by different approaches. Effector functions of an antibody can be reduced or avoided by using antibody fragments lacking the Fc region (e.g., such as a Fab, F(ab')$_2$, single chain Fv (scFv), or a sdAb consisting of a monomeric VH or VL domain). Alternatively, the so-called aglycosylated antibodies can be generated by removing sugars that are linked to particular residues in the Fc region to reduce the effector functions of an antibody while retaining other valuable attributes of the Fc region (e.g., prolonged half-life and heterodimerization). Aglycosylated antibodies can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells). See, e.g., U.S. Pub. No. 20120100140. Another approach is to employ Fc regions from an IgG subclass that have reduced effector function, for example, IgG2 and IgG4 antibodies are characterized by having lower levels of Fc effector functions than IgG1 and IgG3. The residues most proximal to the hinge region in the CH2 domain of the Fc part are responsible for effector functions of antibodies as it contains a largely overlapping binding site for C1q (complement) and IgG-Fc receptors (FcγR) on effector cells of the innate immune system. Vidarsson G. et al., *Front Immunol.* 5:520 (published online Oct. 20, 2014). Accordingly, antibodies with reduced or without Fc effector functions can be prepared by generating, e.g., a chimeric Fc region which comprises a CH2 domain from an IgG antibody of the IgG4 isotype and a CH3 domain from an IgG antibody of the IgG1 isotype, or a chimeric Fc region which comprises hinge region from IgG2 and CH2 region from IgG4 (see, e.g., Lau C. et al., *J. Immunol.* 191:4769-4777 (2013)), or a Fc region with mutations that result in altered Fc effector functions, e.g., reduced or no Fc functions. Such Fc regions with mutations are known in the art. See, e.g., U.S. Pub. No. 20120100140 and U.S. and PCT applications cited therein and An et al., *mAbs* 1:6, 572-579 (2009); the disclosure of which are incorporated by reference to their entirety.

A "hinge", "hinge domain" or "hinge region" or "antibody hinge region" refers to the domain of a heavy chain constant region that joins the CH1 domain to the CH2 domain and includes the upper, middle, and lower portions of the hinge (Roux et al., *J. Immunol.* 1998 161:4083). The hinge provides varying levels of flexibility between the binding and effector regions of an antibody and also provides sites for intermolecular disulfide bonding between the two heavy chain constant regions. As used herein, a hinge starts at Glu216 and ends at Gly237 for all IgG isotypes (Roux et al., 1998 *J Immunol* 161:4083). The sequences of wild-type IgG1, IgG2, IgG3 and IgG4 hinges are known in the art. See, e.g., Kabat E A et al., (1991) Sequences of Proteins of Immunological Interest, Fifth Edition, U.S. Department of Health and Human Services, NIH Publication No. 91-3242; Vidarsson G. et al., *Front Immunol.* 5:520 (published online Oct. 20, 2014).

The term "CH1 domain" refers to the heavy chain constant region linking the variable domain to the hinge in a heavy chain constant domain. As used herein, a CH1 domain starts at A118 and ends at V215. The term "CH1 domain" includes wildtype CH1 domains, as well as naturally existing variants thereof (e.g., allotypes). CH1 domain sequences of IgG1, IgG2, IgG3, and IgG4 (including wildtype and allotypes) are known in the art. See, e.g., Kabat E A et al., (1991) supra and Vidarsson G. et al., *Front Immunol.* 5:520 (published online Oct. 20, 2014). Exemplary CH1 domains include CH1 domains with mutations that modify a biological activity of an antibody, e.g., half-life, e.g., described in U.S. Pub. No. 20120100140 and U.S. patents and publications and PCT publications cited therein.

The term "CH2 domain" refers to the heavy chain constant region linking the hinge to the CH3 domain in a heavy chain constant domain. As used herein, a CH2 domain starts at P238 and ends at K340. The term "CH2 domain" includes wildtype CH2 domains, as well as naturally existing variants thereof (e.g., allotypes). CH2 domain sequences of IgG1, IgG2, IgG3, and IgG4 (including wildtype and allotypes) are known in the art. See, e.g., Kabat E A et al., (1991) supra and Vidarsson G. et al., *Front Immunol.* 5:520 (published online Oct. 20, 2014). Exemplary CH2 domains include CH2 domains with mutations that modify a biological activity of an antibody, e.g., half-life and/or reduced Fc effector function, e.g., described in U.S. Pub. No. 20120100140 and U.S. patents and publications and PCT publications cited therein.

The term "CH3 domain" refers to the heavy chain constant region that is C-terminal to the CH2 domain in a heavy chain constant domain. As used herein, a CH3 domain starts at G341 and ends at K447. The term "CH3 domain" includes wildtype CH3 domains, as well as naturally existing variants thereof (e.g., allotypes). CH3 domain sequences of IgG1, IgG2, IgG3, and IgG4 (including wildtype and allotypes) are known in the art. See, e.g., Kabat E A et al., (1991) supra and Vidarsson G. et al., *Front Immunol.* 5:520 (published online Oct. 20, 2014). Exemplary CH3 domains include CH3 domains with mutations that modify a biological activity of an antibody, e.g., half-life, e.g., described in U.S. Pub. No. 20120100140 and U.S. patents and publications and PCT publications cited therein.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants within a specific isotype group, which variants differ in a few amino acids (see, e.g., Jefferis et al., (2009) *mAbs* 1:1). Antibodies described herein can be of any allotype. Allotypes of IgG1, IgG2, IgG3, and IgG4 are known in the art. See, e.g., Kabat E A et al., (1991) supra; Vidarsson G. et al., *Front Immunol.* 5:520 (published online Oct. 20, 2014); and Lefranc M P, *mAbs* 1:4, 1-7(2009).

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other antibodies having different antigenic specificities (e.g., an isolated antibody that specifically binds to FAM19A5 is substantially free of antibodies that specifically bind antigens other than FAM19A5). An isolated antibody that specifically binds to an epitope of FAM19A5 can, however, have cross-reactivity to other FAM19A5 proteins from different species.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$ and is expressed as a molar concentration (M), whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as immunoassays (e.g., enzyme-linked immunosorbent assay (ELISA)), BIACORE® or kinetic exclusion assay (KinExA).

As used herein, the terms "specifically binds," "specifically recognizes," "specific binding," "selective binding," and "selectively binds," are analogous terms in the context of antibodies and refer to molecules (e.g., antibodies) that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIACORE®, KinExA 3000 instrument (Sapidyne Instruments, Boise, ID), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$M or less, preferably $10^{-8}$ M or less, even more preferably $10^{-9}$ M or less, and most preferably between $10^{-8}$ M and $10^{-10}$M or less, when determined by, e.g., immunoassays (e.g., ELISA) or surface plasmon resonance (SPR) technology in a BIACORE 2000 instrument using the predetermined antigen, but does not bind with high affinity to unrelated antigens.

As used herein, the term "antigen" refers to any natural or synthetic immunogenic substance, such as a protein, peptide, or hapten. An antigen can be FAM19A5 or a fragment thereof.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14, 15, or 20 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from (e.g., from FMAM19A5) are tested for reactivity with a given antibody (e.g., anti-FAM19A5 antibody). Methods of determining spatial conformation of epitopes include techniques in the art and those described herein, for example, x-ray crystallography, 2-dimensional nuclear magnetic resonance and HDX-MS (see, e.g., Epitope Mapping Protocols in Methods in Molecular Biology, Vol. 66, G. E. Morris, Ed. (1996)).

In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giege R et al., (1994) *Acta Crystallogr D Biol Crystallogr* 50(Pt 4): 339-350; McPherson A (1990) *Eur J Biochem* 189: 1-23; Chayen N E (1997) *Structure* 5: 1269-1274; McPherson A (1976) *J Biol Chem* 251: 6300-6303). Antibody:antigen crystals can be studied using well known X-ray diffraction techniques and can be refined using computer software such as X-PLOR (Yale University, 1992, distributed by Molecular Simulations, Inc.; see, e.g., *Meth Enzymol* (1985) volumes 114 & 115, eds Wyckoff H W et al.; U.S. 2004/0014194), and BUSTER (Bricogne G (1993) *Acta Crystallogr D Blot Crystallogr* 49(Pt 1): 37-60; Bricogne G (1997) *Meth Enzymol* 276A: 361-423, ed Carter C W; Roversi P et al., (2000) *Acta Crystallogr D Biol Crystallogr* 56(Pt 10): 1316-1323). Mutagenesis mapping studies can be accomplished using any method known to one of skill in the art. See, e.g., Champe M et al., (1995) *J Blot Chem* 270: 1388-1394 and Cunningham B C & Wells J A (1989) *Science* 244: 1081-1085 for a description of mutagenesis techniques, including alanine scanning mutagenesis techniques.

The term "epitope mapping" refers to the process of identification of the molecular determinants for antibody-antigen recognition.

The term "binds to the same epitope" with reference to two or more antibodies means that the antibodies bind to the same segment of amino acid residues, as determined by a given method. Techniques for determining whether antibodies bind to the "same epitope on FAM19A5" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, NY, USA 1999. Competing antibodies bind to the same epitope, an overlapping epitope or to adjacent epitopes (e.g., as evidenced by steric hindrance).

Other competitive binding assays include: solid phase direct or indirect radioimmunoassay (MA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label MA using 1-125 label (see Morel et al., *Mol. Immunol.* 25(1):7 (1988)); solid phase direct biotin-avidin EIA (Cheung et al., *Virology* 176:546 (1990)); and direct labeled MA. (Moldenhauer et al., *Scand. J. Immunol.* 32:77 (1990)).

The term "single chain Fv" or "scFv" refers to a single chain Fv ("fragment variable") antibody in which the variable domains of the heavy chain and of the light chain of a traditional two chain antibody have been joined to form one chain.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In some embodiments, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) *Nature Biotech.* 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to an antibody in which some, most or all of the amino acids outside the CDR domains of a non-human antibody are replaced with corresponding amino acids derived from human immunoglobulins. In some embodiments of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

The term "cross-reacts," as used herein, refers to the ability of an antibody described herein to bind to FAM19A5 from a different species. For example, an antibody described herein that binds human FAM19A5 can also bind another species of FAM19A5 (e.g., mouse FAM19A5). As used herein, cross-reactivity can be measured by detecting a specific reactivity with purified antigen in binding assays (e.g., SPR, ELISA) or binding to, or otherwise functionally interacting with, cells physiologically expressing FAM19A5. Methods for determining cross-reactivity include standard binding assays as described herein, for example, by BIACORE™ surface plasmon resonance (SPR) analysis using a BIACORE™ 2000 SPR instrument (Biacore AB, Uppsala, Sweden), or flow cytometric techniques.

The term "naturally-occurring," as applied to an object disclosed herein, refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

The term "nucleic acid molecule," as used herein, is intended to include DNA molecules and RNA molecules. A nucleic acid molecule can be single-stranded or double-stranded, and can be cDNA.

The term "recombinant host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

II. Adeno-Associated Virus (AAV) and Vectors Derived Thereof

The AAV vectors disclosed herein include a nucleic acid encoding a protein of interest, e.g., a FAM19A5 antagonist, e.g., an anti-FAM19A5 antibody. In some embodiments, the nucleic acid also can include one or more regulatory sequences allowing expression and, in some embodiments, secretion of the protein of interest, such as e.g., a promoter, enhancer, polyadenylation signal, an internal ribosome entry site (IRES), a sequence encoding a protein transduction domain (PTD), and the like. Thus, in some embodiments, the nucleic acid can comprise a promoter region operably linked to the coding sequence to cause or improve expression of the protein of interest in infected cells. Such a promoter can be ubiquitous, cell- or tissue-specific, strong, weak, regulated, chimeric, etc., for example to allow efficient and stable production of the protein in the infected tissue. The promoter can be homologous to the encoded protein, or heterologous, although generally promoters of use in the disclosed methods are functional in human cells. Examples of regulated promoters include, without limitation, Tet on/off element-containing promoters, rapamycin-inducible promoters, tamoxifen-inducible promoters, and metallothionein promoters. Other promoters that can be used include promoters that are tissue specific for tissues such as kidney, spleen, pancreas, brain, or spinal cord. Examples of ubiquitous promoters include viral promoters, particularly the CMV promoter, the RSV promoter, the SV40 promoter, etc., and cellular promoters such as the PGK (phosphoglycerate kinase) promoter and the β-actin promoter.

In some embodiments of the AAV vectors disclosed herein, one or more feedback elements can be used to dampen over-expression of the protein of interest. For example, some embodiments of the AAV vectors include one or more siRNA sequences that would target the exogenous transcript. In other embodiments, the AAV vector includes one or more additional promoters that can be recognized by inhibitory transcription factors. In various embodiments, the AAV vectors disclosed herein comprise a construct that can create a homoeostatic feedback loop that can maintain expression levels of the protein of interest at a physiological level.

In some embodiments, the AAV vectors disclosed herein comprise a nucleic acid that includes a leader sequence (or signal peptide) allowing secretion of the encoded protein. In some embodiments, fusion of the transgene of interest with a sequence encoding a secretion signal peptide (usually located at the N-terminal of secreted polypeptides) allows the production of the therapeutic protein in a form that can be secreted from the transduced cell. Non-limiting examples of such signal peptides include human beta-globin, albumin, the β-glucuronidase, the alkaline protease or the fibronectin secretory signal peptides.

In some embodiments, the mRNA expressed from the AAV vector of the present disclosure comprises a miRNA binding site of a miRNA that is preferentially expressed in non-CNS tissue. In certain embodiments, the miRNA binding site is a binding site for miR-122. In certain embodiments, the miRNA binding site is a binding site for miR-1. In some embodiments, mRNA expressed from the CNS-associated gene does not comprise a miRNA binding site of a miRNA that is preferentially expressed in CNS tissue.

AAV, a member of Parvoviridae family, is a small non-enveloped, icosahedral virus with single-stranded linear DNA genomes of 4.7 kilobases (kb) to 6 kb. Gonsalves, M., Virol J 2: 43 (2005). This family can be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require co-infection with a helper virus such as adenovirus or herpes virus for productive infection in cell culture. The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996).

Replication, Capsid, and Assembly AAV Genes

The single-stranded genome of AAV comprises three genes, rep (Replication), cap (Capsid), and aap (Assembly). These three genes give rise to at least nine gene products through the use of three promoters, alternative translation start sites, and differential splicing.

The rep gene encodes four proteins (Rep78, Rep68, Rep52, and Rep40), which are required for viral genome replication and packaging. The cap gene expression gives rise to the viral capsid proteins (VP1; VP2; VP3), which form the outer capsid shell that protects the viral genome, as well as being actively involved in cell binding and internalization. It is estimated that the viral coat is comprised of 60 proteins arranged into an icosahedral structure. The aap gene encodes the assembly-activating protein (AAP) in an alternate reading frame overlapping the cap gene. This nuclear protein is thought to provide a scaffolding function for capsid assembly and plays a role in nucleolar localization of VP proteins in some AAV serotypes.

In some embodiments, the AAV vector disclosed herein is a recombinant AAV and lacks one or more of the rep gene, the cap gene, and the aap gene. In some embodiments, the rAAV is modified so that one or more of the rep gene, the cap gene, and the aap gene is mutated so that expression of one or more of the AAV genes is modified. In some embodiments, one or more of the rep, cap, or aap genes are naturally occurring, e.g. the rep, cap, or app genes comprise all or a portion of parvovirus rep, cap, or aap genes. In some embodiments, the one or more of the rep, cap, or aap genes comprise a synthetic sequence.

It is to be understood that a particular AAV genome described herein could have genes from different AAV genomes (e.g., genomes from AAV1, AAV2, AAV3, AAV4, AAV5, AAV6, AAV7, AAV8, AAV9, AAV10, AAV11). Thus, disclosed herein are AAV vectors that comprise any possible permutation of rep, cap, or aap.

Inverted Terminal Repeats

Certain aspects of the present disclosure are directed to a nucleic acid molecule comprising a first ITR, e.g., a 5' ITR, and second ITR, e.g., a 3' ITR. In some embodiments, the ITR comprises a naturally occurring, e.g. the ITR comprises all or a portion of a parvovirus ITR. In some embodiments, the ITR comprises a synthetic sequence.

In some embodiments, the ITR comprises an ITR from an AAV genome. In some embodiments, the ITR is an ITR of an AAV genome selected from AAV1, AAV2, AAV3, AAV4, AAV5, AAV6, AAV7, AAV8, AAV9, AAV10, AAV11, and any combination thereof. In certain embodiments, the ITR is an ITR of the AAV8 or AAV9 genome. In other embodiments, the ITR is a synthetic sequence genetically engineered to include at its 5' and 3' ends ITRs derived from one or more of AAV genomes. In some embodiments, the ITRs are derived from the same genome, e.g., from the genome of the same virus, or from different genomes, e.g., from the genomes of two or more different AAV genomes. In certain embodiments, the ITRs are derived from the same AAV genome. In other embodiments, the two ITRs present in the nucleic acid molecule of the present disclosure are the same, and can in particular be AAV2 ITRs. In some embodiments, the first ITR and the second ITR are identical.

In some embodiments, ITR is a synthetic sequence genetically engineered to include at its 5' and 3' ends ITRs not derived from an AAV genome. In some embodiments, the ITR sequence comprises one or more palindromic sequence. A palindromic sequence of an ITR disclosed herein includes, but is not limited to, native palindromic sequences (i.e., sequences found in nature), synthetic sequences (i.e., sequences not found in nature), such as pseudo palindromic sequences, and combinations or modified forms thereof. A "pseudo palindromic sequence" is a palindromic DNA sequence, including an imperfect palindromic sequence, which shares less than 80% including less than 70%, 60%, 50%, 40%, 30%, 20%, 10%, or 5%, or no nucleic acid sequence identity to sequences in native AAV palindromic sequence which form a secondary structure. The native palindromic sequences can be obtained or derived from any genome disclosed herein. The synthetic palindromic sequence can be based on any genome disclosed herein. The palindromic sequence can be continuous or interrupted. In some embodiments, the palindromic sequence is interrupted, wherein the palindromic sequence comprises an insertion of a second sequence. In some embodiments, the second sequence comprises a promoter, an enhancer, an integration site for an integrase (e.g., sites for Cre or Flp recombinase), an open reading frame for a gene product, or a combination thereof.

In some embodiments, the ITRs form hairpin loop structures. In one embodiment, the first ITR forms a hairpin structure. In another embodiment, the second ITR forms a hairpin structure. Still in another embodiment, both the first ITR and the second ITR form hairpin structures.

In some embodiments, an ITR in a nucleic acid molecule described herein may be a transcriptionally activated ITR. A transcriptionally-activated ITR can comprise all or a portion of a wild-type ITR that has been transcriptionally activated by inclusion of at least one transcriptionally active element. Various types of transcriptionally active elements are suitable for use in this context. In some embodiments, the transcriptionally active element is a constitutive transcriptionally active element. Constitutive transcriptionally active elements provide an ongoing level of gene transcription, and are preferred when it is desired that the transgene be expressed on an ongoing basis. In other embodiments, the transcriptionally active element is an inducible transcriptionally active element. Inducible transcriptionally active elements generally exhibit low activity in the absence of an inducer (or inducing condition), and are up-regulated in the presence of the inducer (or switch to an inducing condition). Inducible transcriptionally active elements may be preferred when expression is desired only at certain times or at certain locations, or when it is desirable to titrate the level of expression using an inducing agent. Transcriptionally active elements can also be tissue-specific; that is, they exhibit activity only in certain tissues or cell types.

Transcriptionally active elements, can be incorporated into an ITR in a variety of ways. In some embodiments, a transcriptionally active element is incorporated 5' to any portion of an ITR or 3' to any portion of an ITR. In other embodiments, a transcriptionally active element of a transcriptionally-activated ITR lies between two ITR sequences. If the transcriptionally active element comprises two or more elements which must be spaced apart, those elements may alternate with portions of the ITR. In some embodiments, a hairpin structure of an ITR is deleted and replaced with inverted repeats of a transcriptional element. This latter arrangement would create a hairpin mimicking the deleted portion in structure. Multiple tandem transcriptionally active elements can also be present in a transcriptionally-activated ITR, and these may be adjacent or spaced apart. In addition, protein binding sites (e.g., Rep binding sites) can be introduced into transcriptionally active elements of the transcriptionally-activated ITRs. A transcriptionally active element can comprise any sequence enabling the controlled transcription of DNA by RNA polymerase to form RNA, and can comprise, for example, a transcriptionally active element, as defined below.

Transcriptionally-activated ITRs provide both transcriptional activation and ITR functions to the nucleic acid molecule in a relatively limited nucleotide sequence length which effectively maximizes the length of a transgene which can be carried and expressed from the nucleic acid molecule. Incorporation of a transcriptionally active element into an ITR can be accomplished in a variety of ways. A comparison of the ITR sequence and the sequence requirements of the transcriptionally active element can provide insight into ways to encode the element within an ITR. For example, transcriptional activity can be added to an ITR through the introduction of specific changes in the ITR sequence that replicates the functional elements of the transcriptionally active element. A number of techniques exist in the art to efficiently add, delete, and/or change particular nucleotide sequences at specific sites (see, for example, Deng and Nickoloff (1992) Anal. Biochem. 200:81-88). Another way to create transcriptionally-activated ITRs involves the introduction of a restriction site at a desired location in the ITR. In addition, multiple transcriptionally activate elements can be incorporated into a transcriptionally-activated ITR, using methods known in the art.

By way of illustration, transcriptionally-activated ITRs can be generated by inclusion of one or more transcriptionally active elements such as: TATA box, GC box, CCAAT box, Sp1 site, Inr region, CRE (cAMP regulatory element) site, ATF-1/CRE site, APBβ box, APBα box, CArG box, CCAC box, or any other element involved in transcription as known in the art.

FAM19A5 Antagonists

AAV vectors of the present disclosure comprise a nucleic acid, which encodes one or more antagonists of a FAM19A5 protein. In some embodiments, the FAM19A5 antagonist is an antibody, or an antigen-binding fragment thereof, that specifically binds to the FAM19A5 protein. In some embodiments, the anti-FAM19A5 antibody comprises a Fab, a Fab', a F(ab')2, a Fv, or a single chain Fv (scFv). In certain embodiments, the anti-FAM19A5 antibody is a scFv.

In some embodiments, the anti-FAM19A5 antibody (e.g., anti-FAM19A5 scFv) expressed by the AAV vectors of the present disclosure is characterized by particular functional features or properties. For example, the antibodies specifically bind human FAM19A5, including soluble FAM19A5 and membrane bound FAM19A5. In addition to binding specifically to soluble and/or membrane bound human FAM19A5, the antibodies described herein exhibit one or more of the following functional properties:

(a) reduce, reverse, and/or prevent fibrosis;
(b) reduce formation of excessive extracellular matrix (ECM);
(c) delay tumor growth or progression;
(d) bind to soluble human FAM19A5 with a $K_D$ of 10 nM or less as measured by enzyme-linked immunosorbent assay (ELISA);
(e) bind to membrane bound human FAM19A5 with a $K_D$ of 10 nM or less as measured by ELISA;
(f) reduce, reverse, delay, and/or prevent an onset of reactive gliosis;
(g) suppress an excessive proliferation of reactive astrocytes;
(h) decrease expression of chondroitin sulfate proteoglycans including neurocan and neuron-glial antigen 2 (NG2);
(i) increase expression of c-fos and pERK in the nucleus of neurons;
(j) promote survival of neurons;
(k) increase expression of GAP43 in neurons; and
(l) promote regrowth of an axon.

In some embodiments, the anti-FAM19A5 antibody (e.g., scFv) specifically binds to soluble human FAM19A5 or membrane-bound human with high affinity, for example, with a $K_D$ of $10^{-7}$ M or less, $10^{-8}$ M or less, $10^{-9}$ M (1 nM) or less, $10^{-10}$ M (0.1 nM) or less, $10^{-11}$ M or less, or $10^{-12}$ M or less, e.g., $10^{-12}$ M to $10^{-7}$ M, $10^{-11}$ M to $10^{-7}$ M, $10^{-10}$ M to $10^{-7}$ M, or $10^{-9}$ M to $10^{-7}$ M, e.g., $10^{-12}$ M, $5 \times 10^{-12}$ M, $10^{-11}$ M, $5 \times 10^{-11}$ M, $10^{-10}$ M, $5 \times 10^{-10}$ M, $10^{-9}$ M, $5 \times 10^{-9}$ M, $10^{-8}$ M, $5 \times 10^{-8}$ M, $10^{-7}$ M, or $5 \times 10^{-7}$ M. Standard assays to evaluate the binding ability of the antibody toward human FAM19A5 of various species are known in the art, including for example, ELISAs, Western blots, and RIAs. The binding kinetics (e.g., binding affinity)

of the antibodies also can be assessed by standard assays known in the art, such as by ELISA, BIACORE™ analysis or KITNEXA®.

In some embodiments, the anti-FAM19A5 antibody (e.g., scFv) binds to soluble human FAM19A5 with a $K_D$, e.g., as determined by ELISA, of $10^{-7}$ M or less, $10^{-8}$ M (10 nM) or less, $10^{-9}$ M (1 nM) or less, $10^{-10}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M. In some embodiments, the anti-FAM19A5 antibody (e.g., scFv) binds to soluble FAM19A5 with a $K_D$ of 10 nM or less, e.g., between 0.1 and 10 nM, between 0.1 and 5 nM, between 0.1 and 1 nM, between 0.5 and 10 nM, between 0.5 and 5 nM, between 0.5 and 1 nM, between 1 and 10 nM, between 1 and 5 nM, or between 5 and 10 nM. In some embodiments, the anti-FAM19A5 antibody (e.g., scFv) specifically binds to soluble human FAM19A5 with a $K_D$ of about 1 pM, 2 pM, 3 pM, 4 pM, 5 pM, 6 pM, 7 pM, 8 pM, 9 pM, 10 pM, 20 pM, 30 pM, 40 pM, 50 pM, 60 pM, 70 pM, 80 pM, 90 pM, 100 pM, 200 pM, 300 pM, 400 pM, 500 pM, 600 pM, 700 pM, 800 pM, or 900 pM, or about 1 nM, 2 nM, 3 nM, 4 nM, 5 nM, 6 nM, 7 nM, 8 nM, or 9 nM, or about 10 nM, 20 nM, 30 nM, 40 nM, 50 nM, 60 nM, 70 nM, 80 nM, or 90 nM, as determined by as determined by ELISA.

In some embodiments, the anti-FAM19A5 antibody (e.g., scFv) binds to membrane-bound human with a $K_D$, e.g., as determined by ELISA, of $10^{-7}$ M or less, $10^{-8}$ M (10 nM) or less, $10^{-9}$ M (1 nM) or less, $10^{-10}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M. In certain embodiments, the anti-FAM19A5 antibody (e.g., scFv) specifically binds to membrane-bound human FAM19A5 with a $K_D$ of 10 nM or less as determined by ELISA, e.g., between 0.1 and 10 nM, between 0.1 and 5 nM, between 0.1 and 1 nM, between 0.5 and 10 nM, between 0.5 and 5 nM, between 0.5 and 1 nM, between 1 and 10 nM, between 1 and 5 nM, or between 5 and 10 nM. In some embodiments, the anti-FAM19A5 antibody (e.g., scFv) binds to membrane-bound human FAM19A5 with a $K_D$ of about 1 pM, 2 pM, 3 pM, 4 pM, 5 pM, 6 pM, 7 pM, 8 pM, 9 pM, 10 pM, 20 pM, 30 pM, 40 pM, 50 pM, 60 pM, 70 pM, 80 pM, 90 pM, 100 pM, 200 pM, 300 pM, 400 pM, 500 pM, 600 pM, 700 pM, 800 pM, or 900 pM, or about 1 nM, 2 nM, 3 nM, 4 nM, 5 nM, 6 nM, 7 nM, 8 nM, or 9 nM, or about 10 nM, 20 nM, 30 nM, 40 nM, 50 nM, 60 nM, 70 nM, 80 nM, or 90 nM, as determined by as determined by ELISA.

In some embodiments, the anti-FAM19A5 antibody (e.g., scFv) suitable for the methods disclosed herewith cross-competes for binding to (or inhibits binding of) a human FAM19A5 epitope with an anti-FAM19A5 antibody comprising CDRs or variable regions disclosed herein.

In some embodiments, anti-FAM19A5 antibodies (e.g., scFvs) inhibit binding of a reference antibody comprising heavy chain CDR1, CDR2, and CDR3, and light chain CDR1, CDR2, and CDR3, (i) wherein the heavy chain CDR1, CDR2, and CDR3 of the reference antibody comprise the amino acid sequence of SEQ ID NO: 11, SEQ ID NO: 12, and SEQ ID NO: 13, respectively, and light chain CDR1, CDR2, and CDR3 of the reference antibody comprise the amino acid sequence of SEQ ID NO: 23, SEQ ID NO: 24, and SEQ ID NO: 25, respectively; (ii) wherein the heavy chain CDR1 comprises the amino acid sequence of SEQ ID NO: 14, the heavy chain CDR2 comprises the amino acid sequence of SEQ ID NO: 15, and the heavy chain CDR3 comprises the amino acid sequence of SEQ ID NO: 16, the light chain CDR1 comprises the amino acid sequence of SEQ ID NO: 26, the light chain CDR2 comprises the amino acid sequence of SEQ ID NO: 27, and the light chain CDR3 comprises the amino acid sequence of SEQ ID NO: 28; (iii) wherein the heavy chain CDR1 comprises the amino acid sequence of SEQ ID NO: 17, the heavy chain CDR2 comprises the amino acid sequence of SEQ ID NO: 18, and the heavy chain CDR3 comprises the amino acid sequence of SEQ ID NO: 19, the light chain CDR1 comprises the amino acid sequence of SEQ ID NO: 29, the light chain CDR2 comprises the amino acid sequence of SEQ ID NO: 30, and the light chain CDR3 comprises the amino acid sequence of SEQ ID NO: 31; (iv) wherein the heavy chain CDR1 comprises the amino acid sequence of SEQ ID NO: 20, the heavy chain CDR2 comprises the amino acid sequence of SEQ ID NO: 21, the heavy chain CDR3 comprises the amino acid sequence of SEQ ID NO: 22, the light chain CDR1 comprises the amino acid sequence of SEQ ID NO: 32, the light chain CDR2 comprises the amino acid sequence of SEQ ID NO: 33, and the light chain CDR3 comprises the amino acid sequence of SEQ ID NO: 34; (v) wherein the heavy chain CDR1 comprises the amino acid sequence of SEQ ID NO: 89, the heavy chain CDR2 comprises the amino acid sequence of SEQ ID NO: 90, the heavy chain CDR3 comprises the amino acid sequence of SEQ ID NO: 91, the light chain CDR1 comprises the amino acid sequence of SEQ ID NO: 92, the light chain CDR2 comprises the amino acid sequence of SEQ ID NO: 93, and the light chain CDR3 comprises the amino acid sequence of SEQ ID NO: 94; (vi) wherein the heavy chain CDR1 comprises the amino acid sequence of SEQ ID NO: 95, the heavy chain CDR2 comprises the amino acid sequence of SEQ ID NO: 96, the heavy chain CDR3 comprises the amino acid sequence of SEQ ID NO: 97, the light chain CDR1 comprises the amino acid sequence of SEQ ID NO: 98, the light chain CDR2 comprises the amino acid sequence of SEQ ID NO: 99, and the light chain CDR3 comprises the amino acid sequence of SEQ ID NO: 100; (vii) wherein the heavy chain CDR1 comprises the amino acid sequence of SEQ ID NO: 101, the heavy chain CDR2 comprises the amino acid sequence of SEQ ID NO: 102, the heavy chain CDR3 comprises the amino acid sequence of SEQ ID NO: 103, the light chain CDR1 comprises the amino acid sequence of SEQ ID NO: 104, the light chain CDR2 comprises the amino acid sequence of SEQ ID NO: 105, and the light chain CDR3 comprises the amino acid sequence of SEQ ID NO: 106; (viii) wherein the heavy chain CDR1 comprises the amino acid sequence of SEQ ID NO: 107, the heavy chain CDR2 comprises the amino acid sequence of SEQ ID NO: 108, the heavy chain CDR3 comprises the amino acid sequence of SEQ ID NO: 109, the light chain CDR1 comprises the amino acid sequence of SEQ ID NO: 110, the light chain CDR2 comprises the amino acid sequence of SEQ ID NO: 111, and the light chain CDR3 comprises the amino acid sequence of SEQ ID NO: 112; (ix) wherein the heavy chain CDR1 comprises the amino acid sequence of SEQ ID NO: 113, the heavy chain CDR2 comprises the amino acid sequence of SEQ ID NO: 114, the heavy chain CDR3 comprises the amino acid sequence of SEQ ID NO: 115, the light chain CDR1 comprises the amino acid sequence of SEQ ID NO: 116, the light chain CDR2 comprises the amino acid sequence of SEQ ID NO: 117, and the light chain CDR3 comprises the amino acid sequence of SEQ ID NO: 118; (x) wherein the heavy chain CDR1 comprises the amino acid sequence of SEQ ID NO: 119, the heavy chain CDR2 comprises the amino acid sequence of SEQ ID NO: 120, the heavy chain CDR3 comprises the amino acid sequence of SEQ ID NO: 121, the light chain CDR1 comprises the amino acid sequence of SEQ ID NO:

122, the light chain CDR2 comprises the amino acid sequence of SEQ ID NO: 123, and the light chain CDR3 comprises the amino acid sequence of SEQ ID NO: 124; (xi) wherein the heavy chain CDR1 comprises the amino acid sequence of SEQ ID NO: 125, the heavy chain CDR2 comprises the amino acid sequence of SEQ ID NO: 126, the heavy chain CDR3 comprises the amino acid sequence of SEQ ID NO: 127, the light chain CDR1 comprises the amino acid sequence of SEQ ID NO: 128, the light chain CDR2 comprises the amino acid sequence of SEQ ID NO: 129, and the light chain CDR3 comprises the amino acid sequence of SEQ ID NO: 130; (xii) wherein the heavy chain CDR1 comprises the amino acid sequence of SEQ ID NO: 131, the heavy chain CDR2 comprises the amino acid sequence of SEQ ID NO: 132, the heavy chain CDR3 comprises the amino acid sequence of SEQ ID NO: 133, the light chain CDR1 comprises the amino acid sequence of SEQ ID NO: 134, the light chain CDR2 comprises the amino acid sequence of SEQ ID NO: 135, and the light chain CDR3 comprises the amino acid sequence of SEQ ID NO: 136; (xiii) wherein the heavy chain CDR1 comprises the amino acid sequence of SEQ ID NO: 137, the heavy chain CDR2 comprises the amino acid sequence of SEQ ID NO: 138, the heavy chain CDR3 comprises the amino acid sequence of SEQ ID NO: 139, the light chain CDR1 comprises the amino acid sequence of SEQ ID NO: 140, the light chain CDR2 comprises the amino acid sequence of SEQ ID NO: 141, and the light chain CDR3 comprises the amino acid sequence of SEQ ID NO: 142; (xiv) wherein the heavy chain CDR1 comprises the amino acid sequence of SEQ ID NO: 143, the heavy chain CDR2 comprises the amino acid sequence of SEQ ID NO: 144, the heavy chain CDR3 comprises the amino acid sequence of SEQ ID NO: 145, the light chain CDR1 comprises the amino acid sequence of SEQ ID NO: 146, the light chain CDR2 comprises the amino acid sequence of SEQ ID NO: 147, and the light chain CDR3 comprises the amino acid sequence of SEQ ID NO: 148; or (xv) wherein the heavy chain CDR1 comprises the amino acid sequence of SEQ ID NO: 149, the heavy chain CDR2 comprises the amino acid sequence of SEQ ID NO: 150, the heavy chain CDR3 comprises the amino acid sequence of SEQ ID NO: 151, the light chain CDR1 comprises the amino acid sequence of SEQ ID NO: 152, the light chain CDR2 comprises the amino acid sequence of SEQ ID NO: 153, and the light chain CDR3 comprises the amino acid sequence of SEQ ID NO: 154. In some embodiments, the heavy chain CDR1, CDR2 and CDR3 of the reference antibody comprises a CDR1, CDR2, and CDR3 sequence as set forth in Table 2, respectively, and the light chain CDR1, CDR2, and CDR3 of the reference antibody comprises a CDR1, CDR2, and CDR3 sequence as set forth in Table 3, respectively.

In some embodiments, the reference antibody comprises (a) heavy and light chain variable region sequences comprising SEQ ID NOs: 35 and 39, respectively; (b) heavy and light chain variable region sequences comprising SEQ ID NOs: 36 and 40, respectively; (c) heavy and light chain variable region sequences comprising SEQ ID NOs: 37 and 41, respectively; (d) heavy and light chain variable region sequences comprising SEQ ID NOs: 38 and 42, respectively; (e) heavy and light chain variable region sequences comprising SEQ ID NOs: 155 and 166, respectively; (f) heavy and light chain variable region sequences comprising SEQ ID NOs: 156 and 167, respectively; (g) heavy and light chain variable region sequences comprising SEQ ID NOs: 157 and 168, respectively; (h) heavy and light chain variable region sequences comprising SEQ ID NOs: 158 and 169, respectively; (i) heavy and light chain variable region sequences comprising SEQ ID NOs: 159 and 170, respectively; (j) heavy and light chain variable region sequences comprising SEQ ID NOs: 160 and 171, respectively; (k) heavy and light chain variable region sequences comprising SEQ ID NOs: 161 and 172, respectively; (l) heavy and light chain variable region sequences comprising SEQ ID NOs: 162 and 173, respectively; (m) heavy and light chain variable region sequences comprising SEQ ID NOs: 163 and 174, respectively; (n) heavy and light chain variable region sequences comprising SEQ ID NOs: 164 and 175, respectively; or (o) heavy and light chain variable region sequences comprising SEQ ID NOs: 165 and 176, respectively. In some embodiments, the reference antibody comprises a heavy chain variable region (VH) and a light chain variable region (VL), wherein the VH comprises an amino acid sequence as set forth in Table 4, and the VL comprises an amino acid sequence as set forth in Table 5.

In some embodiments, the anti-FAM19A5 antibody (e.g., scFvs) inhibits binding of such a reference antibody to human FAM19A5 by at least 10%, 20%, 30%, 40%, 50%, 60%, 70%, 80%, 90% or by 100%. Competing antibodies bind to the same epitope, an overlapping epitope or to adjacent epitopes (e.g., as evidenced by steric hindrance). Whether two antibodies compete with each other for binding to a target can be determined using competition experiments known in the art such as RIA and EIA.

In some embodiments, the anti-FAM19A5 antibody (e.g., scFvs) binds to the same FAM19A5 epitope as a reference antibody disclosed herein comprising heavy chain CDR1, CDR2, and CDR3 and light chain CDR1, CDR2, and CDR3, (i) wherein the heavy chain CDR1 comprises the amino acid sequence of SEQ ID NO: 11, the heavy chain CDR2 comprises the amino acid sequence of SEQ ID NO: 12, and the heavy chain CDR3 comprises the amino acid sequence of SEQ ID NO: 13, the light chain CDR1 comprises the amino acid sequence of SEQ ID NO: 23, the light chain CDR2 comprises the amino acid sequence of SEQ ID NO: 24, and the light chain CDR3 comprises the amino acid sequence of SEQ ID NO: 25; (ii) wherein the heavy chain CDR1 comprises the amino acid sequence of SEQ ID NO: 14, the heavy chain CDR2 comprises the amino acid sequence of SEQ ID NO: 15, and the heavy chain CDR3 comprises the amino acid sequence of SEQ ID NO: 16, the light chain CDR1 comprises the amino acid sequence of SEQ ID NO: 26, the light chain CDR2 comprises the amino acid sequence of SEQ ID NO: 27, and the light chain CDR3 comprises the amino acid sequence of SEQ ID NO: 28; (iii) wherein the heavy chain CDR1 comprises the amino acid sequence of SEQ ID NO: 17, the heavy chain CDR2 comprises the amino acid sequence of SEQ ID NO: 18, and the heavy chain CDR3 comprises the amino acid sequence of SEQ ID NO: 19, the light chain CDR1 comprises the amino acid sequence of SEQ ID NO: 29, the light chain CDR2 comprises the amino acid sequence of SEQ ID NO: 30, and the light chain CDR3 comprises the amino acid sequence of SEQ ID NO: 31; (iv) wherein the heavy chain CDR1 comprises the amino acid sequence of SEQ ID NO: 20, the heavy chain CDR2 comprises the amino acid sequence of SEQ ID NO: 21, the heavy chain CDR3 comprises the amino acid sequence of SEQ ID NO: 22, the light chain CDR1 comprises the amino acid sequence of SEQ ID NO: 32, the light chain CDR2 comprises the amino acid sequence of SEQ ID NO: 33, and the light chain CDR3 comprises the amino acid sequence of SEQ ID NO: 34; (v) wherein the heavy chain CDR1 comprises the amino acid sequence of SEQ ID NO: 89, the heavy chain CDR2 comprises the amino acid sequence of SEQ ID NO: 90, the heavy chain CDR3 comprises the amino acid sequence of SEQ ID NO: 91, the light chain CDR1 comprises the amino acid sequence of SEQ ID NO: 92, the light chain CDR2 comprises the amino acid sequence of SEQ ID NO: 93, and the light chain CDR3 comprises the amino acid sequence of SEQ ID NO: 94; (vi) wherein the heavy chain CDR1 comprises the amino acid sequence of SEQ ID NO: 95, the heavy chain CDR2 comprises the amino acid sequence of SEQ ID NO: 96, the heavy chain CDR3 comprises the amino acid sequence of SEQ ID NO: 97, the light chain CDR1 comprises the amino acid sequence of SEQ ID NO: 98, the light chain CDR2 comprises the amino acid sequence of SEQ ID NO: 99, and the light chain CDR3 comprises the amino acid sequence of SEQ ID NO: 100; (vii) wherein the heavy chain CDR1 comprises the amino acid sequence of SEQ ID NO: 101, the heavy chain CDR2 comprises the amino acid sequence of SEQ ID NO: 102, the heavy chain CDR3 comprises the amino acid sequence of SEQ ID NO: 103, the light chain CDR1 comprises the amino acid sequence of SEQ ID NO: 104, the light chain CDR2 comprises the amino acid sequence of SEQ ID NO: 105, and the light chain CDR3 comprises the amino acid sequence of SEQ ID NO: 106; (viii) wherein the heavy chain CDR1 comprises the amino acid sequence of SEQ ID NO: 107, the heavy chain CDR2 comprises the amino acid sequence of SEQ ID NO: 108, the heavy chain CDR3 comprises the amino acid sequence of SEQ ID NO: 109, the light chain CDR1 comprises the amino acid sequence of SEQ ID NO: 110, the light chain CDR2 comprises the amino acid sequence of SEQ ID NO: 111, and the light chain CDR3 comprises the amino acid sequence of SEQ ID NO: 112; (ix) wherein the heavy chain CDR1 comprises the amino acid sequence of SEQ ID NO: 113, the heavy chain CDR2 comprises the amino acid sequence of SEQ ID NO: 114, the heavy chain CDR3 comprises the amino acid sequence of SEQ ID NO: 115, the light chain CDR1 comprises the amino acid sequence of SEQ ID NO: 116, the light chain CDR2 comprises the amino acid sequence of SEQ ID NO: 117, and the light chain CDR3 comprises the amino acid sequence of SEQ ID NO: 118; (x) wherein the heavy chain CDR1 comprises the amino acid sequence of SEQ ID NO: 119, the heavy chain CDR2 comprises the amino acid sequence of SEQ ID NO: 120, the heavy chain CDR3 comprises the amino acid sequence of SEQ ID NO: 121, the light chain CDR1 comprises the amino acid sequence of SEQ ID NO: 122, the light chain CDR2 comprises the amino acid sequence of SEQ ID NO: 123, and the light chain CDR3 comprises the amino acid sequence of SEQ ID NO: 124; (xi) wherein the heavy chain CDR1 comprises the amino acid sequence of SEQ ID NO: 125, the heavy chain CDR2 comprises the amino acid sequence of SEQ ID NO: 126, the heavy chain CDR3 comprises the amino acid sequence of SEQ ID NO: 127, the light chain CDR1 comprises the amino acid sequence of SEQ ID NO: 128, the light chain CDR2 comprises the amino acid sequence of SEQ ID NO: 129, and the light chain CDR3 comprises the amino acid sequence of SEQ ID NO: 130; (xii) wherein the heavy chain CDR1 comprises the amino acid sequence of SEQ ID NO: 131, the heavy chain CDR2 comprises the amino acid sequence of SEQ ID NO: 132, the heavy chain CDR3 comprises the amino acid sequence of SEQ ID NO: 133, the light chain CDR1 comprises the amino acid sequence of SEQ ID NO: 134, the light chain CDR2 comprises the amino acid sequence of SEQ ID NO: 135, and the light chain CDR3 comprises the amino acid sequence of SEQ ID NO: 136; (xiii) wherein the heavy chain CDR1 comprises the amino acid sequence of SEQ ID NO: 137, the heavy chain CDR2 comprises the amino acid sequence of SEQ ID NO: 138, the heavy chain CDR3 comprises the amino acid sequence of SEQ ID NO: 139, the light chain CDR1 comprises the amino acid sequence of SEQ ID NO: 140, the light chain CDR2 comprises the amino acid sequence of SEQ ID NO: 141, and the light chain CDR3 comprises the amino acid sequence of SEQ ID NO: 142; (xiv) wherein the heavy chain CDR1 comprises the amino acid sequence of SEQ ID NO: 143, the heavy chain CDR2 comprises the amino acid sequence of SEQ ID NO: 144, the heavy chain CDR3 comprises the amino acid sequence of SEQ ID NO: 145, the light chain CDR1 comprises the amino acid sequence of SEQ ID NO: 146, the light chain CDR2 comprises the amino acid sequence of SEQ ID NO: 147, and the light chain CDR3 comprises the amino acid sequence of SEQ ID NO: 148; or (xv) wherein the heavy chain CDR1 comprises the amino acid sequence of SEQ ID NO: 149, the heavy chain CDR2 comprises the amino acid sequence of SEQ ID NO: 150, the heavy chain CDR3 comprises the amino acid sequence of SEQ ID NO: 151, the light chain CDR1 comprises the amino acid sequence of SEQ ID NO: 152, the light chain CDR2 comprises the amino acid sequence of SEQ ID NO: 153, and the light chain CDR3 comprises the amino acid sequence of SEQ ID NO: 154. In some embodiments, the heavy chain CDR1, CDR2 and CDR3 of the reference antibody comprises a CDR1, CDR2, and CDR3 sequence as set forth in Table 2, respectively, and the light chain CDR1, CDR2, and CDR3 of the reference antibody comprises a CDR1, CDR2, and CDR3 sequence as set forth in Table 3, respectively.

In some embodiments, the reference antibody comprises (a) heavy and light chain variable region sequences comprising SEQ ID NOs: 35 and 39, respectively; (b) heavy and light chain variable region sequences comprising SEQ ID NOs: 36 and 40, respectively; (c) heavy and light chain variable region sequences comprising SEQ ID NOs: 37 and 41, respectively; (d) heavy and light chain variable region sequences comprising SEQ ID NOs: 38 and 42, respectively; (e) heavy and light chain variable region sequences comprising SEQ ID NOs: 155 and 166, respectively; (f) heavy and light chain variable region sequences comprising SEQ ID NOs: 156 and 167, respectively; (g) heavy and light chain variable region sequences comprising SEQ ID NOs: 157 and 168, respectively; (h) heavy and light chain variable region sequences comprising SEQ ID NOs: 158 and 169, respectively; (i) heavy and light chain variable region sequences comprising SEQ ID NOs: 159 and 170, respectively; (j) heavy and light chain variable region sequences comprising SEQ ID NOs: 160 and 171, respectively; (k) heavy and light chain variable region sequences comprising SEQ ID NOs: 161 and 172, respectively; (l) heavy and light chain variable region sequences comprising SEQ ID NOs: 162 and 173, respectively; (m) heavy and light chain variable region sequences comprising SEQ ID NOs: 163 and 174, respectively; (n) heavy and light chain variable region sequences comprising SEQ ID NOs: 164 and 175, respectively; or (o) heavy and light chain variable region sequences comprising SEQ ID NOs: 165 and 176, respectively. In some embodiments, the reference antibody comprises a heavy chain variable region (VH) and a light chain variable region (VL), wherein the VH comprises an amino acid sequence as set forth in Table 4, and the VL comprises an amino acid sequence as set forth in Table 5.

Techniques for determining whether two antibodies bind to the same epitope include, e.g., epitope mapping methods, such as, x-ray analyses of crystals of antigen:antibody complexes which provides atomic resolution of the epitope and hydrogen/deuterium exchange mass spectrometry (HDX-MS), methods monitoring the binding of the antibody to antigen fragments or mutated variations of the antigen, where loss of binding due to a modification of an amino acid residue within the antigen sequence is often considered an indication of an epitope component, computational combinatorial methods for epitope mapping.

An anti-FAM19A5 antibody (e.g., scFvs) that would be useful in the methods disclosed herewith can bind to at least one epitope of mature human FAM19A5, as determined, e.g., by binding of the antibodies to fragments of human FAM19A5. In some embodiments, the anti-FAM19A5 antibodies bind to a fragment located within the amino acid sequence of TLDRDSSQPRRTIARQTARC (SEQ ID NO: 6 or amino acid residues 42 to 61 of SEQ ID NO: 2), e.g., an epitope having at least 1, 2, 3, 4, 5, 6, 7, 8, 9, 10, 11, 12, 13, 14, 15, 16, 17, 18, 19, or 20 amino acids of SEQ ID NO: 6. In some embodiments, anti-FAM19A5 antibodies bind to SEQ ID NO: 6 at one or more amino acids corresponding to amino acid residues 46 to 51 (i.e., DSSQPR), e.g., amino acid residues 46, 50, and 52 (i.e., D---P-R), e.g., amino acid residues 46, 47, 48, and 50 (i.e., DSS-P) of SEQ ID NO: 2. In some embodiments, anti-FAM19A5 antibodies bind to a fragment located within the amino acid sequence of CDMLPCLEGEGCDLLINRSG (SEQ ID NO: 9 or amino acids 90 to 109 of SEQ ID NO: 2), e.g., an epitope having at least 1, 2, 3, 4, 5, 6, 7, 8, 9, 10, 11, 12, 13, 14, 15, 16, 17, 18, 19, or 20 amino acids of SEQ ID NO: 9. In certain embodiments, anti-FAM19A5 antibodies bind to SEQ ID NO: 9 at one or more amino acids residues 99 to 107 (i.e., EGCDLLINR), e.g., amino acid residues 102, 103, 105, and 107 (i.e., DL-I-R), e.g., amino acid residues 99, 100, 102, 103, 105, and 107 (i.e., EG-DL-I-R), e.g., amino acid residues 99, 100, and 107 (i.e., EG------R) of SEQ ID NO: 4.

In some embodiments, the at least one epitope has the amino acid sequence that is at least 90%, at least about 95%, at least about 96%, at least about 97%, at least about 98%, at least about 99%, or about 100% identical to SEQ ID NO: 6. In some embodiments, the at least one epitope has the amino acid sequence that is at least 90%, at least about 95%, at least about 96%, at least about 97%, at least about 98%, at least about 99%, or about 100% identical to SEQ ID NO: 9.

In some embodiments, the anti-FAM19A5 antibody (e.g., scFvs) binds to a human FAM19A5 epitope only, which is SEQ ID NO: 5, 6, 7, 8, 9, or 10, or a fragment located within the amino acid sequence of SEQ ID NO: 5, 6, 7, 8, 9, or 10, e.g., an epitope having 3, 4, 5, 6, 7, 8, 9, 10, 11, 12, 13, 14, 15, 16, 17, 18, 19, or 20 amino acids of SEQ ID NO: 5, 6, 7, 8, 9, or 10.

In some embodiments, the anti-FAM19A5 antibody of the present disclosure binds to SEQ ID NO: 6 or a fragment thereof in its native conformation (i.e., un-denatured). In some embodiments, the anti-FAM19A5 antibody binds to SEQ ID NO: 9 or a fragment thereof in its native conformation (i.e., un-denatured). In some embodiments, the anti-FAM19A5 antibody binds to both glycosylated and unglycosylated human FAM19A5.

In some embodiments, the anti-FAM19A5 antibody (e.g., scFvs) further binds to one or more additional FAM19A5 epitopes. Therefore, certain anti-FAM19A5 antibodies bind to (i) an epitope of SEQ ID NO: 6 and an additional epitope, or (ii) an epitope of SEQ ID NO: 9 and an additional epitope. Other anti-FAM19A5 antibodies can bind to an epitope of SEQ ID NO: 5, SEQ ID NO: 9, and an additional epitope.

In some embodiments, anti-FAM19A5 antibodies bind to an epitope of SEQ ID NO: 6, an epitope of SEQ ID NO: 10, and an additional epitope.

In some embodiments, the one or more additional FAM19A5 epitopes are selected from QLAAGTCEIVTLDR (SEQ ID NO: 5, epitope F1), TLDRDSSQPRRTIARQTARC (SEQ ID NO: 6, epitope F2), TARCACRKGQIAGTTRARPA (SEQ ID NO: 7, epitope F3), ARPACVDARIIKTKQWCDML (SEQ ID NO: 8, epitope F4), CDMLPCLEGEGCDLLINRSG (SEQ ID NO: 9, epitope F5), or NRSGWTCTQPGGRIKTTTVS (SEQ ID NO: 10, epitope F6), or a fragment located within the amino acid sequence of SEQ ID NO: 5, SEQ ID NO: 6, SEQ ID NO: 7, SEQ ID NO: 8, SEQ ID NO: 9, or SEQ ID NO: 10, or any combination thereof. A fragment located within the amino acid sequence of SEQ ID NO: 5, SEQ ID NO: 6, SEQ ID NO: 7, SEQ ID NO: 8, SEQ ID NO: 9, or SEQ ID NO: 10, includes a fragment having 1, 2, 3, 4, 5, 6, 7, 8, 9, 10, 11, 12, 13, 14, 15, 16, 17, 18, 19, or 20 amino acids of any of SEQ ID NO: 5, SEQ ID NO: 6, and SEQ ID NO: 7, SEQ ID NO: 8, SEQ ID NO: 9, or SEQ ID NO: 10. In some embodiments, the one or more additional FAM19A5 epitopes are selected from SEQ ID NO: 5, 6, 7, 8, 9, or 10, or a fragment located within the amino acid sequence of SEQ ID NO: 5, 6, 7, 8, 9, or 10, e.g., a fragment having 1, 2, 3, 4, 5, 6, 7, 8, 9, 10, 11, 12, 13, 14, 15, 16, 17, 18, 19, or 20 amino acids of SEQ ID NO: 5, 6, 7, 8, 9, or 10, or any combination thereof. In some embodiments, the anti-FAM19A5 antibody of the disclosure binds to any of the one or more additional epitopes in their native conformation (i.e., un-denatured). In some embodiments, the anti-FAM19A5 antibody binds to both glycosylated and unglycosylated of the one or more additional FAM19A5 epitopes.

In some embodiments, anti-FAM19A5 antibodies of the present disclosure (e.g., scFvs) bind to at least one FAM19A5 epitope identified as EP2, EP4, and/or EP8, wherein EP2 comprises, consists essentially of, or consists of the amino acids DSSQP (SEQ ID NO: 66), wherein EP4 comprises, consists essentially of, or consists of the amino acids ARCACRK (SEQ ID NO: 68), and wherein EP8 comprises, consists essentially of, or consists of the amino acids TCTQPGGR (SEQ ID NO: 72). In some embodiments, the at least one epitope has the amino acid sequence that is at least 90%, at least about 95%, at least about 96%, at least about 97%, at least about 98%, at least about 99%, or about 100% identical to EP2, EP4, or EP8. In some embodiments, anti-FAM19A5 antibodies only bind to EP2. In some embodiments, anti-FAM19A5 antibodies bind to EP4 and EP8.

In some embodiments, the anti-FAM19A5 antibody binds to at least one FAM19A5 epitope identified as EP6, EP7, or EP8, wherein EP6 comprises the amino acids KTKQWCDML (SEQ ID NO: 70), wherein EP7 comprises the amino acids GCDLLINR (SEQ ID NO: 71), and wherein EP8 comprises the amino acids TCTQPGGR (SEQ ID NO: 72). In some embodiments, the at least one epitope has the amino acid sequence that is at least 90%, at least about 95%, at least about 96%, at least about 97%, at least about 98%, at least about 99%, or about 100% identical to EP6, EP7, or EP8. In some embodiments, the anti-FAM19A5 antibody only binds to EP6, EP7, or EP8. In some embodiments, the anti-FAM19A5 antibody binds to EP6, EP7, and EP8. In some embodiments, the anti-FAM19A5 antibody binds to EP7 and EP8. In some embodiments, the anti-FAM19A5 antibody binds to EP7.

In some embodiments, anti-FAM19A5 antibodies bind to one or more FAM19A5 epitopes selected from the group consisting of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, and any combinations thereof.

In some embodiments, provided herein is an antibody that binds to FAM19A5 (e.g., human FAM19A5) with a 20%, 25%, 30%, 35%, 40%, 45%, 50%, 55%, 60%, 65%, 70%, 75%, 80%, 85%, 90%, 95% or higher affinity than to another protein in the FAM19A family as measured by, e.g., a immunoassay (e.g., ELISA), surface plasmon resonance, or kinetic exclusion assay. In a specific embodiment, provided herein is an antibody that binds to FAM19A5 (e.g., human FAM19A5) with no cross reactivity with another protein in the FAM19A family as measured by, e.g., an immunoassay.

In some embodiments, the anti-FAM19A5 antibodies are not native antibodies or are not naturally-occurring antibodies. For example, the anti-FAM19A5 antibodies have post-translational modifications that are different from those of antibodies that are naturally occurring, such as by having more, less or a different type of post-translational modification.

Exemplary Anti-FAM19A5 Antibodies

Particular antibodies that can be expressed by the AAV vectors disclosed herein are antibodies, e.g., scFv, having the CDR and/or variable region sequences of anti-FAM19A5 antibodies 1-65, 3-2, and 2-13, as well as antibodies having at least 80% identity (e.g., at least 85%, at least 90%, at least 95%, or at least 99% identity) to their variable region or CDR sequences. See U.S. Pat. No. 9,579,398; International Application No. PCT/IB2017/001490. Tables 2 and 3 provide exemplary heavy chain and the light chain CDR sequences, respectively. The CDRs for the following antibodies were identified using the Kabat numbering scheme (see supra): 1-65, 3-2, 2-13, 1-28, P2-C12, 13B4, 13F7, 15A9, P1-A03, P1-A08, P1-F02, P2-A01, P2-A03, P2-F07, P2-F11, SS01-13, SS01-13-s5, and S5-2.GKNG. The CDRs for the following antibodies were identified using the IMGT numbering system (see supra): 1-7A-IT, Low-PI, 1-30, 1-17, 1-32, 4-11, 6-10, 2-13D, 2-13D-37, 2-13D-37-1.5W-41, and 2-13D-37-3W-16. The VH and VL amino acid sequences of different anti-FAM19A5 antibodies of the present disclosure are provided in Tables 4 and 5, respectively.

TABLE 2

| Variable heavy chain CDR amino acid sequences | | | |
|---|---|---|---|
| Antibody | VH-CDR1 | VH-CDR2 | VH-CDR3 |
| Anti-FAM19A5 ("1-65") | SYQMG (SEQ ID NO: 17) | VINKSGSDTS (SEQ ID NO: 18) | GSASYITAATIDA (SEQ ID NO: 19) |
| Anti-FAM19A5 ("3-2") | SFNMF (SEQ ID NO: 14) | QISSSGSSTNYAPAVRG (SEQ ID NO: 15) | SSYDCPYGHCSSGVDSAGEIDA (SEQ ID NO: 16) |
| Anti-FAM19A5 ("2-13") | SHGMF (SEQ ID NO: 11) | EITNDGSGTNYGSAVKG (SEQ ID NO: 12) | STYECPGGFSCWGDTGQIDA (SEQ ID NO: 13) |
| Anti-FAM19A5 ("1-28") | GFDFSDYG (SEQ ID NO: 20) | IRSDGSNP (SEQ ID NO: 21) | AKDGNGYCALDAYRSGGYSCGVYPGSIDA (SEQ ID NO: 22) |
| Anti-FAM19A5 ("P2-C12") | TYAVT (SEQ ID NO: 89) | YINWRGGTSYANWAKG (SEQ ID NO: 90) | DASSGAAFGSYGMDP (SEQ ID NO: 91) |
| Anti-FAM19A5 ("13B4") | SSNWWS (SEQ ID NO: 95) | EIYHGGTTNYNPSLKG (SEQ ID NO: 96) | WQLVGGLDV (SEQ ID NO: 97) |
| Anti-FAM19A5 ("13F7") | GYSWT (SEQ ID NO: 101) | EISHFGSANYNPSLKS (SEQ ID NO: 102) | ALRGTYSRFYYGMDV (SEQ ID NO: 103) |
| Anti-FAM19A5 ("15A9") | SYYWS (SEQ ID NO: 107) | YIYPSGSTNYNPSLKS (SEQ ID NO: 108) | VNPFGYYYAMDV (SEQ ID NO: 109) |
| Anti-FAM19A5 ("P1-A03") | SDYMS (SEQ ID NO: 113) | IIYPSTITYYASWAKG (SEQ ID NO: 114) | GSNWSSGMNL (SEQ ID NO: 115) |
| Anti-FAM19A5 ("P1-A08") | TYYMS (SEQ ID NO: 119) | IVYPSGTTYYANWAKG (SEQ ID NO: 120) | GDSFGYGL (SEQ ID NO: 121) |
| Anti-FAM19A5 ("P1-F02") | NYYMG (SEQ ID NO: 125) | IIYASGSTYYASWAKG (SEQ ID NO: 126) | IDIGVGDYGWAYDRLDL (SEQ ID NO: 127) |
| Anti-FAM19A5 ("P2-A01") | GYYMS (SEQ ID NO: 131) | IIYPSGSTDYASWAKG (SEQ ID NO: 132) | VAGYVGYGYETFFDI (SEQ ID NO: 133) |
| Anti-FAM19A5 ("P2-A03") | NYDMS (SEQ ID NO: 137) | FMDTDGSAYYATWAKG (SEQ ID NO: 138) | RGSSYYGGIDI (SEQ ID NO: 139) |
| Anti-FAM19A5 ("P2-F07") | SYYMN (SEQ ID NO: 143) | IIYPSGTTYYAGWAKG (SEQ ID NO: 144) | TVSGYFDI (SEQ ID NO: 145) |
| Anti-FAM19A5 ("P2-F11") | SYGVS (SEQ ID NO: 149) | YIANNYNPHYASWAKG (SEQ ID NO: 150) | DNYGMDP (SEQ ID NO: 151) |
| Anti-FAM19A5 ("SS01-13") | SYQMG (SEQ ID NO: 17) | VINKSGSDTS (SEQ ID NO: 18) | GSASYITAATIDA (SEQ ID NO: 19) |

TABLE 2-continued

Variable heavy chain CDR amino acid sequences

| Antibody | VH-CDR1 | VH-CDR2 | VH-CDR3 |
| --- | --- | --- | --- |
| Anti-FAM19A5 ("SS01-13-s5") | SYQMG (SEQ ID NO: 17) | AINKSGSDTS (SEQ ID NO: 208) | GSASYITAATIDA (SEQ ID NO: 19) |
| Anti-FAM19A5 ("S5-2.GKNG") | SYQMG (SEQ ID NO: 17) | AINKGGSDTS (SEQ ID NO: 209) | GSASYITAATIDA (SEQ ID NO: 19) |
| Anti-FAM19A5 ("1-7A-IT") | GFTFSSFNMF (SEQ ID NO: 210) | QISSSGSSTNYAPAVKG (SEQ ID NO: 211) | SSYDCPYGHCSSGVDSAGEIDA (SEQ ID NO: 16) |
| Anti-FAM19A5 ("Low-PI") | GFDFESFNMF (SEQ ID NO: 212) | QISSSEEDENYAPAVKG (SEQ ID NO: 213) | SSYDCPYGHCSSGVDSAGEIDA (SEQ ID NO: 16) |
| Anti-FAM19A5 ("1-30") | GFDFESFNMF (SEQ ID NO: 212) | QISSSEEDENYAPAVKG (SEQ ID NO: 213) | SSYDCPYGHCSSGVDSAGEIDA (SEQ ID NO: 16) |
| Anti-FAM19A5 ("1-17") | GFDFESFNMF (SEQ ID NO: 212) | QISSSEEDENYAPAVKG (SEQ ID NO: 213) | SSYDCPYGHCSSGVDSAGEIDA (SEQ ID NO: 16) |
| Anti-FAM19A5 ("1-32") | GFDFESFNMF (SEQ ID NO: 212) | QISSSEEDENYAPAVKG (SEQ ID NO: 213) | SSYDCPYGHCSSGVDSAGEIDA (SEQ ID NO: 16) |
| Anti-FAM19A5 ("4-11") | GFDFESFNMF (SEQ ID NO: 212) | QISSSEEDENYAPAVKG (SEQ ID NO: 213) | SSYDCPYGHCSSGVDSAGEIDA (SEQ ID NO: 16) |
| Anti-FAM19A5 ("6-10") | GFDFESFNMF (SEQ ID NO: 212) | QISSSEEDENYAPAVKG (SEQ ID NO: 213) | SSYDCPYGHCSSGVDSAGEIDA (SEQ ID NO: 16) |
| Anti-FAM19A5 ("2-13D") | GFTFSSHGMF (SEQ ID NO: 214) | EITNDGSGTNYGSAVKG (SEQ ID NO: 12) | STYECPGGFSCWGDTGQIDA (SEQ ID NO: 13) |
| Anti-FAM19A5 ("2-13D-37") | GFDFSSHGMF (SEQ ID NO: 215) | EITNDGSGTNYGSAVKG (SEQ ID NO: 12) | STYECPGGFSCWGDTGQIDA (SEQ ID NO: 13) |
| Anti-FAM19A5 ("2-13D-37-1.5W-41") | GFDFSSHGMF (SEQ ID NO: 215) | EITNDGSGTNYGSAVKG (SEQ ID NO: 12) | SSYVCPGGFSCWGDTGQIDA (SEQ ID NO: 216) |
| Anti-FAM19A5 ("2-13D-37-3W-16") | GFDFSSHGMF (SEQ ID NO: 215) | EITNDGSGTNYGSAVKG (SEQ ID NO: 12) | SNYACPGGFSCWGDTGQIDA (SEQ ID NO: 217) |

TABLE 3

Variable light chain CDR amino acid sequences

| Antibody | VL-CDR1 | VL-CDR2 | VL-CDR3 |
| --- | --- | --- | --- |
| Anti-FAM19A5 ("1-65") | SGGGSSGYGYG (SEQ ID NO: 29) | WNDKRPS (SEQ ID NO: 30) | GNDDYSSDSGYVGV (SEQ ID NO: 31) |
| Anti-FAM19A5 ("3-2") | SGGGSYAGSYYYG (SEQ ID NO: 26) | ESNKRPS (SEQ ID NO: 27) | GSWDSSNGGI (SEQ ID NO: 28) |
| Anti-FAM19A5 ("2-13") | SGGSYSYG (SEQ ID NO: 23) | WDDERPS (SEQ ID NO: 24) | GTEDISGTAGV (SEQ ID NO: 25) |
| Anti-FAM19A5 ("1-28") | GYGYG (SEQ ID NO: 32) | QND (SEQ ID NO: 33) | GSEDSSTLAGI (SEQ ID NO: 34) |
| Anti-FAM19A5 ("P2-C12") | QASQSISSYLS (SEQ ID NO: 92) | EASKLAS (SEQ ID NO: 93) | QQGYSSTNVWNA (SEQ ID NO: 94) |
| Anti-FAM19A5 ("13B4") | SGDKLGNVYAS (SEQ ID NO: 98) | QDNKRPS (SEQ ID NO: 99) | QAWDSSTAV (SEQ ID NO: 100) |
| Anti-FAM19A5 ("13F7") | RSSQSLLHSNGYNYLD (SEQ ID NO: 104) | LGSNRAS (SEQ ID NO: 105) | MQARQTPLT (SEQ ID NO: 106) |
| Anti-FAM19A5 ("15A9") | RASQSISTSLN (SEQ ID NO: 110) | GASTLQS (SEQ ID NO: 111) | QESASIPRT (SEQ ID NO: 112) |
| Anti-FAM19A5 ("P1-A03") | LASEDIYSGIS (SEQ ID NO: 116) | GASNLES (SEQ ID NO: 117) | LGGYSYSSTGLT (SEQ ID NO: 118) |

TABLE 3-continued

Variable light chain CDR amino acid sequences

| Antibody | VL-CDR1 | VL-CDR2 | VL-CDR3 |
| --- | --- | --- | --- |
| Anti-FAM19A5 ("P1-A08") | TADTLSRSYAS (SEQ ID NO: 122) | RDTSRPS (SEQ ID NO: 123) | ATSDGSGSNYQYV (SEQ ID NO: 124) |
| Anti-FAM19A5 ("P1-F02") | LASEDIYSGIS (SEQ ID NO: 128 | GASNLES (SEQ ID NO: 129) | LGGYSYSSIT (SEQ ID NO: 130) |
| Anti-FAM19A5 ("P2-A01") | LASEDIYSGIS (SEQ ID NO: 134) | GASNLES (SEQ ID NO: 135) | LGGVTYSSTGTHLT (SEQ ID NO: 136) |
| Anti-FAM19A5 ("P2-A03") | QASQSIGGNLA (SEQ ID NO: 140) | RASTLAS (SEQ ID NO: 141) | QSPAYDPAAYVGNA (SEQ ID NO: 142) |
| Anti-FAM19A5 ("P2-F07") | LASEDIYSALA (SEQ ID NO: 146) | GTSNLES (SEQ ID NO: 147) | QGYSSYPLT (SEQ ID NO: 148) |
| Anti-FAM19A5 ("P2-F11") | QASQSVYNNKNLA (SEQ ID NO: 152) | AASTLAS (SEQ ID NO: 153) | QGEFSCSSADCNA (SEQ ID NO: 154) |
| Anti-FAM19A5 ("SS01-13") | SGGASSGYGYG (SEQ ID NO: 218) | KDDERPS (SEQ ID NO: 219) | GNDDYSSDSGYVGV (SEQ ID NO: 31) |
| Anti-FAM19A5 ("SS01-13-S5") | SGGASSGYGYG (SEQ ID NO: 218) | KDSERPS (SEQ ID NO: 220) | GNDDYSSDSGYVGV (SEQ ID NO: 31) |
| Anti-FAM19A5 ("S5-2.GKNG") | SGGASSGYGYG (SEQ ID NO: 218) | KDSERPS (SEQ ID NO: 220) | GNDDYSSDSGYVGV (SEQ ID NO: 31) |
| Anti-FAM19A5 ("1-7A-IT") | SGGGSYAGSYYYG (SEQ ID NO: 26) | ENNKRPS (SEQ ID NO: 221) | GSWDSSNGGI (SEQ ID NO: 28) |
| Anti-FAM19A5 ("Low-PI") | SGGGSEEEQYYYG (SEQ ID NO: 222) | EDEERPS (SEQ ID NO: 223) | GSWDSEDEDH (SEQ ID NO: 223) |
| Anti-FAM19A5 ("1-30") | SGGGSEEEQYYYG (SEQ ID NO: 222) | QDEERPS (SEQ ID NO: 225) | GSWDSEDEDH (SEQ ID NO: 224) |
| Anti-FAM19A5 ("1-17") | SGGGSYAGSYYYG (SEQ ID NO: 26) | EDEQRPS (SEQ ID NO: 226) | GSWDSEDEDH (SEQ ID NO: 224) |
| Anti-FAM19A5 ("1-32") | SGGGSYAGSYYYG (SEQ ID NO: 26) | QDEERPS (SEQ ID NO: 225) | GSWDSEDEDH (SEQ ID NO: 224) |
| Anti-FAM19A5 ("4-11") | SGGGSYAGSYYYG (SEQ ID NO: 26) | EDHERPS (SEQ ID NO: 227) | GSWDSSDEDH (SEQ ID NO: 228) |
| Anti-FAM19A5 ("6-10") | SGGGSYAGSYYYG (SEQ ID NO: 26) | QDLLRPS (SEQ ID NO: 229) | GSWDSLSSSH (SEQ ID NO: 230) |
| Anti-FAM19A5 ("2-13D") | SGGVYSYG (SEQ ID NO: 231) | WDDERPS (SEQ ID NO: 24) | GTEDISGTAGV (SEQ ID NO: 25) |
| Anti-FAM19A5 ("2-13D-37") | SGGVYSYG (SEQ ID NO: 231) | WDDERPS (SEQ ID NO: 24) | GTEDISGTAGV (SEQ ID NO: 25) |
| Anti-FAM19A5 ("2-13D-37-1.5W-41") | SGGVYSYG (SEQ ID NO: 231) | WDDERPS (SEQ ID NO: 24) | GTEDISGTAGV (SEQ ID NO: 25) |
| Anti-FAM19A5 ("2-13D-37-3W-16") | SGGVYSYG (SEQ ID NO: 231) | WDDERPS (SEQ ID NO: 24) | GTEDISGTAGV (SEQ ID NO: 25) |

TABLE 4

Variable heavy chain amino acid sequence

| Antibody | VH Amino Acid Sequence (SEQ ID NO) |
| --- | --- |
| Anti-FAM19A5 ("1-65") | AVTLDESGGGLQTPGGALSLVCKASGFTFSSYQMGWVRQAPGKGLEWVGVINKSGSDTSYGSAVKGRATISRDNGQSTVRLQLNNLRAEDTGTYFCAKGSASYITAATIDAWGHGTEVIVSSTS (SEQ ID NO: 37) |

TABLE 4-continued

Variable heavy chain amino acid sequence

| Antibody | VH Amino Acid Sequence (SEQ ID NO) |
|---|---|
| Anti-FAM19A5 ("3-2") | AVTLDESGGGLQTPGGALSLVCKASGFTFSSFNMFWVRQAPGKGLEYVAQISSSGSSTNYAPAVRGRATISRDNGQSTVRLQLNNPGAEDTGTYYCAKSSYDCPYGHCSSGVDSAGEIDAWGHGTEVIVSS (SEQ ID NO: 36) |
| Anti-FAM19A5 ("2-13") | AVTLDESGGGLQTPGGALSLVCKASGFTFSSHGMFWVRQTPGKGLEYVAEITNDGSGTNYGSAVKGRATISRDNGQSTVRLQLNNLRAEDTGTYFCARSTYECPGGFSCWGDTGQIDAWGHGTEVIVSS (SEQ ID NO: 35) |
| Anti-FAM19A5 ("1-28") | AVTLDESGGGLQTPGGALSLVCKASGFDFSDYGMGWVRQAPGKGLEWVAAIRSDGSNPSYGSAVKGRATISKDNGRSTVRLQLNNLRAEDTATYYCAKDGNGYCALDAYRSGGYSCGVYPGSIDAWGHGTEVIVSS (SEQ ID NO: 38) |
| Anti-FAM19A5 ("P2-C12") | QSLEESGGRLVTPGTPLTLTCTVSGFSLSTYAVTWVRQAPGKGLEWIGYINWRGGTSYANWAKGRFTISKTSSTTVDLKMTSPTTEDTATYFCARDASSGAAFGSYGMDPWGPGTLVTVSS (SEQ ID NO: 155) |
| Anti-FAM19A5 ("13B4") | QVQLQESGPGLVKPSGTLSLNCAVSGGSISSSNWWSWVRQPPGKGLEWIGEIYHGGTTNYNPSLKGRVTMSVDKTKNQFSLRLSSVTAVDTAVYYCARWQLVGGLDVWGQGTTVTVSS (SEQ ID NO: 156) |
| Anti-FAM19A5 ("13F7") | QVQLQEWGAGLLKPSETLSLTCAINAESFNGYSWTWIRQTPGKGLEWIGEISHFGSANYNPSLKSRATISADKSKNQFSLKLTSVTAVDTAVYYCARALRGTYSRFYYGMDVWGQGTTVTVSS (SEQ ID NO: 157) |
| Anti-FAM19A5 ("15A9") | QVQLQESGPGLVKPSETLSLTCTVSGGSISSYYWSWIRQPPGKGLEWIGYIYPSGSTNYNPSLKSRVTISVDTSKNQFSLNLKSVTAVDTAVYYCARVNPFGYYYAMDVWGQGTTVTVSS (SEQ ID NO: 158) |
| Anti-FAM19A5 ("P1-A03") | QSVEESGGRLVTPGTPLTLTCTVSGFSLSSDYMSWVRQAPGEGLEWIGIIYPSTTTYYASWAKGRFTISKTSSTTVELKMTSLTTEDTATYFCARGSNWSSGMNLWGPGTLVTVSS (SEQ ID NO: 159) |
| Anti-FAM19A5 ("P1-A08") | QSLEESGGRLVTPGTPLTLTCTASGFSLSTYYMSWVRQAPGKGLEWIGIVYPSGTTYYANWAKGRFTISTASTTVDLMITSPTTEDTATYFCARGDSFGYGLWGPGTLVTVSS (SEQ ID NO: 160) |
| Anti-FAM19A5 ("P1-F02") | QSLEESGGRLVTPGTPLTLTCTASGFSLSNYYMGWVRQAPGEGLEWIGIIYASGSTYYASWAKGRFTISKTSTTVDLKMTSLTTEDTATYFCARIDIGVGDYGWAYDRLDLWGQGTLVTVSS (SEQ ID NO: 161) |
| Anti-FAM19A5 ("P2-A01") | QEQLVESGGRLVTPGTPLTLSCTASGFFLSGYYMSWVRQAPGKGLEWIGIIYPSGSTDYASWAKGRFTISKTSTTVDLKITTPTTEDTATYFCARVAGYVGYGYETFFDIWGPGTLVTVSL (SEQ ID NO: 162) |
| Anti-FAM19A5 ("P2-A03") | QSVEESGGRLVTPGTPLTLTCTVSGFSLNNYDMSWVRQAPGKGLEYIGFMDTDGSAYYATWAKGRFTISRTSTTVDLKMTSPTTEDTATYFCARRGSSYYGGIDIWGPGTPVTVSL (SEQ ID NO: 163) |
| Anti-FAM19A5 ("P2-F07") | QSLEESGGRLVTPGTPLTLTCTASGFSLSSYYMNWVRQAPGKGLEWIGIIYPSGTTYYAGWAKGRFTISKTSTTVDLKITSPTSEDTATYFCARTVSGYFDIWGPGTLVTVSL (SEQ ID NO: 164) |
| Anti-FAM19A5 ("P2-F11") | QEQLVESGGRLVTPGTTLTLTCTVSGFSLSSYGVSWVRQAPGKGLEWIGYIANNYNPHYASWAKGRFTISKTSSTTVDLKMTSLTTEDTATYFCARDNYGMDPWGPGTLVTVSS (SEQ ID NO: 165) |
| Anti-FAM19A5 ("SS01-13") | AVTLDESGGGLQTPGGALSLSCKASGFTFSSYQMGWVRQAPGKGLEWVGVINKSGSDTSYGSAVKGRATISRDNGQSTLYLQMNNLRAEDTAVYFCAKGSASYITAATIDAWGHGTEVIVSS (SEQ ID NO: 232) |
| Anti-FAM19A5 ("SS01-13-s5") | AVTLDESGGGLQTPGGALRLSCKASGFTFSSYQMGWVRQAPGKGLEWVSAINKSGSDTSYGSAVKGRATISRDNGQSTLYLQMNSLRAEDTAVYFCAKGSASYITAATIDAWGHGTEVIVSS (SEQ ID NO: 233) |
| Anti-FAM19A5 ("S5-2.GKNG") | AVTLDESGGGLQTPGGALRLSCKASGFTFSSYQMGWVRQAPGKGLEWVSAINKGGSDTSYGSAVKGRATISRDNGQSTLYLQMNSLRAEDTAVYFCAKGSASYITAATIDAWGHGTEVIVSS (SEQ ID NO: 234) |
| Anti-FAM19A5 ("1-7A-IT") | AVTLDESGGGLQTPGGALRLSCKASGFTFSSFNMFWVRQAPGKGLEYVSQISSSGSSTNYAPAVKGRATISRDNGQSTLYLQMNSLRAEDTGTYYCAKSSYDCPYGHCSSGVDSAGEIDAWGHGTEVIVSS (SEQ ID NO: 235) |

TABLE 4-continued

Variable heavy chain amino acid sequence

| Antibody | VH Amino Acid Sequence (SEQ ID NO) |
|---|---|
| Anti-FAM19A5 ("Low-PI") | AVTLDESGGGLQTPGGALRLSCKASGFDFESFNMFWVRQAPGKGLEYVSQISSSEEDENY APAVKGRATISRDNGQSTLYLQMNSLRAEDTGTYYCAKSSYDCPYGHCSSGVDSAGEIDA WGHGTEVIVSS (SEQ ID NO: 236) |
| Anti-FAM19A5 ("1-30") | AVTLDESGGGLQTPGGALRLSCKASGFDFESFNMFWVRQAPGKGLEYVSQISSSEEDENY APAVKGRATISRDNGQSTLYLQMNSLRAEDTGTYYCAKSSYDCPYGHCSSGVDSAGEIDA WGHGTEVIVSS (SEQ ID NO: 236) |
| Anti-FAM19A5 ("1-17") | AVTLDESGGGLQTPGGALRLSCKASGFDFESFNMFWVRQAPGKGLEYVSQISSSEEDENY APAVKGRATISRDNGQSTLYLQMNSLRAEDTGTYYCAKSSYDCPYGHCSSGVDSAGEIDA WGHGTEVIVSS (SEQ ID NO: 236) |
| Anti-FAM19A5 ("1-32") | AVTLDESGGGLQTPGGALRLSCKASGFDFESFNMFWVRQAPGKGLEYVSQISSSEEDENY APAVKGRATISRDNGQSTLYLQMNSLRAEDTGTYYCAKSSYDCPYGHCSSGVDSAGEIDA WGHGTEVIVSS (SEQ ID NO: 236) |
| Anti-FAM19A5 ("4-11") | AVTLDESGGGLQTPGGALRLSCKASGFDFESFNMFWVRQAPGKGLEYVSQISSSEEDENY APAVKGRATISRDNGQSTLYLQMNSLRAEDTGTYYCAKSSYDCPYGHCSSGVDSAGEIDA WGHGTEVIVSS (SEQ ID NO: 236) |
| Anti-FAM19A5 ("6-10") | AVTLDESGGGLQTPGGALRLSCKASGFDFESFNMFWVRQAPGKGLEYVSQISSSEEDENY APAVKGRATISRDNGQSTLYLQMNSLRAEDTGTYYCAKSSYDCPYGHCSSGVDSAGEIDA WGHGTEVIVSS (SEQ ID NO: 236) |
| Anti-FAM19A5 ("2-13D") | AVTLDESGGGLQTPGGALRLSCSASGFTFSSHGMFWVRQAPGKGLEYVSEITNDGSGTNY GSAVKGRATISRDNGQSTLYLQMNSLRAEDTGTYFCARSTYECPGGFSCWGDTGQIDAWG HGTEVIVSS (SEQ ID NO: 237) |
| Anti-FAM19A5 ("2-13D-37") | AVTLDESGGGLQTPGGALRLSCSASGFDFSSHGMFWVRQAPGKGLEYVSEITNDGSGTNY GSAVKGRATISRDNGQSTLYLQMNSLRAEDTGTYFCARSTYECPGGFSCWGDTGQIDAWG HGTEVIVSS (SEQ ID NO: 238) |
| Anti-FAM19A5 ("2-13D-37-1.5W-41") | AVTLDESGGGLQTPGGALRLSCSASGFDFSSHGMFWVRQAPGKGLEYVSEITNDGSGTNY GSAVKGRATISRDNGQSTLYLQMNSLRAEDTGTYFCARSSYVCPGGFSCWGDTGQIDAWG HGTEVIVSS (SEQ ID NO: 239) |
| Anti-FAM19A5 ("2-13D-37-3W-16") | AVTLDESGGGLQTPGGALRLSCSASGFDFSSHGMFWVRQAPGKGLEYVSEITNDGSGTNY GSAVKGRATISRDNGQSTLYLQMNSLRAEDTGTYFCARSNYACPGGFSCWGDTGQIDAWG HGTEVIVSS (SEQ ID NO: 240) |

TABLE 5

Variable light chain amino acid sequence

| Antibody | VL Amino Acid Sequence (SEQ ID NO) |
|---|---|
| Anti-FAM19A5 ("1-65") | ALTQPSSVSANPGETVKITCSGGGSSGYGYGWYQQKSPSSAPLTVIYWNDKRPSDIPSRF SGSKSGSTHTLTITGVQAEDEAVYFCGNDDYSSDSGYVGVFGAGTTLTVL (SEQ ID NO: 41) |
| Anti-FAM19A5 ("3-2") | ALTQPSSVSANPGETVKITCSGGGSYAGSYYYGWYQQKAPGSAPVTLIYESNKRPSDIPS RFSGSTSGSTATLTITGVQADDEAIYYCGSWDSSNGGIFGAGTTLTVL (SEQ ID NO: 40) |
| Anti-FAM19A5 ("2-13") | ALTQPSSVSANPGETVKITCSGGSYSYGWFQQKSPGSALVTVIYWDDERPSDIPSRFSGA LSGSTNTLTITGVQADDEAVYFCGTEDISGTAGVFGAGTTLTVL (SEQ ID NO: 39) |
| Anti-FAM19A5 ("1-28") | ALTQPSSVSANLEGTVEITCSGSGYGYGWYQQKSPGSAPVTVIYQNDKRPSDIPSRFSGS KSGSTGTLTITGVQVEDEAVYYCGSEDSSTLAGIFGAGTTLTVL (SEQ ID NO: 42) |
| Anti-FAM19A5 ("P2-C12") | ELDMTQTPSSVSAAVGGTVTIKCQASQSISSYLSWYQQKPGQPPKLLIYEASKLASGVPS RFSGSGYGTEFTLTISDLECADAATYYCQQGYSSTNVWNAFGGGTNVEIK (SEQ ID NO: 166) |
| Anti-FAM19A5 ("13B4") | SYELTQPLSVSVSPGQTASITCSGDKLGNVYASWYQQKPGQSPTLVIYQDNKRPSGIPER FSGSNSGKTATLTISGTQALDEADYYCQAWDSSTAVFGGGTKLTVL (SEQ ID NO: 167) |

TABLE 5-continued

Variable light chain amino acid sequence

| Antibody | VL Amino Acid Sequence (SEQ ID NO) |
|---|---|
| Anti-FAM19A5 ("13F7") | DIVMTQTPLSLPVAPGEPASISCRSSQSLLHSNGYNYLDWYVQKPGQPPQLLIYLGSNRA SGVPDRFSGSGSGTDFTLKISRVEAEDVGVYYCMQARQTPLTFGGGTKVEIK (SEQ ID NO: 168) |
| Anti-FAM19A5 ("15A9") | DIQMTQSPSSLSASVGDRITISCRASQSISTSLNWYQQTPGKAPRLLIYGASTLQSGVPS RFSGGGSGTDFSLTITSLQPEDFATYYCQESASIPRTFGQGTKLDIK (SEQ ID NO: 169) |
| Anti-FAM19A5 ("P1-A03") | ELVMTQPPSLSASVGETVRIRCLASEDIYSGISWYQQKPEKPPTLLISGASNLESGVPP RFSGSGSGTDYTLTIGGVQAEDAATYYCLGGYSYSSTGLTFGAGTNVEIK (SEQ ID NO: 170) |
| Anti-FAM19A5 ("P1-A08") | ELVLTQSPSVQVNLGQTVSLTCTADTLSRSYASWYQQKPGQAPVLLIYRDTSRPSGVPDR FSGSSSGNTATLTISGAQAGDEADYYCATSDGSGSNYQYVFGGGTQLTVT (SEQ ID NO: 171) |
| Anti-FAM19A5 ("P1-F02") | ELDMTQPPSLSASVGETVRIRCLASEDIYSGISWYQQKPGKPPTLLIYGASNLESGVPP RFSGSGSGTDYTLTIGGVQAEDAATYYCLGGYSYSSITFGAGTNVEIK (SEQ ID NO: 172) |
| Anti-FAM19A5 ("P2-A01") | ELVMTQPPSLSASVGETVRIRCLASEDIYSGISWYQQKPGKPPTLLIYGASNLESGVPP RFSGSGSGSDYTLTIGGVQAEDAATYYCLGGVTYSSTGTHLTFGAGTNVEIK (SEQ ID NO: 173) |
| Anti-FAM19A5 ("P2-A03") | ELDLTQTPASVSEPVGGTVTIKCQASQSIGGNLAWYQQKPGQPPKLLIYRASTLASGVPS RFKGSGSGTDFTLTISDLECADAATYYCQSPAYDPAAYVGNAFGGGTELEIL (SEQ ID NO: 174) |
| Anti-FAM19A5 ("P2-F07") | ELDLTQPPSLSASVGGTVTINCLASEDIYSALAWYQQKPGKPPTLLISGTSNLESGVPP RFSGSGSGTDYTLTIGGVQAEDAATYFCQGYSSYPLTFGAGTNVEIK (SEQ ID NO: 175) |
| Anti-FAM19A5 ("P2-F11") | ELDLTQPSSVSAAVGGTVTINCQASQSVYNNKNLAWYQQKPGQPPKLLIYAASTLASGV SSRFKGSGSGTQFTLTISDVQCDDAATYYCQGEFSCSSADCNAFGGGTELEIL (SEQ ID NO: 176) |
| Anti-FAM19A5 ("SS01-13") | ALTQPSSVSANPGETVRITCSGGASSGYGYGWYQQKPSSAPLTVIYKDDERPSDIPSRFS GSSSGSTHTLTITGVQAEDEAVYFCGNDDYSSDSGYVGVFGAGTTLTVL (SEQ ID NO: 241) |
| Anti-FAM19A5 ("SS01-13-s5") | ALTQPSSVSANPGETARITCSGGASSGYGYGWYQQKPSSAPLTVIYKDSERPSDIPSRFS GSSSGSTHTLTISGVQAEDEAVYFCGNDDYSSDSGYVGVFGAGTTLTVL (SEQ ID NO: 242) |
| Anti-FAM19A5 ("S5-2.GKNG") | ALTQPSSVSANPGETARITCSGGASSGYGYGWYQQKPSSAPLTVIYKDSERPSDIPSRFS GSSSGSTHTLTISGVQAEDEAVYFCGNDDYSSDSGYVGVFGAGTTLTVL (SEQ ID NO: 242) |
| Anti-FAM19A5 ("1-7A-IT") | ALTQPSSVSANPGETVKITCSGGGSYAGSYYYGWYQQKPGSAPVTLIYENNKRPSDIPSR FSGSTSGSTATLTITGVQAGDEADYYCGSWDSSNGGIFGAGTTLTVL (SEQ ID NO: 243) |
| Anti-FAM19A5 ("Low-PI") | ALTQPSSVSANPGETVKITCSGGGSEEEQYYYGWYQQKPGSAPVTLIYEDEERPSDIPSR FSGSTSGSTATLTITGVQAGDEADYYCGSWDSEDEDHFGAGTTLTVL (SEQ ID NO: 244) |
| Anti-FAM19A5 ("1-30") | ALTQPSSVSANPGETVKITCSGGGSEEEQYYYGWYQQKPGSAPVTLIYQDEERPSDIPSR FSGSTSGSTATLTITGVQAGDEADYYCGSWDSEDEDHFGAGTTLTVL (SEQ ID NO: 245) |
| Anti-FAM19A5 ("1-17") | ALTQPSSVSANPGETVKITCSGGGSYAGSYYYGWYQQKPGSAPVTLIYEDEQRPSDIPSR FSGSTSGSTATLTITGVQAGDEADYYCGSWDSEDEDHFGAGTTLTVL (SEQ ID NO: 246) |
| Anti-FAM19A5 ("1-32") | ALTQPSSVSANPGETVKITCSGGGSYAGSYYYGWYQQKPGSAPVTLIYQDEERPSDIPSR FSGSTSGSTATLTITGVQAGDEADYYCGSWDSEDEDHFGAGTTLTVL (SEQ ID NO: 247) |
| Anti-FAM19A5 ("4-11") | ALTQPSSVSANPGETVKITCSGGGSYAGSYYYGWYQQKPGSAPVTLIYEDHERPSDIPSR FSGSTSGSTATLTITGVQAGDEADYYCGSWDSSDEDHFGAGTTLTVL (SEQ ID NO: 248) |

TABLE 5-continued

Variable light chain amino acid sequence

| Antibody | VL Amino Acid Sequence (SEQ ID NO) |
|---|---|
| Anti-FAM19A5 ("6-10") | ALTQPSSVSANPGETVKITCSGGGSYAGSYYYGWYQQKPGSAPVTLIYQDLLRPSDIPSR FSGSTSGSTATLTITGVQAGDEADYYCGSWDSLSSSHFGAGTTLTVL (SEQ ID NO: 249) |
| Anti-FAM19A5 ("2-13D") | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVL (SEQ ID NO: 250) |
| Anti-FAM19A5 ("2-13D-37") | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVL (SEQ ID NO: 250) |
| Anti-FAM19A5 ("2-13D-37-1.5W-41") | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVL (SEQ ID NO: 250) |
| Anti-FAM19A5 ("2-13D-37-3W-16") | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVL (SEQ ID NO: 250) |

In some embodiments, the anti-FAM19A5 antibody comprises heavy and light chain variable regions, wherein the heavy chain variable region comprises the amino acid sequence of SEQ ID NOs: 35-38, 155-165, or 232-240 (see Table 4). In other embodiments, the anti-FAM19A5 antibody comprises the CDRs of the heavy chain variable region selected from the group consisting of SEQ ID NOs: 35-38, 155-165, or 232-240 (see Table 4).

In some embodiments, the anti-FAM19A5 antibody comprises heavy and light chain variable regions, wherein the light chain variable region comprises the amino acid sequence of SEQ ID NOs: 39-42, 166-176, or 241-250 (see Table 5). In other embodiments, the anti-FAM19A5 antibody comprises the CDRs of the light chain variable region selected from the group consisting of SEQ ID NOs: 39-42, 166-176, or 241-250 (see Table 5).

In some embodiments, the anti-FAM19A5 antibody comprises the CDRs of the heavy chain variable region selected from the group consisting of SEQ ID NOs: 35-38, 155-165, or 232-240 (see Table 4) and the CDRs of the light chain variable region selected from the group consisting of SEQ ID NOs: 39-42, 166-176, or 241-250 (see Table 5).

In some embodiments, the anti-FAM19A5 antibody comprises heavy and light chain variable regions, (i) wherein the heavy chain variable region comprises the amino acid sequence of SEQ ID NO: 37 and wherein the light chain variable region comprises the amino acid sequence of SEQ ID NO: 41; (ii) wherein the heavy chain variable region comprises the amino acid sequence of SEQ ID NO: 36 and wherein the light chain variable region comprises the amino acid sequence of SEQ ID NO: 40; (iii) wherein the heavy chain variable region comprises the amino acid sequence of SEQ ID NO: 35 and wherein the light chain variable region comprises the amino acid sequence of SEQ ID NO: 39; (iv) wherein the heavy chain variable region comprises the amino acid sequence of SEQ ID NO: 38 and wherein the light chain variable region comprises the amino acid sequence of SEQ ID NO: 42; (v) wherein the heavy chain variable region comprises the amino acid sequence of SEQ ID NO: 155 and wherein the light chain variable region comprises the amino acid sequence of SEQ ID NO: 166; (vi) wherein the heavy chain variable region comprises the amino acid sequence of SEQ ID NO: 156 and wherein the light chain variable region comprises the amino acid sequence of SEQ ID NO: 167; (vii) wherein the heavy chain variable region comprises the amino acid sequence of SEQ ID NO: 157 and wherein the light chain variable region comprises the amino acid sequence of SEQ ID NO: 168; (viii) wherein the heavy chain variable region comprises the amino acid sequence of SEQ ID NO: 158 and wherein the light chain variable region comprises the amino acid sequence of SEQ ID NO: 169; (ix) wherein the heavy chain variable region comprises the amino acid sequence of SEQ ID NO: 159 and wherein the light chain variable region comprises the amino acid sequence of SEQ ID NO: 170; (x) wherein the heavy chain variable region comprises the amino acid sequence of SEQ ID NO: 160 and wherein the light chain variable region comprises the amino acid sequence of SEQ ID NO: 171; (xi) wherein the heavy chain variable region comprises the amino acid sequence of SEQ ID NO: 161 and wherein the light chain variable region comprises the amino acid sequence of SEQ ID NO: 172; (xii) wherein the heavy chain variable region comprises the amino acid sequence of SEQ ID NO: 162 and wherein the light chain variable region comprises the amino acid sequence of SEQ ID NO: 173; (xiii) wherein the heavy chain variable region comprises the amino acid sequence of SEQ ID NO: 163 and wherein the light chain variable region comprises the amino acid sequence of SEQ ID NO: 174; (xiv) wherein the heavy chain variable region comprises the amino acid sequence of SEQ ID NO: 164 and wherein the light chain variable region comprises the amino acid sequence of SEQ ID NO: 175; and (xv) wherein the heavy chain variable region comprises the amino acid sequence of SEQ ID NO: 165 and wherein the light chain variable region comprises the amino acid sequence of SEQ ID NO: 176. In some embodiments, an isolated anti-FAM19A5 antibody, or an antigen binding fragment thereof, comprises a heavy chain variable region (VH) and a light chain variable region (VL), wherein the VH comprises a VH sequence as set forth in Table 4, and the VL comprises a VL sequence as set forth in Table 5.

In some embodiments, the anti-FAM19A5 antibody comprises a heavy chain variable region and a light chain variable region, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NOs: 35-38, 155-165, or 232-240 (see Table 4).

In some embodiments, the anti-FAM19A5 antibody comprises a heavy chain variable region and a light chain variable region, wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NOs: 39-42, 166-176, or 241-250 (see Table 5).

In some embodiments, the anti-FAM19A5 antibody comprises heavy and light chain variable regions, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NOs: 35-38, 155-165, or 232-240 (see Table 4), and wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NOs: 39-42, 166-176, or 241-250 (see Table 5).

In some embodiments, the anti-FAM19A5 antibody comprises:

(a) heavy and light chain variable region sequences comprising SEQ ID NOs: 35 and 39, respectively;
(b) heavy and light chain variable region sequences comprising SEQ ID NOs: 36 and 40, respectively;
(c) heavy and light chain variable region sequences comprising SEQ ID NOs: 37 and 41, respectively;
(d) heavy and light chain variable region sequences comprising SEQ ID NOs: 38 and 42, respectively;
(e) heavy and light chain variable region sequences comprising SEQ ID NOs: 155 and 166, respectively;
(f) heavy and light chain variable region sequences comprising SEQ ID NOs: 156 and 167, respectively;
(g) heavy and light chain variable region sequences comprising SEQ ID NOs: 157 and 168, respectively;
(h) heavy and light chain variable region sequences comprising SEQ ID NOs: 158 and 169, respectively;
(i) heavy and light chain variable region sequences comprising SEQ ID NOs: 159 and 170, respectively;
(j) heavy and light chain variable region sequences comprising SEQ ID NOs: 160 and 171, respectively;
(k) heavy and light chain variable region sequences comprising SEQ ID NOs: 161 and 172, respectively;
(l) heavy and light chain variable region sequences comprising SEQ ID NOs: 162 and 173, respectively;
(m) heavy and light chain variable region sequences comprising SEQ ID NOs: 163 and 174, respectively;
(n) heavy and light chain variable region sequences comprising SEQ ID NOs: 164 and 175, respectively;
(o) heavy and light chain variable region sequences comprising SEQ ID NOs: 165 and 176, respectively;
(p) heavy and light chain variable region sequences comprising SEQ ID NOs: 232 and 241, respectively;
(q) heavy and light chain variable region sequences comprising SEQ ID NOs: 233 and 242, respectively;
(r) heavy and light chain variable region sequences comprising SEQ ID NOs: 234 and 242, respectively;
(s) heavy and light chain variable region sequences comprising SEQ ID NOs: 235 and 243, respectively;
(t) heavy and light chain variable region sequences comprising SEQ ID NOs: 236 and 244, respectively;
(u) heavy and light chain variable region sequences comprising SEQ ID NOs: 236 and 245, respectively;
(v) heavy and light chain variable region sequences comprising SEQ ID NOs: 236 and 246, respectively;
(w) heavy and light chain variable region sequences comprising SEQ ID NOs: 236 and 247, respectively;
(x) heavy and light chain variable region sequences comprising SEQ ID NOs: 236 and 248, respectively;
(y) heavy and light chain variable region sequences comprising SEQ ID NOs: 236 and 249, respectively;
(z) heavy and light chain variable region sequences comprising SEQ ID NOs: 237 and 250, respectively;
(aa) heavy and light chain variable region sequences comprising SEQ ID NOs: 238 and 250, respectively;
(bb) heavy and light chain variable region sequences comprising SEQ ID NOs: 239 and 250, respectively; or
(cc) heavy and light chain variable region sequences comprising SEQ ID NOs: 240 and 250, respectively.

In certain embodiments, the anti-FAM19A5 antibody comprises (i) the heavy chain CDR1, CDR2 and CDR3 of 1-65, or combinations thereof, and/or the light chain CDR1, CDR2, and CDR3 of 1-65, or combinations thereof; (ii) the heavy chain CDR1, CDR2 and CDR3 of 3-2, or combinations thereof, and/or the light chain CDR1, CDR2, and CDR3 of 3-2, or any combinations thereof; (iii) the heavy chain CDR1, CDR2 and CDR3 of 2-13, or combinations thereof, and/or the light chain CDR1, CDR2, and CDR3 of 2-13, or any combinations thereof; (iv) the heavy chain CDR1, CDR2 and CDR3 of 1-28, or combinations thereof, and/or the light chain CDR1, CDR2, and CDR3 of 1-28, or any combinations thereof; (v) the heavy chain CDR1, CDR2, and CDR3 of P2-C12, or combinations thereof, and/or the light chain CDR1, CDR2, and CDR3 of P2-C12, or any combinations thereof; (vi) the heavy chain CDR1, CDR2, and CDR3 of 13B4, or combinations thereof, and/or the light chain CDR1, CDR2, and CDR3 of 13B4, or any combinations thereof; (vii) the heavy chain CDR1, CDR2, and CDR3 of 13F7, or combinations thereof, and/or the light chain CDR1, CDR2, and CDR3 of 13F7, or any combinations thereof; (viii) the heavy chain CDR1, CDR2, and CDR3 of 15A9, or combinations thereof, and/or the light chain CDR1, CDR2, and CDR3 of 15A9, or any combinations thereof; (ix) the heavy chain CDR1, CDR2, and CDR3 of P1-A03, or combinations thereof, and/or the light chain CDR1, CDR2, and CDR3 of P1-A03, or any combinations thereof; (x) the heavy chain CDR1, CDR2, and CDR3 of P1-A08, or combinations thereof, and/or the light chain CDR1, CDR2, and CDR3 of P1-A08, or any combinations thereof; (xi) the heavy chain CDR1, CDR2, and CDR3 of P1-F02, or combinations thereof, and/or the light chain CDR1, CDR2, and CDR3 of P1-F02, or any combinations thereof; (xii) the heavy chain CDR1, CDR2, and CDR3 of P2-A01, or combinations thereof, and/or the light chain CDR1, CDR2, and CDR3 of P2-A01, or any combinations thereof; (xiii) the heavy chain CDR1, CDR2, and CDR3 of P2-A03, or combinations thereof, and/or the light chain CDR1, CDR2, and CDR3 of P2-A03, or any combinations thereof; (xiv) the heavy chain CDR1, CDR2, and CDR3 of P2-F07, or combinations thereof, and/or the light chain CDR1, CDR2, and CDR3 of P2-F07, or any combinations thereof; (xv) the heavy chain CDR1, CDR2, and CDR3 of P2-F11, or combinations thereof, and/or the light chain CDR1, CDR2, and CDR3 of F2-F11, or any combinations thereof; (xvi) the heavy chain CDR1, CDR2, and CDR3 of SS01-13, or combinations thereof, and/or the light chain CDR1, CDR2, and CDR3 of SS01-13, or any combinations thereof; (xvii) the heavy chain CDR1, CDR2, and CDR3 of SS01-13-s5, or combinations thereof, and/or the light chain CDR1, CDR2, and CDR3 of SS01-13-s5, or any combinations thereof; (xviii) the heavy chain CDR1, CDR2, and CDR3 of S5-2.GKNG, or combinations thereof, and/or the light chain CDR1, CDR2, and CDR3 of S5-2.GKNG, or any combinations thereof; (xix) the heavy chain CDR1, CDR2, and CDR3 of 1-7A-IT, or combinations thereof, and/or the light chain CDR1, CDR2, and CDR3 of 1-7A-IT, or any combinations thereof; (xx) the heavy chain CDR1, CDR2, and CDR3 of Low-PI, or combinations thereof, and/or the light chain CDR1, CDR2, and CDR3 of Low-PI, or any combinations thereof; (xxi) the heavy chain CDR1, CDR2, and CDR3 of 1-30, or combinations thereof, and/or the light chain CDR1, CDR2, and CDR3 of 1-30, or any combinations thereof; (xxii) the heavy chain CDR1, CDR2, and CDR3 of 1-17, or combinations thereof, and/or the light chain CDR1, CDR2, and CDR3 of 1-17, or any combinations thereof; (xxiii) the heavy chain CDR1, CDR2, and CDR3 of 1-32, or combinations thereof, and/or the light chain CDR1, CDR2, and CDR3 of 1-32, or any combinations thereof; (xxiv) the heavy chain CDR1, CDR2, and CDR3 of 4-11, or combinations thereof, and/or the light chain CDR1, CDR2, and CDR3 of 4-11, or any combinations thereof; (xxv) the heavy chain CDR1, CDR2, and CDR3 of 6-10, or combinations thereof, and/or the light chain CDR1, CDR2, and CDR3 of 6-10, or any combinations thereof; (xxvi) the heavy chain CDR1, CDR2, and CDR3 of 2-13D, or combinations thereof, and/or the light chain CDR1, CDR2, and CDR3 of 2-13D, or any combinations thereof; (xxvii) the heavy chain CDR1, CDR2, and CDR3 of 2-13D-37, or combinations thereof, and/or the light chain CDR1, CDR2, and CDR3 of 2-13D-37, or any combinations thereof; (xxviii) the heavy chain CDR1, CDR2, and CDR3 of 2-13D-37-1.5W-41, or combinations thereof, and/or the light chain CDR1, CDR2, and CDR3 of 2-13D-37-1.5W-41, or any combinations thereof; or (xxiv) the heavy chain CDR1, CDR2, and CDR3 of 2-13D-37-3W-16, or combinations thereof, and/or the light chain CDR1, CDR2, and CDR3 of 2-13D-3W-16, or any combinations thereof. The amino acid sequences of the VH CDR1, CDR2, and CDR3 for the different anti-FAM19A5 antibodies disclosed herein are provided in Table 2. The amino acid sequences of the VL CDR1, CDR2, and CDR3 for the different anti-FAM19A5 antibodies disclosed herein are provided in Table 3.

In some embodiments, the anti-FAM19A5 antibody comprises:
(a) a VH CDR1 comprising the amino acid sequence of SEQ ID NO: 17; and/or
(b) a VH CDR2 comprising the amino acid sequence of SEQ ID NO: 18; and/or
(c) a VH CDR3 comprising the amino acid sequence of SEQ ID NO: 19.

In some embodiments, the anti-FAM19A5 antibody comprises one, two, or all three of the VH CDRs above.

In some embodiments, the anti-FAM19A5 antibody comprises:
(a) a VL CDR1 comprising the amino acid sequence of SEQ ID NO: 29; and/or
(b) a VL CDR2 comprising the amino acid sequence of SEQ ID NO: 30; and/or
(c) a VL CDR3 comprising the amino acid sequence of SEQ ID NO: 31.

In some embodiments, the anti-FAM19A5 antibody comprises one, two, or all three of the VL CDRs above.

In some embodiments, the anti-FAM19A5 antibody comprises:
(a) a VH CDR1 comprising the amino acid sequence of SEQ ID NO: 17;
(b) a VH CDR2 comprising the amino acid sequence of SEQ ID NO: 18;
(c) a VH CDR3 comprising the amino acid sequence of SEQ ID NO: 19;
(d) a VL CDR1 comprising the amino acid sequence of SEQ ID NO: 29;
(e) a VL CDR2 comprising the amino acid sequence of SEQ ID NO: 30; and/or
(f) a VL CDR3 comprising the amino acid sequence of SEQ ID NO: 31.

In some embodiments, the anti-FAM19A5 antibody comprises:
(a) a VH CDR1 comprising the amino acid sequence of SEQ ID NO: 14;
(b) a VH CDR2 comprising the amino acid sequence of SEQ ID NO: 15; and/or
(c) a VH CDR3 comprising the amino acid sequence of SEQ ID NO: 16.

In some embodiments, the anti-FAM19A5 antibody comprises one, two, or all three of the VH CDRs above.

In some embodiments, the anti-FAM19A5 antibody comprises:
(a) a VL CDR1 comprising the amino acid sequence of SEQ ID NO: 26;
(b) a VL CDR2 comprising the amino acid sequence of SEQ ID NO: 27; and/or
(c) a VL CDR3 comprising the amino acid sequence of SEQ ID NO: 28.

In some embodiments, the anti-FAM19A5 antibody comprises one, two, or all three of the VL CDRs above.

In some embodiments, the anti-FAM19A5 antibody comprises:
(a) a VH CDR1 comprising the amino acid sequence of SEQ ID NO: 14;
(b) a VH CDR2 comprising the amino acid sequence of SEQ ID NO: 15;
(c) a VH CDR3 comprising the amino acid sequence of SEQ ID NO: 16;
(d) a VL CDR1 comprising the amino acid sequence of SEQ ID NO: 26;
(e) a VL CDR2 comprising the amino acid sequence of SEQ ID NO: 27; and/or
(f) a VL CDR3 comprising the amino acid sequence of SEQ ID NO: 28.

In some embodiments, the anti-FAM19A5 antibody comprises:
(a) a VH CDR1 comprising the amino acid sequence of SEQ ID NO: 11;
(b) a VH CDR2 comprising the amino acid sequence of SEQ ID NO: 12; and/or
(c) a VH CDR3 comprising the amino acid sequence of SEQ ID NO: 13.

In some embodiments, the anti-FAM19A5 antibody comprises one, two, or all three of the VH CDRs above.

In some embodiments, the anti-FAM19A5 antibody comprises:
(a) a VL CDR1 comprising the amino acid sequence of SEQ ID NO: 23;

(b) a VL CDR2 comprising the amino acid sequence of SEQ ID NO: 24; and/or
(c) a VL CDR3 comprising the amino acid sequence of SEQ ID NO: 25.

In some embodiments, the anti-FAM19A5 antibody comprises one, two, or all three of the VL CDRs above.

In some embodiments, the anti-FAM19A5 antibody comprise:
(a) a VH CDR1 comprising the amino acid sequence of SEQ ID NO: 11;
(b) a VH CDR2 comprising the amino acid sequence of SEQ ID NO: 12;
(c) a VH CDR3 comprising the amino acid sequence of SEQ ID NO: 13;
(d) a VL CDR1 comprising the amino acid sequence of SEQ ID NO: 23;
(e) a VL CDR2 comprising the amino acid sequence of SEQ ID NO: 24; and/or
(f) a VL CDR3 comprising the amino acid sequence of SEQ ID NO: 25.

In some embodiments, the anti-FAM19A5 antibody comprises:
(a) a VH CDR1 comprising the amino acid sequence of SEQ ID NO: 20;
(b) a VH CDR2 comprising the amino acid sequence of SEQ ID NO: 21; and/or
(c) a VH CDR3 comprising the amino acid sequence of SEQ ID NO: 22.

In some embodiments, the anti-FAM19A5 antibody comprises one, two, or all three of the VH CDRs above.

In some embodiments, the anti-FAM19A5 antibody comprises:
(a) a VL CDR1 comprising the amino acid sequence of SEQ ID NO: 32;
(b) a VL CDR2 comprising the amino acid sequence of SEQ ID NO: 33; and/or
(c) a VL CDR3 comprising the amino acid sequence of SEQ ID NO: 34.

In some embodiments, the anti-FAM19A5 antibody comprises one, two, or all three of the VL CDRs above.

In some embodiments, the anti-FAM19A5 antibody comprises:
(a) a VH CDR1 comprising the amino acid sequence of SEQ ID NO: 20;
(b) a VH CDR2 comprising the amino acid sequence of SEQ ID NO: 21;
(c) a VH CDR3 comprising the amino acid sequence of SEQ ID NO: 22;
(d) a VL CDR1 comprising the amino acid sequence of SEQ ID NO: 32;
(e) a VL CDR2 comprising the amino acid sequence of SEQ ID NO: 33; and/or
(f) a VL CDR3 comprising the amino acid sequence of SEQ ID NO: 34.

In some embodiments, the anti-FAM19A5 antibody disclosed herein (e.g., scFvs) comprises one, two, three, four, five, or six of the CDRs above. In some embodiments, the anti-FAM19A5 antibody disclosed herein (e.g., scFvs) comprises one, two, three, four, five, or six of the CDRs provided in Table 2 or Table 3.

In some embodiments, a VH domain and a VL domain described herein can be linked by a flexible linker to produce a single chain Fv antibody. Accordingly, in some embodiments, the anti-FAM19A5 antibody, or antigen-binding portion thereof, comprises a VH domain selected from Table 4 and a VL domain selected from Table 5, wherein the VH domain and the VL domain are joined by a flexible linker. In some embodiments, the flexible linker comprises the sequence SGGGGSSGGGGS (SEQ ID NO: 207). In other embodiments, the flexible linker comprises the sequence GQSSRSSGGGGSSGGGGS (SEQ ID NO: 300). Amino acid sequences of exemplary anti-FAM19A5 scFv are provided in Table 6, below (VH domain is underlined, VL domain is bolded, and the linker is italicized).

TABLE 6

| Variable heavy chain amino acid sequence | |
|---|---|
| ScFv Antibody | Amino Acid Sequence (SEQ ID NO) |
| Anti-FAM19A5 ("1-65") | ALTQPSSVSANPGETVKITCSGGGSSGYGYGWYQQKSPSSAPLTVIYWNDKRPSDIPSRF SGSKSGSTHTLTITGVQAEDEAVYFCGNDDYSSDSGYVGVFGAGTTLTVL*SGGGGSSGGG GS*AVTLDESGGGLQTPGGALSLVCKASGFTFSSYQMGWVRQAPGKGLEWVGVINKSGSDT SYGSAVKGRATISRDNGQSTVRLQLNNLRAEDTGTYFCAKGSASYITAATIDAWGHGTEV IVSS (SEQ ID NO: 202) |
| Anti-FAM19A5 ("3-2") | ALTQPSSVSANPGETVKITCSGGGSYAGSYYYGWYQQKAPGSAPVTLIYESNKRPSDIPS RFSGSTSGSTATLTITGVQADDEAIYYCGSWDSSNGGIFGAGTTLTVL*SGGGGSSGGGGS* AVTLDESGGGLQTPGGALSLVCKASGFTFSSFNMFWVRQAPGKGLEYVAQISSSGSSTNY APAVRGRATISRDNGQSTVRLQLNNPGAEDTGTYYCAKSSYDCPYGHCSSGVDSAGEIDA WGHGTEVIVSS (SEQ ID NO: 201) |
| Anti-FAM19A5 ("2-13") | ALTQPSSVSANPGETVKITCSGGSYSYGWFQQKSPGSALVTVIYWDDERPSDIPSRFSGA LSGSTNTLTITGVQADDEAVYFCGTEDISGTAGVEGAGTTLTVL*SGGGGSSGGGGS*AVTL DESGGGLQTPGGALSLVCKASGFTFSSHGMFWVRQTPGKGLEYVAEITNDGSGTNYGSAV KGRATISRDNGQSTVRLQLNNLRAEDTGTYFCARSTYECPGGFSCWGDTGQIDAWGHGTE VIVSS (SEQ ID NO: 203) |
| Anti-FAM19A5 ("SS01-13") scFv | ALTQPSSVSANPGETVRITCSGGASSGYGYGWYQQKPSSAPLTVIYKDDERPSDIPSRFS GSSSGSTHTLTITGVQAEDEAVYFCGNDDYSSDSGYVGVFGAGTTLTVL*GQSSRSSGGGG SSGGGGS*AVTLDESGGGLQTPGGALSLSCKASGFTFSSYQMGWVRQAPGKGLEWVGVINK SGSDTSYGSAVKGRATISRDNGQSTLYLQMNNLRAEDTAVYFCAKGSASYITAATIDAWG HGTEVIVSS (SEQ ID NO: 251) |
| Anti-FAM19A5 ("SS01-13-s5") scFv | ALTQPSSVSANPGETARITCSGGASSGYGYGWYQQKPSSAPLTVIYKDSERPSDIPSRFS GSSSGSTHTLTISGVQAEDEAVYFCGNDDYSSDSGYVGVFGAGTTLTVL*GQSSRSSGGGG SSGGGGS*AVTLDESGGGLQTPGGALRLSCKASGFTFSSYQMGWVRQAPGKGLEWVSAINK SGSDTSYGSAVKGRATISRDNGQSTLYLQMNSLRAEDTAVYFCAKGSASYITAATIDAWG HGTEVIVSS (SEQ ID NO: 252) |

TABLE 6-continued

Variable heavy chain amino acid sequence

| ScFv Antibody | Amino Acid Sequence (SEQ ID NO) |
|---|---|
| Anti-FAM19A5 ("S5-2.GKNG") scFv | ALTQPSSVSANPGETARITCSGGASSGYGYGWYQQKPSSAPLTVIYKDSERPSDIPSRFS GSSSGSTHTLTISGVQAEDEAVYFCGNDDYSSDSGYVGVFGAGTTLTVLGQSSRSSGGGG SSGGGGSAVTLDESGGGLQTPGGALRLSCKASGFTFSSYQMGWVRQAPGKGLEWVSAINK GGSDTSYGSAVKGRATISRDNGQSTLYLQMNSLRAEDTAVYFCAKGSASYITAATIDAWG HGTEVIVSS (SEQ ID NO: 253) |
| Anti-FAM19A5 ("1-7A-IT") scFv | ALTQPSSVSANPGETVKITCSGGGSYAGSYYYGWYQQKPGSAPVTLIYENNKRPSDIPSR FSGSTSGSTATLTITGVQAGDEADYYCGSWDSSNGGIFGAGTTLTVLGQSSRSSGGGGSS GGGGSAVTLDESGGGLQTPGGALRLSCKASGFTFSSFNMFWVRQAPGKGLEYVSQISSSG SSTNYAPAVKGRATISRDNGQSTLYLQMNSLRAEDTGTYYCAKSSYDCPYGHCSSGVDSA GEIDAWGHGTEVIVSS (SEQ ID NO: 254) |
| Anti-FAM19A5 ("Low-PI") scFv | ALTQPSSVSANPGETVKITCSGGGSEEEQYYYGWYQQKPGSAPVTLIYEDEERPSDIPSR FSGSTSGSTATLTITGVQAGDEADYYCGSWDSEDEDHFGAGTTLTVLGQSSRSSGGGGSS GGGGSAVTLDESGGGLQTPGGALRLSCKASGFDFESFNMFWVRQAPGKGLEYVSQISSSE EDENYAPAVKGRATISRDNGQSTLYLQMNSLRAEDTGTYYCAKSSYDCPYGHCSSGVDSA GEIDAWGHGTEVIVSS (SEQ ID NO: 255) |
| Anti-FAM19A5 ("1-30") scFv | ALTQPSSVSANPGETVKITCSGGGSEEEQYYYGWYQQKPGSAPVTLIYQDEERPSDIPSR FSGSTSGSTATLTITGVQAGDEADYYCGSWDSEDEDHFGAGTTLTVLGQSSRSSGGGGSS GGGGSAVTLDESGGGLQTPGGALRLSCKASGFDFESFNMFWVRQAPGKGLEYVSQISSSE EDENYAPAVKGRATISRDNGQSTLYLQMNSLRAEDTGTYYCAKSSYDCPYGHCSSGVDSA GEIDAWGHGTEVIVSS (SEQ ID NO: 256) |
| Anti-FAM19A5 ("1-17") scFv | ALTQPSSVSANPGETVKITCSGGGSYAGSYYYGWYQQKPGSAPVTLIYEDEQRPSDIPSR FSGSTSGSTATLTITGVQAGDEADYYCGSWDSEDEDHFGAGTTLTVLGQSSRSSGGGGSS GGGGSAVTLDESGGGLQTPGGALRLSCKASGFDFESFNMFWVRQAPGKGLEYVSQISSSE EDENYAPAVKGRATISRDNGQSTLYLQMNSLRAEDTGTYYCAKSSYDCPYGHCSSGVDSA GEIDAWGHGTEVIVSS (SEQ ID NO: 257) |
| Anti-FAM19A5 ("1-32") scFv | ALTQPSSVSANPGETVKITCSGGGSYAGSYYYGWYQQKPGSAPVTLIYQDEERPSDIPSR FSGSTSGSTATLTITGVQAGDEADYYCGSWDSEDEDHFGAGTTLTVLGQSSRSSGGGGSS GGGGSAVTLDESGGGLQTPGGALRLSCKASGFDFESFNMFWVRQAPGKGLEYVSQISSSE EDENYAPAVKGRATISRDNGQSTLYLQMNSLRAEDTGTYYCAKSSYDCPYGHCSSGVDSA GEIDAWGHGTEVIVSS (SEQ ID NO: 258) |
| Anti-FAM19A5 ("4-11") scFv | ALTQPSSVSANPGETVKITCSGGGSYAGSYYYGWYQQKPGSAPVTLIYEDHERPSDIPSR FSGSTSGSTATLTITGVQAGDEADYYCGSWDSSDEDHFGAGTTLTVLGQSSRSSGGGGSS GGGGSAVTLDESGGGLQTPGGALRLSCKASGFDFESFNMFWVRQAPGKGLEYVSQISSSE EDENYAPAVKGRATISRDNGQSTLYLQMNSLRAEDTGTYYCAKSSYDCPYGHCSSGVDSA GEIDAWGHGTEVIVSS (SEQ ID NO: 259) |
| Anti-FAM19A5 ("6-10") scFv | ALTQPSSVSANPGETVKITCSGGGSYAGSYYYGWYQQKPGSAPVTLIYQDLLRPSDIPSR FSGSTSGSTATLTITGVQAGDEADYYCGSWDSLSSSHFGAGTTLTVLGQSSRSSGGGGSS GGGGSAVTLDESGGGLQTPGGALRLSCKASGFDFESFNMFWVRQAPGKGLEYVSQISSSE EDENYAPAVKGRATISRDNGQSTLYLQMNSLRAEDTGTYYCAKSSYDCPYGHCSSGVDSA GEIDAWGHGTEVIVSS (SEQ ID NO: 260) |
| Anti-FAM19A5 ("2-13D") scFv | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVLGQSSRSSGGGGSSGGGG SAVTLDESGGGLQTPGGALRLSCSASGFTFSSHGMFWVRQAPGKGLEYVSEITNDGSGTN YGSAVKGRATISRDNGQSTLYLQMNSLRAEDTGTYFCARSTYECPGGFSCWGDTGQIDAW GHGTEVIVSS (SEQ ID NO: 261) |
| Anti-FAM19A5 ("2-13D-37") scFv | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVLGQSSRSSGGGGSSGGGG SAVTLDESGGGLQTPGGALRLSCSASGFDFSSHGMFWVRQAPGKGLEYVSEITNDGSGTN YGSAVKGRATISRDNGQSTLYLQMNSLRAEDTGTYFCARSTYECPGGFSCWGDTGQIDAW GHGTEVIVSS (SEQ ID NO: 262) |
| Anti-FAM19A5 ("2-13D-37-1.5W-41") scFv | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVLGQSSRSSGGGGSSGGGG SAVTLDESGGGLQTPGGALRLSCSASGFDFSSHGMFWVRQAPGKGLEYVSEITNDGSGTN YGSAVKGRATISRDNGQSTLYLQMNSLRAEDTGTYFCARSSYVCPGGFSCWGDTGQIDAW GHGTEVIVSS (SEQ ID NO: 263) |
| Anti-FAM19A5 ("2-13D-37-3W-16") scFv | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVLGQSSRSSGGGGSSGGGG SAVTLDESGGGLQTPGGALRLSCSASGFDFSSHGMFWVRQAPGKGLEYVSEITNDGSGTN YGSAVKGRATISRDNGQSTLYLQMNSLRAEDTGTYFCARSNYACPGGFSCWGDTGQIDAW GHGTEVIVSS (SEQ ID NO: 264) |

A VH domain, or one or more CDRs thereof, described herein can also be linked to a constant domain for forming a heavy chain, e.g., a full length heavy chain. Similarly, a VL domain, or one or more CDRs thereof, described herein can be linked to a constant domain for forming a light chain, e.g., a full length light chain. A full length heavy chain and full length light chain combine to form a full length antibody.

Accordingly, in specific embodiments, provided is an antibody comprising an antibody light chain and heavy chain, e.g., a separate light chain and heavy chain that is useful in the methods disclosed herein. With respect to the light chain, in a specific embodiment, the light chain of an antibody described herein is a kappa light chain. In another specific embodiment, the light chain of an antibody described herein is a lambda light chain. In yet another specific embodiment, the light chain of an antibody described herein is a human kappa light chain or a human lambda light chain. In a particular embodiment, an antibody useful in the methods disclosed herein, which specifically binds to an FAM19A5 polypeptide (e.g., human FAM19A5) comprises a light chain which comprises any VL or VL CDR amino acid sequences described herein, and wherein the constant region of the light chain comprises the amino acid sequence of a human kappa light chain constant region. In a particular embodiment, an antibody described useful in the methods disclosed herein, which specifically binds to an FAM19A5 polypeptide (e.g., human FAM19A5) comprises a light chain which comprises a VL or VL CDR amino acid sequences described herein, and wherein the constant region of the light chain comprises the amino acid sequence of a human lambda light chain constant region. Non-limiting examples of human constant region sequences have been described in the art, e.g., see U.S. Pat. No. 5,693,780 and Kabat E A et al, (1991) supra.

With respect to the heavy chain, in some embodiments, the heavy chain of an antibody described herein can be an alpha (α), delta (δ), epsilon (ε), gamma (γ) or mu (μ) heavy chain. In another specific embodiment, the heavy chain of an antibody described can comprise a human alpha (α), delta (δ), epsilon (ε), gamma (γ) or mu (μ) heavy chain. In some embodiments, an antibody described useful in the methods disclosed herein, which specifically binds to FAM19A5 (e.g., human FAM19A5), comprises a heavy chain which comprises a VH or VH CDR amino acid sequence described herein, and wherein the constant region of the heavy chain comprises the amino acid sequence of a human gamma (γ) heavy chain constant region. In other embodiments, an antibody described herein, which specifically binds to FAM19A5 (e.g., human FAM19A5), comprises a heavy chain which comprises a VH or VH CDR amino acid sequence disclosed herein, and wherein the constant region of the heavy chain comprises the amino acid of a human heavy chain described herein or known in the art. Non-limiting examples of human constant region sequences have been described in the art, e.g., see U.S. Pat. No. 5,693,780 and Kabat E A et al., (1991) supra.

In some embodiments, an antibody described useful in the methods disclosed herein, which specifically binds to FAM19A5 (e.g., human FAM19A5) comprises a VL domain and a VH domain comprising the VH or VH CDRs and VL and VL CDRs described herein, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In another specific embodiment, an antibody described herein, which specifically binds to FAM19A5 (e.g., human FAM19A5) comprises a VL domain and a VH domain comprising any amino acid sequences described herein, and wherein the constant regions comprise the amino acid sequences of the constant regions of an IgG, IgE, IgM, IgD, IgA or IgY immunoglobulin molecule, any subclass (e.g., IgG1, IgG2, IgG3, IgG4, IgA1 and IgA2) of immunoglobulin molecule. In some embodiments, the constant regions comprise the amino acid sequences of the constant regions of a human IgG, which are naturally-occurring, including subclasses (e.g., IgG1, IgG2, IgG3 or IgG4), and allotypes (e.g., G1m, G2m, G3m, and nG4m) and variants thereof. See, e.g., Vidarsson G. et al. *Front Immunol.* 5:520 (published online Oct. 20, 2014) and Jefferis R. and Lefranc M P, *mAbs* 1:4, 1-7(2009). In some embodiments, the constant regions comprise the amino acid sequences of the constant regions of a human IgG1, IgG2, IgG3, or IgG4, or variants thereof.

In certain embodiments, the anti-FAM19A5 antibody disclosed useful in the methods disclosed herein does not have Fc effector functions, e.g., complement-dependent cytotoxicity (CDC) and/or antibody-dependent cellular phagocytosis (ADCP). Effector functions are mediated by the Fc region and the residues most proximal to the hinge region in the CH2 domain of the Fc region are responsible for effector functions of antibodies as it contains a largely overlapping binding site for C1q (complement) and IgG-Fc receptors (FcγR) on effector cells of the innate immune system. Also, IgG2 and IgG4 antibodies have lower levels of Fc effector functions than IgG1 and IgG3 antibodies. Effector functions of an antibody can be reduced or avoided by different approaches known in the art, including (1) using antibody fragments lacking the Fc region (e.g., such as a Fab, F(ab')$_2$, single chain Fv (scFv), or a sdAb consisting of a monomeric VH or VL domain); (2) generating aglycosylated antibodies, which can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells, see, e.g., U.S. Pub. No. 20120100140); (3) employing Fc regions from an IgG subclass that have reduced effector function (e.g., a Fc region from IgG2 or IgG4 antibodies or a chimeric Fc region comprising a CH2 domain from IgG2 or IgG4 antibodies, see, e.g., U.S. Pub. No. 20120100140 and Lau C. et al. *J. Immunol.* 191:4769-4777 (2013)); and (4) generating a Fc region with mutations that result in reduced or no Fc functions. See, e.g., U.S. Pub. No. 20120100140 and U.S. and PCT applications cited therein and An et al., *mAbs* 1:6, 572-579 (2009).

Thus, in some embodiments, the anti-FAM19A5 antibody useful in the methods disclosed herein is a Fab, a Fab', a F(ab')2, a Fv, a single chain Fv (scFv), or a sdAb consisting of a monomeric VH or VL domain. Such antibody fragments are well known in the art and are described supra.

In some embodiments, the anti-FAM19A5 antibody useful in the methods disclosed herein comprises a Fc region with reduced or no Fc effector function. In some embodiments, the constant regions comprise the amino acid sequences of the Fc region of a human IgG2 or IgG4, in some embodiments, the anti-FAM19A5 antibody is of an IgG2/IgG4 isotype. In some embodiments, the anti-FAM19A5 antibody comprises a chimeric Fc region which comprises a CH2 domain from an IgG antibody of the IgG4 isotype and a CH3 domain from an IgG antibody of the IgG1 isotype, or a chimeric Fc region which comprises a hinge region from IgG2 and a CH2 region from IgG4, or a Fc region with mutations that result in reduced or no Fc functions. Fc regions with reduced or no Fc effector function include those known in the art. See, e.g., Lau C. et al., *J. Immunol.* 191:4769-4777 (2013); An et al., *mAbs* 1:6, 572-579 (2009); and U.S. Pub. No. 20120100140 and the U.S.

patents and publications and PCT publications cited therein. Also Fc regions with reduced or no Fc effector function can be readily made by a person of ordinary skill in the art.

Nucleic Acid Molecules

Another aspect described herein pertains to one or more nucleic acid molecules that encode any one of the antibodies, or antigen binding portions thereof, disclosed herein. Such nucleic acid molecules can be expressed in an AAV vector of the present disclosure. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and can or cannot contain intronic sequences. In a certain embodiments, the nucleic acid is a cDNA molecule.

Certain nucleic acids molecules described herein are those encoding the VH and VL sequences of the anti-FAM19A5 antibodies of the present disclosure. Exemplary DNA sequences encoding the VH sequence of such antibodies are set forth in SEQ ID NOs: 43-46, 177, and 265-278 (Table 7). Exemplary DNA sequences encoding the VL sequences of such antibodies are set forth in SEQ ID NOs: 47-50, 178, and 279-292 (Table 8). Exemplary DNA sequences encoding the 1-65, 3-2, and 2-13 scFv antibodies are provided in Table 9.

TABLE 7

Variable heavy chain polynucleotide sequence

| Antibody | Variable Heavy Chain Polynucleotide Sequence (SEQ ID NO) |
|---|---|
| Anti-FAM19A5 (1-65) | GCCGTGACGTTGGACGAGTCCGGGGGCGGCCTCCAGACGCCCGGAGGAGCGCTCAGCCTC GTCTGCAAGGCCTCCGGGTTCACCTTCAGCAGCTATCAGATGGGCTGGGTGCGACAGGCG CCCGGCAAGGGGCTGGAATGGGTCGGTGTTATTAACAAGAGTGGTAGTGACACATCATAC GGGTCGGCGGTGAAGGGCCGTGCCACCATCTCGAGGGACAACGGGCAGAGCACAGTGAGG CTGCAGCTGAACAACCTCAGGGCTGAGGACACCGGCACCTACTTCTGCGCCAAAGGTTCT GCTAGTTATATAACTGCTGCTACCATCGACGCATGGGGCCACGGGACCGAAGTCATCGTC TCCTCCACTAGT (SEQ ID NO: 45) |
| Anti-FAM19A5 (3-2) | GCCGTGACGTTGGACGAGTCCGGGGGCGGCCTCCAGACGCCCGGAGGAGCGCTCAGCCTC GTCTGCAAGGCCTCCGGGTTCACCTTCAGCAGCTTCAACATGTTCTGGGTGCGACAGGCG CCCGGCAAGGGGCTGGAATACGTCGCTCAAATTAGCAGCAGTGGTAGTAGCACAAACTAC GCACCCGCGGTGAGGGCCGTGCCACCATCTCGAGGGACAACGGGCAGAGCACAGTGAGG CTGCAGCTGAACAACCCCGGGGCTGAAGACACCGGCACCTACTACTGCGCCAAAAGTAGT TATGACTGTCCTTACGGTCATTGTAGTAGTGGTGTTGATAGTGCTGGTGAGATCGACGCA TGGGGCCACGGGACCGAAGTCATCGTCTCCTCCA (SEQ ID NO: 44) |
| Anti-FAM19A5 (2-13) | GCCGTGACGTTGGACGAGTCCGGGGGCGGCCTCCAGACGCCCGGAGGAGCGCTCAGCCTC GTCTGCAAGGCCTCCGGGTTCACCTTCAGCAGCCATGGCATGTTCTGGGTGCGACAGACG CCCGGCAAGGGGTTGGAATATGTCGCTGAAATTACCAATGATGGTAGTGGCACAAACTAC GGGTCGGCGGTGAAGGGCCGTGCCACCATCTCGAGGGACAACGGGCAGAGCACAGTGAGG CTGCAGCTGAACAACCTCAGGGCTGAGGACACCGGCACCTACTTCTGCGCCAGATCTACT TATGAATGTCCTGGTGGTTTTAGTTGTTGGGGTGATACTGGTCAAATAGACGCATGGGGC CACGGGACCGAAGTCATCGTCTCCTCCA (SEQ ID NO: 43) |
| Anti-FAM19A5 (1-28) | GCCGTGACGTTGGACGAGTCCGGGGGCGGCCTCCAGACGCCCGGAGGAGCGCTCAGCCTC GTCTGCAAGGCCTCCGGGTTCGACTTCAGCGATTATGGCATGGTTTGGGTGCGACAGGCT CCAGGCAAGGGGCTGGAGTGGGTTGCTGCTATTAGAAGTGATGGTAGTAACCCATCATAC GGGTCGGCGGTGAAGGGCCGTGCCACCATCTCGAAGGACAACGGGCGAAGCACAGTGAGG CTGCAGCTGAACAACCTCAGGGCTGAGGACACCGCCACCTACTACTGCGCCAAGGATGGT AATGGTTACTGTGCTCTCGATGCTTATCGTAGTGGTGGTTATAGTTGTGGTGTTTATCCT GGTAGCATCGACGCATGGGGCCACGGGACCGAAGTCATCGTCTCCTCC (SEQ ID NO: 46) |
| Anti-FAM19A5 (P2-C12) | CAGTCGCTGGAGGAGTCCGGGGGTCGCCTGGTCACGCCTGGGACACCCCTGACACTCACC TGCACCGTCTCTGGATTCTCCCTCAGTACCTATGCAGTGACCTGGGTCCGCCAGGCTCCA GGGAAGGGGCTGGAATGGATCGGATACATTAATTGGCGTGGTGGGACATCCTACGCGAAC TGGGCGAAAGGCCGATTCACCATCTCCAAAACCTCGTCGACCACGGTGGATCTGAAAATG ACCAGTCCGACAACCGAGGACACGGCCACCTATTTCTGTGCCAGAGATGCTAGTAGTGGT GCTGCTTTTGGGTCTTACGGCATGGACCCCTGGGCCCAGGGACCCTCGTCACCGTCTCT TCA (SEQ ID NO: 177) |
| Anti-FAM19A5 (SS01-13) | GCCGTGACGTTGGACGAGTCCGGGGGCGGCCTCCAGACGCCCGGAGGAGCGCTCTCTCTC TCTTGCAAAGCCTCCGGGTTCACCTTCAGCAGCTATCAGATGGGCTGGGTGCGACAGGCG CCCGGCAAGGGGCTGGAATGGGTCGGTGTTATTAACAAGTCTGGTAGTGACACATCATAC GGGTCGGCGGTGAAGGGCCGTGCCACCATCTCGAGGGACAACGGGCAGAGCACACTGTAC CTGCAGATGAACAACCTCAGGGCTGAGGACACCGCTGTTTACTTCTGCGCCAAAGGTTCT GCTAGTTACATAACTGCTGCTACCATCGACGCATGGGGCCACGGGACCGAAGTCATCGTC TCCTCC (SEQ ID NO: 265) |
| Anti-FAM19A5 (SS01-13-S5) | GCCGTGACGTTGGACGAGTCCGGGGGCGGCCTCCAGACGCCCGGAGGAGCGCTCCGCCTC TCTTGCAAGGCCTCCGGGTTCACCTTCAGCAGCTATCAGATGGGCTGGGTGCGACAGGCG CCCGGCAAGGGGCTGGAATGGGTCAGCGCGATTAATAAGAGCGGTAGTGACACATCATAC GGGTCGGCGGTGAAGGGCCGTGCCACCATCTCGAGGGACAACGGGCAGAGCACACTGTAC |

TABLE 7-continued

Variable heavy chain polynucleotide sequence

| Antibody | Variable Heavy Chain Polynucleotide Sequence (SEQ ID NO) |
|---|---|
|  | CTGCAGATGAACAGCCTCAGGGCTGAGGACACCGCTGTTTACTTCTGCGCCAAAGGTTCT<br>GCTAGTTACATAACTGCTGCTACCATCGACGCATGGGGCCACGGGACCGAAGTCATCGTC<br>TCCTCC (SEQ ID NO: 266) |
| Anti-FAM19A5<br>("S5-2.GKNG") | GCCGTGACGTTGGACGAGTCCGGGGGCGGCCTCCAGACGCCCGGAGGAGCGCTCCGCCTC<br>TCTTGCAAGGCCTCCGGGTTCACCTTCAGCAGCTATCAGATGGGCTGGGTGCGACAGGCG<br>CCCGGCAAGGGGCTGGAATGGGTCAGCGCGATTAATAAGGGCGGTAGTGACACATCATAC<br>GGGTCGGCGGTGAAGGGCCGTGCCACCATCTCGAGGGACAACGGGCAGAGCACACTGTAC<br>CTGCAGATGAACAGCCTCAGGGCTGAGGACACCGCTGTTTACTTCTGCGCCAAAGGTTCT<br>GCTAGTTACATAACTGCTGCTACCATCGACGCATGGGGCCACGGGACCGAAGTCATCGTC<br>TCCTCC (SEQ ID NO: 267) |
| Anti-FAM19A5<br>("1-7A-IT") | GCCGTGACGTTGGATGAATCCGGGGGCGGCCTCCAGACGCCCGGAGGAGCGCTCCGCCTC<br>AGCTGCAAGGCCTCTGGGTTCACCTTCAGCAGCTTCAACATGTTCTGGGTGCGACAGGCG<br>CCCGGCAAGGGGCTGGAATACGTCTCGCAGATTAGCAGCAGTGGTAGTAGCACAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 268) |
| Anti-FAM19A5<br>("Low-PI") | GCCGTGACGTTGGATGAATCCGGGGGCGGCCTCCAGACGCCCGGAGGAGCGCTCCGCCTC<br>AGCTGCAAGGCCTCTGGGTTCACCTTCAGCAGCTTCAACATGTTCTGGGTGCGACAGGCG<br>CCCGGCAAGGGGCTGGAATACGTCTCGCAGATTAGCAGCAGTGGTAGTAGCACAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 269) |
| Anti-FAM19A5<br>("1-30") | GCCGTGACGTTGGATGAATCCGGGGGCGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 270) |
| Anti-FAM19A5<br>("1-17") | GCCGTGACGTTGGATGAATCCGGGGGCGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 271) |
| Anti-FAM19A5<br>("1-32") | GCCGTGACGTTGGATGAATCCGGGGGCGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 272) |
| Anti-FAM19A5<br>("4-11") | GCCGTGACGTTGGATGAATCCGGGGGCGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 273) |
| Anti-FAM19A5<br>("6-10") | GCCGTGACGTTGGATGAATCCGGGGGCGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 274) |
| Anti-FAM19A5<br>("2-13D") | GCCGTGACGTTGGACGAGTCCGGGGGCGGCCTCCAGACGCCCGGAGGAGCGCTCCGCCTT<br>AGCTGCAGCGCCTCCGGGTTCACCTTCAGCAGCCATGGCATGTTCTGGGTGCGACAGGCG<br>CCCGGCAAGGGGTTGGAATATGTCTCGGAGATTACCAATGAGTGGTAGTGGCACAAACTAC<br>GGGTCGGCGGTGAAGGGCCGTGCCACCATCTCGAGGGACAACGGGCAGAGCACACTGTAT<br>CTGCAGATGAACAGCCTCAGGGCTGAGGACACCGGCACCTACTTCTGCGCCAGATCTACT<br>TATGAATGTCCTGGTGGTTTTAGTTGTTGGGGTGATACTGGTCAAATAGACGCATGGGGC<br>CACGGGACCGAAGTCATCGTCTCCTCC (SEQ ID NO: 275) |

TABLE 7-continued

Variable heavy chain polynucleotide sequence

| Antibody | Variable Heavy Chain Polynucleotide Sequence (SEQ ID NO) |
|---|---|
| Anti-FAM19A5 ("2-13D-37") | GCCGTGACGTTGGACGAGTCCGGGGGCGGCCTCCAGACGCCCGGAGGAGCGCTCCGCCTT<br>AGCTGCAGCGCCTCCGGGTTCGATTTCAGCAGCCATGGCATGTTCTGGGTGCGACAGGCG<br>CCCGGCAAGGGGTTGGAATATGTCTCGGAGATTACCAATGATGGTAGTGGCACAAACTAC<br>GGGTCGGCGGTGAAGGGCCGTGCCACCATCTCGAGGGACAACGGGCAGAGCACACTGTAT<br>CTGCAGATGAACAGCCTCAGGGCTGAGGACACCGGCACCTACTTCTGCGCGCAGATCTACT<br>TATGAATGTCCTGGTGGTTTTAGTTGTTGGGGTGATACTGGTCAAATAGACGCATGGGGC<br>CACGGGACCGAAGTCATCGTCTCCTCC (SEQ ID NO: 276) |
| Anti-FAM19A5 ("2-13D-37-1.5W-41") | GCCGTGACGTTGGACGAGTCCGGGGGCGGCCTCCAGACGCCCGGAGGAGCGCTCCGCCTT<br>AGCTGCAGCGCCTCCGGGTTCGATTTCAGCAGCCATGGCATGTTCTGGGTGCGACAGGCG<br>CCCGGCAAGGGGTTGGAATATGTCTCGGAGATTACCAATGATGGTAGTGGCACAAACTAC<br>GGGTCGGCGGTGAAGGGCCGTGCCACCATCTCGAGGGACAACGGGCAGAGCACACTGTAT<br>CTGCAGATGAACAGCCTCAGGGCTGAGGACACCGGCACCTACTTCTGCGCGCAGATCTTCT<br>TATGTTTGTCCTGGTGGTTTTAGTTGTTGGGGTGATACTGGTCAAATAGACGCATGGGGC<br>CACGGGACCGAAGTCATCGTCTCCTCC (SEQ ID NO: 277) |
| Anti-FAM19A5 ("2-13D-37-3W-16") | GCCGTGACGTTGGACGAGTCCGGGGGCGGCCTCCAGACGCCCGGAGGAGCGCTCCGCCTT<br>AGCTGCAGCGCCTCCGGGTTCGATTTCAGCAGCCATGGCATGTTCTGGGTGCGACAGGCG<br>CCCGGCAAGGGGTTGGAATATGTCTCGGAGATTACCAATGATGGTAGTGGCACAAACTAC<br>GGGTCGGCGGTGAAGGGCCGTGCCACCATCTCGAGGGACAACGGGCAGAGCACACTGTAT<br>CTGCAGATGAACAGCCTCAGGGCTGAGGACACCGGCACCTACTTCTGCGCGCAGATCTAAT<br>TATGCTTGTCCTGGTGGTTTTAGTTGTTGGGGTGATACTGGTCAAATAGACGCATGGGGC<br>CACGGGACCGAAGTCATCGTCTCCTCC (SEQ ID NO: 278) |

TABLE 8

Variable light chain polynucleotide sequence

| Antibody | Variable Light Chain Polynucleotide Sequence (SEQ ID NO) |
|---|---|
| Anti-FAM19A5 (1-65) | CTGACTCAGCCGTCCTCGGTGTCAGCAAACCCTGGGGAAACTGTCAAGATCACCTGCTCC<br>GGGGGTGGTAGCAGTGGCTATGGTTATGGCTGGTATCAGCAGAAGTCACCTAGCAGTGCC<br>CCTCTCACTGTGATCTACTGGAACGACAAGAGACCCTCGGACATCCCTTCACGATTCTCC<br>GGTTCCAAATCCGGCTCCACACACACATTAACCATCACTGGGGTCCAAGCCGAGGACGAG<br>GCTGTATATTTCTGTGGGAATGATGACTACAGCAGTGATAGTGGATATGTCGGTGTATTT<br>GGGGCCGGGACAACCCTGACCGTCCTA (SEQ ID NO: 49) |
| Anti-FAM19A5 (3-2) | GGCCCTGACTCAGCCGTCCTCGGTGTCAGCAAACCCAGGAGAAACCGTCAAGATCACCTG<br>CTCCGGGGGTGGCAGCTATGCTGGAAGTTACTATTATGGCTGGTACCAGCAGAAGGCACC<br>TGGCAGTGCCCCTGTCACTCTGATCTATGAAAGCAACAAGAGACCCTCGGACATCCCTTC<br>ACGATTCTCCGGTTCCACATCTGGCTCCACAGCCACACTAACCATCACTGGGGTCCAAGC<br>CGATGACGAGGCTATCTATTACTGTGGGAGCTGGGACAGTAGCAATGGTGGTATATTTGG<br>GGCCGGGACAACCCTGACCGTCCTAGG (SEQ ID NO: 48) |
| Anti-FAM19A5 (2-13) | GGCCCTGACTCAGCCGTCCTCGGTGTCAGCAAACCCAGGAGAAACCGTCAAGATAACCTG<br>CTCCGGGGGGTAGCTATAGCTATGGCTGGTTCCAGCAGAAGTCTCCTGGCAGTGCCCTTGT<br>CACTGTGATCTACTGGGATGATGAGAGACCCTCGGACATCCCTTCACGATTCTCCGGTGC<br>CCTATCCGGCTCCACAAACACATTAACCATCACTGGGGTCCAAGCCGACGACGAGGCTGT<br>CTATTTCTGTGGGACTGAAGACATCAGCGGCACTGCTGGTGTATTTGGGGCCGGGACAAC<br>CCTGACCGTCCTGGG (SEQ ID NO: 47) |
| Anti-FAM19A5 (1-28) | GCCCTGACTCAGCCGTCCTCGGTGTCAGCAAACCTGGAAGGAACCGTCGAGATCACCTGC<br>TCCGGGAGTGGCTATGGTTATGGCTGGTATCAGCAGAAGTCTCCTGGCAGTGCCCCTGTC<br>ACTGTGATCTATCAGAACGACAAGAGACCCTCGGACATCCCTTCACGATTCTCCGGTTCC<br>AAATCCGGCTCCACGGGCACATTAACCATCACTGGGGTCCAAGTCGAGGACGAGGCTGTC<br>TATTACTGTGGGAGTGAAGACAGCAGCACTCTTGCTGGTATATTTGGGGCCGGGACAACC<br>CTGACCGTCCTA (SEQ ID NO: 50) |
| Anti-FAM19A5 (P2-C12) | GAGCTCGATATGACCCAGACTCCATCCTCCGTGTCTGCAGCTGTGGGAGGCACAGTCACC<br>ATCAAGTGCCAGGCCAGTCAGAGCATTAGTAGCACTTATCCTGGTATCAGCAGAAACCA<br>GGGCAGCCTCCCAAGCTCCTGATCTATGAAGCATCCAAACTGGCCTCTGGGGTCCCATCG<br>CGGTTCAGCGGCAGTGGATATGGGACAGAGTTCACTCTCACCATCAGCGACCTGGAGTGT<br>GCCGATGCTGCCACTTACTACTGTCAACAGGGTTATAGTAGTACTAATGTTTGGAATGCT<br>TTCGGCGGAGGCACCAATGTGGAAATCAAA (SEQ ID NO: 178) |
| Anti-FAM19A5 (SS01-13) | GCCCTGACTCAGCCGTCCTCGGTGTCAGCAAACCCTGGGGAAACTGTTCGTATCACCTGC<br>TCCGGGGGTGCTAGCAGTGGCTATGGTTATGGCTGGTATCAGCAGAAGCCTAGCAGTGCC<br>CCTCTCACTGTGATCTACAAAGACGACGAAAGACCCTCGGACATCCCTTCACGATTCTCC<br>GGTTCCTCTTCCGGCTCCACACACACATTAACCATCACTGGGGTCCAAGCCGAGGACGAG<br>GCTGTATATTTCTGTGGGAATGATGACTACAGCAGTGATAGTGGATATGTCGGTGTATTT<br>GGGGCCGGGACAACCCTGACCGTCCTA (SEQ ID NO: 279) |

TABLE 8-continued

Variable light chain polynucleotide sequence

| Antibody | Variable Light Chain Polynucleotide Sequence (SEQ ID NO) |
|---|---|
| Anti-FAM19A5 (SS01-13-S5) | GCCCTGACTCAGCCGTCCTCGGTGTCAGCAAACCCTGGGGAAACTGCGCGTATCACCTGC<br>TCCGGTGGTGCTAGCAGTGGCTATGGTTATGGCTGGTATCAGCAGAAGCCTAGCAGTGCC<br>CCTCTCACTGTGATCTACAAAGACTCTGAAAGACCCTCGGACATCCCTTCACGATTCTCC<br>GGTTCCTCTTCCGGCTCCACACACACATTAACCATCAGCGGGGTCCAAGCCGAGGACGAG<br>GCTGTATATTTCTGTGGGAATGATGACTACAGCAGTGATAGTGGATATGTCGGTGTATTT<br>GGGGCCGGGACAACCCTGACCGTCCTA (SEQ ID NO: 280) |
| Anti-FAM19A5 ("S5-2.GKNG") | GCCCTGACTCAGCCGTCCTCGGTGTCAGCAAACCCTGGGGAAACTGCGCGTATCACCTGC<br>TCCGGTGGTGCTAGCAGTGGCTATGGTTATGGCTGGTATCAGCAGAAGCCTAGCAGTGCC<br>CCTCTCACTGTGATCTACAAAGACTCTGAAAGACCCTCGGACATCCCTTCACGATTCTCC<br>GGTTCCTCTTCCGGCTCCACACACACATTAACCATCAGCGGGGTCCAAGCCGAGGACGAG<br>GCTGTATATTTCTGTGGGAATGATGACTACAGCAGTGATAGTGGATATGTCGGTGTATTT<br>GGGGCCGGGACAACCCTGACCGTCCTA (SEQ ID NO: 281) |
| Anti-FAM19A5 ("1-7A-IT") | GCCCTGACTCAGCCGTCCTCGGTGTCAGCAAACCCAGGAGAAACCGTCAAGATCACCTGC<br>TCCGGGGGTGGCAGCTATGCTGGAAGTTACTATTATGGCTGGTATCAGCAGAAGCCTGGC<br>AGTGCCCCTGTCACTCTGATCTATGAAAACAACAAGAGACCCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTAGCAATGGTGGTATATTTGGGGCC<br>GGGACAACCCTGACCGTCCTA (SEQ ID NO: 282) |
| Anti-FAM19A5 ("Low-PI") | GCCCTGACTCAGCCGTCCTCGGTGTCAGCAAACCCAGGAGAAACCGTCAAGATCACCTGC<br>TCCGGGGGTGGCAGCTATGCTGGAAGTTACTATTATGGCTGGTATCAGCAGAAGCCTGGC<br>AGTGCCCCTGTCACTCTGATCTATGAAAACAACAAGAGACCCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTAGCAATGGTGGTATATTTGGGGCC<br>GGGACAACCCTGACCGTCCTA (SEQ ID NO: 283) |
| Anti-FAM19A5 ("1-30") | GCCCTGACTCAGCCGTCCTCGGTGTCAGCAAACCCAGGAGAAACCGTCAAGATCACCTGC<br>TCCGGGGGTGGCAGCGAAGAAGAACAGTACTATTATGGCTGGTATCAGCAGAAGCCTGGC<br>AGTGCCCCTGTCACTCTGATCTATCAGGATGAAGAAAGACCCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTGAAGATGAAGATCATTTTGGGGCC<br>GGGACAACCCTGACCGTCCTA (SEQ ID NO: 284) |
| Anti-FAM19A5 ("1-17") | GCCCTGACTCAGCCGTCCTCGGTGTCAGCAAACCCAGGAGAAACCGTCAAGATCACCTGC<br>TCCGGGGGTGGCAGCTATGCTGGAAGTTACTATTATGGCTGGTATCAGCAGAAGCCTGGC<br>AGTGCCCCTGTCACTCTGATCTATGAAGATGAACAGAGACCCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTGAAGATGAAGATCATTTTGGGGCC<br>GGGACAACCCTGACCGTCCTA (SEQ ID NO: 285) |
| Anti-FAM19A5 ("1-32") | GCCCTGACTCAGCCGTCCTCGGTGTCAGCAAACCCAGGAGAAACCGTCAAGATCACCTGC<br>TCCGGGGGTGGCAGCTATGCTGGAAGTTACTATTATGGCTGGTATCAGCAGAAGCCTGGC<br>AGTGCCCCTGTCACTCTGATCTATCAGGATGAAGAAAGACCCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTGAAGATGAAGATCATTTTGGGGCC<br>GGGACAACCCTGACCGTCCTA (SEQ ID NO: 286) |
| Anti-FAM19A5 ("4-11") | GCCCTGACTCAGCCGTCCTCGGTGTCAGCAAACCCAGGAGAAACCGTCAAGATCACCTGC<br>TCCGGGGGTGGCAGCTATGCTGGAAGTTACTATTATGGCTGGTATCAGCAGAAGCCTGGC<br>AGTGCCCCTGTCACTCTGATCTATGAAGACCACGAGAGACCCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTAGCGATGAAGATCATTTTGGGGCC<br>GGGACAACCCTGACCGTCCTA (SEQ ID NO: 287) |
| Anti-FAM19A5 ("6-10") | GCCCTGACTCAGCCGTCCTCGGTGTCAGCAAACCCAGGAGAAACCGTCAAGATCACCTGC<br>TCCGGGGGTGGCAGCTATGCTGGAAGTTACTATTATGGCTGGTATCAGCAGAAGCCTGGC<br>AGTGCCCCTGTCACTCTGATCTATCAGGATCTGCTGAGACCCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTCTGAGCAGCAGCCATTTTGGGGCC<br>GGGACAACCCTGACCGTCCTA (SEQ ID NO: 288) |
| Anti-FAM19A5 ("2-13D") | GCCCTGACTCAGCCGTCCTCGGTGTCAGCAAACCCAGGAGAAACCGCGAAGATAACCTGC<br>TCCGGGGGTGTGTATAGCTATGCTGGTTCCAGCAGAAGCCTGGCAGTGCCCTTGTCACT<br>GTGATCTACTGGGATGATGAGAGACCCTCGGACATCCCTTCACGATTCTCCGGTGCCCTA<br>TCCGGCTCCACAAACACATTAACCATCACTGGGGTCCAAGCCGAAGACGAGGCTGATTAT<br>TATTGTGGGACTGAAGACATCAGCGGCACTGCTGGTGTATTTGGGGCCGGGACAACCCTG<br>ACCGTCCTG (SEQ ID NO: 289) |

TABLE 8-continued

Variable light chain polynucleotide sequence

| Antibody | Variable Light Chain Polynucleotide Sequence (SEQ ID NO) |
| --- | --- |
| Anti-FAM19A5 ("2-13D-37") | GCCCTGACTCAGCCGTCCTCGGTGTCAGCAAACCCAGGAGAAACCGCGAAGATAACCTGC<br>TCCGGGGGTGTGTATAGCTATGGCTGGTTCCAGCAGAAGCCTGGCAGTGCCCTTGTCACT<br>GTGATCTACTGGGATGATGAGAGACCCTCGGACATCCCTTCACGATTCTCCGGTGCCCTA<br>TCCGGCTCCACAAACACATTAACCATCACTGGGGTCCAAGCCGAAGACGAGGCTGATTAT<br>TATTGTGGGACTGAAGACATCAGCGGCACTGCTGGTGTATTTGGGGCCGGGACAACCCTG<br>ACCGTCCTG (SEQ ID NO: 290) |
| Anti-FAM19A5 ("2-13D-37-1.5W-41") | GCCCTGACTCAGCCGTCCTCGGTGTCAGCAAACCCAGGAGAAACCGCGAAGATAACCTGC<br>TCCGGGGGTGTGTATAGCTATGGCTGGTTCCAGCAGAAGCCTGGCAGTGCCCTTGTCACT<br>GTGATCTACTGGGATGATGAGAGACCCTCGGACATCCCTTCACGATTCTCCGGTGCCCTA<br>TCCGGCTCCACAAACACATTAACCATCACTGGGGTCCAAGCCGAAGACGAGGCTGATTAT<br>TATTGTGGGACTGAAGACATCAGCGGCACTGCTGGTGTATTTGGGGCCGGGACAACCCTG<br>ACCGTCCTG (SEQ ID NO: 291) |
| Anti-FAM19A5 ("2-13D-37-3W-16") | GCCCTGACTCAGCCGTCCTCGGTGTCAGCAAACCCAGGAGAAACCGCGAAGATAACCTGC<br>TCCGGGGGTGTGTATAGCTATGGCTGGTTCCAGCAGAAGCCTGGCAGTGCCCTTGTCACT<br>GTGATCTACTGGGATGATGAGAGACCCTCGGACATCCCTTCACGATTCTCCGGTGCCCTA<br>TCCGGCTCCACAAACACATTAACCATCACTGGGGTCCAAGCCGAAGACGAGGCTGATTAT<br>TATTGTGGGACTGAAGACATCAGCGGCACTGCTGGTGTATTTGGGGCCGGGACAACCCTG<br>ACCGTCCTG (SEQ ID NO: 292) |

TABLE 9

Variable scFv polynucleotide sequence

| ScFv Antibody | Polynucleotide Sequence (SEQ ID NO) |
| --- | --- |
| Anti-FAM19A5 ("1-65") | GCCTTGACACAACCCTCATCAGTATCTGCTAACCCCGGCGAAACAGTTAAAATAACATGC<br>TCAGGAGGTGGTTCATCTGGCTATGGATATGGGTGGTATCAACAGAAATCACCAAGTTCC<br>GCCCCCTTGACCGTGATTTATTGGAATGATAAGCGCCCCTCAGACATTCCCAGTCGCTTC<br>TCAGGCAGTAAATCAGGCTCAACCCATACTCTTACTATCACCGGTGTCCAAGCAGAAGAT<br>GAAGCCGTGTATTTTTGTGGGAATGATGACTATTCCAGCGATTCTGGCTATGTAGGAGTG<br>TTCGGTGCCGGTACTACCCTCACAGTATTGAGTGGTGGTGGCGGAAGTTCAGGTGGTGGT<br>GGAAGCGCTGTCACTTTGGATGAATCAGGTGGAGGCCTCCAAACCCCAGGTGGCGCACTC<br>AGTCTCGTATGTAAAGCCTCTGGTTTCACTTTCAGCTCATATCAAATGGGATGGGTGCGG<br>CAGGCTCCCGGCAAGGGGTTGGAGTGGGTCGGTGTTATCAACAAGAGCGGCTCTGATACT<br>AGCTATGGAAGCGCAGTCAAGGGGAGAGCTACTATAAGCAGGGATAATGGGCAAAGTACC<br>GTCAGGCTTCAATTGAACAATCTCAGGGCTGAGGATACAGGAACCTACTTCTGCGCCAAA<br>GGGTCAGCATCTTATATCACAGCAGCTACCATTGACGCATGGGGACATGGCACAGAGGTC<br>ATTGTTTCCAGT (SEQ ID NO: 205) |
| Anti-FAM19A5 ("SS01-13") scFv | GCCCTGACTCAGCCGTCCTCGGTGTCAGCAAACCCTGGGGAAACTGTTCGTATCACCTGC<br>TCCGGGGGTGCTAGCAGTGGCTATGGTTATGGCTGGTATCAGCAGAAGCCTAGCAGTGCC<br>CCTCTCACTGTGATCTACAAAGACGACGAAAGACCCTCGGACATCCCTTCACGATTCTCC<br>GGTTCCTCTTCCGGCTCCACACACACATTAACCATCACTGGGGTCCAAGCCGAGGACGAG<br>GCTGTATATTTCTGTGGGAATGATGACTACAGCAGTGATAGTGGATATGTCGGTGTATTT<br>GGGGCCGGGACAACCCTGACCGTCCTAGGTCAGTCCTCTAGATCTTCCGGCGGTGGTGGC<br>AGCTCCGGTGGTGGCGGTTCCGCCGTGACGTTGGACGAGTCCGGGGGCGGCCTCCAGACG<br>CCCGGAGGAGCGCTCTCTCTCTTGCAAAGCCTCCGGGTTCACCTTCAGCAGCTATCAG<br>ATGGGCTGGGTGCGACAGGCGCCCGGCAAGGGGCTGGAATGGGTCGGTGTTATTAACAAG<br>TCTGGTAGTGACACATCATACGGGTCGGCGGTGAAGGGCCGTGCCACCATCTCGAGGGAC<br>AACGGGCAGAGCACACTGTACCTGCAGATGAACAACCTCAGGGCTGAGGACACCGCTGTT<br>TACTTCTGCGCCAAAGGTTCTGCTAGTTACATAACTGCTGCTACCATCGACGCATGGGGC<br>CACGGGACCGAAGTCATCGTCTCCTCC (SEQ ID NO: 293) |
| Anti-FAM19A5 ("SS01-13-s5") scFv | GCCCTGACTCAGCCGTCCTCGGTGTCAGCAAACCCTGGGGAAACTGCGCGTATCACCTGC<br>TCCGGTGGTGCTAGCAGTGGCTATGGTTATGGCTGGTATCAGCAGAAGCCTAGCAGTGCC<br>CCTCTCACTGTGATCTACAAAGACTCTGAAAGACCCTCGGACATCCCTTCACGATTCTCC<br>GGTTCCTCTTCCGGCTCCACACACACATTAACCATCAGCGGGGTCCAAGCCGAGGACGAG<br>GCTGTATATTTCTGTGGGAATGATGACTACAGCAGTGATAGTGGATATGTCGGTGTATTT<br>GGGGCCGGGACAACCCTGACCGTCCTAGGTCAGTCCTCTAGATCTTCCGGCGGTGGTGGA<br>TCCTCTGGTGGTGGTGGTTCCGCCGTGACGTTGGACGAGTCCGGGGGCGGCCTCCAGACG<br>CCCGGAGGAGCGCTCCGCCTCTCTTGCAAGGCCTCCGGGTTCACCTTCAGCAGCTATCAG<br>ATGGGCTGGGTGCGACAGGCGCCCGGCAAGGGGCTGGAATGGGTCAGCGCGATTAATAAG<br>AGCGGTAGTGACACATCATACGGGTCGGCGGTGAAGGGCCGTGCCACCATCTCGAGGGAC<br>AACGGGCAGAGCACACTGTACCTGCAGATGAACAGCCTCAGGGCTGAGGACACCGCTGTT<br>TACTTCTGCGCCAAAGGTTCTGCTAGTTACATAACTGCTGCTACCATCGACGCATGGGGC<br>CACGGGACCGAAGTCATCGTCTCCTCC (SEQ ID NO: 294) |

TABLE 9-continued

Variable scFv polynucleotide sequence

| ScFv Antibody | Polynucleotide Sequence (SEQ ID NO) |
|---|---|
| Anti-FAM19A5 ("S5-2.GKNG") scFv | GCCCTGACTCAGCCGTCCTCGGTGTCAGCAAACCCTGGGGAAACTGCGCGTATCACCTGC TCCGGTGGTGCTAGCAGTGGCTATGGTTATGGCTGGTATCAGCAGAAGCCTAGCAGTGCC CCTCTCACTGTGATCTACAAAGACTCTGAAAGACCCTCGGACATCCCTTCACGATTCTCC GGTTCCTCTTCCGGCTCCACACACACATTAACCATCAGCGGGGTCCAAGCCGAGGACGAG GCTGTATATTTCTGTGGGAATGATGACTACAGCAGTGATAGTGGATATGTCGGTGTATTT GGGGCCGGGACAACCCTGACCGTCCTAGGTCAGTCCTCTAGATCTTCCGGCGGTGGTGGA TCCTCTGGTGGTGGTGGTTCCGCCGTGACGTTGGACGAGTCCGGGGGCGGCCTCCAGACG CCCGGAGGAGCGCTCCGCCTCTCTTGCAAGGCCTCCGGGTTCACCTTCAGCAGCTATCAG ATGGGCTGGGTGCGACAGGCGCCCGGCAAGGGGCTGGAATGGGTCAGCGCGATTAATAAG GGCGGTAGTGACACATCATACGGGTCGGCGGTGAAGGGCCGTGCCACCATCTCGAGGGAC AACGGGCAGAGCACACTGTACCTGCAGATGAACAGCCTCAGGGCTGAGGACACCGCTGTT TACTTCTGCGCCAAAGGTTCTGCTAGTTACATAACTGCTGCTACCATCGACGCATGGGGC CACGGGACCGAAGTCATCGTCTCCTCC (SEQ ID NO: 295) |
| Anti-FAM19A5 ("3-2") | GCATTGACTCAGCCCTCTTCCGTGAGTGCTAATCCAGGTGAAACAGTAAAAATAACTTGC AGTGGGGGAGGGTCTTACGCAGGATCTTATTATTATGGATGGTACCAGCAAAAAGCCCCT GGGTCTGCACCAGTCACTCTGATATACGAGAGCAATAAACGCCCTTCCGACATCCCCAGC CGCTTTTCTGGTTCTACCTCTGGCAGTACTGCTACCTTGACTATTACCGGGGTCCAGGCT GACGACGAAGCCATTTATTATTGTGGAAGTTGGGATTCAAGCAACGGGGGTATATTCGGC GCTGGTACTACCCTTACCGTGCTGTCCGGTGGGGGTGGGAGCAGTGGAGGTGGAGGAAGT GCTGTAACTCTTGATGAAAGCGGGGGAGGGCTGCAAACCCCTGGCGGGGCCTTGTCCTTG GTTTGTAAGGCTTCCGGATTTACTTTCTCAAGTTTTAATATGTTTTGGGTGCGACAGGCC CCAGGGAAAGGGTTGGAATATGTTGCACAGATCTCCAGCTCAGGTTCATCCACCAATTAT GCACCTGCCGTCCGAGGGAGGGCTACAATTTCTAGGGACAACGGGCAGTCAACTGTACGG TTGCAGCTTAACAATCCCGGAGCAGAAGATACAGGTACCTATTACTGTGCTAAGAGTTCA TACGACTGTCCCTATGGTCACTGTTCCTCAGGTGTTGACTCCGCAGGGGAGATAGATGCT TGGGGGCATGGGACCGAAGTGATTGTGTCATCT (SEQ ID NO: 204) |
| Anti-FAM19A5 ("1-30") | GCTCTCACACAACCTTCCTCTGTCTCTGCTAATCCTGGCGAGACTGTTAAAATCACCTGC TCCGGGGGGGGTAGTGAGGAAGAACAGTATTACTATGGATGGTACCAACAAAAGCCTGGG TCTGCACCCGTAACCCTTATATACCAAGATGAGGAGCGCCCATCCGATATACCCTCACGC TTCTCAGGCAGTACATCTGGGTCAACTGCAACCCTCACCATTACAGGAGTGCAAGCAGGT GATGAGGCAGATTATTATTGTGGGTCATGGGACTCCGAGGACGAGGATCATTTTGGAGCT GGCACTACATTGACAGTACTGGGCCAGTCATCAAGAAGTTCAGGTGGCGGCGGAAGCTCC GGGGGCGGTGGATCAGCAGTAACTCTCGACGAATCTGGAGGCGGTCTTCAAACCCCTGGG GGGGCTCTGAGACTCTCATGTAAAGCCAGCGGATTCGATTTCGAGTCATTTAACATGTTT TGGGTCCGCCAGGCCCCCGGTAAAGGCCTGGAGTATGTGTCCCAAATATCAAGTTCAGAG GAGGACGAGAACTATGCCCCAGCCGTGAAAGGTCGAGCTACAATTTCCCGAGACAACGGC CAGTCAACACTCTACTTGCAGATGAACAGCCTGAGAGCCAAGACACTGGTACATACTAT TGTGCTAAATCCAGCTACGACTGTCCATACGGCCATTGTTCATCAGGAGTAGACTCCGCA GGTGAGATAGACGCATGGGGTCATGGCACTGAGGTCATTGTGTCCTCT (SEQ ID NO: 301) |
| Anti-FAM19A5 ("2-13") | GCTCTGACACAACCAAGCTCTGTCAGTGCAAATCCAGGAGAGACCGTTAAAATCACTTGC AGCGGAGGCTCTTATTCCTACGGATGGTTCCAGCAAAAAGTCCTGGTTCAGCCCTCGTT ACTGTCATCTACTGGGACGACGAGCGCCCTAGCGATATTCCTAGTAGATTCTCAGGGGCT CTTAGCGGCTCCACTAATACTTTTGACCATTACTGGAGTACAGGCTGATGACGAAGCAGTT TACTTCTGTGGCACCGAAGATATAAGCGGAACTGCAGGGGTATTTGGGGCTGGTACAACA CTCACAGTGCTCTCCGGGGGGGGCGGGAGCTCAGGAGGCGGCGGATCAGCTGTAACCCTG GACGAATCTGGTGGGGGGCTTCAAACACCCGGAGGAGCCCTCTCCCTCGTATGCAAAGCT TCAGGATTCACCTTCTCTTCACATGGAATGTTCTGGGTAAGGCAGACACCTGGCAAAGGG CTTGAATATGTAGCTGAGATCACTAATGACGGTAGCGGTACAAACTATGGGTCTGCTGTA AAAGGCCGGGCTACAATAAGTCGAGACAATGGACAAAGTACCGTTAGACTCCAGCTCAAC AACCTGCGAGCTGAGGACACAGGCACTTACTTTTGTGCACGCAGTACTTACGAGTGTCCA GGTGGATTTTCATGTTGGGGAGATACCGGACAGATCGACGCTTGGGGGCACGGCACCGAG GTCATTGTAAGTAGC (SEQ ID NO: 206) |
| Anti-FAM19A5 ("2-13D") | CTGACTCAGCCGTCCTCGGTGTCAGCAAACCCAGGAGAAACCGCGAAGATAACCTGCTCC GGGGGTGTGTATAGCTATGGCTGGTTCCAGCAGAAGCCTGGCAGTGCCCTTGTCACTGTG ATCTACTGGGATGATGAGAGACCCTCGGACATCCCTTCACGATTCTCCGGTGCCCTATCC GGCTCCACAAACACATTAACCATCACTGGGGTCCAAGCCGAAGACGAGGCTGATTATTAT TGTGGGACTGAAGACATCAGCGGCACTGCTGGTGTATTTGGGGCCGGGACAACCCTGACC GTCCTGGGTCAGTCCTCTAGATCTTCCGGCGGTGGTGGATCCTCTGGTGGTGGTGGTTCC GCCGTGACGTTGGACGAGTCCGGGGGCGGCCTCCAGACGCCCGGAGGAGCGCTCCGCCTT AGCTGCAGCGCCTCCGGGTTCACCTTCAGCAGCCATGGCATGTTCTGGGTGCGACAGGCG CCCGGCAAGGGGTTGGAATATGTCTCGGAGATTACCAATGATGGTAGTGGCACAAACTAC GGGTCGGCGGTGAAGGGCCGTGCCACCATCTCGAGGGACAACGGGCAGAGCACACTGTAT CTGCAGATGAACAGCCTCAGGGCTGAGGACACCGGCACTTACTTCTGCGCCAGATCTACT TATGAATGTCCTGGTGGTTTTAGTTGTTGGGTGATACTGGTCAAATAGACGCATGGGGC CACGGGACCGAAGTCATCGTCTCCTCC (SEQ ID NO: 296) |

TABLE 9-continued

Variable scFv polynucleotide sequence

| ScFv Antibody | Polynucleotide Sequence (SEQ ID NO) |
|---|---|
| Anti-FAM19A5 ("2-13D-37") | CTGACTCAGCCGTCCTCGGTGTCAGCAAACCCAGGAGAAACCGCGAAGATAACCTGCTCC<br>GGGGGTGTGTATAGCTATGGCTGGTTCCAGCAGAAGCCTGGCAGTGCCCTTGTCACTGTG<br>ATCTACTGGGATGATGAGAGACCCTCGGACATCCCTTCACGATTCTCCGGTGCCCTATCC<br>GGCTCCACAAACACATTAACCATCACTGGGGTCCAAGCCGAAGACGAGGCTGATTATTAT<br>TGTGGGACTGAAGACATCAGCGGCACTGCTGGTGTATTTGGGGCCGGGACAACCCTGACC<br>GTCCTGGGTCAGTCCTCTAGATCTTCCGGCGGTGGTGGATCCTCTGGTGGTGGTGGTTCC<br>GCCGTGACGTTGGACGAGTCCGGGGGCGGCCTCCAGACGCCCGGAGGAGCGCTCCGCCTT<br>AGCTGCAGCGCCTCCGGGTTCGATTTCAGCAGCCATGGCATGTTCTGGGTGCGACAGGCG<br>CCCGGCAAGGGGTTGGAATATGTCTCGGAGATTACCAATGATGGTAGTGGCACAAACTAC<br>GGGTCGGCGGTGAAGGGCCGTGCCACCATCTCGAGGGACAACGGGCAGAGCACACTGTAT<br>CTGCAGATGAACAGCCTCAGGGCTGAGGACACCGGCACCTACTTCTGCGCCAGATCTACT<br>TATGAATGTCCTGGTGGTTTTAGTTGTTGGGGTGATACTGGTCAAATAGACGCATGGGGC<br>CACGGGACCGAAGTCATCGTCTCCTCC (SEQ ID NO: 297) |
| Anti-FAM19A5 ("2-13D-37-1.5W-41") | GCCCTGACTCAGCCGTCCTCGGTGTCAGCAAACCCAGGAGAAACCGCGAAGATAACCTGC<br>TCCGGGGGTGTGTATAGCTATGGCTGGTTCCAGCAGAAGCCTGGCAGTGCCCTTGTCACT<br>GTGATCTACTGGGATGATGAGAGACCCTCGGACATCCCTTCACGATTCTCCGGTGCCCTA<br>TCCGGCTCCACAAACACATTAACCATCACTGGGGTCCAAGCCGAAGACGAGGCTGATTAT<br>TATTGTGGGACTGAAGACATCAGCGGCACTGCTGGTGTATTTGGGGCCGGGACAACCCTG<br>ACCGTCCTGGGTCAGTCCTCTAGATCTTCCGGCGGTGGTGGATCCTCTGGTGGTGGTGGT<br>TCCGCCGTGACGTTGGACGAGTCCGGGGGCGGCCTCCAGACGCCCGGAGGAGCGCTCCGC<br>CTTAGCTGCAGCGCCTCCGGGTTCGATTTCAGCAGCCATGGCATGTTCTGGGTGCGACAG<br>GCGCCCGGCAAGGGGTTGGAATATGTCTCGGAGATTACCAATGATGGTAGTGGCACAAAC<br>TACGGGTCGGCGGTGAAGGGCCGTGCCACCATCTCGAGGGACAACGGGCAGAGCACACTG<br>TATCTGCAGATGAACAGCCTCAGGGCTGAGGACACCGGCACCTACTTCTGCGCCAGATCT<br>TCTTATGTTTGTCCTGGTGGTTTTAGTTGTTGGGGTGATACTGGTCAAATAGACGCATGG<br>GGCCACGGGACCGAAGTCATCGTCTCCTCC (SEQ ID NO: 298) |
| Anti-FAM19A5 ("2-13D-37-3W-16") | GCCCTGACTCAGCCGTCCTCGGTGTCAGCAAACCCAGGAGAAACCGCGAAGATAACCTGC<br>TCCGGGGGTGTGTATAGCTATGGCTGGTTCCAGCAGAAGCCTGGCAGTGCCCTTGTCACT<br>GTGATCTACTGGGATGATGAGAGACCCTCGGACATCCCTTCACGATTCTCCGGTGCCCTA<br>TCCGGCTCCACAAACACATTAACCATCACTGGGGTCCAAGCCGAAGACGAGGCTGATTAT<br>TATTGTGGGACTGAAGACATCAGCGGCACTGCTGGTGTATTTGGGGCCGGGACAACCCTG<br>ACCGTCCTGGGTCAGTCCTCTAGATCTTCCGGCGGTGGTGGATCCTCTGGTGGTGGTGGT<br>TCCGCCGTGACGTTGGACGAGTCCGGGGGCGGCCTCCAGACGCCCGGAGGAGCGCTCCGC<br>CTTAGCTGCAGCGCCTCCGGGTTCGATTTCAGCAGCCATGGCATGTTCTGGGTGCGACAG<br>GCGCCCGGCAAGGGGTTGGAATATGTCTCGGAGATTACCAATGATGGTAGTGGCACAAAC<br>TACGGGTCGGCGGTGAAGGGCCGTGCCACCATCTCGAGGGACAACGGGCAGAGCACACTG<br>TATCTGCAGATGAACAGCCTCAGGGCTGAGGACACCGGCACCTACTTCTGCGCCAGATCT<br>AATTATGCTTGTCCTGGTGGTTTTAGTTGTTGGGGTGATACTGGTCAAATAGACGCATGG<br>GGCCACGGGACCGAAGTCATCGTCTCCTCC (SEQ ID NO: 299) |

To create an anti-FAM19A5 scFv antibody disclosed herein, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see, e.g., Bird et al., (1988) Science 242:423-426; Huston et al., (1988) Proc. Natl. Acad. Sci. USA 85:5879-5883; McCafferty et al., (1990) Nature 348:552-554). Such nucleic acid sequence can then be inserted into an AAV vector disclosed herein, which can then be used to produce the scFv antibody, e.g., as demonstrated in the Examples.

Alternatively, nucleotide sequences encoding the heavy and light chains of the anti-FAM19A5 antibodies (with or without a signal peptide), e.g., SEQ ID NOs: 43 and 47, SEQ ID NOs: 44 and 48, SEQ ID NOs: 45 and 49, SEQ ID NOs: 46 and 50, SEQ ID NOs: 177 and 178, respectively, can be inserted into one or more AAV vectors of the present disclosure. Such AAV vectors can then be used to produce full length antibodies. Host cells that have been transduced with AAV vectors of the present disclosure are encompassed herein.

Methods of producing AAV vectors as disclosed herein are well known in the art, including methods, for example, using packaging cells, auxiliary viruses or plasmids, and/or baculovirus systems (see, e.g., Samulski et al., J. Virology 63, 3822 (1989); Xiao et al., J. Virology 72, 2224 (1998); Inoue et al., J. Virol. 72, 7024 (1998); WO1998/022607; and WO2005/072364).

Methods of producing pseudotyped AAV vectors are also known (see, e.g., WO00/28004), as well as various modifications or formulations of AAV vectors, to reduce their immunogenicity upon in vivo administration (see, e.g., WO01/23001; WO00/73316; WO04/112727; WO05/005610; and WO99/06562). In some embodiments, AAV vectors may be prepared or derived from various serotypes of AAVs which may be mixed together or mixed with other types of viruses to produce chimeric (e.g., pseudotyped) AAV viruses.

III. Pharmaceutical Compositions

Provided herein are compositions comprising an AAV vector of the present disclosure having the desired degree of purity in a physiologically acceptable carrier, excipient or stabilizer (Remington's Pharmaceutical Sciences (1990) Mack Publishing Co., Easton, PA). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some embodiments, pharmaceutical compositions comprise an AAV vector described herein, and optionally one or more additional prophylactic or therapeutic agents, in a pharmaceutically acceptable carrier. In a specific embodiment, pharmaceutical compositions comprise an effective amount of an antibody or antigen-binding portion thereof described herein, and optionally one or more additional prophylactic of therapeutic agents, in a pharmaceutically acceptable carrier. In some embodiments, the antibody is the only active ingredient included in the pharmaceutical composition. Pharmaceutical compositions described herein can be useful in reducing FAM19A5 activity and treating a condition, such as a central nervous system damage, disease, or disorder, e.g., neuropathic pain.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition of the present disclosure can be formulated for any route of administration to a subject. Specific examples of routes of administration include intranasal, oral, parenterally, intrathecally, intracerebroventricularly, pulmonarily, subcutaneously, intraperitoneally, intravitreally, epidurally, subretinally, or intraventricularly. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An AAV vector described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma). These formulations for administration to the respiratory tract can be in the form of an aerosol or solution for a nebulizer, or as a microtine powder for insufflations, alone or in combination with an inert carrier such as lactose. In such a case, the particles of the formulation will, in some embodiments, have diameters of less than 50 microns, in some embodiments less than 10 microns.

An AAV vector described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

In some embodiments, a pharmaceutical composition comprising an AAV vector described herein is a lyophilized powder, which can be reconstituted for administration as solutions, emulsions and other mixtures. It can also be reconstituted and formulated as solids or gels. The lyophilized powder is prepared by dissolving an antibody or antigen-binding portion thereof described herein, or a pharmaceutically acceptable derivative thereof, in a suitable solvent. In some embodiments, the lyophilized powder is sterile. The solvent can contain an excipient which improves the stability or other pharmacological component of the powder or reconstituted solution, prepared from the powder.

Excipients that can be used include, but are not limited to, dextrose, sorbitol, fructose, corn syrup, xylitol, glycerin, glucose, sucrose or other suitable agent. The solvent can also contain a buffer, such as citrate, sodium or potassium phosphate or other such buffer known to those of skill in the art at, in some embodiments, about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The AAV vector described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In certain embodiments, an AAV vector described herein is targeted to treat a disease or disorder, e.g., a central nervous system damage, degenerative brain disease, or neuropathic pain.

The compositions to be used for in vivo administration can be sterile. This is readily accomplished by filtration through, e.g., sterile filtration membranes.

IV. Kits

Also provided herein are kits comprising one or more AAV vectors described herein. In some embodiments, provided herein is a pharmaceutical pack or kit comprising one or more containers filled with one or more of the ingredients of the pharmaceutical compositions described herein, such as one or more AAV vectors provided herein, optional an instructing for use. In some embodiments, the kits contain a pharmaceutical composition described herein and any prophylactic or therapeutic agent, such as those described herein.

V. Therapeutic Uses and Methods

In certain aspects, presented herein are methods for mitigating injury or damage to the CNS in a subject, comprising administering an AAV vector of the present disclosure to the subject.

In other aspects, presented herein are methods for inhibiting, slowing down, suppressing, curbing, reducing, reversing, or preventing the beginning or initiation of gliosis and its associated detrimental effects of the CNS in a subject, comprising administering to the subject an AAV vector disclosed herein. In some embodiments, presented herein are methods for inhibiting, slowing down, suppressing, curbing, reducing, reversing, or preventing excessive or abnormal proliferation of reactive astrocytes and its associated detrimental effects of the CNS in a subject, comprising administering to the subject an AAV vector of the present disclosure. In some embodiments, presented herein are methods for decreasing, inhibiting, or reducing the expression of chondroitin sulfate proteoglycans (including the level of neurocan, NG2, or both), or reducing the activity of, or rendering inactive neurocan, NG2, or both in a subject comprising administering to the subject an AAV vector described herein. In some embodiments, presented herein are methods for stimulating, promoting, increasing, or activating the growth of neurons, preferably after injury or damage in a subject comprising administering to the subject an AAV vector as described herein. In other embodiments, presented herein are methods for increasing the level of c-fos mRNA, c-fos protein, or c-fos protein activity, and increasing the level of ERK mRNA, ERK protein, or pERK activity, preferably in the nucleus of neurons, in a subject in need thereof, comprising administering to the subject an AAV vector of the present disclosure. In certain embodiments, presented herein are methods for enhancing or increasing the level of GAP43 mRNA, GAP43 protein, or increasing the activity of GAP43 protein, preferably in the neurons, in a subject in need thereof, comprising administering to the subject an AAV vector as disclosed herein. In certain embodiments, presented herein are methods for enhancing or promoting the survival of neurons and/or promoting the regrowth of an axon, in a subject in need thereof comprising administering to the subject an AAV vector disclosed herein. In some embodiments, the subject is a human, preferably a human having an injury or damage to a neuron from e.g., CNS damage, trauma, injury, cerebrospinal damage, brain tumor, infection, ischemia, stroke, autoimmune responses, and/or neurodegenerative disease.

In some aspects, also presented herein are methods for treating a disease or disorder including a central nervous system damage, a cerebrospinal system damage, a degenerative brain disorder, a degenerative cerebrospinal or nerve disorder, or a neuropathic pain, in a subject in need thereof, comprising administering to the subject an AAV vector of the present disclosure. In some embodiments, the central nervous system damage is a traumatic brain injury, a cerebrospinal damage, a stroke, a brain tumor, or a combination thereof. In some embodiments, the degenerative brain disorder is Huntington's disease, Parkinson's disease, Alzheimer's disease, multiple sclerosis, Amyotrophic Lateral Sclerosis (ALS), or a combination thereof. Thus, in certain embodiments, disclosed herein is a method for treating a traumatic brain injury, a cerebrospinal damage, a stroke, a brain tumor, or a combination thereof in a subject in need thereof comprising administering to the subject an AAV vector disclosed herein or a composition thereof. In some embodiments, disclosed herein is a method for treating Huntington's disease, Parkinson's disease, Alzheimer's disease, multiple sclerosis, ALS in a subject in need thereof comprising administering to the subject an AAV vector disclosed herein, or a composition thereof. In some embodiments, the subject is a human.

In certain embodiments, presented herein are methods for treating, reducing, reversing, preventing, ameliorating, controlling, or inhibiting a fibrosis in a subject in need thereof, comprising administering to the subject an AAV vector disclosed herein, or a composition thereof. In some embodiments, the fibrosis is benign (i.e., causes no symptoms). In other embodiments, the fibrosis is associated with a pathological state, which can or cannot be reversible. In some embodiments, the fibrosis is selected from the group consisting of a hepatic fibrosis, pulmonary fibrosis, renal fibrosis, myelofibrosis, pancreatic fibrosis, skin fibrosis, cardiac fibrosis, arterial fibrosis, arthrofibrosis, breast fibrosis, muscle fibrosis, retroperitoneal Fibrosis, thyroid fibrosis, lymph node fibrosis, bladder fibrosis, and pleural fibrosis. In one embodiment, the fibrosis is a liver fibrosis or a pulmonary fibrosis. In another embodiment, the fibrosis is associated with a tumor derived from a cancer, such as a liver cancer, a lung cancer, a renal cancer, a breast cancer, and/or a pancreatic cancer. In one embodiment, the method lessens, reverses, alleviates, ameliorates, inhibits, or slows down or prevents a fibrosis, a symptom associated with the fibrosis, an underlining cause of the fibrosis, or a combination thereof.

In other embodiments, the AAV vectors disclosed herein can treat, reduce, reverse, prevent, ameliorate, control, or inhibit a fibrosis associated disease or disorder in a subject in need thereof. The term "a fibrosis associated with a disease or disorder" refers to a fibrosis that accompanies a disease or disorder, or caused by or resulting from a disease or a disorder. The term includes a fibrosis that results from or is caused by the disease or disorder disclosed above, or a fibrosis that accompanies the disease or disorder.

In yet other embodiments, the AAV vector of the present disclosure can treat, reduce, reverse, prevent, delay, ameliorate, control, or inhibit a liver cancer, a lung cancer, a renal cancer, a breast cancer, and/or a pancreatic cancer in a subject in need thereof, wherein the method comprises administering to the subject the AAV vector. In some embodiments, the liver cancer, lung cancer, renal cancer, breast cancer, and/or pancreatic cancer is associated with or caused by fibrosis.

In some embodiments, a therapeutically effective amount of an AAV vector of the present disclosure, or an composition thereof, is administered. When treating a subject (e.g., a human), a therapeutically effective amount of the AAV vector disclosed herein depends on factors such as age, gender, severity of the disease.

In some embodiments, an AAV vector of the present disclosure, or a composition thereof, is administered intravenously, orally, parenterally, transthecally, intrathecally, intra-cerebroventricularly, intramuscularly, pulmonarily, intraperitoneally, intravitreally, subcutaneously, epidurally, subretinally, or intraventricularly.

In some embodiments, an AAV vector disclosed herein, or a composition thereof, can be administered in combination with one or more additional agent for treating a fibrosis (e.g., pirfenidone (ESBRIET) or nintedanib (OFEV) for idiopathic pulmonary fibrosis). Dose and administration of the one or more additional therapeutic drugs are known in the art, e.g., as instructed by the product label of the respective drug.

In some embodiments, an AAV vector described herein, or a composition thereof, can be administered in combination with one or more additional agent for treating a central nervous system damage (e.g., a traumatic brain injury, a cerebrospinal damage, a stroke, or a brain tumor), a cerebrospinal system damage, a degenerative brain disorder (e.g., Huntington's disease, Parkinson's disease, Alzheimer's disease, multiple sclerosis, ALS), a degenerative cerebrospinal or nerve disorder, or a neuropathic pain. For example, non-limiting exemplary agents for treating Huntington's disease include Tetrabenazine (XENAZINE®), antipsychotic drugs, such as haloperidol (HALDOL®), chlorpromazine, risperidone (RISPERDAL®) and quetiapine (SEROQUEL®).

Non-limiting exemplary agents for treating Parkinson's disease include levodopa (with or without Carbidopa), dopamine agonists such as pramipexole (MIRAPEX®), ropinirole (REQUIP®), and rotigotine (NEUPRO®), and apomorphine (APOKYN®), selegiline (ELDEPRYL® and ZELAPAR®), rasagiline (AZILECT®), Entacapone (COMTAN®), benztropine (COGENTIN®), trihexyphenidyl, and amantadine.

Non-limiting exemplary agents for treating Alzheimer's disease include Donepezil (ARICEPT®), Galantamine (RAZADYNE®), and Rivastigmine (EXELON®).

Non-limiting exemplary agents for treating multiple sclerosis include Glatiramer acetate (COPAXONE®), Dimethyl fumarate (TECFIDERA®), Fingolimod (GILENYA®), Teriflunomide (AUBAGIO®), Natalizumab (TYSABRI®), Alemtuzumab (LEMTRADA®), and Mitoxantrone.

Non-limiting exemplary agents for treating ALS include riluzole (RILUTEK®).

Dose and administration of the one or more additional therapeutic drugs are known in the art, e.g., as instructed by the product label of the respective drug.

The following examples are offered by way of illustration and not by way of limitation.

Example 1: Adeno-Associated Viral (AAV) Vector Construction

AAV vectors encoding a single-chain variable fragment (scFv) of anti-FAM19A5 antibody clones 1-65, 2-13, or 3-2 were constructed as follows. Briefly, to construct the AAV vector encoding the 3-2 scFv, the pscAAV-MCS expression vector (Cell biolabs, cat. #VPK-430) was digested with EcoRI and NotI. Then, a transgene encoding human beta globin intron under a CMV promoter and 3-2 scFv were inserted into the pscAAV-MCS vector as shown in FIG. 1. The human beta globin intron was inserted to maximize gene expression. To generate AAV vectors encoding the 1-65 or 2-13 scFv, the above AAV vector was digested with EcoRV and NotI to remove the 3-2 scFv transgene. Then, transgene encoding the 1-65 or 2-13 ScFv were inserted into the AAV vector. Transgenes encoding the 3-2, 1-65, or 2-13 ScFv were codon-optimized for optimal expression in mice. All the AAV vectors included a mouse IgG kappa chain signal peptide in front of the scFv transgene to promote secretion from cells. The AAV vectors also included a FLAG-tag at the back of the scFv transgene to assist in detecting gene expression. Once constructed, the AAV vectors were transformed into E. coli, cultivated, and large amounts of the AAV vectors were obtained using maxiprep. AAV vectors encoding 1-30 scFv or mouse IL-10 or GFP were generated and provided by Signagen Laboratories (Rockville, Maryland).

The following recombinant AAVs were used for the examples described below: (i) scAAV8-CMV-3-2-ScFv (Sirion, Germany), (ii) scAAV9-CMV-3-2-ScFv (Signagen Laboratories, USA), (iii) scAAV9-CMV-1-65-ScFv (Signagen Laboratories, USA), scAAV9-CMV-2-13-ScFv (Signagen Laboratories, USA); (iv) scAAV1-CMV-3-2-ScFv (Signagen Laboratories, USA). (v) scAAV9-CMV-1-30-ScFv (Signagen Laboratories, USA). (vi) scAAV9-CMV-mIL-10 (Signagen Laboratories, USA). (vii) scAAV9-CMV-GFP (Signagen Laboratories, USA). (viii) scAAV1-CMV-GFP (Signagen Laboratories, USA).

Example 2: Analysis of Anti-FAM19A5 ScFv Gene Expression

The expression of the anti-FAM19A5 ScFv was tested using the above constructed AAV vectors (scAAV8-CMV-3-2-ScFv, scAAV9-CMV-3-2-ScFv, scAAV9-CMV-1-65-

ScFv, and scAAV9-CMV-2-13-ScFv). Briefly, HEK293 cells ($1.2\times10^6$) cells were seeded in a 60 mm² dish and cultured for 24 hours. Afterwards, the media was replaced with opti-MEM medium (low serum) and the HEK293 cells were transduced with the different AAV vectors (using multiple multiplicity of infection (MOI)). Supernatant was recovered on days 1, 4, and 8 post transduction. To confirm gene expression, ABSbio™ DYKDDDK tag ELISA kit (Advanced Bioreagent, cat. #SE002-flag) was used to detect the FLAG tag that was included at the back of the scFv gene (see FIG. 1 and Example 1). The collected supernatant was diluted 1 to 10 fold, then 100 μL of the diluted supernatant was added to a well of the ELISA plate and allowed to react at room temperature for 2 hours at 350 rpm. Afterwards, the plate was washed and 100 μL of the detection antibody was added to each of the wells and allowed to react at room temperature for 1 hour at 350 rpm. Next, the plate was washed again, 100 μL of the TMB solution was added to each well and allowed to reach for 10-30 minutes. Then, 100 μL of the stop solution was added to wells and absorbance was measured at 450 nm. The amount of FLAG was measured through the calibration curve and the amount of scFv was calculated by multiplying the ratio of FLAG expression to the molecular weight of the standard.

Figure 2A:
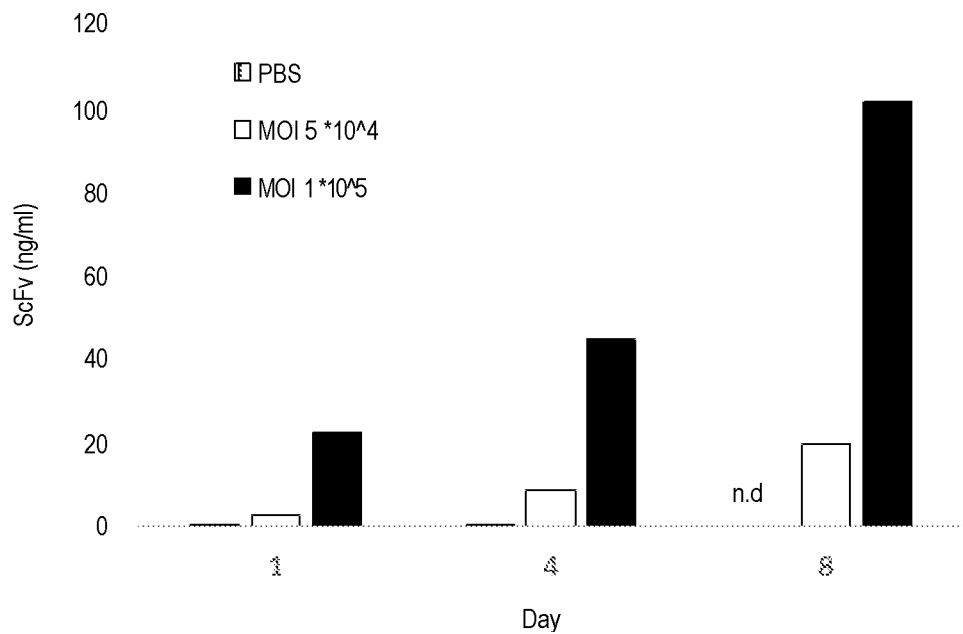
FIGS. 2A, 2B, and 2C show the expression level of the anti-FAM19A5 scFv after transduction of HEK293 cells with one of the following AAV constructs: (i) scAAV8-CMV-3-2-ScFv; (ii) scAAV9-CMV-3-2-ScFv; (iii) scAAV9-CMV-1-65-ScFv; or (iv) scAAV9-2-13-ScFv.
Figure 2B:
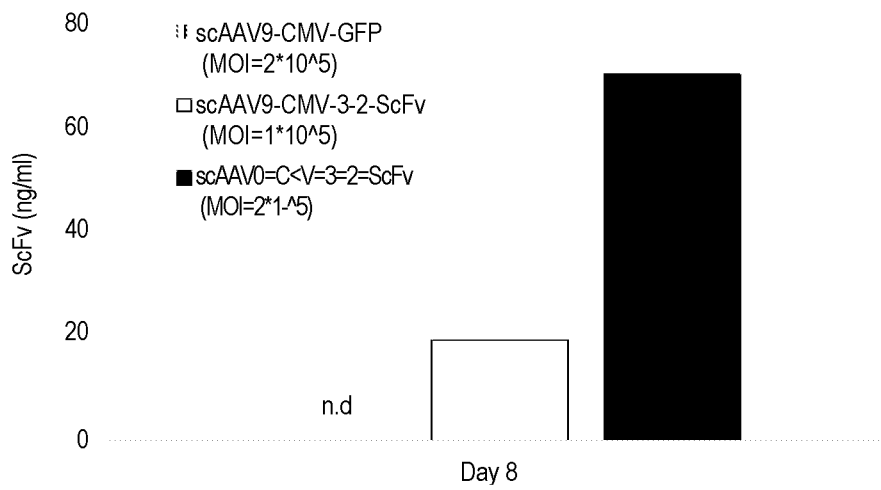
Figure 2C:
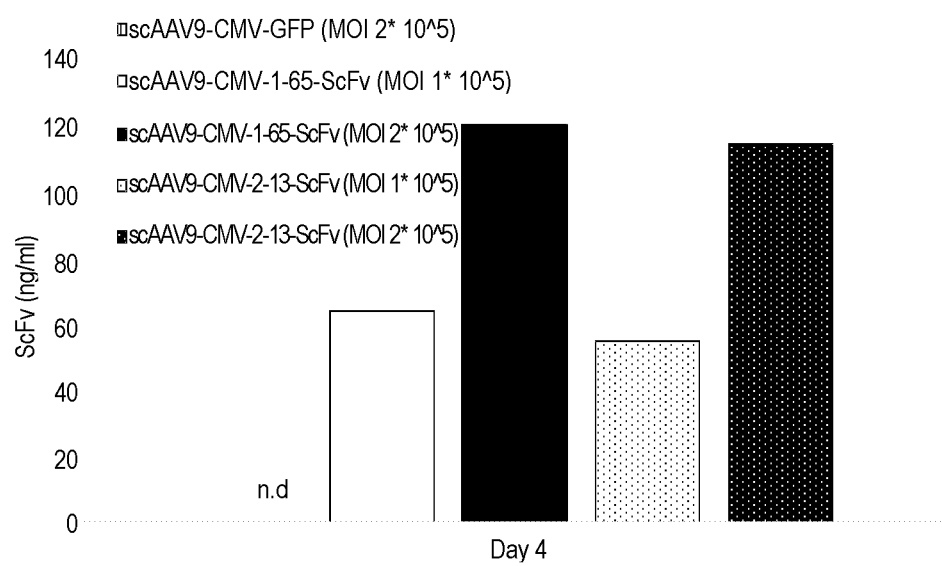

As shown in FIG. 2A, for the scAAV8-CMV-3-2-scFv vector, anti-FAM19A5 scFv could be detected in the supernatant as early as day 1 post-transduction (at $1\times10^5$ MOI). By day 8 post-transduction, approximately 100 ng/mL of 3-2 scFv was detected in the supernatant (at $1\times10^5$ MOI). With the scAAV9-CMV-3-2-scFv vector, by day 8 post transduction, approximately 70 ng/mL of 3-2 scFv was detected in the supernatant (at 2×105 MOI). Similar results were observed with scAAV9-CMV-1-65-ScFv and scAAV9-CMV-2-13-ScFv. As shown in FIG. 2C, approximately 120 ng/mL and 115 ng/mL of 1-65 scFv and 2-13 scFv, respectively, were detected in the supernatant at day 4 post-transduction.

The above data demonstrate that all the AAV vectors constructed in Example 1 were properly constructed and that they can induce anti-FAM19A5 scFv expression when transduced into cells.

Example 3: Inhibition of FAM19A5 Binding in U87MG Cells

To assess the binding capability of the anti-FAM19A5 scFv produced by the above AAV constructs, a binding inhibition assay using U87MG cells (a human primary glioblastoma cell line and can bind to human FAM19A5-Fc protein) was performed. Briefly, the U87MG cells were transduced with scAAV8-CMV-2-3-ScFv (MOI $1\times10^5$), scAAV9-CMV-1-65-ScFv (MOI $2\times10^5$), or scAAV9-CMV-2-13-ScFv (MOI $2\times10^5$). Then, at day 4 post-transduction, 0.1 μg of human FAM19A5-Fc protein was mixed with 200 μL of supernatant, and the mixture was allowed to incubate for 30 minutes at 4° C. Negative control consisted of either PBS or supernatant from HEK293 cells transduced with scAAV9-CMV-GFP vector. After the 30 minute incubation, 100 μL of the mixture (human FAM19A5-Fc+supernatant from cells transfected with the anti-FAM19A5 scFv AAV construct) was added to U87MG cells ($2\times10^5$) and allowed to react for 1 hour at 4° C. Then, the cells were washed with PBS, treated with 100 μL of goat anti-human IgG 488 antibody (Invitrogen, cat. #A11013) (diluted 1:50), allowed to incubate for an additional 30 minutes at 4° C. The cells were then washed again and binding of human FAM19A5-Fc to the U87MG cells was analyzed using flow cytometry.

Figure 3A:
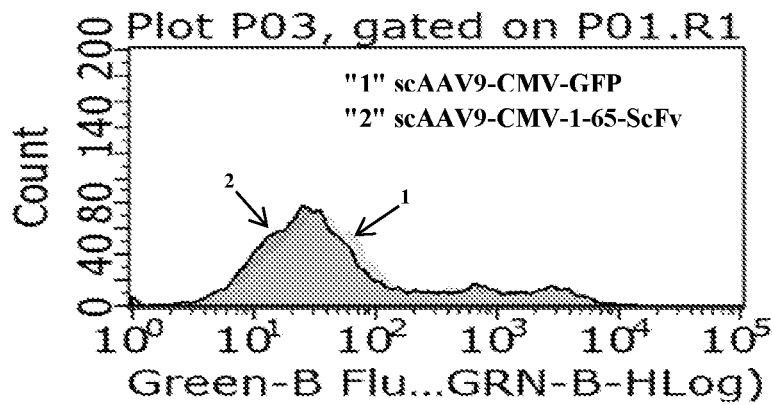
FIGS. 3A, 3B, and 3C show the mean fluorescence intensity (MFI) of human FAM19A5-Fc binding to U87MG cells in the presence or absence of supernatant from cells transduced with different anti-FAM19A5 AAV constructs.
Figure 3B:
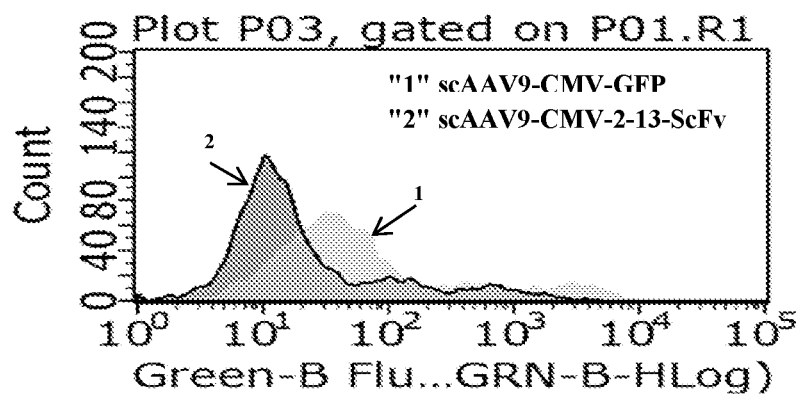
Figure 3C:
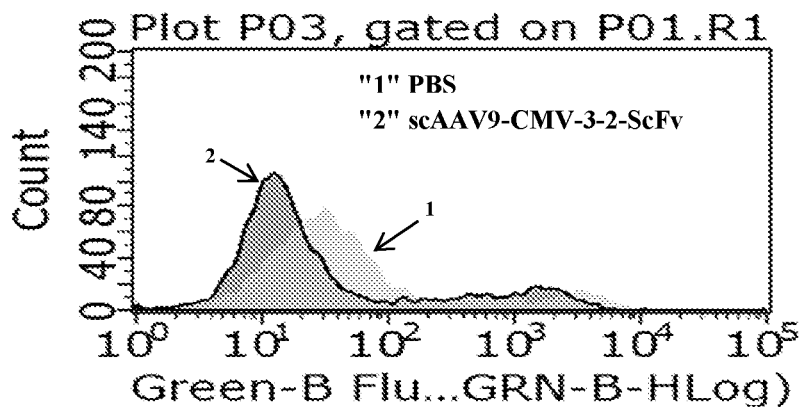

As shown in FIGS. 3A, 3B, and 3C, when the U87MG cells were treated with the mixture (human FAM19A5-Fc+ supernatant from cells transfected with the anti-FAM19A5 scFv AAV construct), there was reduced binding of human FAM19A5-Fc to the cells as compared to when the cells were treated with a control mixture (human FAM19A5-Fc+ supernatant from cells transfected with scAAV9-CMV-GFP construct). This was true for all of anti-FAM19A5 scFv AAV constructs tested. The supernatants from cells transduced with scAAV9-CMV-1-65-ScFv, scAAV9-CMV-2-13-ScFv, scAAV8-CMV-3-2-ScFv reduced the mean fluorescence intensity (MFI) of the binding of human FAM19A5-Fc to U87MG cells by 19% (FIG. 3A), 68% (FIG. 3B), and 42% (FIG. 3C), respectively, compared to corresponding control (supernatant from cells transfected with a AAV-GFP vector or treated with PBS).

These results demonstrate that the anti-FAM19A5 scFv produced by the AAV constructs described in Example 1 can effectively bind to human FAM19A5 with high affinity.

Example 4: Inhibition of FAA/119A5 Binding in C8-D1A Cells

To confirm the inhibition of binding observed in Example 3, C8-D1A cells were used for the binding inhibition assay. C8-D1A cells are an astrocyte cell line and can secrete FAM19A5 into the surrounding medium when cultured. If the anti-FAM19A5 scFv produced by the AAV constructs can effectively bind to human FAM19A5, then treating the C8-D1A cell culture medium with supernatants from cells transduced with the anti-FAM19A5 scFv AAV should result in a decrease in the level of FAM19A5 protein in the culture medium.

Briefly, C8-D1A cells were plated onto a 6-well plate (2×105 cells/well) and cultured for approximately 24 hours. The anti-FAM19A5 scFv containing supernatants were produced by transfecting HEK293 cells with one of the following: (i) scAAV8-CMV-3-2-ScFv (MOI 1×105); (ii) scAAV9-CMV-1-65-ScFv (MOI=2×105); or (iii) scAAV9-CMV-2-13-ScFv (MOI=2×105) and then the supernatant collected at day 8 post-transduction. To activate the C8-DIA cells, TGF-β (20 ng/ml) was added to the cells with the supernatant containing the anti-FAM19A5 scFv. PBS or supernatant from cells transduced with scAAV-9-CMV-GFP were used as a negative control. Cells were allowed to incubate for 24 hours, and then the FAM19A5 protein level in the culture was measured using an ELISA assay (see Example 1 for methods used in the ELISA assay).

Figure 4A:
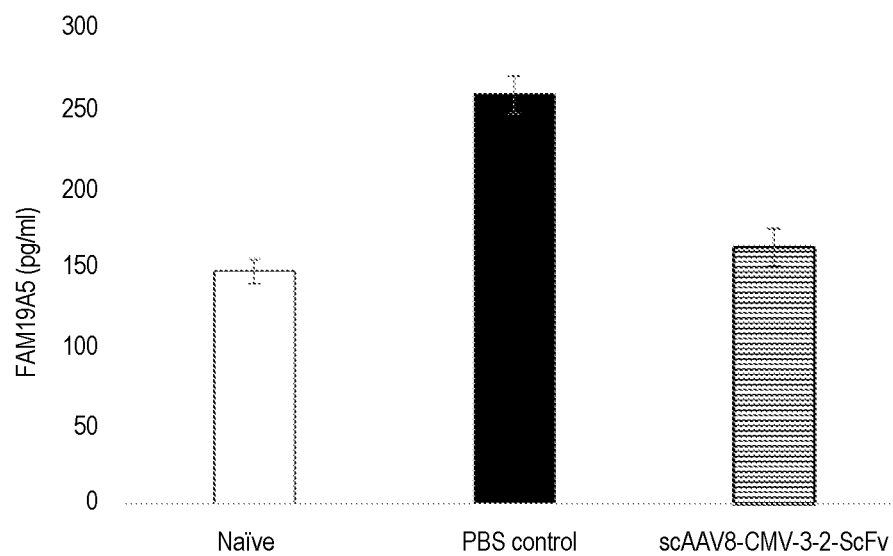
FIGS. 4A and 4B show the level of human FAM19A5 protein in C8-D1A cell culture after treatment with supernatant from cells transduced with the different anti-FAM19A5 AAV constructions.
Figure 4B:
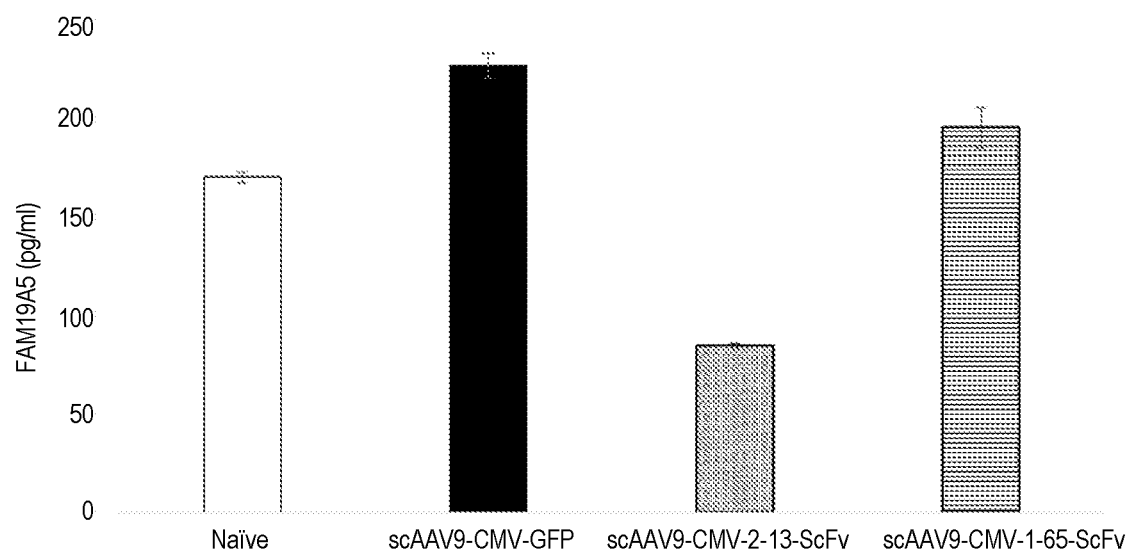

As shown in FIG. 4A, when the C8-D1A cells were activated in the presence of supernatant from cells transduced with scAAV8-CMV-3-2-ScFv, there was about a 38% reduction in the level of FAM19A5 protein detected in the culture medium, compared to a corresponding control (PBS). Supernatant from cells transduced with scAAV9-CMV-2-13-ScFv and scAAV9-CMV-1-65-ScFv reduced the level of FAM19A5 protein in the culture medium by about 63% and 14%, respectively, compared to a corresponding control (supernatant from cells transfected with a GFP AAV vector). See FIG. 4B.

The above data further confirms that the anti-FAM19A5 scFv produced by the AAV vectors can effectively bind to human FAM19A5.

Example 5: In Vivo Expression Analysis

To confirm anti-FAM19A5 scFv expression in vivo, scAAV8-CMV-3-2-ScFv construct was administered to C57BL/6 mice intrathecally ($1\times10^{11}$ viral genome (vg)/mouse). The mice were then sacrificed at 1 and 2 weeks post-administration, and spinal cord tissue (Lumbar spinal cord) were analyzed. To detect gene expression, anti-FLAG antibody and fluorescence microscopy were used.

Figure 5:
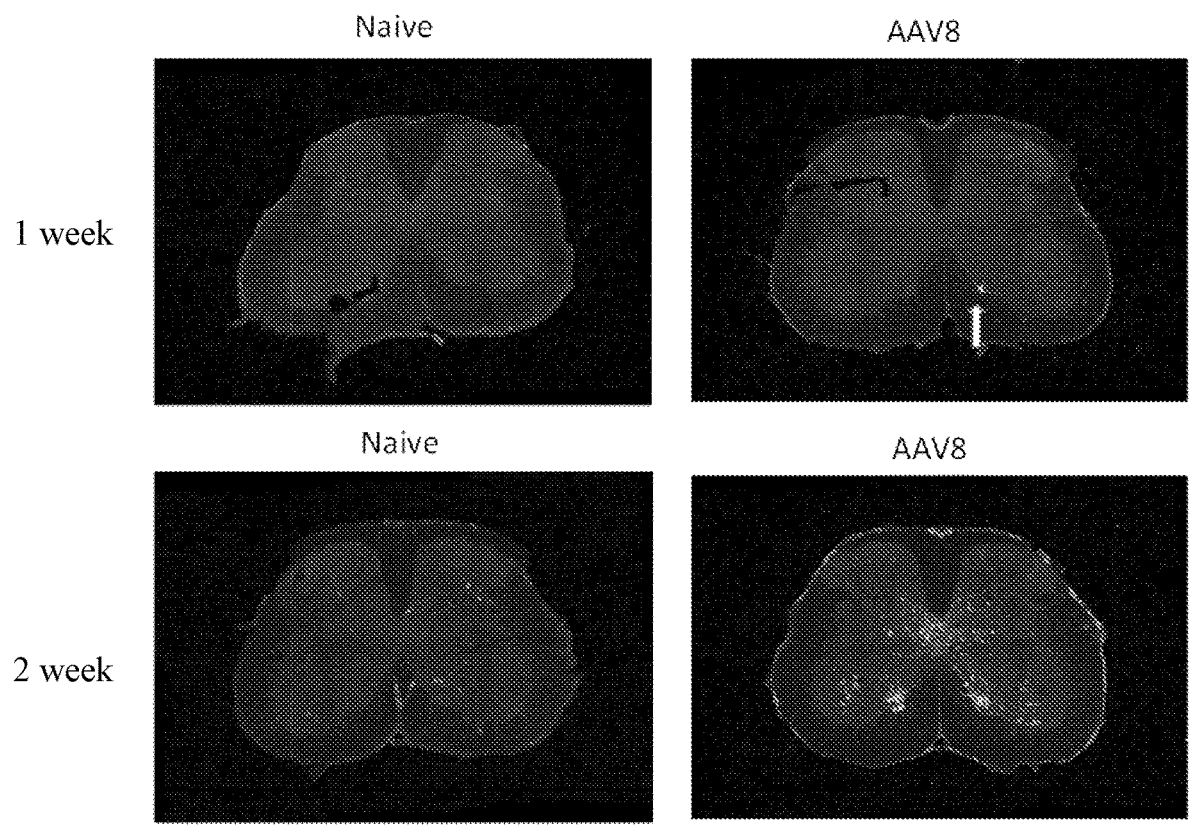
FIG. 5 shows the expression of anti-FAM19A5 (3-2) scFv in the brain at one week (top row) and 2 weeks (bottom row) after intrathecal administration of scAAV8-CMV-3-2-ScFv into C57BL/6 mice. The images to the left are from the naïve animals (no administration). The images to the right are from mice that received the AAV construct. The arrow in the top right image indicates positive staining.

As shown in FIG. 5, there was no positive antibody expression in naïve animals (i.e., no administration of the AAV vector) both at week 1 (upper left image) and at week 2 (bottom left image) post-administration. In contrast, in the scAAV8-CMV-3-2-ScFv treated animals, anti-FLAG (i.e., anti-FAM19A5 scFv) expression were observed in the ventral horn neuron at week 1 post-administration (upper right image). By week 2, there was much higher expression, including in the dorsal horn region.

This data confirmed the earlier in vitro expression data (see Example 2) and indicated that when the anti-FAM19A5 AAV vectors are administered intrathecally, they can transduce the surrounding cells, resulting in anti-FAM19A5 scFv production.

Example 6: Assessment of Pain Relief in a Chronic Neuropathic Pain Model (CCI) Using scAAV8-CMV-3-2-ScFv To assess the in vivo effects of administering the anti-FAM19A5 scFv AAV constructs, a mouse model of chronic constriction injury (CCI) was used. Briefly, either PBS (control) or scAAV8-CMV-3-2-ScFv were administered to C57BL/6 mice intrathecally (into the vertebrae). Then, at about 1 week post-administration, peripheral nerve injury was induced in the animals through scrotum nerve ligation. At various time points after injury, both mechanical allodynia (response to physical external stimuli) and thermal hyperalgesia (response to elevated temperature) were assessed in the animals. Mechanical allodynia was assessed by applying Von Frey monofilaments (0.16 g) to the injured foot multiple times and observing the frequency in which the animals reacted in pain. Thermal hyperalgesia was assessed using the Hargreaves test, in which a radial thermal stimulus (intensity: 30) was applied to the injured foot and the paw withdrawal latency was determined.

Figure 6A:
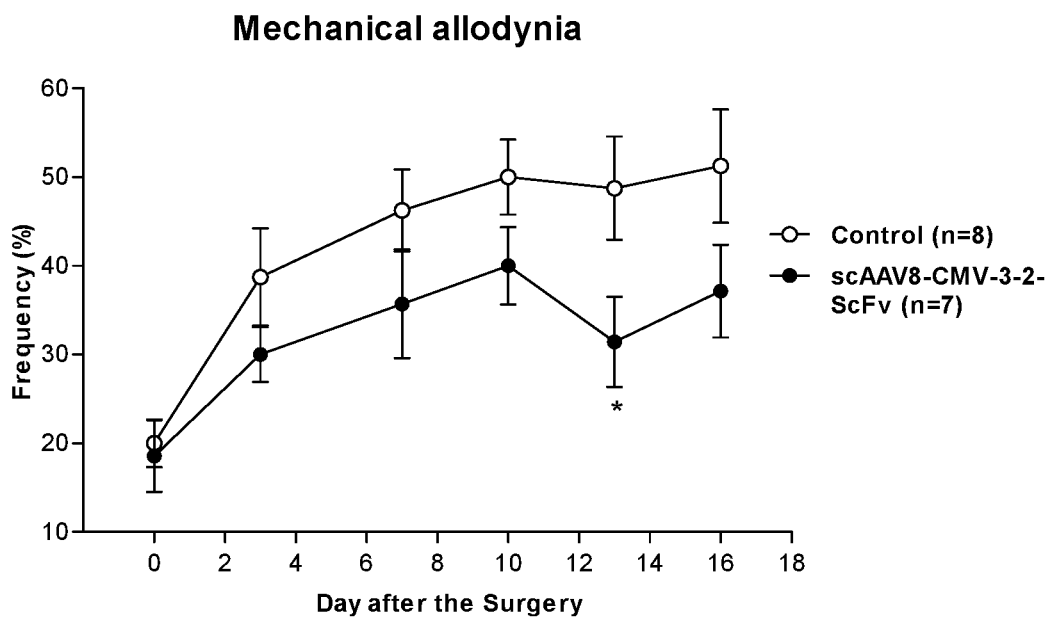
FIGS. 6A and 6B show the effect of scAAV8-CMV-3-2-ScFv administration on mechanical allodynia (FIG. 6A) and thermal hyperalgesia (FIG. 6B) after peripheral nerve injury.
Figure 6B:
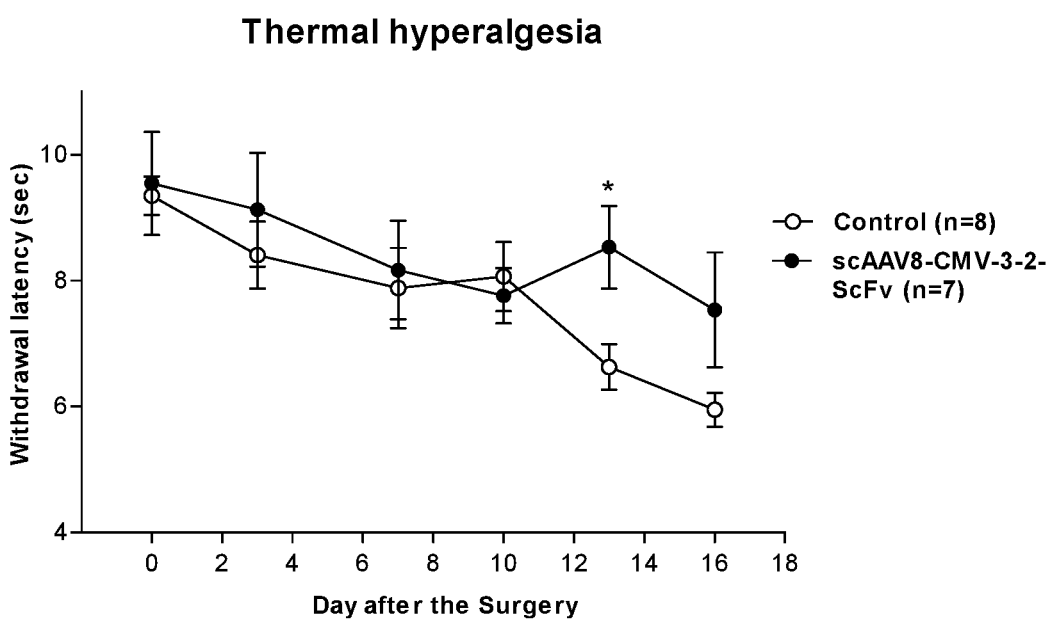

As shown in FIG. 6A, animals that received scAAV8-CMV-3-2 responded to the Von Frey monofilament less frequently compared to the control animals (PBS only). Similar results were observed for thermal hyperalgesia. See FIG. 6B. These results demonstrate that in vivo administration of anti-FAM19A5 AAV constructs can reduce neuropathic pain after a peripheral nerve injury.

Example 7: Assessment of Pain Relief in a Chronic Neuropathic Pain Model (CCI) Using scAAV9-CMV-3-2-ScFv The in vivo effects of scAAV9-CMV-3-2-ScFv was also tested using a mouse model of chronic constriction injury (CCI) as described in Example 6. Briefly, the scAAV9-CMV-3-2-ScFv construct was intrathecally administered to C57BL6 mice. The control animals received scAAV9-CMV-GFP construct. Then, about 1 week after administration, peripheral nerve injury was induced. Then, both mechanical allodynia and thermal hyperalgesia were assessed in the animals at various time points as described in Example 6.

Figure 7A:
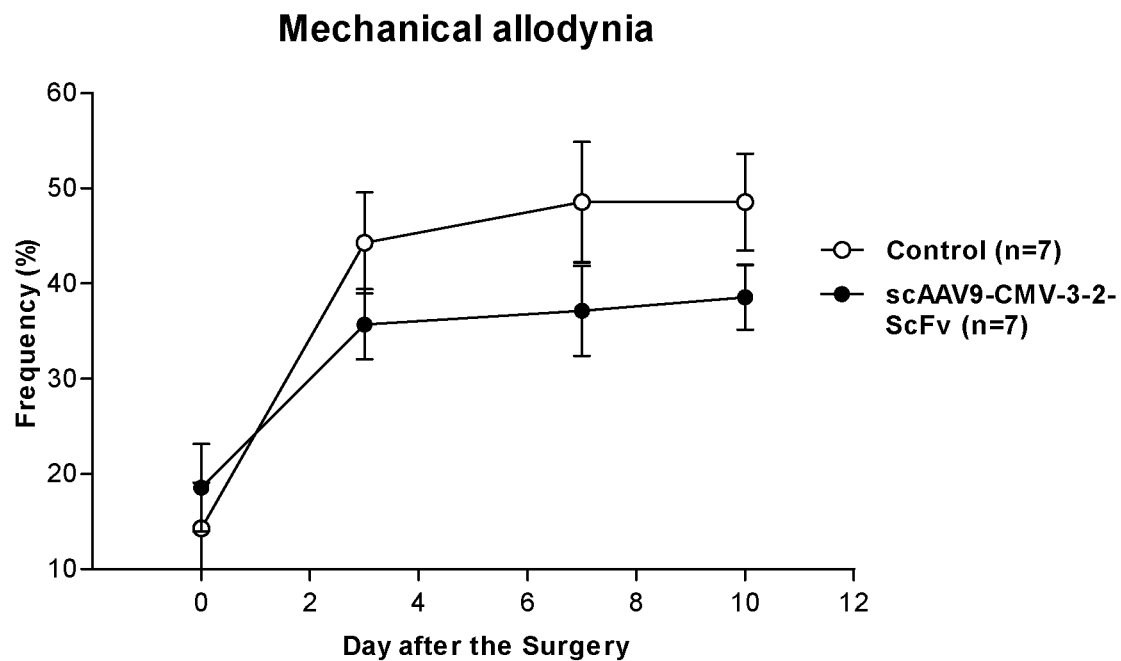
FIGS. 7A and 7B show the effect of scAAV9-CMV-3-2-ScFv administration on mechanical allodynia (FIG. 7A) and thermal hyperalgesia (FIG. 7B) after peripheral nerve injury.
Figure 7B:
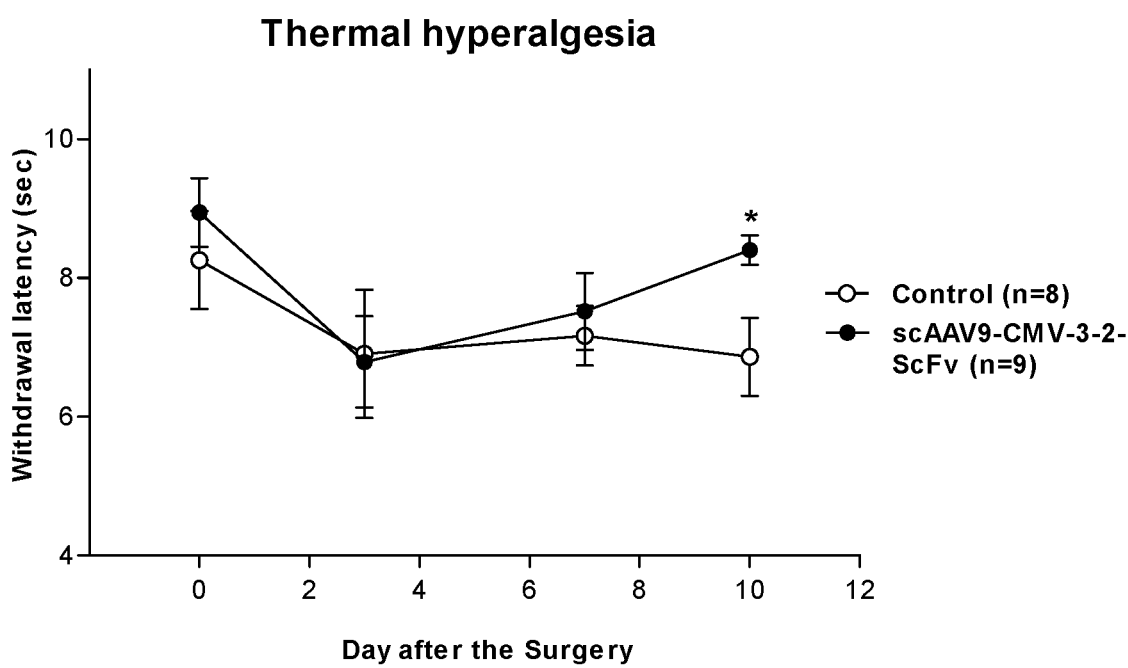

As shown in FIGS. 7A and 7B, animals that received scAAV9-CMV-3-2-ScFv appeared to be more pain tolerant after peripheral nerve injury. For instance, compared to the control animals, mice that received scAAV9-CMV-3-2-ScFv responded to the Von Frey monofilament less frequently (FIG. 7A) and had higher latency time to elevated temperature (FIG. 7B).

Collectively, these results demonstrate that anti-FAM19A5 scFv can be effectively delivered in vivo using AAV vectors and that the anti-FAM19A5 scFv produced by the AAV vectors are fully functional (e.g., binds to human FAM19A5 and reduce neuropathic pain).

Example 8: Assessment of Pain Relief in a Chronic Neuropathic Pain Model (CCI) Using scAAV1-CMV-3-2-ScFv To further assess whether the above effects were dependent on the type of AAV used, the in vivo effects of scAAV1-CMV-3-2-ScFv was tested. Briefly, C57BL/6 mice received two doses (each dose=$1\times10^{11}$ vg/mouse) of scAAV1-CMV-3-2-ScFv at a two-week interval via intrathecal administration. One week after the last administration, peripheral nerve injury was induced, and both mechanical allodynia and thermal hyperalgesia were assessed as described in Example 6.

Figure 8A:
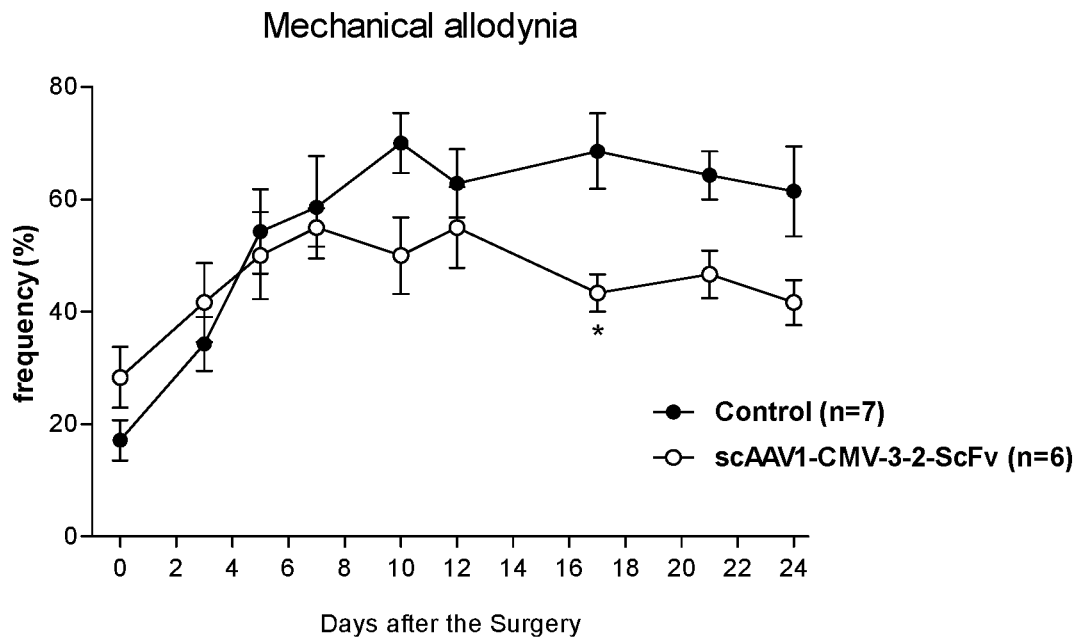
FIGS. 8A and 8B show the effect of scAAV1-CMV-3-2-ScFv administration on mechanical allodynia and thermal hyperalgesia, respectively.
Figure 8B:
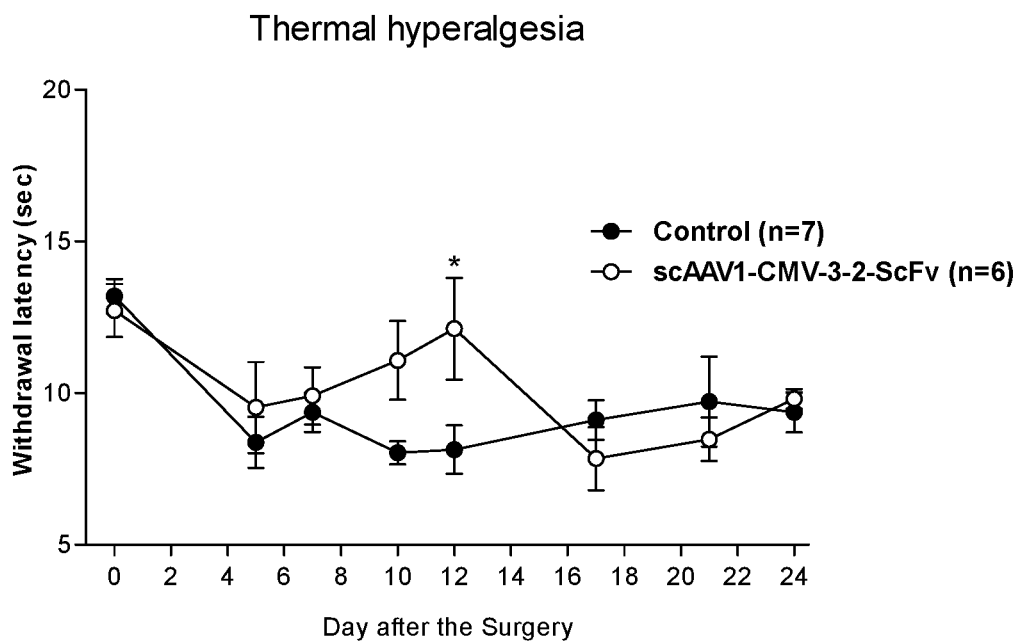
Figure 9A:
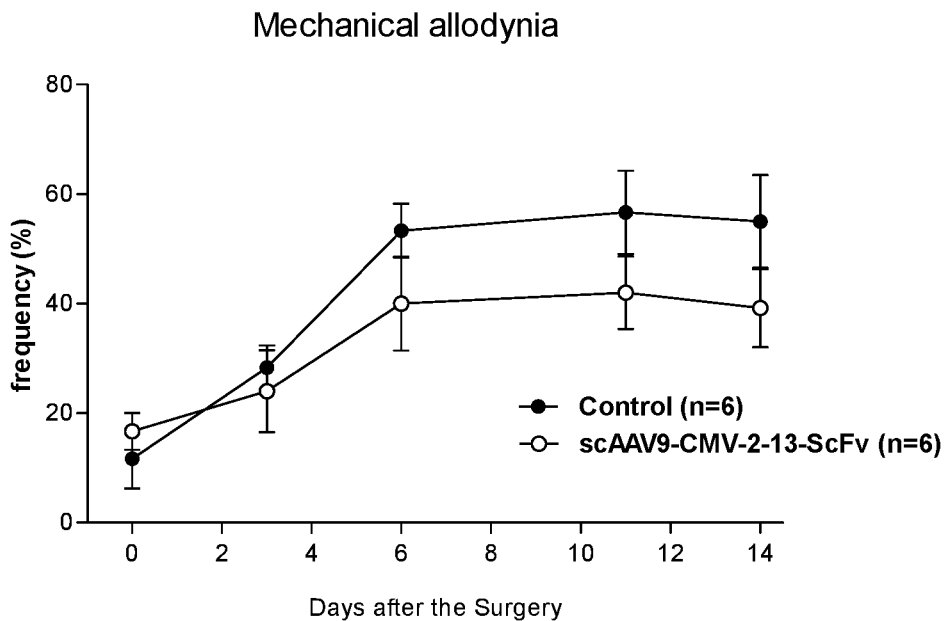
FIGS. 9A and 9B show the effect of scAAV9-CMV-2-13-ScFv administration on mechanical allodynia and thermal hyperalgesia, respectively.
Figure 9B:
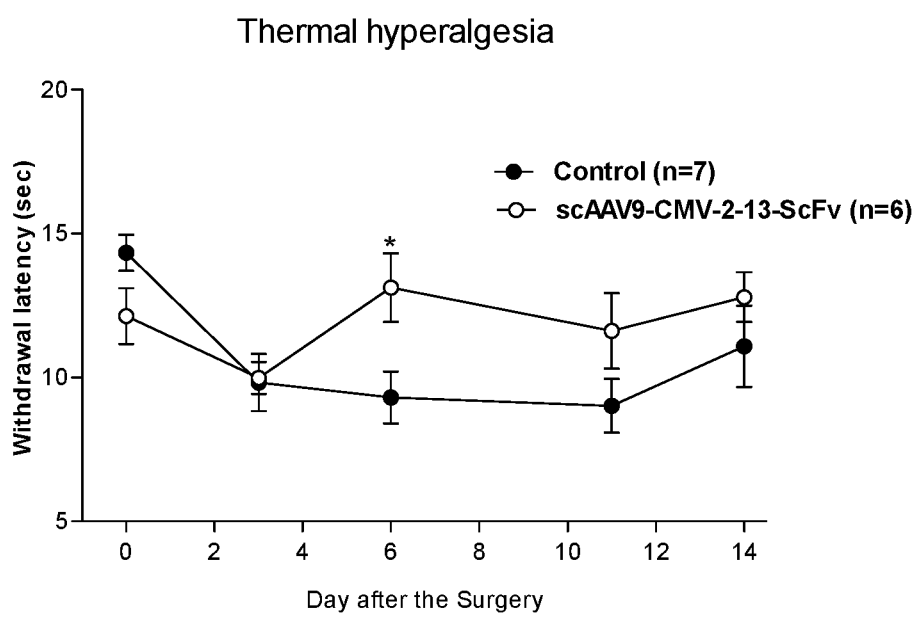
Figure 10A:
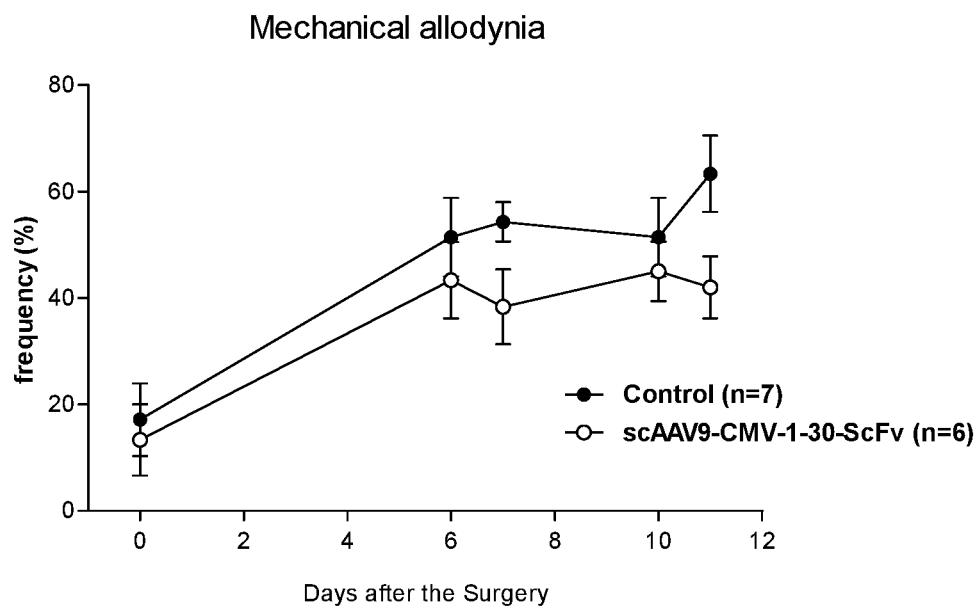
FIGS. 10A and 10B show the effect of scAAV9-CMV-1-30-ScFv administration on mechanical allodynia and thermal hyperalgesia, respectively.
Figure 10B:
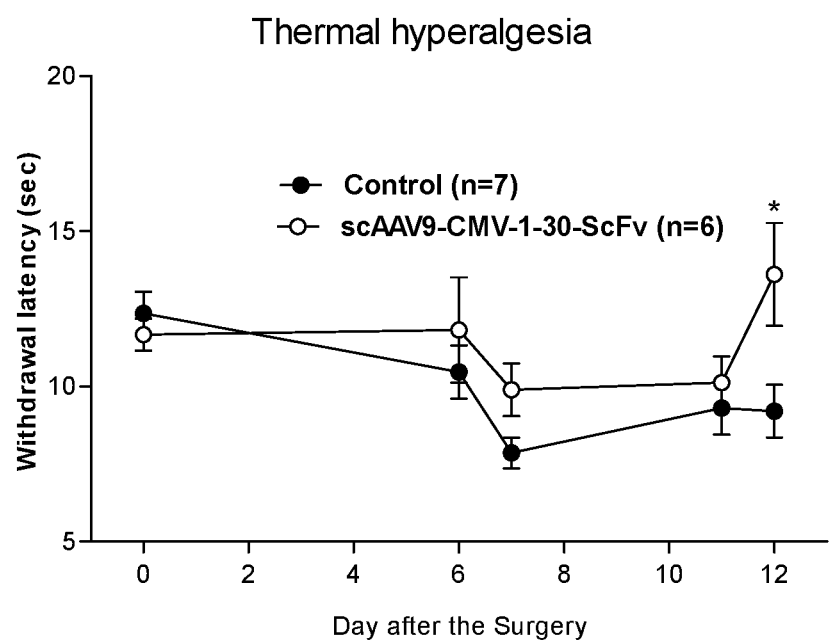

As observed in Examples 6 and 7, compared to the control group, animals treated with scAAV1-CMV-3-2-ScFv showed improvement of mechanical allodynia (i.e., responded less frequently to the Von Frey monofilament stimulation) starting at about day 4 post injury induction (i.e., days after surgery). FIG. 8A. This improvement was maintained until the end of the experiment at day 24 post injury induction. For thermal hyperalgesia, improvement was also observed in animals treated with scAAV1-CMV-3-2-ScFv (i.e., greater latency time in response to the heat stimulus) starting at about day 5 post injury induction and lasted at least until day 12 post injury induction. FIG. 8B.

These results further confirm the efficacy of the 3-2 anti-FAM19A5 scFv in treating neuropathic pain and demonstrate that the therapeutic benefits are not dependent on the type of AAV vector used.

Example 9: Assessment of Pain Relief in a Chronic Neuropathic Pain Model (CCI) Using scAAV9-CMV-2-13-ScFv or scAAV9-CMV-1-30-ScFv To assess whether other clones of the anti-FAM19A5 antibody can also treat neuropathic pain, the mouse model of chronic constriction injury (CCI) described in Example 6 was again used. Briefly, scAAV9-CMV-2-13-ScFv (two doses at two-week interval; each dose=$1\times10^{11}$ vg/mouse) or scAAV9-CMV-1-30-ScFv (single dose; $1\times10^{11}$ vg/mouse) was administered to C57BL/6 mice via intrathecal administration. Control animals received scAAV9-CMV-GFP. Approximately a week after the last administration, peripheral nerve injury was induced, and both mechanical allodynia and thermal hyperalgesia were assessed at various time points post injury induction (see Example 6).

As shown in FIGS. 9A, 9B, 10A, and 10B, animals treated with either scAAV9-CMV-2-13-ScFv or scAAV9-CMV-1-30-ScFv showed improvement for both mechanical allodynia and thermal hyperalgesia. These results demonstrate that different clones of the anti-FAM19A5 antibody can be used to treat neuropathic pain.

Example 10: Assessment of Pain Relief in a Chronic Neuropathic Pain Model (CCI) Using Anti-FAM19A5 ScFv in Combination with IL-10

To determine the efficacy of anti-FAM19A5 ScFv in combination with other therapeutic agents (i.e., IL-10), one of the following regimens was administered to C57BL/6 mice via intrathecal administration: (i) scAAV1-CMV-GFP; (ii) scAAV1-CMV-3-2-ScFv; (iii) scAAV1-CMV-3-2-ScFv+scAAV9-CMV-mIL-10; and (iv) scAAV9-CMV-mIL-10. The different treatment regimens were administered to the mice twice (two-week interval) at a dose of $1\times10^{11}$ µg/mouse. One week after the last administration, peripheral nerve injury was induced, and mechanical allodynia was assessed at various time points (see Example 6).

Figure 11A:
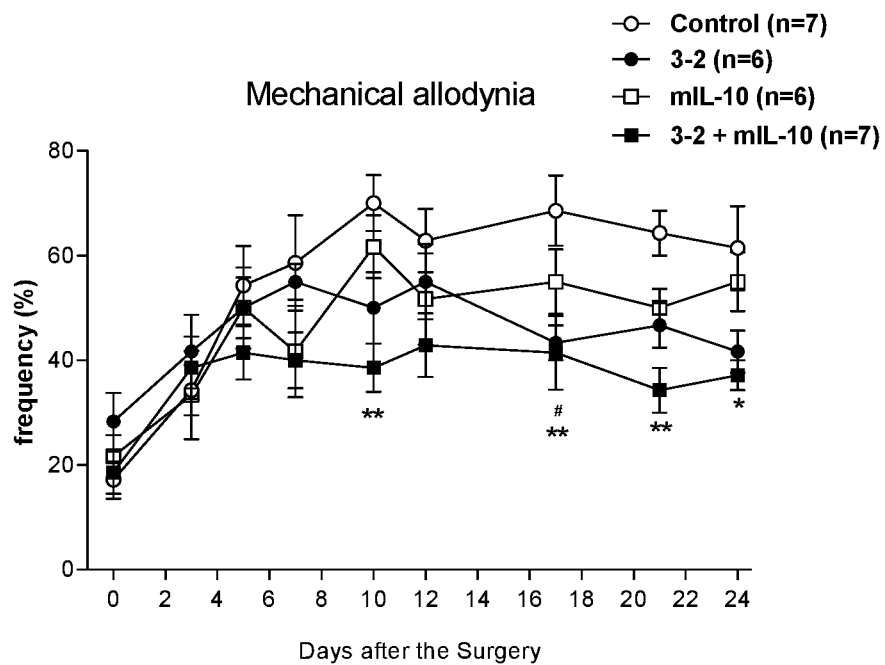
FIGS. 11A, 11B, and 11C provides a comparison of the effect of different anti-FAM19A5 scFv AAV constructs alone or in combination with another therapeutic agent.
Figure 11B:
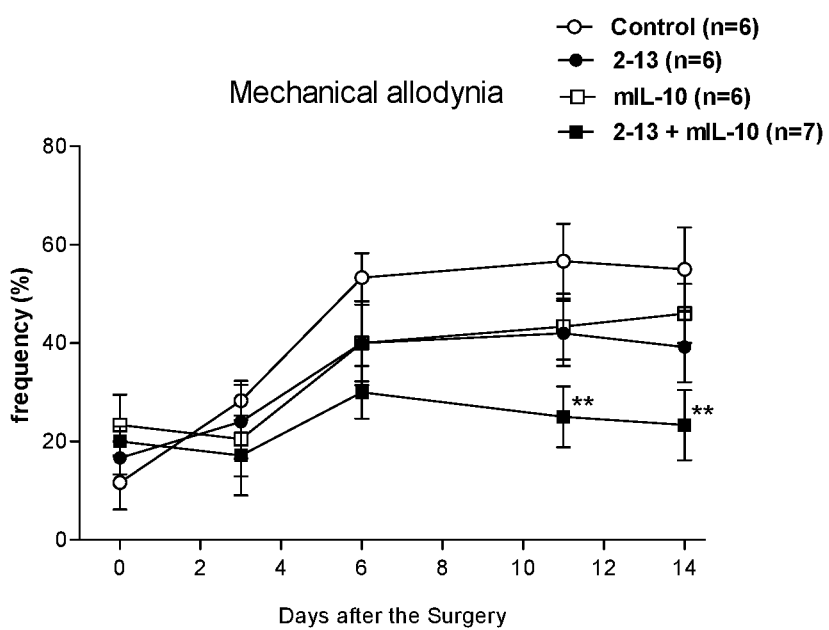
Figure 11C:
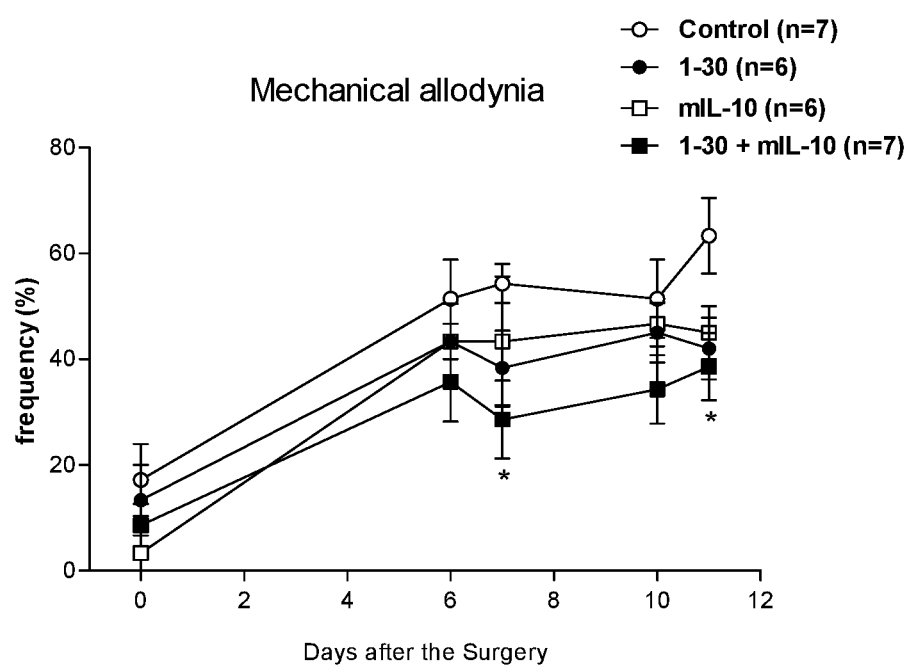

As observed in the earlier Examples, animals treated with scAAV1-CMV-3-2-ScFv alone were more tolerant of the physical stimuli (i.e., responded less frequently to the application of the Von Frey monofilament) compared to the control group (i.e., scAAV1-CMV-GFP). Similar responses were observed in animals treated with scAAV9-CMV-mIL-10 alone (FIG. 11A). When animals were treated with the combination of scAAV1-CMV-3-2-ScFv and scAAV9-CMV-mIL-10, they exhibited even greater improved response, compared to animals treated with a single treatment regimen. Similar results were observed for scAAV9-CMV-2-13-ScFv (FIG. 11B) and scAAV9-CMV-1-30-ScFv (FIG. 11C).

These results further demonstrate the efficacy of anti-FAM19A5 scFv delivered via AAV vectors in treating neuropathic pain. The results also demonstrate that this efficacy can be further enhanced when combined with other therapeutic agents, such as IL-10.

This PCT application claims priority benefit of U.S. Provisional Application No. 62/668,634, filed May 8, 2018, which is incorporated herein by reference in its entirety.

What is claimed is:

1. An adeno-associated virus (AAV) vector comprising a nucleic acid that encodes an antibody, or an antigen-binding portion thereof, which specifically binds to a family with sequence similarity 19, member A5 (FAM19A5) protein (anti-FAM19A5 antibody), wherein the anti-FAM19A5 antibody comprises a heavy chain CDR1, CDR2, and CDR3 and a light chain CDR1, CDR2, and CDR3, and wherein:
   (i) the heavy chain CDR3 comprises the amino acid sequence set forth in SEQ ID NO: 16;
   (ii) the heavy chain CDR1 comprises the amino acid sequence set forth in SEQ ID NO: 212;
   (iii) the heavy chain CDR2 comprises the amino acid sequence set forth in SEQ ID NO: 213;
   (iv) the light chain CDR1 comprises the amino acid sequence set forth in SEQ ID NO: 222;
   (v) the light chain CDR2 comprises the amino acid sequence set forth in SEQ ID NO: 225; and
   (vi) the light chain CDR3 comprises the amino acid sequence set forth in SEQ ID NO: 224.

2. The AAV vector of claim 1, further comprising an intron, a signal peptide, one or more adeno-associated virus inverted terminal repeats (ITRs), or any combination thereof.

3. The AAV vector of claim 1, wherein the anti-FAM19A5 antibody comprises a Fab, a Fab', a F (ab')2, a Fv, a single chain Fv (scFv), or a combination thereof.

4. The AAV vector of claim 3, wherein the anti-FAM19A5 antibody is a scFv.

5. The AAV vector of claim 1, wherein the nucleic acid is codon optimized.

6. An adeno-associated virus (AAV) vector comprising a nucleic acid that encodes an antibody, or an antigen-binding portion thereof, which specifically binds to a family with sequence similarity 19, member A5 (FAM19A5) protein (anti-FAM19A5 antibody), wherein the nucleic acid comprises the nucleotide sequence set forth in SEQ ID NO: 204, or SEQ ID NO: 301.

7. An adeno-associated virus (AAV) vector comprising a nucleic acid that encodes an antibody, or an antigen-binding portion thereof, which specifically binds to a family with sequence similarity 19, member A5 (FAM19A5) protein (anti-FAM19A5 antibody), wherein the scFv comprises the amino acid sequence set forth in SEQ ID NO: 201 or SEQ ID NO: 256.

8. The AAV vector of claim 1, wherein the anti-FAM19A5 antibody comprises
   a heavy chain variable region comprising the amino acid sequence set forth in SEQ ID NO: 236 and a light chain variable region comprising the amino acid sequence set forth in SEQ ID NO: 245.

9. The AAV vector of claim 1, wherein the anti-FAM19A5 antibody comprises a heavy chain variable region and a light chain variable region, wherein the heavy chain variable region comprises an amino acid sequence which is at least about 80% identical to the amino acid sequence set forth in SEQ ID NO: 236; and/or wherein the light chain variable region comprises an amino acid sequence which is at least about 80% identical to the amino acid sequence set forth in SEQ ID NO: 245.

10. The AAV vector of claim 1, wherein: (i) the anti-FAM19A5 antibody, or antigen-binding portion thereof, is capable of inhibiting the binding of a reference antibody, or antigen-binding portion thereof, to a human FAM19A5 protein by at least about 10%, as measured by a binding inhibition assay; (ii) the anti-FAM19A5 antibody, or antigen-binding portion thereof, is capable of reducing a concentration of FAM19A5 protein in a culture medium comprising an astrocyte cell line by at least about 10%, as measured by ELISA; or (iii) both (i) and (ii).

11. A composition comprising the AAV vector of claim 1 and a carrier.

12. An isolated host cell comprising the AAV vector of claim 1.

13. The AAV vector of claim 6, wherein the nucleic acid comprises the nucleotide sequence set forth in SEQ ID NO: 301.

14. A composition comprising the AAV vector of claim 13 and a carrier.

15. A composition comprising the AAV vector of claim 7 and a carrier.

16. An isolated host cell comprising the AAV vector of claim 7.

17. A composition comprising the AAV vector of claim 8 and a carrier.

18. An isolated host cell comprising the AAV vector of claim 8.

19. A composition comprising the AAV vector of claim 9 and a carrier.

20. An isolated host cell comprising the AAV vector of claim 9.

* * * * *